United States Patent
Ko et al.

(10) Patent No.: US 9,932,560 B2
(45) Date of Patent: Apr. 3, 2018

(54) USE OF ZSCAN4 AND ZSCAN4-DEPENDENT GENES FOR DIRECT REPROGRAMMING OF SOMATIC CELLS

(75) Inventors: Minoru S. H. Ko, Cockeysville, MD (US); Tetsuya Hirata, Minato-ku (JP)

(73) Assignee: ELIXIRGEN, LLC, Baltimore, MD (US)

(*) Notice: Subject to any disclaimer, the term of this patent is extended or adjusted under 35 U.S.C. 154(b) by 257 days.

(21) Appl. No.: 14/117,589

(22) PCT Filed: May 11, 2012

(86) PCT No.: PCT/US2012/037643
§ 371 (c)(1),
(2), (4) Date: Apr. 25, 2014

(87) PCT Pub. No.: WO2012/158561
PCT Pub. Date: Nov. 22, 2012

(65) Prior Publication Data
US 2014/0287511 A1  Sep. 25, 2014

Related U.S. Application Data

(60) Provisional application No. 61/486,004, filed on May 13, 2011, provisional application No. 61/529,055, filed on Aug. 30, 2011.

(51) Int. Cl.
| | |
|---|---|
| C12N 5/00 | (2006.01) |
| C12N 15/00 | (2006.01) |
| C12N 15/63 | (2006.01) |
| C07H 21/04 | (2006.01) |
| C07K 1/00 | (2006.01) |
| C12N 5/074 | (2010.01) |
| C12N 15/85 | (2006.01) |
| C12N 5/0735 | (2010.01) |
| C12N 15/79 | (2006.01) |
| C07K 14/47 | (2006.01) |
| C12N 15/86 | (2006.01) |

(52) U.S. Cl.
CPC ........... *C12N 5/0696* (2013.01); *C12N 15/85* (2013.01); *C07H 21/04* (2013.01); *C07K 14/47* (2013.01); *C12N 5/0606* (2013.01); *C12N 15/63* (2013.01); *C12N 15/79* (2013.01); *C12N 15/86* (2013.01); *C12N 2501/60* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2506/00* (2013.01); *C12N 2506/1307* (2013.01)

(58) Field of Classification Search
CPC ...... C12N 5/0606; C12N 15/63; C12N 15/79; C12N 15/86; C12N 2501/60; C12N 2506/00; C12N 2506/1307; C07H 21/04; C07K 14/47
USPC ...... 435/320.1, 377, 455; 530/350; 536/23.5
See application file for complete search history.

(56) References Cited

FOREIGN PATENT DOCUMENTS

| | | |
|---|---|---|
| JP | 2010-522565 A | 7/2010 |
| WO | 2008/118957 A2 | 10/2008 |
| WO | 2010/138517 A1 | 12/2010 |
| WO | 2011/028880 A2 | 3/2011 |
| WO | 2012/129342 A1 | 9/2012 |
| WO | 2012/158561 A1 | 11/2012 |

OTHER PUBLICATIONS

Bellin et al., 2012, Nature reviews/Molecular Cell Biology, vol. 13, p. 713-726.*
Zhang et al., 2012, Cell Cycle, vol. 11, No. 24, p. 1-9.*
Sommer et al., 2013, J. Cell. Physiol., vol. 228, p. 267-275.*
Li et al., 2014, Journal of Hematology & Oncology, 7:50, p. 1-18.*
Extended European Search Report (includes Supplementary European Search Report and Search Opinion) received for European Patent Application No. 12785169.9, dated Oct. 29, 2014, 8 pages.
International Search Report and Written Opinion received for PCT Patent Application No. PCT/US2012/037643, dated Jul. 19, 2012, 8 pages.
International Preliminary Report on Patentability received for PCT Patent Application No. PCT/US2012/037643, dated Nov. 28, 2013, 6 pages.
Brambrink et al., "ES Cells Derived from Cloned and Fertilized Blastocysts are Transcriptionally and Functionally Indistinguishable", Proceedings of the National Academy of Sciences, vol. 103, No. 4, Jan. 24, 2006, pp. 933-938.
Falco et al., "Zscan4: A Novel Gene Expressed Exclusively in Late 2-Cell Embryos and Embryonic Stem Cells", Developmental Biology, vol. 307, 2007, pp. 539-550.
Hirata et al., "Zscan4 Transiently Reactivates Early Embryonic Genes During the Generation of Induced Pluripotent Stem Cells", Science Reports, vol. 2:208, Jan. 4, 2012, pp. 1-11.
Huang et al., "Association of Telomere Length with Authentic Pluripotency of ES/iPS Cells", Cell Research, vol. 21, 2011, pp. 779-792.
Zalzman et al., "Zscan4 Regulates Telomere Elongation and Genomic Stability in ES Cells", Nature, vol. 464, No. 7290, Apr. 8, 2010, pp. 858-863.

(Continued)

*Primary Examiner* — Shin Lin Chen
(74) *Attorney, Agent, or Firm* — Morrison & Foerster LLP

(57) ABSTRACT

Disclosed herein is the finding that Zscan4 is an early embryonic factor that facilitates cellular reprogramming. In particular, Zscan4 can replace the oncogenic reprogramming factor c-Myc to produce induced pluripotent stem cells when co-expressed with Klf4, Oct4 and Sox2. In addition, several Zscan4-dependent genes were identified that promote iPSC formation when co-expressed with known reprogramming factors. Thus, the present disclosure provides an ex vivo method of producing an iPS cell by reprogramming of a somatic cell. The method includes contacting the somatic cell with a Zscan4, or a Zscan4-dependent gene, and at least one reprogramming factor. Also provided are iPS cells produced by the disclosed method and non-human animals generated from such iPS cells.

23 Claims, 23 Drawing Sheets

(56) References Cited

OTHER PUBLICATIONS

Takahashi et al., "Induction of Pluripotent Stem Cells from Mouse Embryonic and Adult Fibroblast Cultures by Defined Factors," Cell, vol. 126, Aug. 25, 2006, pp. 663-676.
Amano et al., "Correction of Down Syndrome and Edwards Syndrome Aneuploidies in Human Cell Cultures", DNA Research, 2015, pp. 1-12.
Gadalla et al., "Telomere Biology in Hematopoiesis and Stem Cell Transplantation", Blood Rev, vol. 25, 2011, pp. 261-269.
Office Action received for European Patent Application No. 14762788.9, dated Oct. 23, 2017, 15 pages.
Response to Office Action for European Patent Application No. 14762788.9, filed on Jan. 27, 2017, 5 pages.
Response to Office Action for European Patent Application No. 14762788.9, filed on Sep. 28, 2017, 8 pages.
Response to Written Opinion for Singapore Patent Application No. 11201507334V, filed on Feb. 24, 2017, 60 pages.
Written Opinion received for Singapore Patent Application No. 11201507334V, dated Aug. 17, 2017, 5 pages.
Written Opinion received for Singapore Patent Application No. 11201507334V, dated Jun. 13, 2016, 9 pages.

\* cited by examiner

FIGURE 3A-B
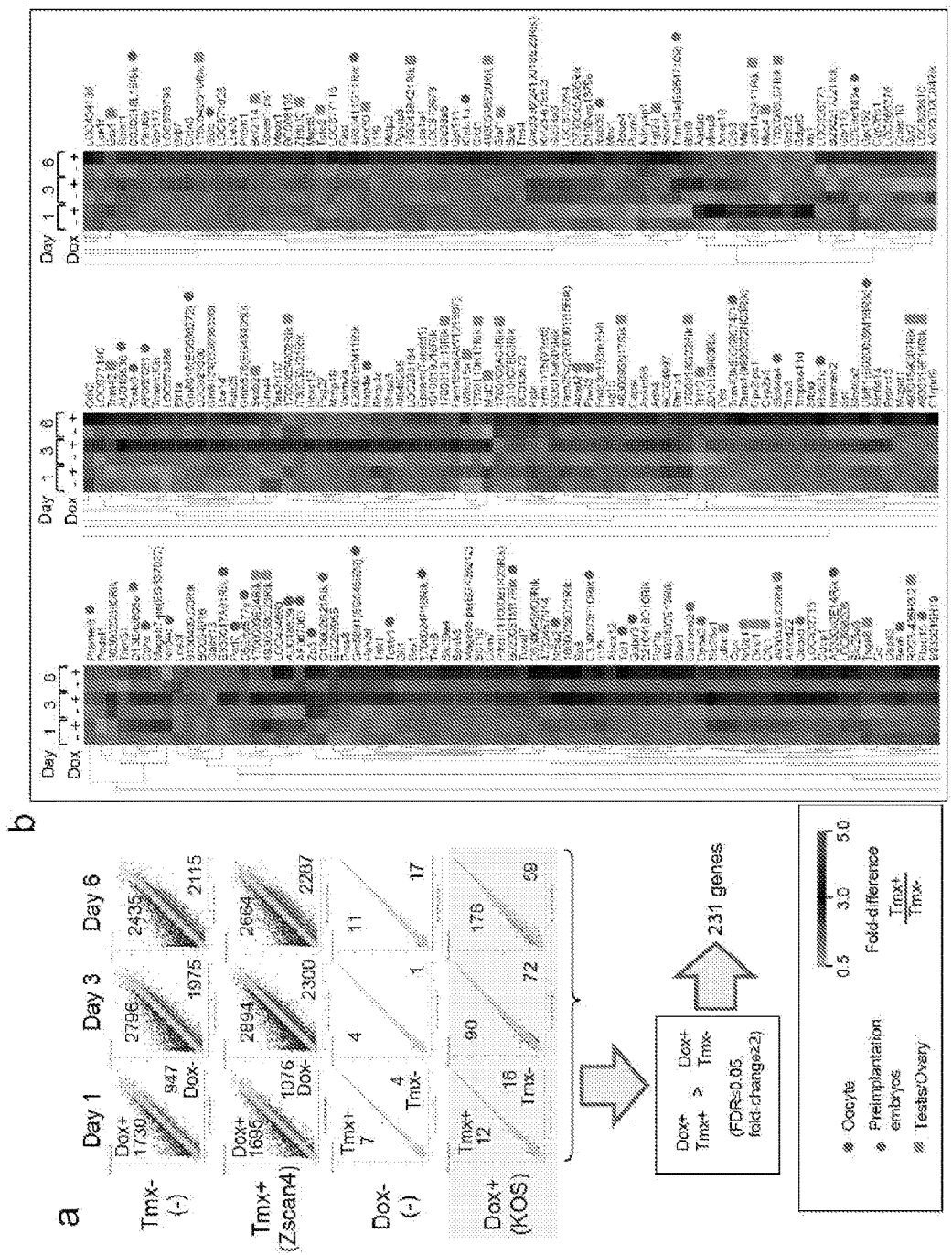

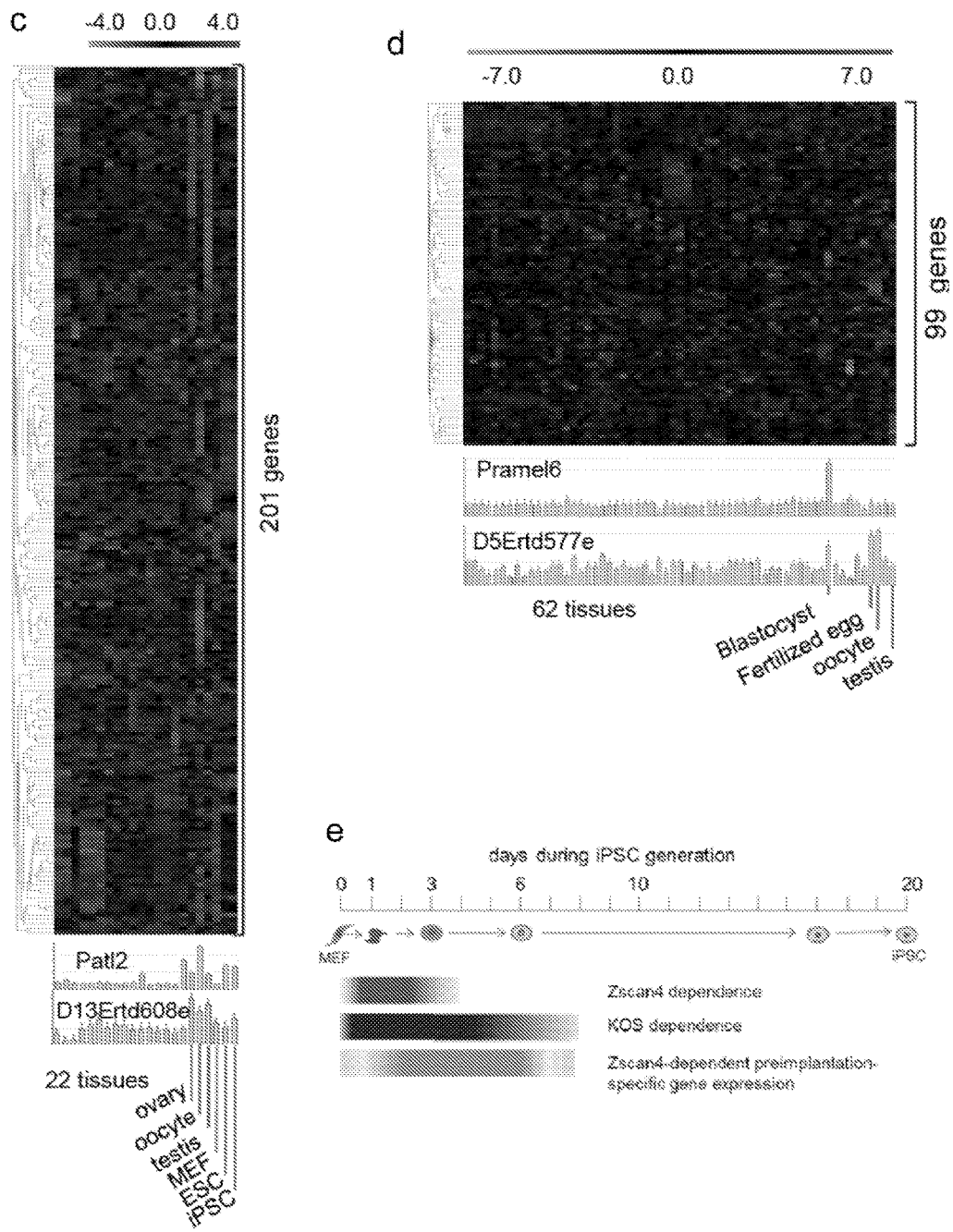
FIGURE 3C-E

FIGURE 17

| Purpose | Primer Name | Primer Sequence | SEQ ID NO: |
|---|---|---|---|
| For construction | attB1-koz-Zscan4c forward primer | GGGGACAAGTTTGTACAAAAAAGCAGGCTCCACCatggcttcacagcaggcac | 15 |
| | attB2-Zscan4c reverse primer | GGGGACCACTTTGTACAAGAAAGCTGGGTtcagtcagatctgtgtaat | 16 |
| | attB2-Zscan4c-ERT2 reverse primer | GGGGACCACTTTGTACAAGAAAGCTGGGTtcagcgtggcagggaaac | 17 |
| | attB1-koz-KLF4 forward primer | GGGGACAAGTTTGTACAAAAAAGCAGGCTCCACCatgagtcagccacctggc | 18 |
| | attB2-SOX2 reverse primer | GGGGACCACTTTGTACAAGAAAGCTGGGTtcacatgtgcgacagcggca | 19 |
| | attB1-kozak-human Zscan4 forward primer | GGGGACAAGTTTGTACAAAAAAGCAGGCTCCACCatggctttag atctaagaat | 20 |
| | attB2-human Zscan4 reverse primer | GGGGACCACTTTGTACAAGAAAGCTGGGTttaggaagcttctggtgtgg | 21 |
| For RT-PCR | endo-oct4 F | TCTTTCCACCAGGCCCCCGGCTC | 22 |
| | endo-oct4 R | TGCGGGCCGACATGGGGAGATCC | 23 |
| | endo-SOX2 F | TAGAGCTAGACTCCGGGCGATGA | 24 |
| | endo-SOX2 R | TTGCCTTAAACAAGACCACGAAA | 25 |
| | Nanog F | CACCCACCCATGCTAGTCTT | 26 |
| | Nanog R | ACCCTCAAACTCCTGGTCCT | 27 |
| | Dax1 F | TGCTGCGGTCCAGGCCATCAAGAG | 28 |
| | Dax1 R | GGGCACTGTTCAGTTCAGCGGATC | 29 |
| | Rex1 F | ACGAGTGGCAGTTTCTTCTTGGGA | 30 |
| | Rex1 R | TATGACTCACTTCCAGGGGGCACT | 31 |
| | GAPDH ON 025 | CGGAGTCAACGGATTTGGTCGTAT | 32 |
| | GAPDH ON 032 | GAAGATGGTGATGGGCTTCC | 33 |
| For RT-qPCR | Zscan4c_ON995 | AGTCTGACTGATGAGTGCTGAAGCC | 34 |
| | Zscan4c_ON996 | GGCCTTGTTGCCAGATTGCTGTTG | 35 |
| For methylation analysis | Me-Oct3/4-S | GGTTTTTTAGAGGATGGTTGAGTG | 36 |
| | Me-Oct3/4-AS | TCCAACCCTACTAACCCATCACC | 37 |

FIGURE 18
A
| iPSC cell line | Zscan4 [z] | Factors | Euploid [%] | No. Injected 4N blastocysts | No. embryos at E13.5 [%] | No. live embryos at E13.5 [%] |
|---|---|---|---|---|---|---|
| MEF-ZERT-KOS #2 | Z | KOS | 80 | 45 | 9 (20%) | 2 (4.4%) |
| B5+1 | Z | MKOS | 58 | 46 | 1 (2%) | 1 (2%) |
| B5+2 | Z | MKOS | 76 | 25 | 0 (0%) | 0 (0%) |
| B5+4 | Z | MKOS | 81 | N.D. | N.D. | N.D. |
| B5-1 | - | MKOS | 47 | N.D. | N.D. | N.D. |
| B5-3 | - | MKOS | 0 | N.D. | N.D. | N.D. |
B
Karyotype examples
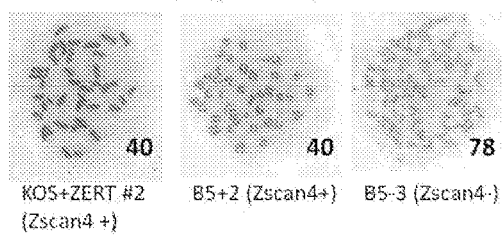
C
Live embryos derived entirely from iPSC
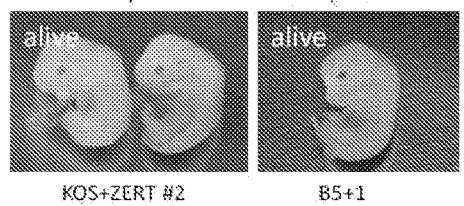

SEQUENCE LISTING

<160> NUMBER OF SEQ ID NOS: 73

<210> SEQ ID NO 1
<211> LENGTH: 2230
<212> TYPE: DNA
<213> ORGANISM: Homo sapiens

<400> SEQUENCE: 1

```
ccttgtaatt cataaatctc tgaaaactta aaagtttgag caaaagtttg tcatgtttct      60
atgagtaatt tataataaaa cttgatcaga atttgtgaga ctagcgtttg tctttatatt     120 ttccttttt tttttttttt tttgagacac agtctcgctc tgtcgtccag gctggagtgc     180
cgtggcgtaa tctcggctca ctgcaacctc tgcctcctgg attcaaacaa ttcttctgcc     240
tcagcctcct gagtagctgg gattacagga ccagtgatgg tatagaacac tgtattagag     300
acatggagct ggggctggat gaagattcca tcagtaattc aatcaacaga caagtgttat     360
ccaatcacgt ctttaaatca atcactgaca tggagctggg gctggatgaa gattccatca     420
gtaattcaat caacagacaa gtgttatcca atcacgtctt taaatcaatc actgatccca     480 gccccctataa aagggagcag ccttaggagg cacatcagat aaacccagtg tggaaagcta     540
```

| | |
|---|---|
| gtcacacatc agctcagtgt tcggcccggg attacccagt caaccaagga gcttgcagtt | 600 |
| ttaaagaatc caccaactgt tgaaacaaat ccctagagac acaaggcaag agactgaatc | 660 |
| atcaaagtaa agtctctctg agaattattg ctaagaatgg ctttagatct aagaaccata | 720 |
| tttcagtgtg aaccatccga gaataatctt ggatcagaaa attcagcgtt tcaacaaagc | 780 |
| caaggacctg ctgttcagag agaagaaggg atttctgagt tctcaagaat ggtgctcaat | 840 |
| tcatttcaag acagcaataa ttcatatgca aggcaggaat tgcaaagact ttataggatc | 900 |
| tttcactcat ggctgcaacc agaaaagcac agcaaggatg aaattatttc tctattagtc | 960 |
| ctggagcagt ttatgattgg tggccactgc aatgacaaag ccagtgtgaa agagaaatgg | 1020 |
| aaatcaagtg gcaaaaactt ggagagattc atagaagacc tgactgatga cagcataaat | 1080 |
| ccacctgcct tagtccacgt ccacatgcag ggacaggaag ctctcttttc tgaggatatg | 1140 |
| cccttaagag atgtcattgt tcatctcaca aaacaagtga atgcccaaac cacaagagaa | 1200 |
| gcaaacatgg ggacaccctc ccagacttcc caagatactt ccttagaaac aggacaagga | 1260 |
| tatgaagatg aacaagatgg ctggaacagt tcttcgaaaa ctactcgagt aaatgaaaat | 1320 |
| attactaatc aaggcaatca aatagttttc ctaatcatca tccaggaaga gaacggtcct | 1380 |
| aggcctgaag agggaggtgt ttcttctgac aacccataca actcaaaaag agcagagcta | 1440 |
| gtcactgcta gatctcagga agggtccata aatggaatca ctttccaagg tgtccctatg | 1500 |
| gtgatgggag cagggtgtat ctctcaacca gagcagtcct cccctgagtc tgcccttacc | 1560 |
| caccagagca atgagggaaa ttccacatgt gaggtacatc agaaaggatc ccatggagtc | 1620 |
| caaaaatcat acaaatgtga agaatgcccc aaggtcttta gtatctctg tcacttatta | 1680 |
| gctcaccaga agacacag gaatgagagg ccatttgttt gtcccgagtg tcaaaaaggc | 1740 |
| ttcttccaga tatcagacct acgggtgcat cagataattc acacaggaaa gaagcctttc | 1800 |
| acatgcagca tgtgtaaaaa gtccttcagc cacaaaacca acctgcggtc tcatgagaga | 1860 |
| atccacacag gagaaaagcc ttatacatgt ccctttgta agacaagcta ccgccagtca | 1920 |
| tccacatacc accgccatat gaggactcat gagaaaatta ccctgccaag tgttccctcc | 1980 |
| acaccagaag cttcctaagc tgctggtctg ataatgtgta taatatgta tgcaagtatg | 2040 |
| tatattccta tagtatttat ctacttagga tataagatat aatctcctga ttatgctttc | 2100 |
| aatttattgt cttgcttcat taaaatgtaa ggctaaggag agcatggaat ttgtcagttt | 2160 |
| tgttcactaa agtattccaa gtggttggga aagtggaaca tttccaagaa ccaataaatt | 2220 |
| tctgttgaat | 2230 |

```
<210> SEQ ID NO 2
<211> LENGTH: 433
<212> TYPE: PRT
<213> ORGANISM: Homo sapiens
<220> FEATURE:
<221> NAME/KEY: DOMAIN
<222> LOCATION: (44)..(126)
<223> OTHER INFORMATION: SCAN box
<220> FEATURE:
<221> NAME/KEY: DOMAIN
<222> LOCATION: (312)..(334)
<223> OTHER INFORMATION: C2H2-type 1
<220> FEATURE:
<221> NAME/KEY: DOMAIN
<222> LOCATION: (340)..(362)
<223> OTHER INFORMATION: C2H2-type 2
<220> FEATURE:
<221> NAME/KEY: DOMAIN
<222> LOCATION: (368)..(390)
<223> OTHER INFORMATION: C2H2-type 3
```

```
<220> FEATURE:
<221> NAME/KEY: DOMAIN
<222> LOCATION: (396)..(418)
<223> OTHER INFORMATION: C2H2-type 4

<400> SEQUENCE: 2
```

| | | | | | | | | | | | | | | |
|---|---|---|---|---|---|---|---|---|---|---|---|---|---|---|
| Met | Ala | Leu | Asp | Leu | Arg | Thr | Ile | Phe | Gln | Cys | Glu | Pro | Ser | Glu | Asn |
| 1 | | | | 5 | | | | | 10 | | | | | 15 | |
| Asn | Leu | Gly | Ser | Glu | Asn | Ser | Ala | Phe | Gln | Gln | Ser | Gln | Gly | Pro | Ala |
| | | | 20 | | | | | 25 | | | | | 30 | | |
| Val | Gln | Arg | Glu | Glu | Gly | Ile | Ser | Glu | Phe | Ser | Arg | Met | Val | Leu | Asn |
| | | 35 | | | | | 40 | | | | | 45 | | | |
| Ser | Phe | Gln | Asp | Ser | Asn | Asn | Ser | Tyr | Ala | Arg | Gln | Glu | Leu | Gln | Arg |
| | 50 | | | | | 55 | | | | | 60 | | | | |
| Leu | Tyr | Arg | Ile | Phe | His | Ser | Trp | Leu | Gln | Pro | Glu | Lys | His | Ser | Lys |
| 65 | | | | | 70 | | | | | 75 | | | | | 80 |
| Asp | Glu | Ile | Ile | Ser | Leu | Leu | Val | Leu | Glu | Gln | Phe | Met | Ile | Gly | Gly |
| | | | | 85 | | | | | 90 | | | | | 95 | |
| His | Cys | Asn | Asp | Lys | Ala | Ser | Val | Lys | Glu | Lys | Trp | Lys | Ser | Ser | Gly |
| | | | 100 | | | | | 105 | | | | | 110 | | |
| Lys | Asn | Leu | Glu | Arg | Phe | Ile | Glu | Asp | Leu | Thr | Asp | Asp | Ser | Ile | Asn |
| | | 115 | | | | | 120 | | | | | 125 | | | |
| Pro | Pro | Ala | Leu | Val | His | Val | His | Met | Gln | Gly | Gln | Glu | Ala | Leu | Phe |
| | 130 | | | | | 135 | | | | | 140 | | | | |
| Ser | Glu | Asp | Met | Pro | Leu | Arg | Asp | Val | Ile | Val | His | Leu | Thr | Lys | Gln |
| 145 | | | | | 150 | | | | | 155 | | | | | 160 |
| Val | Asn | Ala | Gln | Thr | Thr | Arg | Glu | Ala | Asn | Met | Gly | Thr | Pro | Ser | Gln |
| | | | | 165 | | | | | 170 | | | | | 175 | |
| Thr | Ser | Gln | Asp | Thr | Ser | Leu | Glu | Thr | Gly | Gln | Gly | Tyr | Glu | Asp | Glu |
| | | | 180 | | | | | 185 | | | | | 190 | | |
| Gln | Asp | Gly | Trp | Asn | Ser | Ser | Ser | Lys | Thr | Thr | Arg | Val | Asn | Glu | Asn |
| | | 195 | | | | | 200 | | | | | 205 | | | |
| Ile | Thr | Asn | Gln | Gly | Asn | Gln | Ile | Val | Ser | Leu | Ile | Ile | Gln | Glu |
| | 210 | | | | | 215 | | | | | 220 | | | | |
| Glu | Asn | Gly | Pro | Arg | Pro | Glu | Glu | Gly | Gly | Val | Ser | Ser | Asp | Asn | Pro |
| 225 | | | | | 230 | | | | | 235 | | | | | 240 |
| Tyr | Asn | Ser | Lys | Arg | Ala | Glu | Leu | Val | Thr | Ala | Arg | Ser | Gln | Glu | Gly |
| | | | | 245 | | | | | 250 | | | | | 255 | |
| Ser | Ile | Asn | Gly | Ile | Thr | Phe | Gln | Gly | Val | Pro | Met | Val | Met | Gly | Ala |
| | | | 260 | | | | | 265 | | | | | 270 | | |
| Gly | Cys | Ile | Ser | Gln | Pro | Glu | Gln | Ser | Ser | Pro | Glu | Ser | Ala | Leu | Thr |
| | | 275 | | | | | 280 | | | | | 285 | | | |
| His | Gln | Ser | Asn | Glu | Gly | Asn | Ser | Thr | Cys | Glu | Val | His | Gln | Lys | Gly |
| | 290 | | | | | 295 | | | | | 300 | | | | |
| Ser | His | Gly | Val | Gln | Lys | Ser | Tyr | Lys | Cys | Glu | Glu | Cys | Pro | Lys | Val |
| 305 | | | | | 310 | | | | | 315 | | | | | 320 |
| Phe | Lys | Tyr | Leu | Cys | His | Leu | Leu | Ala | His | Gln | Arg | Arg | His | Arg | Asn |
| | | | | 325 | | | | | 330 | | | | | 335 | |
| Glu | Arg | Pro | Phe | Val | Cys | Pro | Glu | Cys | Gln | Lys | Gly | Phe | Phe | Gln | Ile |
| | | | 340 | | | | | 345 | | | | | 350 | | |
| Ser | Asp | Leu | Arg | Val | His | Gln | Ile | Ile | His | Thr | Gly | Lys | Lys | Pro | Phe |
| | | 355 | | | | | 360 | | | | | 365 | | | |
| Thr | Cys | Ser | Met | Cys | Lys | Lys | Ser | Phe | Ser | His | Lys | Thr | Asn | Leu | Arg |
| | 370 | | | | | 375 | | | | | 380 | | | | |

```
Ser His Glu Arg Ile His Thr Gly Glu Lys Pro Tyr Thr Cys Pro Phe
385                 390                 395                 400

Cys Lys Thr Ser Tyr Arg Gln Ser Ser Thr Tyr His Arg His Met Arg
                405                 410                 415

Thr His Glu Lys Ile Thr Leu Pro Ser Val Pro Ser Thr Pro Glu Ala
                420                 425                 430

Ser

<210> SEQ ID NO 3
<211> LENGTH: 2275
<212> TYPE: DNA
<213> ORGANISM: Mus musculus

<400> SEQUENCE: 3
cacagtgcct ccctgggctt cttggcatca cccttgaagt tcactggaga aagagttgag      60
gtggaggaat aggtaaactt cccttcctag tggtcttgaa tgtcttttac agtacatcca     120
tcaactgtta gcattttcgt aaagtcacaa aacagatatt aaactactat agttgaatct     180
ttcacaccat tgtcaccaca atggcttcac agcaggcacc agcaaaagac cttcagacca     240
acaatttaga gtttactcca actgatagtt ctggtgtgca gtgggcagaa gacatctcta     300
actcaccaag tgctcagcta aacttttccc caagtaacaa tggctgctgg gcaactcagg     360
agctgcaaag tctctggaag atgttcaact cctggttgca gccagaaaag cagactaagg     420
agcagatgat ttctcaactg gtcttggagc agtttctcct cactgggcac tgcaaggaca     480
agtatgcttt gacagagaag tggaaagcca gtggtagcga tatgaggaga ttcatggaga     540
gtctgactga tgagtgcttg aagcctcctg tcatggtcca tgtctcaatg caaggacaag     600
aagccctctt ttctgaaaac atgccattaa agaagtcat caagcttttg aaacaacagc      660
aatctgcaac aaggccaaca ccagataatg cacagatgcc agtagacacc acacaagata     720
gattattggc cacaggacaa gaaaacagtg aaaatgaatg caacacctct tgtaatgcta     780
ctgaaggaaa tgttggtgag agctgtagtg gaaatgaaat ggactcctct cttattatcc     840
agaaagaaca gtaccctgag catgaagagg ggaatgttgt ttgtcaattc cctcttgatg     900
ccagaagagc aagtcaaggc acctccagtc atcatgtaga cttcctgagt gctctgacta     960
ctgccgatgt ccccatggag gaacaaccaa aggatttatc cagagaaaac atctctgagg    1020
acaagaacaa ttgctataac acttccagga atgcagctac taaagtatat agtggtgata    1080
atattcccag gaaaaagaca gactcccttt ccattaacaa gaggatatat catcctgagc    1140
ctgaggtggg agatattcct tatggagttc ctcaggattc tacaagagca agtcaaggaa    1200
catctacatg cctgcaagag tcacttgggg gatgttttc cgaaaaagac cctagggagg     1260 taccaggggtt gcagtctagg taagagcagc ctatctctga tcctgtcctt cttggtaaga    1320
atcatgaggc aaacttacca tgtgaaagtc atcaaaagag attctgtaga gatgccaaac    1380
tatacaagtg tgaagaatgt tctaggatgt caaacatgc caggagcctt tcatcccacc      1440
agagaactca cctgaataag aagagtgaat tgctttgtgt cacctgtcag aaaattttca    1500
aacgagtctc tgaccgccga acccatgaga tcatacacat gccagaaaag cctttcaagt    1560
gcagcacatg tgaaaagtcc ttcagccaca agaccaacct gaagtctcat gagatgattc    1620
acacaggaga aatgccttat gtctgttccc tatgtagccg tcgctttcgc caatcatcca    1680
cttaccatcg tcacctgagg aattatcaca gatctgactg aagtatctaa catcctcagc    1740
agagactggt agggcttcag cctcagtatg tcatcttcaa agagagaaga atgttgcaag    1800
```

-continued

```
taaattgtac tgtcccaata atgatataac atgcttgtgg attgccactt ttatgttttg   1860
ttttgttttg tttttattt tgtgtgtgtg tatgtaattt tttgtctgta tttccatagt    1920
tccacagcat aagttattag aatactttgc tgttaattct tgagttgctt cttgctttta   1980
gacagtgtct ttctggttgg cagctttata cacctgtctt tctggcacta gagtttccaa   2040 acatttctg atctccactt ttattttcta cagtggtcct gacagaggcc tgccattccc    2100
tctgacattt ttctacatgt tggggtttca tcccaagtct tagggttgca agttaaatgc   2160
attgcctctt cagacatctc atgtcatgtc tactgcttac agttcaagaa tatttctcta   2220
cattactaga acgacgttca aagtggaata ataaataaat aaataatcaa caatt        2275
```

<210> SEQ ID NO 4
<211> LENGTH: 360
<212> TYPE: PRT
<213> ORGANISM: Mus musculus

<400> SEQUENCE: 4

```
Met Ala Ser Gln Gln Ala Pro Ala Lys Asp Leu Gln Thr Asn Asn Leu
 1               5                  10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Thr
145                 150                 155                 160

Pro Asp Asn Ala Gln Met Pro Val Asp Thr Thr Gln Asp Arg Leu Leu
                165                 170                 175

Ala Thr Gly Gln Glu Asn Ser Glu Asn Glu Cys Asn Thr Ser Cys Asn
            180                 185                 190

Ala Thr Glu Gly Asn Val Gly Glu Ser Cys Ser Gly Asn Glu Met Asp
        195                 200                 205

Ser Ser Leu Ile Ile Gln Lys Glu Gln Tyr Pro Glu His Glu Glu Gly
    210                 215                 220

Asn Val Val Cys Gln Phe Pro Leu Asp Ala Arg Arg Ala Ser Gln Gly
225                 230                 235                 240

Thr Ser Ser His His Val Asp Phe Leu Ser Ala Leu Thr Thr Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Lys
        275                 280                 285

Val Tyr Ser Gly Asp Asn Ile Pro Arg Lys Lys Thr Asp Ser Leu Ser
```

```
                  290                 295                 300
Ile Asn Lys Arg Ile Tyr His Pro Glu Pro Glu Val Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Gly Cys Phe Ser Glu Lys Asp Pro Arg
            340                 345                 350

Glu Val Pro Gly Leu Gln Ser Arg
            355                 360

<210> SEQ ID NO 5
<211> LENGTH: 1774
<212> TYPE: DNA
<213> ORGANISM: Mus musculus

<400> SEQUENCE: 5
cacagtgcct ccctgggctt cttggcatca cccttgaagt tcactggaga aagaggtgat    60
gtggagaagt aggtaaactt cccttcttg tggtcttgaa tgtcttttac agtacatccg    120
tcaactgtta gcattttcct aaagtcacaa aacagatact aaactgctat agttgaatct    180
ttcagaccat tgtcaccaca atggcttcac agcaggcacc agcaaaagac cttcagacca    240
acaatttaga gtttactcca actgatagtt ctggtgtgca gtgggcagaa gacatctcta    300
actcaccaag tgctcagcta aacttttccc caagtaacaa tggctgctgg gcaactcagg    360
agctgcaaag tctctggaag atgttcaact cctggttgca gccagaaaag cagactaagg    420
agcagatgat ttctcaattg gtcttggagc agtttctcct cactgggcac tgcaaggaca    480
agtatgcttt gacagagaag tggaaagcca gtggtagcga tatgaggaga ttcatggaga    540
gtctgactga tgagtgcttg aagcctcctg tcatggtcca tgtttcaatg caaggacaag    600
aagccctctt ttctgaaaac atgccattaa agaagtcat caagcttttg aaacaacagc    660
aatctgcaac aaggccaata ccagataatg cacagatgcc agtagacacc acacaagata    720
gattattggc cacaggcaag aaaacagtga aatgaatgc aacacctctt gcaatgctac    780
tgaagtaaat gttggtgaaa gctgtagtgg aaatgaaaag gactccttc ttattaccca    840 gaaagaacaa accatgagc atgaagaggg gaatgttgtt tgtcaattcc ctcgtggtgc    900
cagaagagca agtcaagaca cctccagtca tcatgtagac ttcccgagtg ctctgactcc    960
tgcagatgtc cccatggagg aacaaccaat ggatttatcc agagaaaaca tctctgagga    1020
caagaacaat tgctataaca cttccaggaa tgcagctact caagtatata gtggtgataa    1080
tattcccagg aacaagacag actccctttt cattaacaag agaatatatc atcctgagcc    1140
tgaggtggga gatattcctt atggagttcc tcaggattct acaagagcaa gtcaaggaac    1200
atctacatgc ctgcaagagt cacttgggga atgttttct gaaaaagacc caagggaggt    1260
accagggttg cagtctaggc aagagcagcc tatctctgat cctgtccttg gtaagaatca    1320
tgaggcaaac ttaccatgtg aaagtcatca aaagagattc catagagatg ccaaactata    1380
caagtgtgaa gaatgttcta ggatgttcaa acatgccagg agcctttcat cccaccagag    1440
aactcacctg aataagaaga gtgaattgct tgcatcacc tgtcagaaaa tattcaaacg    1500
agtttctgac cttcgaaccc atgagatcat acacatgtca gaaaagcctt tcaagtgcag    1560
cacatgtgaa aagtccttca gccacaagac caacctgaag tatcatgaga tgattcacac    1620
aggagaaatg ccttatgtct gttccctatg tagccgtcgc tttcgccaat catccactta    1680
ccatcgtcac ctgaggaatt accacagatc tgactgaagt atctaacatc ctcagcagag    1740
```

```
actggtaggg cttcagcctc agtatgtcat cttc                               1774
```

<210> SEQ ID NO 6
<211> LENGTH: 195
<212> TYPE: PRT
<213> ORGANISM: Mus musculus

<400> SEQUENCE: 6

```
Met Ala Ser Gln Gln Ala Pro Ala Lys Asp Leu Gln Thr Asn Asn Leu
 1               5                  10                  15

Glu Phe Thr Pro Thr Asp Ser Ser Gly Val Gln Trp Ala Glu Asp Ile
             20                  25                  30

Ser Asn Ser Pro Ser Ala Gln Leu Asn Phe Ser Pro Ser Asn Asn Gly
         35                  40                  45

Cys Trp Ala Thr Gln Glu Leu Gln Ser Leu Trp Lys Met Phe Asn Ser
     50                  55                  60

Trp Leu Gln Pro Glu Lys Gln Thr Lys Glu Gln Met Ile Ser Gln Leu
 65                  70                  75                  80

Val Leu Glu Gln Phe Leu Leu Thr Gly His Cys Lys Asp Lys Tyr Ala
                 85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Ile
145                 150                 155                 160

Pro Asp Asn Ala Gln Met Pro Val Asp Thr Thr Gln Asp Arg Leu Leu
                165                 170                 175

Ala Thr Gly Lys Lys Thr Val Lys Met Asn Ala Thr Pro Leu Ala Met
            180                 185                 190

Leu Leu Lys
        195
```

<210> SEQ ID NO 7
<211> LENGTH: 2275
<212> TYPE: DNA
<213> ORGANISM: Mus musculus

<400> SEQUENCE: 7

```
cacagtgcct ccctgggctt cttggcatca cccttgaagt tcaccggaga aagcagtgag    60
gtggaggaat aggtaaactt tccttcctag tggtcttgaa tgtcttttac agtacatcca   120
tcaactgtta gcattttcgt aaagtcacaa aacagatatt aaactactat agttgaatct   180
ttcacaccat tgtcaccaca atggcttcac agcaggcacc agcaaaagac cttcagacca   240
acaatttaga gtttactcca actgatagtt ctggtgtgca gtgggcagaa gacatctcta   300
actcaccaag tgctcagcta aacttttccc caagtaacaa tggctgctgg gcaactcagg   360
agctgcaaag tctctggaag atgttcaact cctggttgca gccagaaaag cagactaagg   420
agcagatgat ttctcaactg gtcttggagc agtttctcct cactgggcac tgcaaggaca   480
agtatgcttt gacagagaag tggaaagcca gtggtagcga tatgaggaga ttcatggaga   540
gtctgactga tgagtgcttg aagcctcctg tcatggtcca tgtttcaatg caaggacaag   600
aagcccttct ttctgaaaac atgccattaa aagaagtcat caagcttttg aaacaacagc   660
```

-continued

```
aatctgcaac aaggccaaca ccagataatg agcagatgcc agtagacacc acacaagata      720
gattattggc cacaggacaa gaaaacagtg aaaatgaatg caacaactct tgtaatgcta      780
ctgaagcaaa tgttggtgaa agctgtagtg gaaatgaaat ggactcccett cttattatcc     840 agaaagaaca gcaccctgag catgaagagg ggaatgttgt tgtcaattc cctcatggtg       900 ccagaagagc aagtcaaggc accccagtc atcatgtaga cttcccgagt gctccgacta       960
ctgccgatgt ccccatggag gaacaaccaa aggatttatc cagagaaaac atctctgagg     1020
acaagaacaa ttgctataac acttccagaa atgcagctac tcaagtatat agtggtgata     1080
atattcccag gaacaagtca gactccctt tcattaacaa gagaatatat catcctgagc      1140
ctgaggtggg agatattcct tatggagttc ctcaggattc tacaagagca agtcaaggaa     1200
catctacatg cctgcaagag tcacttgggg aatgtttttc tgaaaacgac caagggagg      1260 taccagggtt gcagtctagg caagagcagc ctatctctga tcctgtcctt cttggtaaga     1320
atcatgaggc aaacttacca tgtgaaagtc atcaaaagag attctgtaga gatgccaaac     1380
tatacaagtg tgaagaatgt tctaggatgt tcaaacatgc caggagcctt tcatcccacc     1440
agagaactca cctgaataag aagagtgaat tgctttgtgt cacctgtcag aaaatgttca     1500
aacgagtctc tgaccgccga acccatgaga tcatacacat gccagaaaag cctttcaagt     1560
gcagcacatg tgaaaagtcc ttcagccaca agaccaacct gaagtctcat gagatgattc     1620
acacaggaga aatgccttat gtctgttccc tatgtagccg tcgctttcgc caatcatcca     1680
cttaccatcg tcacctgagg aattaccaca gatctgactg aactatctaa catcctcagc     1740
agagactggt agggcttcag cctcagtatg tcatcttcaa agagagaaga atgttgcaag     1800
taaattgtac tgtcccaata atgatataac atgcttgtgg attgccactt ttatgttttg     1860
ttttgttttg ttwtttatkt tgtgtgtgtg tatgtaattt tttgtctgta tttccatatt     1920
tccacagcat aagttattag aatactttgc tgttaattct tgagttgctt cttgcttta     1980 gacagtgtct ttctggttgg cagctttata cacctgtctt tctggcacta gagtttccaa     2040
acattttctg atctccactt ttattttcta cagtgttctt gacagaagcc tggcattccc     2100
tctgacattt tctacatgtt gggttttca tcccaagtct tagggttgca agttaaatgc      2160
attgcctctt cagacatctc atgccatgtc tactgcttac agttcaagaa tatttctcta     2220
cattactaga acgacgttca aagtggaata ataaataaat aaataatcaa caatt          2275
```

<210> SEQ ID NO 8
<211> LENGTH: 506
<212> TYPE: PRT
<213> ORGANISM: Mus musculus
<220> FEATURE:
<221> NAME/KEY: DOMAIN
<222> LOCATION: (37)..(119)
<223> OTHER INFORMATION: SCAN box
<220> FEATURE:
<221> NAME/KEY: DOMAIN
<222> LOCATION: (395)..(417)
<223> OTHER INFORMATION: C2H2-type 1
<220> FEATURE:
<221> NAME/KEY: DOMAIN
<222> LOCATION: (424)..(449)
<223> OTHER INFORMATION: C2H2-type 2
<220> FEATURE:
<221> NAME/KEY: DOMAIN
<222> LOCATION: (452)..(474)
<223> OTHER INFORMATION: C2H2-type 3
<220> FEATURE:
<221> NAME/KEY: DOMAIN
<222> LOCATION: (480)..(503)

<223> OTHER INFORMATION: C2H2-type 4

<400> SEQUENCE: 8

```
Met Ala Ser Gln Gln Ala Pro Ala Lys Asp Leu Gln Thr Asn Asn Leu
 1               5                  10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
130                 135                 140

Glu Val Ile Lys Leu Leu Lys Gln Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Val Ser Cys Ser Gly Asn Glu Met Asp
        195                 200                 205

Ser Leu Leu Ile Ile Gln Lys Glu Gln His Pro Glu His Glu Glu Gly
210                 215                 220

Asn Val Val Cys Gln Phe Pro His Gly Ala Arg Arg Ala Ser Gln Gly
225                 230                 235                 240

Thr Pro Ser His His Val Asp Phe Pro Ser Ala Pro Thr Thr Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Ser Gly Asp Asn Ile Pro Arg Asn Lys Ser Asp Ser Leu Phe
290                 295                 300

Ile Asn Lys Arg Ile Tyr His Pro Glu Pro Glu Val Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Glu Cys Phe Ser Glu Asn Asp Pro Arg
            340                 345                 350

Glu Val Pro Gly Leu Gln Ser Arg Gln Glu Gln Pro Ile Ser Asp Pro
        355                 360                 365

Val Leu Leu Gly Lys Asn His Glu Ala Asn Leu Pro Cys Glu Ser His
370                 375                 380

Gln Lys Arg Phe Cys Arg Asp Ala Lys Leu Tyr Lys Cys Glu Glu Cys
385                 390                 395                 400
```

```
Ser Arg Met Phe Lys His Ala Arg Ser Leu Ser His Gln Arg Thr
            405                 410                 415

His Leu Asn Lys Lys Ser Glu Leu Leu Cys Val Thr Cys Gln Lys Met
            420                 425                 430

Phe Lys Arg Val Ser Asp Arg Arg Thr His Glu Ile Ile His Met Pro
            435                 440                 445

Glu Lys Pro Phe Lys Cys Ser Thr Cys Glu Lys Ser Phe Ser His Lys
            450                 455                 460

Thr Asn Leu Lys Ser His Glu Met Ile His Thr Gly Glu Met Pro Tyr
465                 470                 475                 480

Val Cys Ser Leu Cys Ser Arg Arg Phe Arg Gln Ser Ser Thr Tyr His
            485                 490                 495

Arg His Leu Arg Asn Tyr His Arg Ser Asp
            500                 505

<210> SEQ ID NO 9
<211> LENGTH: 2268
<212> TYPE: DNA
<213> ORGANISM: Mus musculus

<400> SEQUENCE: 9
cacagtgcct ccctgggctt cttggcatca cccttgaagt tcactggaca aagaggtgag      60
gtggaggagt aggtaaactt cccttcctag tggtcgtgaa tgtcttttac agtacatcca     120
tcaactgtta gcattttcat aaagtcacaa aacagatact aaactgctat agttgaatct     180
ttcacaccat tgtcaccaca atggcttcac agcaggcacc agcaaaagac cttcagacca     240
acaatttaga gtttactcca tctcatagtt ctggtgtgca gtgggtagaa gacatctcta     300
actcaccaag tgctcagcta aacttttctc caagtaacaa tggctgctgg gcaactcagg     360
agctgcaaag tctctggaag atgttcaact cctggttgca gccagaaaag cagactaagg     420
agcagatgat ttctcaactg gtcttggagc agtttctcct cattgggcac tgcaaggaca     480
agtatgcttt gacagagaag tggaaagcca gtggtagcga tatgaggaga ttcatggaga     540
gtctgactga tgagtgcttg aagcctcctg tcatggtcca tgtttcaatg caaggacaag     600
aagctctctt ttctgaaaac atgccattaa agaagtcat caagcttttg aaacaacagc      660
aatctgcaac aaggccaaca ccagataatg agcagatgcc agtagacacc acacaagata     720
gattattggc cacaggacaa gaaaacagtg aaaatgaatg caacaactct tgtaatgcta     780
ctgaagcaaa tgttggtgaa agctgtagtg gaaatgaaat ggactcccctt cttattatcc     840 agaaagaaca gcaccctgag catgaagagg ggaatgttgt ttttcaattc cctcttgatg     900
ccagaagagc aagtcaaggc aactccagtc atcatgtaga cttccggagt gctccgactc     960
ctgcggatgt ccccatggag gaacaaccaa aggatttatc cagagaaaac atctctgagg    1020
acaagaacaa ttgctataac acttccagga atgcagctac tcaagtatat gaagtgata     1080 atattcccag gaaaaagaca gactcccttt ccattaacaa gagaatatat cattctgagc    1140
ctgaggaggg agatattcct tatggagttc ctcaggattc tacaagagca agtcaaggaa    1200 catctcatg cttgcaagag tcacttgggg aatgttttc tgaaaagac cctagggagc       1260 taccagggtt ggagtctagg caagaggagc ctatctctga tcctgtcttt cttggtaagg    1320
atcatgaggc aaacttacca tgtgaaagtc atcaaaagag attccgtaga gatgccaaac    1380
tattcaagtg tgaagaatgt tctaggatgt caaacatgc caggagcctt tcgtcccacc     1440
agagaactca cctgaataag aagagtgaat tgctttgtgt cacctgtcag aaaatgttca    1500
```

-continued

```
aacgagtctc tgaccgccga acccatgaga tcatacacat gccagaaaag cctttcaagt    1560
gcagcacatg tgaaaagtcc ttcagccaca agaccaacct gaagtctcat gagatgattc    1620
acacaggaga aatgccttat gtctgttccc tatgtagccg tcgctttcgc caatcatcca    1680
cttaccatcg tcacctgagg aattaccaca gatctgactg aagtatctaa catcctcagc    1740
agagactggt agggcttcag cctcagtatg tcatcttcaa agagagaaga atgttgcaag    1800
taaattgtac tgtcccaata atgatataac atgcttgtgg attgccactt ttatgttttg    1860
ttttttattg tgtgtgtgtg tgtatgtaat ttttttgtctg taatttccat agttccacag    1920
cataagttat tagaatactt tgctgttaat tcttgagttg cttcttgctt ttagacagtg    1980
tctttctggt tggcagcttt atacacctgt ctttctggca ctagagtttc caaacattttt   2040 ctgatctcca cttttattct ctacagtggg cctgacagag gcctgccatt ccctctgaca    2100
ttttttaaca tgttggggtt tcatcccaag tcttagggtt gcaagttaaa tgcattgcct    2160
cttcagacat ctcatgtcat gtctactgct tacagttcaa gaatatttct ctacattact    2220
agaatgacgt tcaaagtgga ataataaata aaaaaataat caacaatt                 2268
```

<210> SEQ ID NO 10
<211> LENGTH: 506
<212> TYPE: PRT
<213> ORGANISM: Mus musculus

<400> SEQUENCE: 10

```
Met Ala Ser Gln Gln Ala Pro Ala Lys Asp Leu Gln Thr Asn Asn Leu
 1               5                  10                  15

Glu Phe Thr Pro Ser His Ser Ser Gly Val Gln Trp Val Glu Asp Ile
             20                  25                  30

Ser Asn Ser Pro Ser Ala Gln Leu Asn Phe Ser Pro Ser Asn Asn Gly
         35                  40                  45

Cys Trp Ala Thr Gln Glu Leu Gln Ser Leu Trp Lys Met Phe Asn Ser
     50                  55                  60

Trp Leu Gln Pro Glu Lys Gln Thr Lys Glu Gln Met Ile Ser Gln Leu
 65                  70                  75                  80

Val Leu Glu Gln Phe Leu Leu Ile Gly His Cys Lys Asp Lys Tyr Ala
                 85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
        195                 200                 205

Ser Leu Leu Ile Ile Gln Lys Glu Gln His Pro Glu His Glu Glu Gly
    210                 215                 220

Asn Val Val Phe Gln Phe Pro Leu Asp Ala Arg Arg Ala Ser Gln Gly
225                 230                 235                 240
```

Asn Ser Ser His His Val Asp Phe Arg Ser Ala Pro Thr Pro Ala Asp
            245                 250                 255

Val Pro Met Glu Glu Gln Pro Lys Asp Leu Ser Arg Glu Asn Ile Ser
        260                 265                 270

Glu Asp Lys Asn Asn Cys Tyr Asn Thr Ser Arg Asn Ala Ala Thr Gln
            275                 280                 285

Val Tyr Arg Ser Asp Asn Ile Pro Arg Lys Lys Thr Asp Ser Leu Ser
        290                 295                 300

Ile Asn Lys Arg Ile Tyr His Ser Glu Pro Glu Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Glu Cys Phe Ser Glu Lys Asp Pro Arg
            340                 345                 350

Glu Leu Pro Gly Leu Glu Ser Arg Gln Glu Glu Pro Ile Ser Asp Pro
        355                 360                 365

Val Phe Leu Gly Lys Asp His Glu Ala Asn Leu Pro Cys Glu Ser His
    370                 375                 380

Gln Lys Arg Phe Arg Arg Asp Ala Lys Leu Phe Lys Cys Glu Glu Cys
385                 390                 395                 400

Ser Arg Met Phe Lys His Ala Arg Ser Leu Ser Ser His Gln Arg Thr
                405                 410                 415

His Leu Asn Lys Lys Ser Glu Leu Leu Cys Val Thr Cys Gln Lys Met
            420                 425                 430

Phe Lys Arg Val Ser Asp Arg Arg Thr His Glu Ile Ile His Met Pro
        435                 440                 445

Glu Lys Pro Phe Lys Cys Ser Thr Cys Glu Lys Ser Phe Ser His Lys
    450                 455                 460

Thr Asn Leu Lys Ser His Glu Met Ile His Thr Gly Glu Met Pro Tyr
465                 470                 475                 480

Val Cys Ser Leu Cys Ser Arg Arg Phe Arg Gln Ser Ser Thr Tyr His
                485                 490                 495

Arg His Leu Arg Asn Tyr His Arg Ser Asp
            500                 505

<210> SEQ ID NO 11
<211> LENGTH: 1774
<212> TYPE: DNA
<213> ORGANISM: Mus musculus

<400> SEQUENCE: 11
cacagtgcct ccctgggctt cttggcatca ccattgaagt tcactggaga aagaggtgag      60
gtggagaagt aggtaaactt ccctttcttg tggtcttgaa tgtcttttac agtacatccg     120
tcaactgtta gcattttcct aaagtcacaa acagatact  aaactgctat agttgaatct     180
ttcagaccat tgtcaccaca atggcttcac agcaggcacc agcaaaagac cttcagacca     240
acaatttaga gtttactcca actgatagtt ctggtgtgca gtgggcagaa gacatctcta     300
actcaccaag tgctcagcta aacttttccc caagtaacaa tggctgctgg gcaactcagg     360
agctgcaaag tctctggaag atgttcaact cctggttgca gccagaaaag cagactaagg     420
agcagatgat ttctcaactg gtcttggagc agtttctcct cactgggcac tgcaaggaca     480
agtatgcttt gacagagaag tggaaagcca gtggtagcga tatgaggaga ttcatggaga     540
gtctgactga tgagtgcttg aagcctcctg tcatggtcca tgtttcaatg caaggacaag     600

```
aagccctctt ttctgaaaac atgccattaa agaagtcat caagcttttg aaacaacagc      660
aatctgcaac aaggccaata ccagataatg agcagatgcc agtagacacc acacaagata      720
gattattggc cacaggcaag aaaacagtga aatgaatgc aacacctctt gcaatgctac      780
tgaagtaaat gttggtgaaa gctgtagtgg aaatgaaaag gactcccttc ttattaccca      840
gaaagaacaa aaccatgagc atgaagaggg gaatgttgtt tgtcaattcc ctcgtggtgc      900
cagaagagca agtcaagaca cctccagtca tcatgtagac ttcccgagtg ctctgactcc      960
tgcagatgtc cccatggagg aacaaccaat ggatttatcc agagaaaaca tctctgagga     1020
caagaacaat tgctataaca cttccaggaa tgcagctact caagtatata atggtgataa     1080
tattcccagg aacaagacag actccctttt cattaacaag agaatatatc atcctgagcc     1140
tgaggtggga gatattcctt atggagttcc tcaggattct acaagagcaa gtcaaggaac     1200
atctacatgc ctgcaagagt cacttgggga atgtttttct gaaaagacc caagggaggt     1260
accaggggttg cagtctaggc aagagcagcc tatctctgat cctgtccttg gtaagaatca     1320
tgaggcaaac ttaccatgtg aaagtcatca aaagagattc catagagatg ccaaactata     1380
caagtgtgaa gaatgttcta ggatgttcaa acatgccagg agcctttcat cccaccagag     1440
aactcacctg aataagaaga gtgaattgct ttgcatcacc tgtcagaaaa tattcaaacg     1500
agtttctgac cttcgaaccc atgagatcat acacatgtca gaaaagcctt tcaagtgcag     1560
cacatgtgaa aagtccttca gccacaagac caacctgaag tatcatgaga tgattcacac     1620
aggagaaatg ccttatgtct gttccctatg tagccgtcgc tttcgccaat catccactta     1680
ccatcgtcac ctgaggaatt accacagatc tgactgaagt atctaacatc ctcagcagag     1740
actggtaggg cttcagcctc agtatgtcat cttc                                 1774
```

<210> SEQ ID NO 12  
<211> LENGTH: 195  
<212> TYPE: PRT  
<213> ORGANISM: Mus musculus

<400> SEQUENCE: 12

```
Met Ala Ser Gln Gln Ala Pro Ala Lys Asp Leu Gln Thr Asn Asn Leu
 1               5                  10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Ile
145                 150                 155                 160

Pro Asp Asn Glu Gln Met Pro Val Asp Thr Thr Gln Asp Arg Leu Leu
```

|  | 165 |  |  | 170 |  |  | 175 |  |  |
|---|---|---|---|---|---|---|---|---|---|
| Ala | Thr | Gly | Lys | Lys | Thr | Val | Lys | Met | Asn | Ala | Thr | Pro | Leu | Ala | Met |
|  |  |  | 180 |  |  |  |  | 185 |  |  |  |  | 190 |  |  |

Leu Leu Lys
    195

<210> SEQ ID NO 13
<211> LENGTH: 2273
<212> TYPE: DNA
<213> ORGANISM: Mus musculus

<400> SEQUENCE: 13

| cacagtgcct | ccctgggctt | cttggcatca | cccttgaagt | tcactggaga | aagaggtgag | 60 |
| gtggaggaat | aggtaaactt | tccttcctag | tggtcttgaa | tgtcttttac | agtacatcca | 120 |
| tcaactgtta | gcattttcgt | aaagtcacaa | aacagatatt | aaactactat | agttgaatct | 180 |
| ttcacaccat | tgtcaccaca | atggcttcac | agcaggcacc | agcaaaagac | cttcagacca | 240 |
| acaatttaga | gttactcca  | actgatagtt | ctggtgtgca | gtgggcagaa | gacatctcta | 300 |
| actcaccaag | tgctcagcta | aacttttccc | caagtaacaa | tggctgctgg | gcaactcagg | 360 |
| agctgcaaag | tctctggaag | atgttcaact | cctggttgca | gccagaaaag | cagactaagg | 420 |
| agcagatgat | ttctcaactg | gtcttggagc | agtttctcct | cactgggcac | tgcaaggaca | 480 |
| agtatgcttt | gactgagaag | tggaaagcca | gtggtagcga | tatgaggaga | ttcatggaga | 540 |
| gtctgactga | tgagtgcttg | aagcctcctg | tcatggtcca | tgtttcaatg | caaggacaag | 600 |
| aagccctctt | ttctgaaaac | atgccattaa | agaagtcat  | caagcttttg | aaacaacagc | 660 |
| aatctgcaac | aaggccaaca | ccagataatg | agcagatgcc | agtagacacc | acacaagata | 720 |
| gattattggc | cacaggacaa | gaaaacagtg | aaaatgaatg | caacaactct | tgtaatgcta | 780 |
| ctgaagcaaa | tgttggtgaa | agctgtagtg | gaaatgaaat | ggactcccct | cttattatgc | 840 |
| agaaagaaca | gcaccctgag | catgaagagg | ggaatgttgt | ttgtcaattc | cctcatggtg | 900 |
| ccagaagagc | aagtcaaggc | accccagtc  | atcatgtaga | cttcccgagt | gctccgacta | 960 |
| ctgccgatgt | ccccatggag | gaacaaccaa | aggatttatc | cagagaaaac | atctctgagg | 1020 |
| acaagaacaa | ttgctataac | acttccagaa | atgcagctac | tcaagtatat | agtggtgata | 1080 |
| atattcccag | gaacaagtca | gactcccttt | tcattaacaa | gagaatatat | catcctgagc | 1140 |
| ctgaggtggg | agatattcct | tatggagttc | ctcaggattc | tacaagagca | agtcaaggaa | 1200 |
| catctacatg | cctgcaagag | tcacttgggg | aatgtttttc | tgaaaagac  | cctagggagg | 1260 |
| taccagggtt | gcagtctagg | caagagcagc | ttatctctga | tcctgtcctt | cttggtaaga | 1320 |
| atcatgaggc | aaacttacca | tgtgaaagtc | atcaaaagag | attctgtaga | gatgccaaac | 1380 |
| tatacaagtg | tgaagaatgt | tctaggatgt | tcaaacatgc | caggagcctt | tcatcccacc | 1440 |
| agagaactca | cctgaataag | aagagtgaat | tgctttgtgt | cacctgtcag | aaaatgttca | 1500 |
| aacgagtctc | tgaccgccga | acccatgaga | tcatacacat | gccagaaaag | cctttcaagt | 1560 |
| gcagcacatg | tgaaaagtcc | ttcagccaca | agaccaacct | gaagtctcat | gagatgattc | 1620 |
| acacaggaga | aatgccttat | gtctgttccc | tatgtagccg | tcgctttcgc | caatcatcca | 1680 |
| cttaccatcg | tcacctgagg | aattaccaca | gatctgactg | aactatctaa | catcctcagc | 1740 |
| agagactggt | agggcttcag | cctcagtatg | tcatcttcaa | agagagaaga | atgttgcaag | 1800 |
| taaattgtac | tgtcccaata | atgatataac | atgcttgtgg | attgccactt | ttatgttttg | 1860 |
| ttttgttttt | tattttgtgt | gtgtgtgtat | gtaattttt  | gtctgtattt | ccatagttcc | 1920 |

-continued

```
acagcataag ttattagaat actttgctgt taattcttga gttgcttctt gcttttagac   1980
agtgtctttc tggttgacag ctttataaac ctgtctttct ggcactagag tttccaaaca   2040
ttttctgatc tccactttta ttctctacag tgttcttgac agaagcctgg cattccctct   2100 gacattttc tacatgttgg ggttttcatc ccaagtctta gggttgcaag ttaaatgcat    2160
tgcctcttca gacatctcat gccctgtcta ctgcttacag ttcaagaata tttctctaca   2220
ttactagaac gacattcaaa gtggaataat aaataaataa ataatcaaca att          2273
```

<210> SEQ ID NO 14
<211> LENGTH: 506
<212> TYPE: PRT
<213> ORGANISM: Mus musculus

<400> SEQUENCE: 14

```
Met Ala Ser Gln Gln Ala Pro Ala Lys Asp Leu Gln Thr Asn Asn Leu
 1               5                  10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Ser Cys Ser Gly Asn Glu Met Asp
        195                 200                 205

Ser Leu Leu Ile Met Gln Lys Glu Gln His Pro Glu His Glu Glu Gly
    210                 215                 220

Asn Val Val Cys Gln Phe Pro His Gly Ala Arg Arg Ala Ser Gln Gly
225                 230                 235                 240

Thr Pro Ser His His Val Asp Phe Pro Ser Ala Pro Thr Thr Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Ser Gly Asp Asn Ile Pro Arg Asn Lys Ser Asp Ser Leu Phe
    290                 295                 300

Ile Asn Lys Arg Ile Tyr His Pro Glu Pro Glu Val Gly Asp Ile Pro
```

```
                305                 310                 315                 320
Tyr Gly Val Pro Gln Asp Ser Thr Arg Ala Ser Gln Gly Thr Ser Thr
                    325                 330                 335

Cys Leu Gln Glu Ser Leu Gly Glu Cys Phe Ser Glu Lys Asp Pro Arg
                340                 345                 350

Glu Val Pro Gly Leu Gln Ser Arg Gln Glu Gln Leu Ile Ser Asp Pro
            355                 360                 365

Val Leu Leu Gly Lys Asn His Glu Ala Asn Leu Pro Cys Glu Ser His
    370                 375                 380

Gln Lys Arg Phe Cys Arg Asp Ala Lys Leu Tyr Lys Cys Glu Glu Cys
385                 390                 395                 400

Ser Arg Met Phe Lys His Ala Arg Ser Leu Ser Ser His Gln Arg Thr
                405                 410                 415

His Leu Asn Lys Lys Ser Glu Leu Leu Cys Val Thr Cys Gln Lys Met
                420                 425                 430

Phe Lys Arg Val Ser Asp Arg Arg Thr His Glu Ile Ile His Met Pro
            435                 440                 445

Glu Lys Pro Phe Lys Cys Ser Thr Cys Glu Lys Ser Phe Ser His Lys
        450                 455                 460

Thr Asn Leu Lys Ser His Glu Met Ile His Thr Gly Glu Met Pro Tyr
465                 470                 475                 480

Val Cys Ser Leu Cys Ser Arg Arg Phe Arg Gln Ser Ser Thr Tyr His
                485                 490                 495

Arg His Leu Arg Asn Tyr His Arg Ser Asp
            500                 505

<210> SEQ ID NO 15
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 15
ggggacaagt ttgtacaaaa aagcaggctc caccatggct tcacagcagg cac            53

<210> SEQ ID NO 16
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 16
ggggaccact ttgtacaaga aagctgggtt cagtcagatc tgtggtaat                49

<210> SEQ ID NO 17
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 17
ggggaccact ttgtacaaga aagctgggtt caagctgtgg cagggaaac                49

<210> SEQ ID NO 18
<211> LENGTH: 52
<212> TYPE: DNA
<213> ORGANISM: Artificial Sequence
```

```
<220> FEATURE:
<223> OTHER INFORMATION: Synthetic oligonucleotide

<400> SEQUENCE: 18
ggggacaagt ttgtacaaaa aagcaggctc caccatgagg cagccacctg gc            52

<210> SEQ ID NO 19
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 19
ggggaccact ttgtacaaga aagctgggtt cacatgtgcg acaggggca                49

<210> SEQ ID NO 20
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 20
ggggacaagt ttgtacaaaa aagcaggctc caccatggct ttagatctaa gaa           53

<210> SEQ ID NO 21
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 21
ggggaccact ttgtacaaga aagctgggtt taggaagctt ctggtgtgg                49

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 22
tctttccacc aggcccccgg ctc                                            23

<210> SEQ ID NO 23
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 23
tgcgggcgga catggggaga tcc                                            23

<210> SEQ ID NO 24
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 24
tagagctaga ctccgggcga tga                                            23
```

<210> SEQ ID NO 25
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 25
ttgccttaaa caagaccacg aaa                                    23

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
cacccaccca tgctagtctt                                        20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
accctcaaac tcctggtcct                                        20

<210> SEQ ID NO 28
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 28
tgctgcggtc caggccatca agag                                   24

<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 29
gggcactgtt cagttcagcg gatc                                   24

<210> SEQ ID NO 30
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 30
acgagtggca gtttcttctt ggga                                   24

<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide

```
<400> SEQUENCE: 31
tatgactcac ttccaggggg cact                                              24

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 32
cggagtcaac ggatttggtc gtat                                              24

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
gaagatggtg atgggcttcc                                                   20

<210> SEQ ID NO 34
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 34
agtctgactg atgagtgctt gaagcc                                            26

<210> SEQ ID NO 35
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 35
ggccttgttg cagattgctg ttg                                               23

<210> SEQ ID NO 36
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 36 ggtttttag aggatggttg agtg                                               24

<210> SEQ ID NO 37
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 37 tccaaccta ctaacccatc acc                                                23

<210> SEQ ID NO 38
```

```
<211> LENGTH: 2434
<212> TYPE: DNA
<213> ORGANISM: Mus musculus
<220> FEATURE:
<221> NAME/KEY: CDS
<222> LOCATION: (479)..(2068)

<400> SEQUENCE: 38
```

| | | |
|---|---|---|
| gggaaaggcc tcaggaagca ggcaaagaga cactgaaaga atagctgtgg aggacaaagg | 60 | |
| gttcccaagc atcacagact cgagtagttg cactttgctc cagaaacaag acatgaggac | 120 | |
| tatacccaga gtactctcgt gccttagaag accccagaga agcagaacgt tatcttgaat | 180 | |
| ggctccagca aaatctgtgt gggcaactga aatccttgtg acgtccaggc tggcctcaag | 240 | |
| tttcctaggt agctgaggct tcccttgaac tcctgagcct cctgtctcca tctctcaagt | 300 | |
| actggcatca ccggcctgtg cttccacacc tgactaagga ttttctttat tagagttctc | 360 | |
| atacttctac accacctcca tagtgaagca tcccagccct ttaacaggtt gcccccttca | 420 | |
| agaggtttct ctatcactgg aggacacagc tggcaaggaa gcccaccagg ctgccaac | 478 |

```
atg aaa tgc ctt gaa ggt ctg cac tta cag cag aga ccc agc aag ttc      526
Met Lys Cys Leu Glu Gly Leu His Leu Gln Gln Arg Pro Ser Lys Phe
 1               5                  10                  15 tct gtc tcc ttg gct cct gaa gaa ggc tta gtg tgt gcc ttc caa ctg      574
Ser Val Ser Leu Ala Pro Glu Glu Gly Leu Val Cys Ala Phe Gln Leu
             20                  25                  30 gag gaa gag aag gag aat gaa gat gaa tgt gtg tgt tca gat cag gct      622
Glu Glu Glu Lys Glu Asn Glu Asp Glu Cys Val Cys Ser Asp Gln Ala
         35                  40                  45 cca gaa gtg aag gag gaa ggg tgt ggt ctc ggg gat cca gcc ata gtg      670
Pro Glu Val Lys Glu Glu Gly Cys Gly Leu Gly Asp Pro Ala Ile Val
     50                  55                  60 agc gcc ttc caa aat acc caa gta cca cag cag aga ggg ctg cac agt      718
Ser Ala Phe Gln Asn Thr Gln Val Pro Gln Gln Arg Gly Leu His Ser
 65                  70                  75                  80 tcc cac aga gtc aag gtc tct ggt gcc ttg ggg atg tca tca gcc tcc      766
Ser His Arg Val Lys Val Ser Gly Ala Leu Gly Met Ser Ser Ala Ser
                 85                  90                  95 ctg cat ttt atg tgg cag tct gtg ttt cca aga gcc agt tct cca gcc      814
Leu His Phe Met Trp Gln Ser Val Phe Pro Arg Ala Ser Ser Pro Ala
            100                 105                 110 cat cat ttt gga ccg caa cag cct tca cca gat cct ttt ctg ttc tac      862
His His Phe Gly Pro Gln Gln Pro Ser Pro Asp Pro Phe Leu Phe Tyr
        115                 120                 125 agc cca ctg acc ccg tgg ccc cct aag ctc agc ctt ccc agt cat ctg      910
Ser Pro Leu Thr Pro Trp Pro Pro Lys Leu Ser Leu Pro Ser His Leu
    130                 135                 140 acc cag ctc cac cct cag cac cag cag atc ctg cag cag cag caa cgg      958
Thr Gln Leu His Pro Gln His Gln Gln Ile Leu Gln Gln Gln Gln Arg
145                 150                 155                 160 tgg cgt agg agg cgg agt cca aca gca aga agt gtc ccc gcc cag aag      1006
Trp Arg Arg Arg Arg Ser Pro Thr Ala Arg Ser Val Pro Ala Gln Lys
                165                 170                 175 cct tgg tct cgt gag cca gct gcc tca gat gcc tat gct aac ctc atg      1054
Pro Trp Ser Arg Glu Pro Ala Ala Ser Asp Ala Tyr Ala Asn Leu Met
            180                 185                 190 acc cga aaa gag aag gac tgg gtg ata aga gtg cag atg gtt caa ctg      1102
Thr Arg Lys Glu Lys Asp Trp Val Ile Arg Val Gln Met Val Gln Leu
        195                 200                 205 cag agt gag aac ccc cgc ctg gat gat tac tac tac cag aaa tac tat      1150
Gln Ser Glu Asn Pro Arg Leu Asp Asp Tyr Tyr Tyr Gln Lys Tyr Tyr
```

```
                210                 215                 220
cag aag ctg gag aag aga cag gca gac aaa gag ctg ctt gga caa aag    1198
Gln Lys Leu Glu Lys Arg Gln Ala Asp Lys Glu Leu Leu Gly Gln Lys
225                 230                 235                 240 acc agg gct gag tct ctc aag ttg gtc acg cct tac atc cag aag cct    1246
Thr Arg Ala Glu Ser Leu Lys Leu Val Thr Pro Tyr Ile Gln Lys Pro
                245                 250                 255 gaa gtt tat gag tca gtg gtg cgg att gag ggt tcc ctg ggc cag gta    1294
Glu Val Tyr Glu Ser Val Val Arg Ile Glu Gly Ser Leu Gly Gln Val
            260                 265                 270 gct gta tca aca tgt ttt agc cct cgc cga gct att gac gct gta tct    1342
Ala Val Ser Thr Cys Phe Ser Pro Arg Arg Ala Ile Asp Ala Val Ser
        275                 280                 285 cac gga acc caa gag cag gat aca gga gct gcg agc agc cag agg ctt    1390
His Gly Thr Gln Glu Gln Asp Thr Gly Ala Ala Ser Ser Gln Arg Leu
    290                 295                 300 cgg gta ttg tcc cag att gag aag atg ttc ctt cag tta cta aaa ata    1438
Arg Val Leu Ser Gln Ile Glu Lys Met Phe Leu Gln Leu Leu Lys Ile
305                 310                 315                 320 gag gag ggc cag aat gat ggg ctc cca caa ctc tac cac act cgg gaa    1486
Glu Glu Gly Gln Asn Asp Gly Leu Pro Gln Leu Tyr His Thr Arg Glu
                325                 330                 335 cag agc agc cag gtt gag aag ctc ttt cag gcc tta aaa acc cag gag    1534
Gln Ser Ser Gln Val Glu Lys Leu Phe Gln Ala Leu Lys Thr Gln Glu
            340                 345                 350 cag aac aac ctg gag gag gca gca gat aac ctc ctg caa gtg ctg tct    1582
Gln Asn Asn Leu Glu Glu Ala Ala Asp Asn Leu Leu Gln Val Leu Ser
        355                 360                 365 gtg agg aaa ggg aaa gtt ttg gtg gct cgg ctg ctc ccc ttc ctg ccc    1630
Val Arg Lys Gly Lys Val Leu Val Ala Arg Leu Leu Pro Phe Leu Pro
    370                 375                 380 ccg gat caa gct gtt agc ctc ctc ctg tac atc acc tac cat ctg ccc    1678
Pro Asp Gln Ala Val Ser Leu Leu Leu Tyr Ile Thr Tyr His Leu Pro
385                 390                 395                 400 ctc ctg atc cag agg gac atg gct gac cag ggt cta cac atg cta ttc    1726
Leu Leu Ile Gln Arg Asp Met Ala Asp Gln Gly Leu His Met Leu Phe
                405                 410                 415 aaa cct ctg ggg aaa tat atc agt cat ctg acc ttc cat cag ctc ctc    1774
Lys Pro Leu Gly Lys Tyr Ile Ser His Leu Thr Phe His Gln Leu Leu
            420                 425                 430 cat gca atg caa gga cta atg ttg cta tca cct ggc tcc tca gag cgg    1822
His Ala Met Gln Gly Leu Met Leu Leu Ser Pro Gly Ser Ser Glu Arg
        435                 440                 445 cca gtc tct gtg gta ctt cag aat cag ttt ggg ata tct ctg cta tat    1870
Pro Val Ser Val Val Leu Gln Asn Gln Phe Gly Ile Ser Leu Leu Tyr
    450                 455                 460 gcc ttg ctg agt cat gga gag cag ctg gta tcc ctg gat cct tcc ctc    1918
Ala Leu Leu Ser His Gly Glu Gln Leu Val Ser Leu Asp Pro Ser Leu
465                 470                 475                 480 cga tcc agc agt gac tgt gca acc tgg aca gac ttg gtg att ctg att    1966
Arg Ser Ser Ser Asp Cys Ala Thr Trp Thr Asp Leu Val Ile Leu Ile
                485                 490                 495 gcc tgg gag ata gct cag ttg cct gca gca tcc ttg gcg gag cct cta    2014
Ala Trp Glu Ile Ala Gln Leu Pro Ala Ala Ser Leu Ala Glu Pro Leu
            500                 505                 510 gcc ttc ccc agg aat ctg ctt ccc tgt tct gcc atc aca tgg aca agc    2062
Ala Phe Pro Arg Asn Leu Leu Pro Cys Ser Ala Ile Thr Trp Thr Ser
        515                 520                 525 aat tag ttcagcagct ggaagccaga atggagcttg cctgtatcta ctgatgtatt    2118
```

Asn agttaatgtg agaagctgaa atatcagaaa cggaactcca tcacctgtct acagtgacag     2178
ttgaggccat ttcctatact ttgttatgtt ggaggaccct gccacattgt catatccttt     2238
cttaaaatct aggtgacttg cctaaaatta aggcatgact actttaggta tgattaaaga     2298
aatatcaaat gatatgttga aacttgtttg taagtttgga attacaacga aggacatttt     2358
tttgaatatg tcaagaatat ccttcctaat aaggggaaag gccttgtatt taataaaagt     2418
ctaatctggg atgttg     2434

<210> SEQ ID NO 39
<211> LENGTH: 529
<212> TYPE: PRT
<213> ORGANISM: Mus musculus

<400> SEQUENCE: 39

Met Lys Cys Leu Glu Gly Leu His Leu Gln Gln Arg Pro Ser Lys Phe
1               5                   10                  15

Ser Val Ser Leu Ala Pro Glu Glu Gly Leu Val Cys Ala Phe Gln Leu
            20                  25                  30

Glu Glu Glu Lys Glu Asn Glu Asp Glu Cys Val Cys Ser Asp Gln Ala
        35                  40                  45

Pro Glu Val Lys Glu Gly Cys Gly Leu Gly Asp Pro Ala Ile Val
    50                  55                  60

Ser Ala Phe Gln Asn Thr Gln Val Pro Gln Gln Arg Gly Leu His Ser
65                  70                  75                  80

Ser His Arg Val Lys Val Ser Gly Ala Leu Gly Met Ser Ser Ala Ser
                85                  90                  95

Leu His Phe Met Trp Gln Ser Val Phe Pro Arg Ala Ser Ser Pro Ala
            100                 105                 110

His His Phe Gly Pro Gln Gln Pro Ser Pro Asp Pro Phe Leu Phe Tyr
        115                 120                 125

Ser Pro Leu Thr Pro Trp Pro Pro Lys Leu Ser Leu Pro Ser His Leu
130                 135                 140

Thr Gln Leu His Pro Gln His Gln Gln Ile Leu Gln Gln Gln Gln Arg
145                 150                 155                 160

Trp Arg Arg Arg Ser Pro Thr Ala Arg Ser Val Pro Ala Gln Lys
                165                 170                 175

Pro Trp Ser Arg Glu Pro Ala Ala Ser Asp Ala Tyr Ala Asn Leu Met
            180                 185                 190

Thr Arg Lys Glu Lys Asp Trp Val Ile Arg Val Gln Met Val Gln Leu
        195                 200                 205

Gln Ser Glu Asn Pro Arg Leu Asp Asp Tyr Tyr Tyr Gln Lys Tyr Tyr
    210                 215                 220

Gln Lys Leu Glu Lys Arg Gln Ala Asp Lys Glu Leu Leu Gly Gln Lys
225                 230                 235                 240

Thr Arg Ala Glu Ser Leu Lys Leu Val Thr Pro Tyr Ile Gln Lys Pro
                245                 250                 255

Glu Val Tyr Glu Ser Val Val Arg Ile Glu Gly Ser Leu Gly Gln Val
            260                 265                 270

Ala Val Ser Thr Cys Phe Ser Pro Arg Arg Ala Ile Asp Ala Val Ser
        275                 280                 285

His Gly Thr Gln Glu Gln Asp Thr Gly Ala Ala Ser Ser Gln Arg Leu
    290                 295                 300

```
Arg Val Leu Ser Gln Ile Glu Lys Met Phe Gln Leu Leu Lys Ile
305                 310                 315                 320

Glu Glu Gly Gln Asn Asp Gly Leu Pro Gln Leu Tyr His Thr Arg Glu
            325                 330                 335

Gln Ser Ser Gln Val Glu Lys Leu Phe Gln Ala Leu Lys Thr Gln Glu
            340                 345                 350

Gln Asn Asn Leu Glu Glu Ala Ala Asp Asn Leu Leu Gln Val Leu Ser
            355                 360                 365

Val Arg Lys Gly Lys Val Leu Val Ala Arg Leu Leu Pro Phe Leu Pro
    370                 375                 380

Pro Asp Gln Ala Val Ser Leu Leu Leu Tyr Ile Thr Tyr His Leu Pro
385                 390                 395                 400

Leu Leu Ile Gln Arg Asp Met Ala Asp Gln Gly Leu His Met Leu Phe
                405                 410                 415

Lys Pro Leu Gly Lys Tyr Ile Ser His Leu Thr Phe His Gln Leu Leu
            420                 425                 430

His Ala Met Gln Gly Leu Met Leu Leu Ser Pro Gly Ser Ser Glu Arg
            435                 440                 445

Pro Val Ser Val Val Leu Gln Asn Gln Phe Gly Ile Ser Leu Leu Tyr
    450                 455                 460

Ala Leu Leu Ser His Gly Glu Gln Leu Val Ser Leu Asp Pro Ser Leu
465                 470                 475                 480

Arg Ser Ser Ser Asp Cys Ala Thr Trp Thr Asp Leu Val Ile Leu Ile
                485                 490                 495

Ala Trp Glu Ile Ala Gln Leu Pro Ala Ala Ser Leu Ala Glu Pro Leu
            500                 505                 510

Ala Phe Pro Arg Asn Leu Leu Pro Cys Ser Ala Ile Thr Trp Thr Ser
            515                 520                 525

Asn

<210> SEQ ID NO 40
<211> LENGTH: 1540
<212> TYPE: DNA
<213> ORGANISM: Mus musculus
<220> FEATURE:
<221> NAME/KEY: CDS
<222> LOCATION: (1)..(1458)

<400> SEQUENCE: 40 atg agt gtt gac tcc cta ccc acc ctc ttt cag tgg gca aga gac aat       48
Met Ser Val Asp Ser Leu Pro Thr Leu Phe Gln Trp Ala Arg Asp Asn
1               5                   10                  15 cta ctg aag gag gaa gct tta gcc att tct gct ctg gag gaa ctg ccc       96
Leu Leu Lys Glu Glu Ala Leu Ala Ile Ser Ala Leu Glu Glu Leu Pro
            20                  25                  30 att cat cta ttc cca gag atg ttc aag gta gcc ttc act gat agg cat      144
Ile His Leu Phe Pro Glu Met Phe Lys Val Ala Phe Thr Asp Arg His
        35                  40                  45 aca aag gtc ctg att gca atg gtg tct gcc tgg ccc ttc cca tgc ctt      192
Thr Lys Val Leu Ile Ala Met Val Ser Ala Trp Pro Phe Pro Cys Leu
    50                  55                  60 cct gta gga acc cta ata gag gac cca cat ctg gag act ttg aaa gca      240
Pro Val Gly Thr Leu Ile Glu Asp Pro His Leu Glu Thr Leu Lys Ala
65                  70                  75                  80 gtg ctt gat ggg ttg aat gtc ctg gta aca ggg aag gtt cat tcc agt      288
Val Leu Asp Gly Leu Asn Val Leu Val Thr Gly Lys Val His Ser Ser
                85                  90                  95
```

| | | |
|---|---|---|
| agg tgc aaa ctc aga gtc ctt gat ttg agg agg aat gtg cac cat gac<br>Arg Cys Lys Leu Arg Val Leu Asp Leu Arg Arg Asn Val His His Asp<br>100                          105                      110 | 336 |
| ttc tgg agc ata cag act gga tcc cat gaa gat aac tgc cca gca cag<br>Phe Trp Ser Ile Gln Thr Gly Ser His Glu Asp Asn Cys Pro Ala Gln<br>115                          120                      125 | 384 |
| atc gtg gca cag aag cag cca gtg gag acc tgc cct aac cct aga agg<br>Ile Val Ala Gln Lys Gln Pro Val Glu Thr Cys Pro Asn Pro Arg Arg<br>130                          135                      140 | 432 |
| gag ata cct ttt atg gtg gtg acc gac ttt gaa ctc acg cag gag agt<br>Glu Ile Pro Phe Met Val Val Thr Asp Phe Glu Leu Thr Gln Glu Ser<br>145                          150                      155                      160 | 480 |
| ttc gat gaa tgg acc ata tac ttg atg cag tgg atc cag gag aga aaa<br>Phe Asp Glu Trp Thr Ile Tyr Leu Met Gln Trp Ile Gln Glu Arg Lys<br>                        165                      170                      175 | 528 |
| tct tcc att cat cta tgc tgt agg aag ctg aac agt tgt gcc tca cca<br>Ser Ser Ile His Leu Cys Cys Arg Lys Leu Asn Ser Cys Ala Ser Pro<br>                  180                      185                      190 | 576 |
| gtc tct aat gtc ata gag atc ttt aaa ttg gtg gat tta aac tgt atc<br>Val Ser Asn Val Ile Glu Ile Phe Lys Leu Val Asp Leu Asn Cys Ile<br>              195                      200                      205 | 624 |
| ctg gag cta cag ctg agt cag tgg tgg cct gaa gtc ctg gaa gaa ctt<br>Leu Glu Leu Gln Leu Ser Gln Trp Trp Pro Glu Val Leu Glu Glu Leu<br>210                          215                      220 | 672 |
| gat cct tac ctg gag gga atg aat aat ctt cac aca ctc atg tta gag<br>Asp Pro Tyr Leu Glu Gly Met Asn Asn Leu His Thr Leu Met Leu Glu<br>225                          230                      235                      240 | 720 |
| gga ttg aag ccc ttc aga ttt act gct tgt gaa gaa gac cag gaa gac<br>Gly Leu Lys Pro Phe Arg Phe Thr Ala Cys Glu Glu Asp Gln Glu Asp<br>                        245                      250                      255 | 768 |
| gag tgg caa agc acg ttg cct tct ctg ctc tcc aac ttt ggc agt ctc<br>Glu Trp Gln Ser Thr Leu Pro Ser Leu Leu Ser Asn Phe Gly Ser Leu<br>                  260                      265                      270 | 816 |
| cag aat ctc tat ttg aat gat atc tac ctt cta gaa gac tcc ctt gac<br>Gln Asn Leu Tyr Leu Asn Asp Ile Tyr Leu Leu Glu Asp Ser Leu Asp<br>              275                      280                      285 | 864 |
| aag tgg ctt ggc tgc ctg aag acc cct ttg aag acc ttg tca att acg<br>Lys Trp Leu Gly Cys Leu Lys Thr Pro Leu Lys Thr Leu Ser Ile Thr<br>290                          295                      300 | 912 |
| gac tgc cct agg ctc tta cag tca gac ttc gag tgc ctg cca aat tgt<br>Asp Cys Pro Arg Leu Leu Gln Ser Asp Phe Glu Cys Leu Pro Asn Cys<br>305                          310                      315                      320 | 960 |
| ccg aat att tgt aag ctc aag cat ctg aac ctg aat gct ctg ttt cta<br>Pro Asn Ile Cys Lys Leu Lys His Leu Asn Leu Asn Ala Leu Phe Leu<br>                        325                      330                      335 | 1008 |
| tct gat gta ggc tat gag att cca ggg ctc atc ctt gag aaa gtc aca<br>Ser Asp Val Gly Tyr Glu Ile Pro Gly Leu Ile Leu Glu Lys Val Thr<br>                  340                      345                      350 | 1056 |
| agt acc ctg caa att ctg gaa ctg gag agg tgt gga atg aca gac cct<br>Ser Thr Leu Gln Ile Leu Glu Leu Glu Arg Cys Gly Met Thr Asp Pro<br>              355                      360                      365 | 1104 |
| cat ttc aaa gcc ctc atg cct gct ctg agc aaa tgc tcc cag ctc ctt<br>His Phe Lys Ala Leu Met Pro Ala Leu Ser Lys Cys Ser Gln Leu Leu<br>370                          375                      380 | 1152 |
| aaa gtc agc ttc tgt cat aat gat atc tcc ctg cgt gtc ctg aag acc<br>Lys Val Ser Phe Cys His Asn Asp Ile Ser Leu Arg Val Leu Lys Thr<br>385                          390                      395                      400 | 1200 |
| ctt ctt tgt cac aca gcc aaa ctg agc cag ctg acc cag gag ctg tac<br>Leu Leu Cys His Thr Ala Lys Leu Ser Gln Leu Thr Gln Glu Leu Tyr<br>                        405                      410                      415 | 1248 |

```
cct gcc cct cag gaa tgc tat gag gat tac aag ata ctt aaa gac aga      1296
Pro Ala Pro Gln Glu Cys Tyr Glu Asp Tyr Lys Ile Leu Lys Asp Arg
            420                 425                 430 ttt aag aaa ctt tgt cca gaa ctg ctg aac ata ctt aag gcc aaa agg      1344
Phe Lys Lys Leu Cys Pro Glu Leu Leu Asn Ile Leu Lys Ala Lys Arg
            435                 440                 445 cag ccc aag aaa gtc tct ttt act aca caa acc tgc ttg aag tgt tta      1392
Gln Pro Lys Lys Val Ser Phe Thr Thr Gln Thr Cys Leu Lys Cys Leu
    450                 455                 460 cat tcc tgt cat tat tat tat aac ctg gag gct aca gat tgc ctt tgt      1440
His Ser Cys His Tyr Tyr Tyr Asn Leu Glu Ala Thr Asp Cys Leu Cys
465                 470                 475                 480 cag tgc att tgt cag taa gtagaataag gttgcttctg gtaccaagaa             1488
Gln Cys Ile Cys Gln
                485 ttgagcacta tgtatgtgga tgtccttatt tgcatgtaat aaatattctg ag            1540

<210> SEQ ID NO 41
<211> LENGTH: 485
<212> TYPE: PRT
<213> ORGANISM: Mus musculus

<400> SEQUENCE: 41

Met Ser Val Asp Ser Leu Pro Thr Leu Phe Gln Trp Ala Arg Asp Asn
 1               5                  10                  15

Leu Leu Lys Glu Glu Ala Leu Ala Ile Ser Ala Leu Glu Glu Leu Pro
            20                  25                  30

Ile His Leu Phe Pro Glu Met Phe Lys Val Ala Phe Thr Asp Arg His
        35                  40                  45

Thr Lys Val Leu Ile Ala Met Val Ser Ala Trp Pro Phe Pro Cys Leu
    50                  55                  60

Pro Val Gly Thr Leu Ile Glu Asp Pro His Leu Glu Thr Leu Lys Ala
65                  70                  75                  80

Val Leu Asp Gly Leu Asn Val Leu Val Thr Gly Lys Val His Ser Ser
                85                  90                  95

Arg Cys Lys Leu Arg Val Leu Asp Leu Arg Arg Asn Val His His Asp
            100                 105                 110

Phe Trp Ser Ile Gln Thr Gly Ser His Glu Asp Asn Cys Pro Ala Gln
        115                 120                 125

Ile Val Ala Gln Lys Gln Pro Val Glu Thr Cys Pro Asn Pro Arg Arg
    130                 135                 140

Glu Ile Pro Phe Met Val Val Thr Asp Phe Glu Leu Thr Gln Glu Ser
145                 150                 155                 160

Phe Asp Glu Trp Thr Ile Tyr Leu Met Gln Trp Ile Gln Glu Arg Lys
                165                 170                 175

Ser Ser Ile His Leu Cys Cys Arg Lys Leu Asn Ser Cys Ala Ser Pro
            180                 185                 190

Val Ser Asn Val Ile Glu Ile Phe Lys Leu Val Asp Leu Asn Cys Ile
        195                 200                 205

Leu Glu Leu Gln Leu Ser Gln Trp Trp Pro Glu Val Leu Glu Glu Leu
    210                 215                 220

Asp Pro Tyr Leu Glu Gly Met Asn Asn Leu His Thr Leu Met Leu Glu
225                 230                 235                 240

Gly Leu Lys Pro Phe Arg Phe Thr Ala Cys Glu Glu Asp Gln Glu Asp
                245                 250                 255
```

Glu Trp Gln Ser Thr Leu Pro Ser Leu Leu Ser Asn Phe Gly Ser Leu
                260                 265                 270

Gln Asn Leu Tyr Leu Asn Asp Ile Tyr Leu Leu Glu Asp Ser Leu Asp
            275                 280                 285

Lys Trp Leu Gly Cys Leu Lys Thr Pro Leu Lys Thr Leu Ser Ile Thr
290                 295                 300

Asp Cys Pro Arg Leu Leu Gln Ser Asp Phe Glu Cys Leu Pro Asn Cys
305                 310                 315                 320

Pro Asn Ile Cys Lys Leu Lys His Leu Asn Leu Asn Ala Leu Phe Leu
                325                 330                 335

Ser Asp Val Gly Tyr Glu Ile Pro Gly Leu Ile Leu Glu Lys Val Thr
            340                 345                 350

Ser Thr Leu Gln Ile Leu Glu Leu Glu Arg Cys Gly Met Thr Asp Pro
        355                 360                 365

His Phe Lys Ala Leu Met Pro Ala Leu Ser Lys Cys Ser Gln Leu Leu
    370                 375                 380

Lys Val Ser Phe Cys His Asn Asp Ile Ser Leu Arg Val Leu Lys Thr
385                 390                 395                 400

Leu Leu Cys His Thr Ala Lys Leu Ser Gln Leu Thr Gln Glu Leu Tyr
                405                 410                 415

Pro Ala Pro Gln Glu Cys Tyr Glu Asp Tyr Lys Ile Leu Lys Asp Arg
            420                 425                 430

Phe Lys Lys Leu Cys Pro Glu Leu Asn Ile Leu Lys Ala Lys Arg
        435                 440                 445

Gln Pro Lys Lys Val Ser Phe Thr Thr Gln Thr Cys Leu Lys Cys Leu
450                 455                 460

His Ser Cys His Tyr Tyr Tyr Asn Leu Glu Ala Thr Asp Cys Leu Cys
465                 470                 475                 480

Gln Cys Ile Cys Gln
            485

<210> SEQ ID NO 42
<211> LENGTH: 4913
<212> TYPE: DNA
<213> ORGANISM: Mus musculus
<220> FEATURE:
<221> NAME/KEY: CDS
<222> LOCATION: (198)..(3113)

<400> SEQUENCE: 42
agtgtgtggg aggaacgcag gggctggaat aggagggaaa ggaggtggct ccaggagaga    60
gcgagagagg gagcgctcgc atcggggctc agtggcacca gacctaaaaa gaaatctagg   120
caaggctccg gcacagtcca cgtggtggaa agataaggaa ttggaacaga accaacagtc   180
gtttctacag cctctca atg gat cct gtc agg ccg ttg ttc agg ggg ccc      230
                    Met Asp Pro Val Arg Pro Leu Phe Arg Gly Pro
                     1               5                   10 acc cca gtc cac cca tct cag tgt gtg cgg atg cca ggc tgt tgg cct    278
Thr Pro Val His Pro Ser Gln Cys Val Arg Met Pro Gly Cys Trp Pro
             15                  20                  25 caa gct cct aga cct ttg gaa cca gct tgg ggt agg gca gga cct gca    326
Gln Ala Pro Arg Pro Leu Glu Pro Ala Trp Gly Arg Ala Gly Pro Ala
         30                  35                  40 ggc aga ggc ctt gtg ttt aga aaa cca gaa gac tcc agc cca cca ctc    374
Gly Arg Gly Leu Val Phe Arg Lys Pro Glu Asp Ser Ser Pro Pro Leu
     45                  50                  55 cag cca gta caa aag gat tct gta ggt ttg gtg tcc atg ttc cgt ggc    422

-continued

```
Gln Pro Val Gln Lys Asp Ser Val Gly Leu Val Ser Met Phe Arg Gly
 60              65                  70                  75 atg ggt ctt gac aca gca ttc cgg cct cct tca aaa cga gaa gtg cct        470
Met Gly Leu Asp Thr Ala Phe Arg Pro Pro Ser Lys Arg Glu Val Pro
                 80                  85                  90 cct tta ggc aga gga gtt cta ggt cga ggc ttg tct gct aac atg gtc        518
Pro Leu Gly Arg Gly Val Leu Gly Arg Gly Leu Ser Ala Asn Met Val
             95                 100                 105 cgc aag gac aga gaa gaa ccc cgt tcc tct ttg cct gat cct tcg gtg        566
Arg Lys Asp Arg Glu Glu Pro Arg Ser Ser Leu Pro Asp Pro Ser Val
         110                 115                 120 ctg gca gct ggg gac agc aaa ctg gca gag gct tct gtt ggt tgg agt        614
Leu Ala Ala Gly Asp Ser Lys Leu Ala Glu Ala Ser Val Gly Trp Ser
     125                 130                 135 aga atg ctg gga aga ggt agt tct gag gtc tct ctg tta cca ctg gga        662
Arg Met Leu Gly Arg Gly Ser Ser Glu Val Ser Leu Leu Pro Leu Gly
140                 145                 150                 155 cga gca gcc agt agt ata ggc aga gga atg gac aaa cct ccc agt gcc        710
Arg Ala Ala Ser Ser Ile Gly Arg Gly Met Asp Lys Pro Pro Ser Ala
                160                 165                 170 ttt ggc ctc aca gct cgg gat ccc cca cgg ctg cca cag cct cca gct        758
Phe Gly Leu Thr Ala Arg Asp Pro Pro Arg Leu Pro Gln Pro Pro Ala
            175                 180                 185 ctg tct cca act tca ctg cac tct gcc gat ccc cct ccg gtc ctg act        806
Leu Ser Pro Thr Ser Leu His Ser Ala Asp Pro Pro Pro Val Leu Thr
        190                 195                 200 atg gaa cga aag gaa aaa gag ctt ttg gtc aag caa gga tca aaa gga        854
Met Glu Arg Lys Glu Lys Glu Leu Leu Val Lys Gln Gly Ser Lys Gly
    205                 210                 215 act cct cag tct ttg gga ctg aac ctc atc aaa atc cag tgt cat aac        902
Thr Pro Gln Ser Leu Gly Leu Asn Leu Ile Lys Ile Gln Cys His Asn
220                 225                 230                 235 gaa gca gtt tat cag tac cat gtg act ttc agc ccc agt gtg gaa tgc        950
Glu Ala Val Tyr Gln Tyr His Val Thr Phe Ser Pro Ser Val Glu Cys
                240                 245                 250 aaa agc atg agg ttt ggc atg ttg aag gac cac cag tct gtc act gga        998
Lys Ser Met Arg Phe Gly Met Leu Lys Asp His Gln Ser Val Thr Gly
            255                 260                 265 aac gtc act gct ttt gat ggc tct att ctt tat ctt cct gtt aag ctt       1046
Asn Val Thr Ala Phe Asp Gly Ser Ile Leu Tyr Leu Pro Val Lys Leu
        270                 275                 280 caa caa gtt gtt gag tta aaa agt cag agg aaa act gac gat gcc gag       1094
Gln Gln Val Val Glu Leu Lys Ser Gln Arg Lys Thr Asp Asp Ala Glu
    285                 290                 295 atc agt atc aag att cag ctg aca aag atc ctg gag ccg tgt tct gac       1142
Ile Ser Ile Lys Ile Gln Leu Thr Lys Ile Leu Glu Pro Cys Ser Asp
300                 305                 310                 315 ctg tgc atc ccc ttc tac aat gtt gtc ttc cgg cgg gta atg aaa ctt       1190
Leu Cys Ile Pro Phe Tyr Asn Val Val Phe Arg Arg Val Met Lys Leu
                320                 325                 330 ctg gat atg aag ctt gtg ggg aga aac ttc tat gac cct aca agt gcc       1238
Leu Asp Met Lys Leu Val Gly Arg Asn Phe Tyr Asp Pro Thr Ser Ala
            335                 340                 345 atg gta ctg cag caa cac aga ttg cag atc tgg cct ggc tat gcg gct       1286
Met Val Leu Gln Gln His Arg Leu Gln Ile Trp Pro Gly Tyr Ala Ala
        350                 355                 360 agt atc cgg agg aca gac ggg ggt ctc ttc ctg ctc gct gat gtc tct       1334
Ser Ile Arg Arg Thr Asp Gly Gly Leu Phe Leu Leu Ala Asp Val Ser
    365                 370                 375
```

-continued

| | | |
|---|---|---|
| cat aag gtc att cgg aac gac tct gtg ctg gat gtc atg cat gct atc<br>His Lys Val Ile Arg Asn Asp Ser Val Leu Asp Val Met His Ala Ile<br>380                        385                          390                        395 | 1382 | |
| tac cag cag aac aag gag cac ttc cag gac gag tgc agc aag ctt ctg<br>Tyr Gln Gln Asn Lys Glu His Phe Gln Asp Glu Cys Ser Lys Leu Leu<br>                      400                          405                        410 | 1430 | |
| gtt ggc agc att gtc atc acg cgc tac aac aat cgt acc tac cga atc<br>Val Gly Ser Ile Val Ile Thr Arg Tyr Asn Asn Arg Thr Tyr Arg Ile<br>                      415                        420                          425 | 1478 | |
| gat gat gtg gac tgg aac aag acc cct aaa gac agc ttt gtc atg tcg<br>Asp Asp Val Asp Trp Asn Lys Thr Pro Lys Asp Ser Phe Val Met Ser<br>        430                        435                        440 | 1526 | |
| gac ggg aag gaa atc aca ttc ctg gaa tac tac agc aaa aac tat ggg<br>Asp Gly Lys Glu Ile Thr Phe Leu Glu Tyr Tyr Ser Lys Asn Tyr Gly<br>        445                        450                        455 | 1574 | |
| atc aca gtc aag gaa gat gac cag ccg ctg ctc atc cac cgg ccc agt<br>Ile Thr Val Lys Glu Asp Asp Gln Pro Leu Leu Ile His Arg Pro Ser<br>460                        465                          470                        475 | 1622 | |
| gag aga cag aat aac cat ggc atg ttg ctg aag ggc gag atc ctg ctg<br>Glu Arg Gln Asn Asn His Gly Met Leu Leu Lys Gly Glu Ile Leu Leu<br>                      480                          485                        490 | 1670 | |
| ctg ccc gag ctc tcc ttc atg acg ggg atc cct gag aag atg aag aag<br>Leu Pro Glu Leu Ser Phe Met Thr Gly Ile Pro Glu Lys Met Lys Lys<br>                      495                        500                        505 | 1718 | |
| gac ttc agg gcc atg aag gac ttg act cag cag att aac ctg agc ccc<br>Asp Phe Arg Ala Met Lys Asp Leu Thr Gln Gln Ile Asn Leu Ser Pro<br>        510                        515                        520 | 1766 | |
| aag cag cac cac ggt gct ttg gaa tgc ctg ctg cag aga att tca caa<br>Lys Gln His His Gly Ala Leu Glu Cys Leu Leu Gln Arg Ile Ser Gln<br>525                        530                          535 | 1814 | |
| aac gag aca gcc agc aat gag ctg acc cgc tgg ggg ctc agt ctg cat<br>Asn Glu Thr Ala Ser Asn Glu Leu Thr Arg Trp Gly Leu Ser Leu His<br>540                        545                          550                        555 | 1862 | |
| aaa gat gtc cac aag att gaa ggt cgg ctt ctg cca atg gag agg atc<br>Lys Asp Val His Lys Ile Glu Gly Arg Leu Leu Pro Met Glu Arg Ile<br>                      560                        565                        570 | 1910 | |
| aac tta agg aac act tca ttt gtc aca tcg gag gac ctg aac tgg gtt<br>Asn Leu Arg Asn Thr Ser Phe Val Thr Ser Glu Asp Leu Asn Trp Val<br>            575                        580                        585 | 1958 | |
| aag gaa gtg acc aga gat gct tcc att cta act att ccc atg cat ttc<br>Lys Glu Val Thr Arg Asp Ala Ser Ile Leu Thr Ile Pro Met His Phe<br>                      590                        595                        600 | 2006 | |
| tgg gca ctc ttt tat cca aag aga gca atg gac caa gcc aga gaa ctg<br>Trp Ala Leu Phe Tyr Pro Lys Arg Ala Met Asp Gln Ala Arg Glu Leu<br>        605                        610                        615 | 2054 | |
| gtt aac atg ttg gaa aag att gcc ggg ccc att ggc atg cgc ata agc<br>Val Asn Met Leu Glu Lys Ile Ala Gly Pro Ile Gly Met Arg Ile Ser<br>620                        625                          630                        635 | 2102 | |
| ccc cca gcc tgg gtt gag ctg aag gat gac cga ata gag acc tat atc<br>Pro Pro Ala Trp Val Glu Leu Lys Asp Asp Arg Ile Glu Thr Tyr Ile<br>                        640                        645                        650 | 2150 | |
| agg acc att cag tcc tta ctg gga gtt gag ggg aag ata caa atg gtc<br>Arg Thr Ile Gln Ser Leu Leu Gly Val Glu Gly Lys Ile Gln Met Val<br>                      655                        660                        665 | 2198 | |
| gtt tgc atc atc atg ggc aca cgt gat gat ctc tat gga gcc atc aag<br>Val Cys Ile Ile Met Gly Thr Arg Asp Asp Leu Tyr Gly Ala Ile Lys<br>                  670                        675                        680 | 2246 | |
| aag ctg tgc tgc gtg cag tcc cca gtg ccc tca cag gtc atc aat gtc<br>Lys Leu Cys Cys Val Gln Ser Pro Val Pro Ser Gln Val Ile Asn Val<br>685                        690                        695 | 2294 | |

```
cga acc att ggt cag ccc acc agg ctt cgg agc gtg gct cag aaa att      2342
Arg Thr Ile Gly Gln Pro Thr Arg Leu Arg Ser Val Ala Gln Lys Ile
700             705                 710                 715 tta ctt cag atg aac tgt aaa ctg ggt ggt gag ctc tgg gga gtg gat      2390
Leu Leu Gln Met Asn Cys Lys Leu Gly Gly Glu Leu Trp Gly Val Asp
                720                 725                 730 att ccg ctg aaa caa cta atg gtg att gga atg gat gtg tac cat gac      2438
Ile Pro Leu Lys Gln Leu Met Val Ile Gly Met Asp Val Tyr His Asp
            735                 740                 745 ccc agc aga ggc atg cgc tct gtg gtc ggc ttc gtg gcc agc ata aat      2486
Pro Ser Arg Gly Met Arg Ser Val Val Gly Phe Val Ala Ser Ile Asn
        750                 755                 760 ctc aca ctc acc aaa tgg tac tcg agg gtg gtg ttc cag atg cca cat      2534
Leu Thr Leu Thr Lys Trp Tyr Ser Arg Val Val Phe Gln Met Pro His
765                 770                 775 cag gag att gtg gac agc ctg aag ctc tgc ctg gtg ggt tcc ttg aaa      2582
Gln Glu Ile Val Asp Ser Leu Lys Leu Cys Leu Val Gly Ser Leu Lys
780                 785                 790                 795 aag tat tat gag gtg aac cat tgt ctc cca gag aaa att gtg gtg tac      2630
Lys Tyr Tyr Glu Val Asn His Cys Leu Pro Glu Lys Ile Val Val Tyr
                800                 805                 810 cga gat gga gtg tct gat ggc cag cta aag aca gtt gcc aac tac gag      2678
Arg Asp Gly Val Ser Asp Gly Gln Leu Lys Thr Val Ala Asn Tyr Glu
            815                 820                 825 atc cct cag ctg cag aag tgt ttt gaa gcc ttt gat aac tac cac ccc      2726
Ile Pro Gln Leu Gln Lys Cys Phe Glu Ala Phe Asp Asn Tyr His Pro
        830                 835                 840 aag atg gtg gtg ttt gta gtt cag aag aaa atc agc acc aat ctg tac      2774
Lys Met Val Val Phe Val Val Gln Lys Lys Ile Ser Thr Asn Leu Tyr
845                 850                 855 ctt gct gct cct gat cac ttc gta acc ccc tcc ccc ggg act gtg gtt      2822
Leu Ala Ala Pro Asp His Phe Val Thr Pro Ser Pro Gly Thr Val Val
860                 865                 870                 875 gat cat acc ata acc agc tgt gag tgg gtg gat ttc tac ctt ctt gcc      2870
Asp His Thr Ile Thr Ser Cys Glu Trp Val Asp Phe Tyr Leu Leu Ala
                880                 885                 890 cat cat gtg cga cag ggc tgt ggc ata cct aca cac tac atc tgt gtt      2918
His His Val Arg Gln Gly Cys Gly Ile Pro Thr His Tyr Ile Cys Val
            895                 900                 905 ctg aac act gca aat ctg agc cct gat cac atg cag agg ttg act ttc      2966
Leu Asn Thr Ala Asn Leu Ser Pro Asp His Met Gln Arg Leu Thr Phe
        910                 915                 920 aaa cta tgc cac atg tac tgg aat tgg cct ggt acc atc cga gtt cca      3014
Lys Leu Cys His Met Tyr Trp Asn Trp Pro Gly Thr Ile Arg Val Pro
925                 930                 935 gct cct tgc aag tat gcc cac aag cta gct ttc ctg tcc gga cag att      3062
Ala Pro Cys Lys Tyr Ala His Lys Leu Ala Phe Leu Ser Gly Gln Ile
940                 945                 950                 955 ttg cat cat gag cca gcc atc cag ctg tgt ggg aac ctg ttc ttc ctg      3110
Leu His His Glu Pro Ala Ile Gln Leu Cys Gly Asn Leu Phe Phe Leu
                960                 965                 970 taa ctgggaactt ggacaccggc tgcaaggagc aactggactc agctcagctc           3163
ctccttacag aatcaacaga aatggcagtg aatttatg tttgcatttt ctctttctcc     3223
atccttgtag aattagattt ctgttcttct tttaaccctg atatcatagt agggtgttgt    3283
ggtgcatgcc ttttatccca gcacttggga gactgaagca ggagtatctt tagttcaagg   3343
ccagcctaga ctacatggtg agttctaggc tagccaagat tacagagtga gaccctgtct   3403
```

```
caaaaaacaa aaacaaacca ctgtcccctc aaagcccaca acaaaaccaa agcctggggt    3463
caaggaagca agtttgtagg tagccgctgg ctgcccgctg ccttcatgga gtgtgtgccg    3523
tcagcgctgc ttctcctcag ccgagcgtgg agcttcggac agggcagtga tgacatgttc    3583
ttagcatgtc aaatccccct accaaataag tcaagcaagg aaaaaatagc ccccaaggca    3643
gcctgagcat cagttcctag aggttatgcc tacagaacca tcctatttct ggtggcagaa    3703
gtgacatgaa gtcattgcag acatcttaaa ggagagttac tgtgcagctg tctacatgtg    3763
tgaaagacat gtagaaaaac cagcgtaggg tacagtcggg cgtatgtgcc cacctgaccc    3823
agggctgtga gtctgacttc ccgagagtct ggctagagct gcttttctgg tccttttggt    3883
tatttgcaac catcatcaga ttgctttcct gcagcccgac tgatacacgc atgtgcgcac    3943
gcacacactt ttgttctttg tgactaatct tgaataaatt caattagaac acatggaaag    4003
gattcagcag acctaggaac atttggggtg gagtgtagtt tttctgcaaa agtctgtaaa    4063
tgagattacg caagagtctc ttccagctgt gggctggtgt tgcttggaaa atttcaaaat    4123
cccaaagttt caggcttccc aaagttggct tggaaaaatg tgatagtctc acctgagtct    4183
agacatgtag gaaattttcc tagggcctct gggcttcagt atttggggga agcactggtt    4243
ttctgtgtta ttttttttcct tctgtttcag aatcttcaag tttcttcagg cttcagtggg    4303
ccatcccttt actgggctct aaaagctaat tttacttaac cttttcaaat gtgtatgtat    4363
ctatttatgt tttggtgtgg tggatggatg gtaggggact gagcagaaat agtcatttta    4423
aataacagtg tgctaggaga gcctcagtgt gaagtcctga ggagcagcgg gggctgtggg    4483
agtcagtgtc agccctcact cagacaggcc aagcctgggc tcgaagacaa cattgtccag    4543
ggaagccttt agtttgctat agcacccaga ggttggcgag gaataagggt tagggtcctc    4603
aaatacaccc atggcttttg gagtctatga ccaaggccag gctgagacct gaaatgtaaa    4663
agccatagaa ttaaacagaa cagactgaaa aacgagtctt aagttccact ttctggattt    4723
ctctggaagt cttttgaatt tgtctgtaga agttgctgtt cctagcactc cttttctctt    4783
taggtagaac agatacttga ccataatgcc agaatgtact ttctctgcct tggttttttct    4843 atgccttgtt tttcagtttc agggccaaac aattgggccc tgtggtgtaa aataaaaaca    4903
atgtatgtgt                                                          4913
```

<210> SEQ ID NO 43
<211> LENGTH: 971
<212> TYPE: PRT
<213> ORGANISM: Mus musculus

<400> SEQUENCE: 43

```
Met Asp Pro Val Arg Pro Leu Phe Arg Gly Pro Thr Pro Val His Pro
 1               5                  10                  15

Ser Gln Cys Val Arg Met Pro Gly Cys Trp Pro Gln Ala Pro Arg Pro
            20                  25                  30

Leu Glu Pro Ala Trp Gly Arg Ala Gly Pro Ala Gly Arg Gly Leu Val
        35                  40                  45

Phe Arg Lys Pro Glu Asp Ser Ser Pro Leu Gln Pro Val Gln Lys
    50                  55                  60

Asp Ser Val Gly Leu Val Ser Met Phe Arg Gly Met Gly Leu Asp Thr
65                  70                  75                  80

Ala Phe Arg Pro Pro Ser Lys Arg Glu Val Pro Pro Leu Gly Arg Gly
                85                  90                  95

Val Leu Gly Arg Gly Leu Ser Ala Asn Met Val Arg Lys Asp Arg Glu
```

```
                100                 105                 110
Glu Pro Arg Ser Ser Leu Pro Asp Pro Ser Val Leu Ala Ala Gly Asp
            115                 120                 125

Ser Lys Leu Ala Glu Ala Ser Val Gly Trp Ser Arg Met Leu Gly Arg
130                 135                 140

Gly Ser Ser Glu Val Ser Leu Leu Pro Leu Gly Arg Ala Ala Ser Ser
145                 150                 155                 160

Ile Gly Arg Gly Met Asp Lys Pro Pro Ser Ala Phe Gly Leu Thr Ala
                165                 170                 175

Arg Asp Pro Pro Arg Leu Pro Gln Pro Pro Ala Leu Ser Pro Thr Ser
            180                 185                 190

Leu His Ser Ala Asp Pro Pro Val Leu Thr Met Glu Arg Lys Glu
            195                 200                 205

Lys Glu Leu Leu Val Lys Gln Gly Ser Lys Gly Thr Pro Gln Ser Leu
    210                 215                 220

Gly Leu Asn Leu Ile Lys Ile Gln Cys His Asn Glu Ala Val Tyr Gln
225                 230                 235                 240

Tyr His Val Thr Phe Ser Pro Ser Val Glu Cys Lys Ser Met Arg Phe
                245                 250                 255

Gly Met Leu Lys Asp His Gln Ser Val Thr Gly Asn Val Thr Ala Phe
            260                 265                 270

Asp Gly Ser Ile Leu Tyr Leu Pro Val Lys Leu Gln Gln Val Val Glu
        275                 280                 285

Leu Lys Ser Gln Arg Lys Thr Asp Asp Ala Glu Ile Ser Ile Lys Ile
    290                 295                 300

Gln Leu Thr Lys Ile Leu Glu Pro Cys Ser Asp Leu Cys Ile Pro Phe
305                 310                 315                 320

Tyr Asn Val Val Phe Arg Arg Val Met Lys Leu Leu Asp Met Lys Leu
                325                 330                 335

Val Gly Arg Asn Phe Tyr Asp Pro Thr Ser Ala Met Val Leu Gln Gln
            340                 345                 350

His Arg Leu Gln Ile Trp Pro Gly Tyr Ala Ala Ser Ile Arg Arg Thr
        355                 360                 365

Asp Gly Gly Leu Phe Leu Leu Ala Asp Val Ser His Lys Val Ile Arg
    370                 375                 380

Asn Asp Ser Val Leu Asp Val Met His Ala Ile Tyr Gln Gln Asn Lys
385                 390                 395                 400

Glu His Phe Gln Asp Glu Cys Ser Lys Leu Leu Val Gly Ser Ile Val
                405                 410                 415

Ile Thr Arg Tyr Asn Asn Arg Thr Tyr Arg Ile Asp Asp Val Asp Trp
            420                 425                 430

Asn Lys Thr Pro Lys Asp Ser Phe Val Met Ser Asp Gly Lys Glu Ile
        435                 440                 445

Thr Phe Leu Glu Tyr Tyr Ser Lys Asn Tyr Gly Ile Thr Val Lys Glu
    450                 455                 460

Asp Asp Gln Pro Leu Leu Ile His Arg Pro Ser Glu Arg Gln Asn Asn
465                 470                 475                 480

His Gly Met Leu Leu Lys Gly Glu Ile Leu Leu Pro Glu Leu Ser
                485                 490                 495

Phe Met Thr Gly Ile Pro Glu Lys Met Lys Lys Asp Phe Arg Ala Met
            500                 505                 510

Lys Asp Leu Thr Gln Gln Ile Asn Leu Ser Pro Lys Gln His His Gly
        515                 520                 525
```

```
Ala Leu Glu Cys Leu Leu Gln Arg Ile Ser Gln Asn Glu Thr Ala Ser
        530                 535                 540

Asn Glu Leu Thr Arg Trp Gly Leu Ser Leu His Lys Asp Val His Lys
545                 550                 555                 560

Ile Glu Gly Arg Leu Leu Pro Met Glu Arg Ile Asn Leu Arg Asn Thr
                565                 570                 575

Ser Phe Val Thr Ser Glu Asp Leu Asn Trp Val Lys Glu Val Thr Arg
            580                 585                 590

Asp Ala Ser Ile Leu Thr Ile Pro Met His Phe Trp Ala Leu Phe Tyr
        595                 600                 605

Pro Lys Arg Ala Met Asp Gln Ala Arg Glu Leu Val Asn Met Leu Glu
    610                 615                 620

Lys Ile Ala Gly Pro Ile Gly Met Arg Ile Ser Pro Pro Ala Trp Val
625                 630                 635                 640

Glu Leu Lys Asp Asp Arg Ile Glu Thr Tyr Ile Arg Thr Ile Gln Ser
                645                 650                 655

Leu Leu Gly Val Glu Gly Lys Ile Gln Met Val Val Cys Ile Ile Met
            660                 665                 670

Gly Thr Arg Asp Asp Leu Tyr Gly Ala Ile Lys Lys Leu Cys Cys Val
        675                 680                 685

Gln Ser Pro Val Pro Ser Gln Val Ile Asn Val Arg Thr Ile Gly Gln
    690                 695                 700

Pro Thr Arg Leu Arg Ser Val Ala Gln Lys Ile Leu Leu Gln Met Asn
705                 710                 715                 720

Cys Lys Leu Gly Gly Glu Leu Trp Gly Val Asp Ile Pro Leu Lys Gln
                725                 730                 735

Leu Met Val Ile Gly Met Asp Val Tyr His Asp Pro Ser Arg Gly Met
            740                 745                 750

Arg Ser Val Val Gly Phe Val Ala Ser Ile Asn Leu Thr Leu Thr Lys
        755                 760                 765

Trp Tyr Ser Arg Val Val Phe Gln Met Pro His Gln Glu Ile Val Asp
    770                 775                 780

Ser Leu Lys Leu Cys Leu Val Gly Ser Leu Lys Lys Tyr Tyr Glu Val
785                 790                 795                 800

Asn His Cys Leu Pro Glu Lys Ile Val Val Tyr Arg Asp Gly Val Ser
                805                 810                 815

Asp Gly Gln Leu Lys Thr Val Ala Asn Tyr Glu Ile Pro Gln Leu Gln
            820                 825                 830

Lys Cys Phe Glu Ala Phe Asp Asn Tyr His Pro Lys Met Val Val Phe
        835                 840                 845

Val Val Gln Lys Lys Ile Ser Thr Asn Leu Tyr Leu Ala Ala Pro Asp
    850                 855                 860

His Phe Val Thr Pro Ser Pro Gly Thr Val Val Asp His Thr Ile Thr
865                 870                 875                 880

Ser Cys Glu Trp Val Asp Phe Tyr Leu Leu Ala His His Val Arg Gln
                885                 890                 895

Gly Cys Gly Ile Pro Thr His Tyr Ile Cys Val Leu Asn Thr Ala Asn
            900                 905                 910

Leu Ser Pro Asp His Met Gln Arg Leu Thr Phe Lys Leu Cys His Met
        915                 920                 925

Tyr Trp Asn Trp Pro Gly Thr Ile Arg Val Pro Ala Pro Cys Lys Tyr
    930                 935                 940
```

```
Ala His Lys Leu Ala Phe Leu Ser Gly Gln Ile Leu His Glu Pro
945                 950                 955                 960

Ala Ile Gln Leu Cys Gly Asn Leu Phe Phe Leu
                965                 970

<210> SEQ ID NO 44
<211> LENGTH: 2501
<212> TYPE: DNA
<213> ORGANISM: Mus musculus
<220> FEATURE:
<221> NAME/KEY: CDS
<222> LOCATION: (124)..(1569)

<400> SEQUENCE: 44 ggcttttttgc tccagaggag tcaggaaaac tttcagagtt gtagaaccta aaacttcagc      60
ctgtccttgc ttgcagtagg aacactgtca cctcaggagc cttcttcctg aagacctgag     120 agg atg agt ggt cag acc cca ccc aca ctc cag aag cta gca agg cag      168
    Met Ser Gly Gln Thr Pro Pro Thr Leu Gln Lys Leu Ala Arg Gln
    1               5                   10                  15 aca ctg ctg aga gat gag gct ttg gcc ata tcc tct ctg gag gag ctg      216
Thr Leu Leu Arg Asp Glu Ala Leu Ala Ile Ser Ser Leu Glu Glu Leu
                20                  25                  30 cca gct gtg gtc ttc cca cca ctg ttc caa gag gcc ttt gct ggc aga      264
Pro Ala Val Val Phe Pro Pro Leu Phe Gln Glu Ala Phe Ala Gly Arg
            35                  40                  45 ctc aac aag ctc ata aag gca atg gtg gca gcc tgg cct ttc cac gat      312
Leu Asn Lys Leu Ile Lys Ala Met Val Ala Ala Trp Pro Phe His Asp
        50                  55                  60 ctc cct gtg ggg cca ttg ata aat atg cat aac ctg gaa acc ttg caa      360
Leu Pro Val Gly Pro Leu Ile Asn Met His Asn Leu Glu Thr Leu Gln
    65                  70                  75 gct ctg cta gat gga gta gac atg aga cta aca aga aaa ttt cac ccc      408
Ala Leu Leu Asp Gly Val Asp Met Arg Leu Thr Arg Lys Phe His Pro
80                  85                  90                  95 tgg agg cca aaa ctt cag gtt ctc gac atg aga aac gtg gac cat gtc      456
Trp Arg Pro Lys Leu Gln Val Leu Asp Met Arg Asn Val Asp His Val
                100                 105                 110 ttc tgg aac ata tgg agc gat gca aat gac agt gac tct gat gca gag      504
Phe Trp Asn Ile Trp Ser Asp Ala Asn Asp Ser Asp Ser Asp Ala Glu
            115                 120                 125 acc ttg gat gaa aag caa gta gtg aag gcc cct cgc aga tat gca ctg      552
Thr Leu Asp Glu Lys Gln Val Val Lys Ala Pro Arg Arg Tyr Ala Leu
        130                 135                 140 agg cag cgt ctg aag atc ata gtt gat ctg tca atc agt tct cag ctc      600
Arg Gln Arg Leu Lys Ile Ile Val Asp Leu Ser Ile Ser Ser Gln Leu
    145                 150                 155 aat gaa caa aaa gca tat ttc ttg aat tgg gcc aag cag aga aag ggg      648
Asn Glu Gln Lys Ala Tyr Phe Leu Asn Trp Ala Lys Gln Arg Lys Gly
160                 165                 170                 175 tcc ata aat ttc tgc tgt aca aag atg aag atc tgg gat gca cca gac      696
Ser Ile Asn Phe Cys Cys Thr Lys Met Lys Ile Trp Asp Ala Pro Asp
                180                 185                 190 gaa gtt atc aga gaa atc atg aat gtt ttc cat cca gag cac att aca      744
Glu Val Ile Arg Glu Ile Met Asn Val Phe His Pro Glu His Ile Thr
            195                 200                 205 gaa tta gaa ctg tat acc gac tgg act ctg ttg cgg ctg gca cat ttt      792
Glu Leu Glu Leu Tyr Thr Asp Trp Thr Leu Leu Arg Leu Ala His Phe
        210                 215                 220 gct ccc tac att ggg cag atg aaa aat ctt gaa aga gtc ttc ctg gca      840
Ala Pro Tyr Ile Gly Gln Met Lys Asn Leu Glu Arg Val Phe Leu Ala
```

```
                225                 230                 235
cca ctc cac aag aat acc tcc cct att atg aat ttg aca agg gac tca    888
Pro Leu His Lys Asn Thr Ser Pro Ile Met Asn Leu Thr Arg Asp Ser
240                 245                 250                 255 aaa gtc aag tgt att aaa aaa att att tct cag ttt tcc aaa ttc aac    936
Lys Val Lys Cys Ile Lys Lys Ile Ile Ser Gln Phe Ser Lys Phe Asn
                260                 265                 270 tgt ctc caa cat gtc ttc atg aaa cgt gtc cat ttt ctc aga gac cac    984
Cys Leu Gln His Val Phe Met Lys Arg Val His Phe Leu Arg Asp His
            275                 280                 285 ctg cat cag ata cta ggg tgc ctg agg acg ccc ttg cag acc ctc tcc   1032
Leu His Gln Ile Leu Gly Cys Leu Arg Thr Pro Leu Gln Thr Leu Ser
        290                 295                 300 atc act cac tgc cta att tca cag aca gac ttg gat tcc ttt tcc tgc   1080
Ile Thr His Cys Leu Ile Ser Gln Thr Asp Leu Asp Ser Phe Ser Cys
    305                 310                 315 tgt cac aac ctt ttt aag tta aaa aat ctg gaa atc aga gga gtg aca   1128
Cys His Asn Leu Phe Lys Leu Lys Asn Leu Glu Ile Arg Gly Val Thr
320                 325                 330                 335 tta ttt gct ctc gat ctt atg cct ctg aga ggt ctc cta gga aaa ctg   1176
Leu Phe Ala Leu Asp Leu Met Pro Leu Arg Gly Leu Leu Gly Lys Leu
                340                 345                 350 gca ggt act ctt gag tct ctg gat ttt cag tgg tgt agc atg aag gac   1224
Ala Gly Thr Leu Glu Ser Leu Asp Phe Gln Trp Cys Ser Met Lys Asp
            355                 360                 365 tcc cag ctc att gtc ctc tta cct gcc ctc agt caa tgc tct cag ctc   1272
Ser Gln Leu Ile Val Leu Leu Pro Ala Leu Ser Gln Cys Ser Gln Leu
        370                 375                 380 aac cag atc aac ttc tac agc aat gac ttc tcc atg gcc atc ctg aag   1320
Asn Gln Ile Asn Phe Tyr Ser Asn Asp Phe Ser Met Ala Ile Leu Lys
    385                 390                 395 gac ctt ttg cag cac aca gcc aac tgg agc aag atg aat gtg gaa caa   1368
Asp Leu Leu Gln His Thr Ala Asn Trp Ser Lys Met Asn Val Glu Gln
400                 405                 410                 415 tac cct gtc cct ctg gag tgc tat gat gca ttg ggt cat gtc tcc aga   1416
Tyr Pro Val Pro Leu Glu Cys Tyr Asp Ala Leu Gly His Val Ser Arg
                420                 425                 430 gaa aga ttt gtg gaa ctt tgt cag gag ctc atg gat acc ctc agg gcc   1464
Glu Arg Phe Val Glu Leu Cys Gln Glu Leu Met Asp Thr Leu Arg Ala
            435                 440                 445 aaa aga gag cct aag agc ata tct ttt gca aca aat gtc tgc caa aat   1512
Lys Arg Glu Pro Lys Ser Ile Ser Phe Ala Thr Asn Val Cys Gln Asn
        450                 455                 460 tgt ggc aag acc tgt gtc tat ggc cag ggg gca aga ctt tgt tcc tgt   1560
Cys Gly Lys Thr Cys Val Tyr Gly Gln Gly Ala Arg Leu Cys Ser Cys
    465                 470                 475 ttg cag taa acatggatac aggacttctg aatatgaata aatgacatgc           1609
Leu Gln
480 ttgggacaca tctctcatcc agggtgctca gagactgtga cttcagacac ttcccatatg  1669 gttagaagta aagagatgtg tagtgactgg gaccctgaat gcttagatag aaatgtggac  1729 tattccaata gactgttgga ccagggacat gatggaatca gaaaaacagt ttggcattta  1789 tatgtggctt ctgcccagac agtatattta gatgcttttt tgtgtaccta aacctctct   1849 ctccagggtc tttgactttt accaacctta ctaccaggtt cagggtcagg atgatagaat  1909 aggtccagga ttggaaagac actgttattt tatgaaggaa gcaaagttcc aggtgaatat  1969 ggcatgtata aaataaaagt tttcttgaca catctttccc tggtctcttg cctgggctac  2029
```

-continued

```
atgtataaca cttttgtgtg gctgatcagt tatgtgcaca aaacatttac attaatgtga    2089
ggaagataaa cacaaatctt gtgaaggggg gattaagagg atcacagatg gttaatatcc    2149
agtatgttga gaccacaagg caccttggac ccatcaaaga tgcctaaagg taggaagaca    2209
acatagagca aagtaaacag gctttccatt ctagctttaa atcctgatct ttttgtcatg    2269
ccttaatgag cttactaacc agaacctcta tatacagtct ttatgccaca tgtctctaga    2329
gctctattcc tatggagtcc caaactctat gaagtaacca tagtgtataa aaaggtgcca    2389
acaattatgc aggtaccttt gctacataaa gtatttactt tcaaaaagac ttgtatttta    2449
aatcttcagt tgtaataaaa ataaagaaa caaaaatcaa aaaaaaaaa aa              2501
```

<210> SEQ ID NO 45
<211> LENGTH: 481
<212> TYPE: PRT
<213> ORGANISM: Mus musculus

<400> SEQUENCE: 45

```
Met Ser Gly Gln Thr Pro Pro Thr Leu Gln Lys Leu Ala Arg Gln Thr
 1               5                  10                  15

Leu Leu Arg Asp Glu Ala Leu Ala Ile Ser Ser Leu Glu Glu Leu Pro
            20                  25                  30

Ala Val Val Phe Pro Pro Leu Phe Gln Glu Ala Phe Ala Gly Arg Leu
        35                  40                  45

Asn Lys Leu Ile Lys Ala Met Val Ala Ala Trp Pro Phe His Asp Leu
    50                  55                  60

Pro Val Gly Pro Leu Ile Asn Met His Asn Leu Glu Thr Leu Gln Ala
65                  70                  75                  80

Leu Leu Asp Gly Val Asp Met Arg Leu Thr Arg Lys Phe His Pro Trp
                85                  90                  95

Arg Pro Lys Leu Gln Val Leu Asp Met Arg Asn Val Asp His Val Phe
            100                 105                 110

Trp Asn Ile Trp Ser Asp Ala Asn Asp Ser Asp Ser Asp Ala Glu Thr
        115                 120                 125

Leu Asp Glu Lys Gln Val Val Lys Ala Pro Arg Arg Tyr Ala Leu Arg
    130                 135                 140

Gln Arg Leu Lys Ile Ile Val Asp Leu Ser Ile Ser Ser Gln Leu Asn
145                 150                 155                 160

Glu Gln Lys Ala Tyr Phe Leu Asn Trp Ala Lys Gln Arg Lys Gly Ser
                165                 170                 175

Ile Asn Phe Cys Cys Thr Lys Met Lys Ile Trp Asp Ala Pro Asp Glu
            180                 185                 190

Val Ile Arg Glu Ile Met Asn Val Phe His Pro Glu His Ile Thr Glu
        195                 200                 205

Leu Glu Leu Tyr Thr Asp Trp Thr Leu Leu Arg Leu Ala His Phe Ala
    210                 215                 220

Pro Tyr Ile Gly Gln Met Lys Asn Leu Glu Arg Val Phe Leu Ala Pro
225                 230                 235                 240

Leu His Lys Asn Thr Ser Pro Ile Met Asn Leu Thr Arg Asp Ser Lys
                245                 250                 255

Val Lys Cys Ile Lys Lys Ile Ile Ser Gln Phe Ser Lys Phe Asn Cys
            260                 265                 270

Leu Gln His Val Phe Met Lys Arg Val His Phe Leu Arg Asp His Leu
        275                 280                 285
```

-continued

```
His Gln Ile Leu Gly Cys Leu Arg Thr Pro Leu Gln Thr Leu Ser Ile
            290                 295                 300

Thr His Cys Leu Ile Ser Gln Thr Asp Leu Asp Ser Phe Ser Cys Cys
305                 310                 315                 320

His Asn Leu Phe Lys Leu Lys Asn Leu Glu Ile Arg Gly Val Thr Leu
                325                 330                 335

Phe Ala Leu Asp Leu Met Pro Leu Arg Gly Leu Leu Gly Lys Leu Ala
            340                 345                 350

Gly Thr Leu Glu Ser Leu Asp Phe Gln Trp Cys Ser Met Lys Asp Ser
                355                 360                 365

Gln Leu Ile Val Leu Leu Pro Ala Leu Ser Gln Cys Ser Gln Leu Asn
370                 375                 380

Gln Ile Asn Phe Tyr Ser Asn Asp Phe Ser Met Ala Ile Leu Lys Asp
385                 390                 395                 400

Leu Leu Gln His Thr Ala Asn Trp Ser Lys Met Asn Val Glu Gln Tyr
                405                 410                 415

Pro Val Pro Leu Glu Cys Tyr Asp Ala Leu Gly His Val Ser Arg Glu
            420                 425                 430

Arg Phe Val Glu Leu Cys Gln Glu Leu Met Asp Thr Leu Arg Ala Lys
                435                 440                 445

Arg Glu Pro Lys Ser Ile Ser Phe Ala Thr Asn Val Cys Gln Asn Cys
450                 455                 460

Gly Lys Thr Cys Val Tyr Gly Gln Gly Ala Arg Leu Cys Ser Cys Leu
465                 470                 475                 480

Gln
```

<210> SEQ ID NO 46
<211> LENGTH: 1967
<212> TYPE: DNA
<213> ORGANISM: Homo sapiens
<220> FEATURE:
<221> NAME/KEY: CDS
<222> LOCATION: (99)..(1730)

<400> SEQUENCE: 46

```
gaaaggacag caacagtcag gtggtttacc ttccagaggc tggcaatgct gtttcactgg      60
aggacacggc taagaaggaa gtccaccagc ctgccaag atg aat tgc ctt gaa ggg     116
                                         Met Asn Cys Leu Glu Gly
                                         1               5 cca ggt aag acc tgt ggc ccc ttg gct tct gag gag gag ctg gtg tct      164
Pro Gly Lys Thr Cys Gly Pro Leu Ala Ser Glu Glu Glu Leu Val Ser
            10                  15                  20 gcc tgc cag ttg gaa aaa gaa gaa gag aat gaa ggg gag gag gag gaa      212
Ala Cys Gln Leu Glu Lys Glu Glu Glu Asn Glu Gly Glu Glu Glu Glu
        25                  30                  35 gag gag gag gac gag gag gat ctg gac cca gat ctg gac cca gac cta      260
Glu Glu Glu Asp Glu Glu Asp Leu Asp Pro Asp Leu Asp Pro Asp Leu
40                  45                  50 gag gag gaa gag aat gat ctt ggg gat cca gct gta ctt ggt gct gtc      308
Glu Glu Glu Glu Asn Asp Leu Gly Asp Pro Ala Val Leu Gly Ala Val
55                  60                  65                  70 cac aac acc cag aga gct ctg ctt agc tcc cct gga gtc aag gcc cct      356
His Asn Thr Gln Arg Ala Leu Leu Ser Ser Pro Gly Val Lys Ala Pro
                75                  80                  85 ggt atg ctg gga atg tca ctt gcc tcc ttg cat ttt ctg tgg cag acc      404
Gly Met Leu Gly Met Ser Leu Ala Ser Leu His Phe Leu Trp Gln Thr
            90                  95                  100
```

-continued

| | |
|---|---|
| ttg gac tac ctg tcg ccc atc cct ttc tgg cct aca ttt ccc agc acc<br>Leu Asp Tyr Leu Ser Pro Ile Pro Phe Trp Pro Thr Phe Pro Ser Thr<br>          105                    110                        115 | 452 |
| agc tct cca gca cag cac ttt gga cct cgg ctg ccc tca cca gac cca<br>Ser Ser Pro Ala Gln His Phe Gly Pro Arg Leu Pro Ser Pro Asp Pro<br>120                          125                        130 | 500 |
| act ctc ttc tgc agc ctg ctg acc tcg tgg ccc cct agg ttc agt cat<br>Thr Leu Phe Cys Ser Leu Leu Thr Ser Trp Pro Pro Arg Phe Ser His<br>135                        140                      145                  150 | 548 |
| ctg acc cag ctc cac cct cgg cac caa cga atc ttg cag cag cag cag<br>Leu Thr Gln Leu His Pro Arg His Gln Arg Ile Leu Gln Gln Gln Gln<br>                  155                        160                        165 | 596 |
| cat agt caa aca cca agt ccc cca gcc aag aag cct tgg tct cag cag<br>His Ser Gln Thr Pro Ser Pro Pro Ala Lys Lys Pro Trp Ser Gln Gln<br>170                          175                        180 | 644 |
| cca gac ccc tat gct aac ctc atg acc aga aaa gag aag gac tgg gtg<br>Pro Asp Pro Tyr Ala Asn Leu Met Thr Arg Lys Glu Lys Asp Trp Val<br>                  185                        190                        195 | 692 |
| ata aaa gtg cag atg gtg cag ctg cag agt gca aaa ccc cgc ctg gat<br>Ile Lys Val Gln Met Val Gln Leu Gln Ser Ala Lys Pro Arg Leu Asp<br>200                          205                        210 | 740 |
| gac tac tat tac cag gaa tat tac cag aag cta gag aag aag cag gca<br>Asp Tyr Tyr Tyr Gln Glu Tyr Tyr Gln Lys Leu Glu Lys Lys Gln Ala<br>215                        220                      225                  230 | 788 |
| gac gaa gag cta ctt gga cga aga aac cgg gtt gag tcc ctc aag ctg<br>Asp Glu Glu Leu Leu Gly Arg Arg Asn Arg Val Glu Ser Leu Lys Leu<br>                  235                        240                        245 | 836 |
| gta acg cct tac att ccg aag gca gag gct tat gag tcc gtg gtc cga<br>Val Thr Pro Tyr Ile Pro Lys Ala Glu Ala Tyr Glu Ser Val Val Arg<br>                      250                        255                        260 | 884 |
| atc gag ggt tcc ctg ggc cag gta gct gtg tcg aca tgc ttc agc cct<br>Ile Glu Gly Ser Leu Gly Gln Val Ala Val Ser Thr Cys Phe Ser Pro<br>265                          270                        275 | 932 |
| cgc cga gct att gat gcg gta ccc cat gga act caa gag cag gat ata<br>Arg Arg Ala Ile Asp Ala Val Pro His Gly Thr Gln Glu Gln Asp Ile<br>                  280                        285                        290 | 980 |
| gaa gct gca agc agt cag agg ctt cgg gta tta tac cgg att gag aag<br>Glu Ala Ala Ser Ser Gln Arg Leu Arg Val Leu Tyr Arg Ile Glu Lys<br>295                          300                      305                  310 | 1028 |
| atg ttc ctt cag tta cta gaa ata gag gaa ggc tgg aag tat agg cct<br>Met Phe Leu Gln Leu Leu Glu Ile Glu Glu Gly Trp Lys Tyr Arg Pro<br>                  315                        320                        325 | 1076 |
| cca ccg ccc tgc ttt tct gag cag caa agc aac cag gtt gag aag ctc<br>Pro Pro Pro Cys Phe Ser Glu Gln Gln Ser Asn Gln Val Glu Lys Leu<br>                  330                        335                        340 | 1124 |
| ttc cag acc tta aag acc cag gag cag aac aac ctg gaa gag gca gca<br>Phe Gln Thr Leu Lys Thr Gln Glu Gln Asn Asn Leu Glu Glu Ala Ala<br>345                          350                      355 | 1172 |
| gat ggc ttc ctg cag gtg ctc tct gtg agg aag ggg aag gcc ctg gtg<br>Asp Gly Phe Leu Gln Val Leu Ser Val Arg Lys Gly Lys Ala Leu Val<br>                  360                        365                        370 | 1220 |
| gcc cgg ctg ctc ccc ttc ctg ccc cag gat cag gct gtt acc att ctt<br>Ala Arg Leu Leu Pro Phe Leu Pro Gln Asp Gln Ala Val Thr Ile Leu<br>375                          380                      385                  390 | 1268 |
| ttg gct atc acc cac cat ctg ccc ctc ctg gtc cgg agg gat gtg gct<br>Leu Ala Ile Thr His His Leu Pro Leu Leu Val Arg Arg Asp Val Ala<br>                      395                        400                        405 | 1316 |
| gat cag gcc cta caa atg tta ttc aaa cct ctg ggc aaa tgt att agt<br>Asp Gln Ala Leu Gln Met Leu Phe Lys Pro Leu Gly Lys Cys Ile Ser<br>                  410                        415                  420 | 1364 |

-continued

```
cac ttg acc ctc cac gaa ctc ctc caa gga ctt cag gga tta acg ctg    1412
His Leu Thr Leu His Glu Leu Leu Gln Gly Leu Gln Gly Leu Thr Leu
        425                 430                 435 ttg cca cct ggc tcc tca gag cgg cca gtc acc gtg gtg ctt cag aat    1460
Leu Pro Pro Gly Ser Ser Glu Arg Pro Val Thr Val Val Leu Gln Asn
    440                 445                 450 cag ttt gga ata tct ttg ctc tat gcc ctg ctg agc cat ggg gag caa    1508
Gln Phe Gly Ile Ser Leu Leu Tyr Ala Leu Leu Ser His Gly Glu Gln
455                 460                 465                 470 ctg gta tcg ctg cat tct tcc cta gag gaa ccc aac agt gac cat aca    1556
Leu Val Ser Leu His Ser Ser Leu Glu Glu Pro Asn Ser Asp His Thr
                475                 480                 485 gct tgg aca gac atg gtg gtt ctg att gcc tgg gag ata gcc caa atg    1604
Ala Trp Thr Asp Met Val Val Leu Ile Ala Trp Glu Ile Ala Gln Met
        490                 495                 500 cct aca gcc tct ctg gca gaa ccc cta gct ttc ccc agc aac cta ctt    1652
Pro Thr Ala Ser Leu Ala Glu Pro Leu Ala Phe Pro Ser Asn Leu Leu
    505                 510                 515 ccc ctg ttc tgt cac cac gtg gac aaa caa ttg gtt cag cag ctg gag    1700
Pro Leu Phe Cys His His Val Asp Lys Gln Leu Val Gln Gln Leu Glu
520                 525                 530 gcc agg atg gag ttt gcc tgg att tac tga tctgtttgtt ctggaatacg      1750
Ala Arg Met Glu Phe Ala Trp Ile Tyr
535                 540 tgtatgtggg aagttgaatc atcagacact agctacatag actatgttta cagggatcca  1810
gagagtctga agacatttct tatgccttta tatattggag aacccttccc cattttcata  1870
tcctttcttc aaaaatctaa atgatgtgcc taaaaataag acatggcata ataaggtata  1930
attaaagaga taatagaatg aaaaaaaaaa aaaaaaa                           1967
```

<210> SEQ ID NO 47
<211> LENGTH: 543
<212> TYPE: PRT
<213> ORGANISM: Artificial Sequence
<220> FEATURE:
<223> OTHER INFORMATION: Synthetic oligonucleotide

<400> SEQUENCE: 47

```
Met Asn Cys Leu Glu Gly Pro Gly Lys Thr Cys Gly Pro Leu Ala Ser
1               5                   10                  15

Glu Glu Glu Leu Val Ser Ala Cys Gln Leu Glu Lys Glu Glu Glu Asn
                20                  25                  30

Glu Gly Glu Glu Glu Glu Glu Glu Asp Glu Glu Asp Leu Asp Pro
        35                  40                  45

Asp Leu Asp Pro Asp Leu Glu Glu Glu Asn Asp Leu Gly Asp Pro
    50                  55                  60

Ala Val Leu Gly Ala Val His Asn Thr Gln Arg Ala Leu Leu Ser Ser
65                  70                  75                  80

Pro Gly Val Lys Ala Pro Gly Met Leu Gly Met Ser Leu Ala Ser Leu
                85                  90                  95

His Phe Leu Trp Gln Thr Leu Asp Tyr Leu Ser Pro Ile Pro Phe Trp
                100                 105                 110

Pro Thr Phe Pro Ser Thr Ser Ser Pro Ala Gln His Phe Gly Pro Arg
            115                 120                 125

Leu Pro Ser Pro Asp Pro Thr Leu Phe Cys Ser Leu Leu Thr Ser Trp
        130                 135                 140

Pro Pro Arg Phe Ser His Leu Thr Gln Leu His Pro Arg His Gln Arg
```

```
           145                 150                 155                 160
Ile Leu Gln Gln Gln His Ser Gln Thr Pro Ser Pro Ala Lys
                165                 170                 175
Lys Pro Trp Ser Gln Pro Asp Pro Tyr Ala Asn Leu Met Thr Arg
                180                 185                 190
Lys Glu Lys Asp Trp Val Ile Lys Val Gln Met Val Gln Leu Gln Ser
                195                 200                 205
Ala Lys Pro Arg Leu Asp Asp Tyr Tyr Gln Glu Tyr Tyr Gln Lys
210                 215                 220
Leu Glu Lys Lys Gln Ala Asp Glu Glu Leu Leu Gly Arg Arg Asn Arg
225                 230                 235                 240
Val Glu Ser Leu Lys Leu Val Thr Pro Tyr Ile Pro Lys Ala Glu Ala
                245                 250                 255
Tyr Glu Ser Val Val Arg Ile Glu Gly Ser Leu Gly Gln Val Ala Val
                260                 265                 270
Ser Thr Cys Phe Ser Pro Arg Arg Ala Ile Asp Ala Val Pro His Gly
                275                 280                 285
Thr Gln Glu Gln Asp Ile Glu Ala Ala Ser Ser Gln Arg Leu Arg Val
                290                 295                 300
Leu Tyr Arg Ile Glu Lys Met Phe Leu Gln Leu Leu Glu Ile Glu Glu
305                 310                 315                 320
Gly Trp Lys Tyr Arg Pro Pro Pro Cys Phe Ser Glu Gln Gln Ser
                325                 330                 335
Asn Gln Val Glu Lys Leu Phe Gln Thr Leu Lys Thr Gln Glu Gln Asn
                340                 345                 350
Asn Leu Glu Glu Ala Ala Asp Gly Phe Leu Gln Val Leu Ser Val Arg
                355                 360                 365
Lys Gly Lys Ala Leu Val Ala Arg Leu Leu Pro Phe Leu Pro Gln Asp
                370                 375                 380
Gln Ala Val Thr Ile Leu Leu Ala Ile Thr His His Leu Pro Leu Leu
385                 390                 395                 400
Val Arg Arg Asp Val Ala Asp Gln Ala Leu Gln Met Leu Phe Lys Pro
                405                 410                 415
Leu Gly Lys Cys Ile Ser His Leu Thr Leu His Glu Leu Leu Gln Gly
                420                 425                 430
Leu Gln Gly Leu Thr Leu Leu Pro Pro Gly Ser Ser Glu Arg Pro Val
                435                 440                 445
Thr Val Val Leu Gln Asn Gln Phe Gly Ile Ser Leu Leu Tyr Ala Leu
                450                 455                 460
Leu Ser His Gly Glu Gln Leu Val Ser Leu His Ser Ser Leu Glu Glu
465                 470                 475                 480
Pro Asn Ser Asp His Thr Ala Trp Thr Asp Met Val Val Leu Ile Ala
                485                 490                 495
Trp Glu Ile Ala Gln Met Pro Thr Ala Ser Leu Ala Glu Pro Leu Ala
                500                 505                 510
Phe Pro Ser Asn Leu Leu Pro Leu Phe Cys His His Val Asp Lys Gln
                515                 520                 525
Leu Val Gln Gln Leu Glu Ala Arg Met Glu Phe Ala Trp Ile Tyr
                530                 535                 540

<210> SEQ ID NO 48
<211> LENGTH: 3997
<212> TYPE: DNA
<213> ORGANISM: Artificial Sequence
```

<220> FEATURE:
<223> OTHER INFORMATION: Synthetic oligonucleotide

<400> SEQUENCE: 48

```
attcgaggcc cggcgccgcg gccccaagaa ggtgtccagg ttggggcggc aggggaggcc      60
ctccggaggc ccaagtggac gtcttatttg gcctgagaga ggagatagaa cccctggcag     120
ggctgtggct ttggggaaag gtgcttttct cggggtggaa aggggatggg actcgccttc     180
gggggccttg cttctggtta ggcccgagtc gcgaggcctc agcgcggagc acgcacccag     240
ggatgcgagg gaggcaggcc cagcccgtcc tgggttcgct ccccattgaa cctttcggac     300
agccaagtat ctgctacctg atcccagggg gaaacccaca ctgggagagg gccctctggg     360
ggagctacct gaatctatag aagtggtgct ggaggttgag ggaagcgtgg acaaagagga     420
agattccaga tgtcccttaa gggaggccgt ccagcgcttc tgagtaatta accagaacag     480
gatcgacacg tgttctctac agcccgtcc atg gat cct ttc cga cca tcg ttc       533
                                  Met Asp Pro Phe Arg Pro Ser Phe
                                   1               5 agg ggc cag tct cct atc cac cca tcc cag tgc cag gct gta cgg atg       581
Arg Gly Gln Ser Pro Ile His Pro Ser Gln Cys Gln Ala Val Arg Met
 10                  15                  20 cca ggc tgt tgg cca caa gct tct aaa cct ttg gac cca gct ctg ggc       629
Pro Gly Cys Trp Pro Gln Ala Ser Lys Pro Leu Asp Pro Ala Leu Gly
 25                  30                  35                  40 agg gga gca cct gca ggc aga ggc cat gta ttt gga aag cca gag gaa       677
Arg Gly Ala Pro Ala Gly Arg Gly His Val Phe Gly Lys Pro Glu Glu
                 45                  50                  55 cca agc aca cag agg ggg cca gca caa agg gag tct gtg ggt ttg gtc       725
Pro Ser Thr Gln Arg Gly Pro Ala Gln Arg Glu Ser Val Gly Leu Val
 60                  65                  70 tcc atg ttc cga ggc ctg ggc att gaa aca gtt tct aag acc cct ctg       773
Ser Met Phe Arg Gly Leu Gly Ile Glu Thr Val Ser Lys Thr Pro Leu
             75                  80                  85 aaa cgg gaa atg ctt cca tca ggt aga ggc att tta ggt cga ggc ttg       821
Lys Arg Glu Met Leu Pro Ser Gly Arg Gly Ile Leu Gly Arg Gly Leu
 90                  95                 100 tct gct aat ctg gta cgc aag gac agg gag gaa ctc tct ccc act ttt       869
Ser Ala Asn Leu Val Arg Lys Asp Arg Glu Glu Leu Ser Pro Thr Phe
105                 110                 115                 120 tgg gat cca aaa gtg ttg gcg gct ggg gac agc aag atg gca gag acc       917
Trp Asp Pro Lys Val Leu Ala Ala Gly Asp Ser Lys Met Ala Glu Thr
                125                 130                 135 tcc gtt ggt tgg agt agg acg ctt gga aga ggg agt tca gat gcg tct       965
Ser Val Gly Trp Ser Arg Thr Leu Gly Arg Gly Ser Ser Asp Ala Ser
            140                 145                 150 tta tta cca ctg gga aga gca gca ggt ggt atc agc aga gaa gtg gac      1013
Leu Leu Pro Leu Gly Arg Ala Ala Gly Gly Ile Ser Arg Glu Val Asp
        155                 160                 165 aag cct ccc tgt acc ttc agc aca ccg tcc cgg ggt ccc ccg cag ctg      1061
Lys Pro Pro Cys Thr Phe Ser Thr Pro Ser Arg Gly Pro Pro Gln Leu
    170                 175                 180 tca tca cca cca gct ctg ccc cag tct ccc ctg cac tct cca gat cgc      1109
Ser Ser Pro Pro Ala Leu Pro Gln Ser Pro Leu His Ser Pro Asp Arg
185                 190                 195                 200 cct ctg gtc ctg act gtg gaa cac aag gaa aaa gag ctt att gtg aag      1157
Pro Leu Val Leu Thr Val Glu His Lys Glu Lys Glu Leu Ile Val Lys
                205                 210                 215 caa gga tca aaa gga aca cct cag tct ttg gga ctg aac ctc gtc aaa      1205
Gln Gly Ser Lys Gly Thr Pro Gln Ser Leu Gly Leu Asn Leu Val Lys
```

-continued

```
                    220                 225                 230
ata cag tgt cat aat gaa gca gtt tat caa tat cat gtg act ttc agc    1253
Ile Gln Cys His Asn Glu Ala Val Tyr Gln Tyr His Val Thr Phe Ser
        235                 240                 245 ccc aat gtg gag tgc aaa agc atg agg ttc ggc atg ttg aag gac cat    1301
Pro Asn Val Glu Cys Lys Ser Met Arg Phe Gly Met Leu Lys Asp His
250                 255                 260 caa gct gtc acc ggc aac gtc act gcg ttt gat gga tct att ctc tat    1349
Gln Ala Val Thr Gly Asn Val Thr Ala Phe Asp Gly Ser Ile Leu Tyr
265                 270                 275                 280 ctg cct gtt aag ctt caa caa gtt ctt gag tta aaa agt caa agg aaa    1397
Leu Pro Val Lys Leu Gln Gln Val Leu Glu Leu Lys Ser Gln Arg Lys
                285                 290                 295 aca gac agt gct gaa atc agc att aag att cag atg aca aag atc ctg    1445
Thr Asp Ser Ala Glu Ile Ser Ile Lys Ile Gln Met Thr Lys Ile Leu
            300                 305                 310 gag ccc tgc tct gac ctg tgc att ccc ttc tac aat gtt gtt ttc cgt    1493
Glu Pro Cys Ser Asp Leu Cys Ile Pro Phe Tyr Asn Val Val Phe Arg
        315                 320                 325 cgg gta atg aaa ctt tta gat atg aag ctt gtg gga aga aac ttt tat    1541
Arg Val Met Lys Leu Leu Asp Met Lys Leu Val Gly Arg Asn Phe Tyr
330                 335                 340 gac cct aca agt gct atg gta cta cag caa cac aga ttg cag atc tgg    1589
Asp Pro Thr Ser Ala Met Val Leu Gln Gln His Arg Leu Gln Ile Trp
345                 350                 355                 360 cca ggc tat gca gct agc atc cga agg aca gat gga ggg ctc ttc ctg    1637
Pro Gly Tyr Ala Ala Ser Ile Arg Arg Thr Asp Gly Gly Leu Phe Leu
                365                 370                 375 cta gct gat gtc tcc cat aag gtc att cgg aat gac tgt gtg ctg gat    1685
Leu Ala Asp Val Ser His Lys Val Ile Arg Asn Asp Cys Val Leu Asp
            380                 385                 390 gtc atg cat gcc att tat cag cag aat aaa gaa cac ttc cag gat gag    1733
Val Met His Ala Ile Tyr Gln Gln Asn Lys Glu His Phe Gln Asp Glu
        395                 400                 405 tgt act aag ctt ctg gtt ggc aat att gtt atc acc cga tat aac aat    1781
Cys Thr Lys Leu Leu Val Gly Asn Ile Val Ile Thr Arg Tyr Asn Asn
410                 415                 420 cgt acc tat cgt att gat gat gtg gat tgg aat aag act cca aag gat    1829
Arg Thr Tyr Arg Ile Asp Asp Val Asp Trp Asn Lys Thr Pro Lys Asp
425                 430                 435                 440 agc ttc acg atg tct gat ggg aaa gag atc aca ttc ttg gaa tac tac    1877
Ser Phe Thr Met Ser Asp Gly Lys Glu Ile Thr Phe Leu Glu Tyr Tyr
                445                 450                 455 agc aaa aat tat ggg atc aca gtt aag gaa gag gac cag cca ttg ctg    1925
Ser Lys Asn Tyr Gly Ile Thr Val Lys Glu Glu Asp Gln Pro Leu Leu
            460                 465                 470 att cac agg ccc agt gag aga cag gat aat cat ggg atg ctg cta aaa    1973
Ile His Arg Pro Ser Glu Arg Gln Asp Asn His Gly Met Leu Leu Lys
        475                 480                 485 ggg gaa atc ctg ctg cct gag ctt tct ttt atg acc gga atc cca        2021
Gly Glu Ile Leu Leu Leu Pro Glu Leu Ser Phe Met Thr Gly Ile Pro
490                 495                 500 gag aag atg aag aag gac ttc aga gcc atg aag gat ttg gct cag caa    2069
Glu Lys Met Lys Lys Asp Phe Arg Ala Met Lys Asp Leu Ala Gln Gln
505                 510                 515                 520 atc aat ctg agc ccc aag caa cac cat agt gct ttg gaa tgc ttg ctg    2117
Ile Asn Leu Ser Pro Lys Gln His His Ser Ala Leu Glu Cys Leu Leu
                525                 530                 535 caa aga att gca aag aac gag gca gcc acc aat gaa ctg atg cgt tgg    2165
Gln Arg Ile Ala Lys Asn Glu Ala Ala Thr Asn Glu Leu Met Arg Trp
```

```
                Gln Arg Ile Ala Lys Asn Glu Ala Ala Thr Asn Glu Leu Met Arg Trp
                            540                 545                 550 ggg ctc cgt ctg caa aag gat gta cat aag att gaa gga cgt gtt ctg          2213
Gly Leu Arg Leu Gln Lys Asp Val His Lys Ile Glu Gly Arg Val Leu
            555                 560                 565 cca atg gaa aga att aac tta aaa aat act tcg ttt atc aca tct cag          2261
Pro Met Glu Arg Ile Asn Leu Lys Asn Thr Ser Phe Ile Thr Ser Gln
570                 575                 580 gaa cta aac tgg gtt aag gaa gta acc aga gac cct tcc atc ttg act          2309
Glu Leu Asn Trp Val Lys Glu Val Thr Arg Asp Pro Ser Ile Leu Thr
585                 590                 595                 600 atc ccc atg cat ttc tgg gca ctt ttt tac cca aag aga gca atg gac          2357
Ile Pro Met His Phe Trp Ala Leu Phe Tyr Pro Lys Arg Ala Met Asp
                605                 610                 615 cag gct cga gaa ctg gtc aac atg ttg gag aag ata gcc ggc ccc att          2405
Gln Ala Arg Glu Leu Val Asn Met Leu Glu Lys Ile Ala Gly Pro Ile
            620                 625                 630 ggc atg cgt atg agc cca ccg gcc tgg gtt gaa cta aag gat gac cga          2453
Gly Met Arg Met Ser Pro Pro Ala Trp Val Glu Leu Lys Asp Asp Arg
            635                 640                 645 ata gag act tat gtc aga acc att caa tcc acg tta gga gct gag ggg          2501
Ile Glu Thr Tyr Val Arg Thr Ile Gln Ser Thr Leu Gly Ala Glu Gly
650                 655                 660 aag ata cag atg gtt gtt tgc atc atc atg ggc cca cgt gat gat ctc          2549
Lys Ile Gln Met Val Val Cys Ile Ile Met Gly Pro Arg Asp Asp Leu
665                 670                 675                 680 tat ggg gcc atc aag aag ctg tgc tgt gtg cag tcc cca gtg ccc tcc          2597
Tyr Gly Ala Ile Lys Lys Leu Cys Cys Val Gln Ser Pro Val Pro Ser
                685                 690                 695 cag gtt gtc aat gtt cga acc att ggt cag ccc acc agg ctt cgg agt          2645
Gln Val Val Asn Val Arg Thr Ile Gly Gln Pro Thr Arg Leu Arg Ser
            700                 705                 710 gtg gcc cag aag att tta ctt cag att aac tgt aaa ttg ggt ggt gag          2693
Val Ala Gln Lys Ile Leu Leu Gln Ile Asn Cys Lys Leu Gly Gly Glu
            715                 720                 725 ctc tgg gga gtg gat att cct ctg aaa cag tta atg gtg atc ggg atg          2741
Leu Trp Gly Val Asp Ile Pro Leu Lys Gln Leu Met Val Ile Gly Met
730                 735                 740 gat gtt tac cat gac ccc agt aga ggc atg cgc tcc gtg gtt ggc ttc          2789
Asp Val Tyr His Asp Pro Ser Arg Gly Met Arg Ser Val Val Gly Phe
745                 750                 755                 760 gtg gca agc atc aat ctc acc ctc aca aaa tgg tat tcc cgg gtg gtg          2837
Val Ala Ser Ile Asn Leu Thr Leu Thr Lys Trp Tyr Ser Arg Val Val
                765                 770                 775 ttc cag atg ccg cat cag gag att gtg gac agc ctg aag cta tgc ctc          2885
Phe Gln Met Pro His Gln Glu Ile Val Asp Ser Leu Lys Leu Cys Leu
            780                 785                 790 gtg ggc tcc tta aaa aag ttt tat gag gtg aac cac tgt cta cca gag          2933
Val Gly Ser Leu Lys Lys Phe Tyr Glu Val Asn His Cys Leu Pro Glu
            795                 800                 805 aag att gtg gtg tac cgt gat gga gtg tct gat ggc caa ctg aag aca          2981
Lys Ile Val Val Tyr Arg Asp Gly Val Ser Asp Gly Gln Leu Lys Thr
810                 815                 820 gtt gcc aac tat gag att cct caa cta cag aag tgt ttt gaa gct ttt          3029
Val Ala Asn Tyr Glu Ile Pro Gln Leu Gln Lys Cys Phe Glu Ala Phe
825                 830                 835                 840 gag aat tat cag ccc aag atg gtg gtg ttt gta gtt cag aag aaa atc          3077
Glu Asn Tyr Gln Pro Lys Met Val Val Phe Val Val Gln Lys Lys Ile
                845                 850                 855
```

| | | | | | | | | | | | | | | | | |
|---|---|---|---|---|---|---|---|---|---|---|---|---|---|---|---|---|
| agt | act | aat | cta | tat | ctg | gct | gct | cct | cag | aac | ttt | gta | act | ccc | act | 3125 |
| Ser | Thr | Asn | Leu | Tyr | Leu | Ala | Ala | Pro | Gln | Asn | Phe | Val | Thr | Pro | Thr | |
| | | 860 | | | | | 865 | | | | | 870 | | | | |
| cct | gga | act | gtg | gta | gat | cat | aca | ata | aca | agc | tgt | gag | tgg | gtg | gat | 3173 |
| Pro | Gly | Thr | Val | Val | Asp | His | Thr | Ile | Thr | Ser | Cys | Glu | Trp | Val | Asp | |
| | | 875 | | | | | 880 | | | | | 885 | | | | |
| ttc | tat | ctt | ctt | gcc | cat | cat | gta | cgg | cag | ggc | tgt | ggc | att | cct | acg | 3221 |
| Phe | Tyr | Leu | Leu | Ala | His | His | Val | Arg | Gln | Gly | Cys | Gly | Ile | Pro | Thr | |
| | | 890 | | | | | 895 | | | | | 900 | | | | |
| cat | tat | gtc | tgt | gtt | ctc | aac | acc | gca | aac | ctg | agc | cct | gat | cat | atg | 3269 |
| His | Tyr | Val | Cys | Val | Leu | Asn | Thr | Ala | Asn | Leu | Ser | Pro | Asp | His | Met | |
| 905 | | | | | 910 | | | | | 915 | | | | | 920 | |
| cag | agg | ctg | act | ttc | aaa | ctg | tgc | cac | atg | tac | tgg | aat | tgg | cct | ggc | 3317 |
| Gln | Arg | Leu | Thr | Phe | Lys | Leu | Cys | His | Met | Tyr | Trp | Asn | Trp | Pro | Gly | |
| | | | | 925 | | | | | 930 | | | | | 935 | | |
| acc | atc | aga | gtt | cca | gct | cct | tgc | aag | tat | gcc | cac | aag | cta | gct | ttc | 3365 |
| Thr | Ile | Arg | Val | Pro | Ala | Pro | Cys | Lys | Tyr | Ala | His | Lys | Leu | Ala | Phe | |
| | | | 940 | | | | | 945 | | | | | 950 | | | |
| ctg | tca | gga | cac | atc | ttg | cat | cat | gaa | cca | gcc | atc | cag | ctg | tgc | gag | 3413 |
| Leu | Ser | Gly | His | Ile | Leu | His | His | Glu | Pro | Ala | Ile | Gln | Leu | Cys | Glu | |
| | | 955 | | | | | 960 | | | | | 965 | | | | |
| aac | ctg | ttc | ttc | ctg | tga | ctgcacagct | | tggagatggg | | ctggtgagaa | | | | | | 3461 |
| Asn | Leu | Phe | Phe | Leu | | | | | | | | | | | | |
| 970 | | | | | | | | | | | | | | | | |

```
gaaaggcggc ctcagaactc agctgtgact cttgcagaat caacagagac tgaagtgggc    3521
ttttgtgtta taattttccc tttctccaac cctgtagaat aagatttctt tcttgtcttt    3581
taaacctaat atcaccaaga agcaagtttc tgagtaacag ctgaaaatgg ccttgttgcc    3641
tgtgtagagc aagttacggt ggtactgcca ctctgcaggt ggagcgggtg actctggggg    3701
accattaaga cctccagacc gggtgcggtg gttcacacct gtaatccaag cactttggga    3761
ggccgaggcg ggtggatcat gaggtcagga gatcaagacc atcctggcca acatggtgaa    3821
accccgtctc tactaaaata caaaaaaatt agccgggtgt ggcggtgcac gcctgtagtc    3881
ccagctactc aggaggctaa ggcaggagaa tcgcttgaac ccgggaggtg gaggttgcag    3941
tgagccgaga tcacgccact gcactccagc ctgttgacaa agcaagactc tgtctc       3997
```

<210> SEQ ID NO 49
<211> LENGTH: 973
<212> TYPE: PRT
<213> ORGANISM: Homo sapiens

<400> SEQUENCE: 49

```
Met Asp Pro Phe Arg Pro Ser Phe Arg Gly Gln Ser Pro Ile His Pro
 1               5                  10                  15

Ser Gln Cys Gln Ala Val Arg Met Pro Gly Cys Trp Pro Gln Ala Ser
             20                  25                  30

Lys Pro Leu Asp Pro Ala Leu Gly Arg Gly Ala Pro Ala Gly Arg Gly
         35                  40                  45

His Val Phe Gly Lys Pro Glu Glu Pro Ser Thr Gln Arg Gly Pro Ala
     50                  55                  60

Gln Arg Glu Ser Val Gly Leu Val Ser Met Phe Arg Gly Leu Gly Ile
 65                  70                  75                  80

Glu Thr Val Ser Lys Thr Pro Leu Lys Arg Glu Met Leu Pro Ser Gly
                 85                  90                  95

Arg Gly Ile Leu Gly Arg Gly Leu Ser Ala Asn Leu Val Arg Lys Asp
            100                 105                 110
```

```
Arg Glu Glu Leu Ser Pro Thr Phe Trp Asp Pro Lys Val Leu Ala Ala
            115                 120                 125

Gly Asp Ser Lys Met Ala Glu Thr Ser Val Gly Trp Ser Arg Thr Leu
        130                 135                 140

Gly Arg Gly Ser Ser Asp Ala Ser Leu Leu Pro Leu Gly Arg Ala Ala
145                 150                 155                 160

Gly Gly Ile Ser Arg Glu Val Asp Lys Pro Pro Cys Thr Phe Ser Thr
                165                 170                 175

Pro Ser Arg Gly Pro Pro Gln Leu Ser Ser Pro Ala Leu Pro Gln
            180                 185                 190

Ser Pro Leu His Ser Pro Asp Arg Pro Leu Val Leu Thr Val Glu His
        195                 200                 205

Lys Glu Lys Glu Leu Ile Val Lys Gln Gly Ser Lys Gly Thr Pro Gln
    210                 215                 220

Ser Leu Gly Leu Asn Leu Val Lys Ile Gln Cys His Asn Glu Ala Val
225                 230                 235                 240

Tyr Gln Tyr His Val Thr Phe Ser Pro Asn Val Glu Cys Lys Ser Met
                245                 250                 255

Arg Phe Gly Met Leu Lys Asp His Gln Ala Val Thr Gly Asn Val Thr
            260                 265                 270

Ala Phe Asp Gly Ser Ile Leu Tyr Leu Pro Val Lys Leu Gln Gln Val
        275                 280                 285

Leu Glu Leu Lys Ser Gln Arg Lys Thr Asp Ser Ala Glu Ile Ser Ile
    290                 295                 300

Lys Ile Gln Met Thr Lys Ile Leu Glu Pro Cys Ser Asp Leu Cys Ile
305                 310                 315                 320

Pro Phe Tyr Asn Val Val Phe Arg Arg Val Met Lys Leu Leu Asp Met
                325                 330                 335

Lys Leu Val Gly Arg Asn Phe Tyr Asp Pro Thr Ser Ala Met Val Leu
            340                 345                 350

Gln Gln His Arg Leu Gln Ile Trp Pro Gly Tyr Ala Ala Ser Ile Arg
        355                 360                 365

Arg Thr Asp Gly Gly Leu Phe Leu Leu Ala Asp Val Ser His Lys Val
    370                 375                 380

Ile Arg Asn Asp Cys Val Leu Asp Val Met His Ala Ile Tyr Gln Gln
385                 390                 395                 400

Asn Lys Glu His Phe Gln Asp Glu Cys Thr Lys Leu Leu Val Gly Asn
                405                 410                 415

Ile Val Ile Thr Arg Tyr Asn Asn Arg Thr Tyr Arg Ile Asp Asp Val
            420                 425                 430

Asp Trp Asn Lys Thr Pro Lys Asp Ser Phe Thr Met Ser Asp Gly Lys
        435                 440                 445

Glu Ile Thr Phe Leu Glu Tyr Tyr Ser Lys Asn Tyr Gly Ile Thr Val
    450                 455                 460

Lys Glu Glu Asp Gln Pro Leu Leu Ile His Arg Pro Ser Glu Arg Gln
465                 470                 475                 480

Asp Asn His Gly Met Leu Leu Lys Gly Glu Ile Leu Leu Pro Glu
                485                 490                 495

Leu Ser Phe Met Thr Gly Ile Pro Glu Lys Met Lys Lys Asp Phe Arg
            500                 505                 510

Ala Met Lys Asp Leu Ala Gln Gln Ile Asn Leu Ser Pro Lys Gln His
        515                 520                 525

His Ser Ala Leu Glu Cys Leu Leu Gln Arg Ile Ala Lys Asn Glu Ala
```

```
                530             535             540
Ala Thr Asn Glu Leu Met Arg Trp Gly Leu Arg Leu Gln Lys Asp Val
545             550             555             560

His Lys Ile Glu Gly Arg Val Leu Pro Met Glu Arg Ile Asn Leu Lys
                565             570             575

Asn Thr Ser Phe Ile Thr Ser Gln Glu Leu Asn Trp Val Lys Glu Val
            580             585             590

Thr Arg Asp Pro Ser Ile Leu Thr Ile Pro Met His Phe Trp Ala Leu
        595             600             605

Phe Tyr Pro Lys Arg Ala Met Asp Gln Ala Arg Glu Leu Val Asn Met
    610             615             620

Leu Glu Lys Ile Ala Gly Pro Ile Gly Met Arg Met Ser Pro Pro Ala
625             630             635             640

Trp Val Glu Leu Lys Asp Asp Arg Ile Glu Thr Tyr Val Arg Thr Ile
                645             650             655

Gln Ser Thr Leu Gly Ala Glu Gly Lys Ile Gln Met Val Val Cys Ile
            660             665             670

Ile Met Gly Pro Arg Asp Asp Leu Tyr Gly Ala Ile Lys Lys Leu Cys
        675             680             685

Cys Val Gln Ser Pro Val Pro Ser Gln Val Val Asn Val Arg Thr Ile
    690             695             700

Gly Gln Pro Thr Arg Leu Arg Ser Val Ala Gln Lys Ile Leu Leu Gln
705             710             715             720

Ile Asn Cys Lys Leu Gly Gly Glu Leu Trp Gly Val Asp Ile Pro Leu
                725             730             735

Lys Gln Leu Met Val Ile Gly Met Asp Val Tyr His Asp Pro Ser Arg
            740             745             750

Gly Met Arg Ser Val Val Gly Phe Val Ala Ser Ile Asn Leu Thr Leu
        755             760             765

Thr Lys Trp Tyr Ser Arg Val Val Phe Gln Met Pro His Gln Glu Ile
    770             775             780

Val Asp Ser Leu Lys Leu Cys Leu Val Gly Ser Leu Lys Lys Phe Tyr
785             790             795             800

Glu Val Asn His Cys Leu Pro Glu Lys Ile Val Val Tyr Arg Asp Gly
                805             810             815

Val Ser Asp Gly Gln Leu Lys Thr Val Ala Asn Tyr Glu Ile Pro Gln
            820             825             830

Leu Gln Lys Cys Phe Glu Ala Phe Glu Asn Tyr Gln Pro Lys Met Val
        835             840             845

Val Phe Val Val Gln Lys Lys Ile Ser Thr Asn Leu Tyr Leu Ala Ala
850             855             860

Pro Gln Asn Phe Val Thr Pro Thr Pro Gly Thr Val Val Asp His Thr
865             870             875             880

Ile Thr Ser Cys Glu Trp Val Asp Phe Tyr Leu Leu Ala His His Val
                885             890             895

Arg Gln Gly Cys Gly Ile Pro Thr His Tyr Val Cys Val Leu Asn Thr
            900             905             910

Ala Asn Leu Ser Pro Asp His Met Gln Arg Leu Thr Phe Lys Leu Cys
        915             920             925

His Met Tyr Trp Asn Trp Pro Gly Thr Ile Arg Val Pro Ala Pro Cys
    930             935             940

Lys Tyr Ala His Lys Leu Ala Phe Leu Ser Gly His Ile Leu His His
945             950             955             960
```

Glu Pro Ala Ile Gln Leu Cys Glu Asn Leu Phe Phe Leu
                965                 970

<210> SEQ ID NO 50
<211> LENGTH: 2160
<212> TYPE: DNA
<213> ORGANISM: Homo sapiens

<400> SEQUENCE: 50

| | | | | | |
|---|---|---|---|---|---|
| acccacagca | ctcattcctg | aagctactgg | ttggttccct | gagaggtccc | agaactctgc | 60 |
| gaagtgagtc | cagcgctgag | attttccttg | cagatctatc | aggatgagca | tccaggcccc | 120 |
| acccagacta | ctggagctgg | cagggcagag | cctgctgaga | gaccaggcct | tgtccatctc | 180 |
| tgccatggag | gagctgccca | gggtgctcta | tctcccactc | ttcatggagg | ccttcagcag | 240 |
| gagacacttc | cagactctga | cggtgatggt | tcaggcctgg | cccttcacct | gcctccctct | 300 |
| gggatcactg | atgaagacgc | ttcatttgga | gaccttaaaa | gcattgctgg | aagggcttca | 360 |
| tatgctgctt | acacagaagg | atcgccccag | gaggtggaaa | cttcaagtgc | tggatttgcg | 420 |
| ggatgttgac | gagaatttct | gggccagatg | gcctggagcc | tgggccctgt | cctgcttccc | 480 |
| agagaccacg | agtaagaggc | agacagcaga | ggactgtcca | aggatgggag | agcaccagcc | 540 |
| cttaaaggtg | ttcatagaca | tctgcctcaa | ggaaataccc | caggatgaat | gcctgagata | 600 |
| cctcttccag | tgggtttacc | aaaggagagg | tttagtacac | ctgtgctgta | gtaagctggt | 660 |
| caattatcta | acgccgatta | aatatctcag | aaagtcattg | aaaataatat | acctgaatag | 720 |
| tattcaagag | ctggaaattc | gcaacatgtc | ctggccacgt | ctgataagaa | agcttcgttg | 780 |
| ttacctgaag | gagatgaaga | atcttcgcaa | actcgttttc | tccaggtgcc | atcattacac | 840 |
| gtcagataat | gaactccaag | gacggttagt | tgccaaattc | agctctgtgt | tcctcaggct | 900 |
| ggaacacctt | cagttgctta | aaataaaatt | gatcaccttc | ttcagtgggc | acctggaaca | 960 |
| gctgatcagg | tgcctccaga | acccttgga | gaacttggaa | ttaacttatg | ctacctatt | 1020 |
| ggaagaagac | atgaagtgtc | tctcccagta | cccaagcctc | ggttacctaa | agcatctgaa | 1080 |
| tctcagctac | gtgctgctgt | tccgcatcag | tcttgaaccc | ctcggagctc | tgctggagaa | 1140 |
| aattgctgcc | tctctcaaaa | ccctcatctt | ggagggctgt | cagatccact | actcccaact | 1200 |
| cagtgccatc | ctgcctgccc | tgagccggtg | ctcccagctc | accaccttct | actttggcag | 1260 |
| aaattgcatg | tctattgacg | ccctgaagga | cctgctgcgc | cacaccagtg | ggctgagcaa | 1320 |
| gttaagcctg | gagacgtatc | ctgcccctga | ggagagtttg | aattccttgg | ttcgtgtcaa | 1380 |
| ttgggagatc | ttcaccccac | ttcgggctga | gctgatgtgt | acactgaggg | aagtcaggca | 1440 |
| gcccaagagg | atcttcattg | cccccacccc | ctgcccttcc | tgtggctcat | caccgtctga | 1500 |
| ggaactggag | ctccatcttt | gctgctaggg | aaggcgtgcc | cagtggggta | gagaaatcca | 1560 |
| aagttctctt | ccaggcactt | ggacactaaa | atctactatg | tgggtgcaaa | ctatttttct | 1620 |
| cttttcttat | ttatttcatt | ttttaataat | tccaaaattt | ttattaaaga | caatttgaga | 1680 |
| cagggtttcg | ctgtgttgct | ccagctggtc | tcaaactgct | gggcttatgg | gatcctcctg | 1740 |
| cctcagcttc | ctaaagtgct | gggattactg | gcatgagtga | ctgtgtccag | gccacatgca | 1800 |
| acttaaagga | agcacaggca | agtgttcagt | gtgagggaaa | aaacataaca | gcaggggca | 1860 |
| aggttggagg | aaaatgttga | ggtgacatca | gtgagaactt | cagggacccg | tgtcctagag | 1920 |
| tcggaaagag | aagctaaagt | tctacagtga | tgagactgtt | atccctgcaa | ggatggttac | 1980 |
| caaggaatat | cagcaataaa | gagcacctga | atgaaaactt | ttaacctgtt | gtgcaattta | 2040 |

```
tccatcagaa atctctagtt atcgagttac ggatggaaaa ataacgaaat actaatttgt      2100
ctgtgattga gtttcagttg tagaacatca aagcaaccaa ataaaaatta gatcattttg      2160

<210> SEQ ID NO 51
<211> LENGTH: 1786
<212> TYPE: DNA
<213> ORGANISM: Homo sapiens

<400> SEQUENCE: 51 gatgttttttt tctctagatt catcaggatg agcctccagg ccccacctag actcctggag      60
ctggctgagc agagtctgct gagagaccgg gccttggcca tccccaccct ggaggagctg      120
cccagggagc tctttccccc actgttcatg gaggccttta ccaggagatg ctgcgagacc      180
ctgacaacta tggtgcaggc ctggcccttc acctgcctcc ctctagggtc cctgatgaag      240
tcatgtaatc tagagatctt tcgagctgtg ctggaggggc ttgatgcact gcttgcccag      300
aaggttcgcc ccaggcggtg gaaacttcaa gtgttggact tgcggaatgt ggatgagaac      360
ttctggggca tatggtctgg agcttctgca ctctccccag aggccctgag taagagacga      420
acagcaggga actgtccaag gccgggtggg cagcagccct tgatggtgat cctagacctt      480
tgcttcaaga atgggatgct ggatgaatgc ctcacccact tcttagagtg gggcaagcag      540
agaaaaggct tactgcacgt gtgttgcaag gagctgcaga tttttggaat agccatccac      600
aggatcatag aggtcctgaa cacggtggag ctagactgta tccaggaggt ggaagtgtgc      660
tgcccgtggg agctgtccat tcttataagg ttcgccccctt acctgggcca gatgaggaat      720
ctccgcaaac ttgttctctt caacatccat gtctctgcct gcattcccct agacaggaag      780
gagcagtttg tcatccagtt cacctctcag ttcctcaagc tggactactt ccagaagctt      840
tacatgcact ctgtctcttt cctcgaaggc cacctggacc agctgctcag gtgtctccag      900 gccccccttgg agacagtcgt aatgaccgaa tgcctgctgt cagagtcgga cctgaagcat      960
ctctcttggt gcccgagcat ccgtcagcta aaagagctag acctgagggg catcacactg      1020
acccatttca gtcctgagcc cctctcagtt ctgctggagc aagctgaggc caccctgcag      1080
accctggact tagaggactg tgggatcgtg gattcccaac tcagcgccat cctgcctgcc      1140
ctgagccgct gctcccagct cagcaccttc agcttctgtg gaacctcat ctccatggcc      1200 gccctggaga acctgctgcg ccacaccgtc gggctgagca agctaagcct ggagctgtat      1260
cctgcccctc tggagagtta tgatgcccag ggtgctctct gctggggaag attttctcaa      1320
cttggggctg agctgatgaa gacactgagg gacttaaggc agcccaagat tattgtgttc      1380
agcactgtcc cctgccctcg ctgtggcatc agggcctcct atgacctgga gcccagtcac      1440
tgtctgttga atgcctgctg tcagggtgga tttatttaaa gctttcttct ggtcatttgg      1500
caactgaatc ctaggccatg agtgtatgtc aaagggagca cagacccatc gtttcatatg      1560
cctgctcaat gtgaacggga aaggaaaggg gatgcaggaa gggagggact gggggaaaag      1620
ttgagttgga gtcaatagga gctttagaga cctgtgtccc agagaatcag aaatgggaat      1680
ctgaattgct agaatgagaa tcaggtagga gagacacatg agacagttac ccctgcacgg      1740
atggttgtaa agaaacagtc agaaataaag ggaagctgag tggaaa                    1786

<210> SEQ ID NO 52
<211> LENGTH: 1642
<212> TYPE: DNA
<213> ORGANISM: Homo sapiens
```

<400> SEQUENCE: 52

```
cctgaagcta ctggttggtt ccctgagagg tcccagaact ctgcaaagtg agtccagcgc      60
tgagattttt cttgcagatc catcaggatg agcatccagg ccccaccgag actactggag     120
ctggcgggc agagcctgct gagagaccag gccttgtcca tctctgccat ggaggagctg      180
cccagggtgc tctatctccc actcttcagg gaggccttca gcaggagaca cttccagact     240
ctgacggtga tggtgcaggc ctggcctttc acctgcctcc ctctggtatc gctgatgaag     300
acgcttcatc tggagccatt gaaagcattg ctggaagggc ttcatatgct gcttacacag     360
aaggatcgcc ccaggaggtg gaaacttcaa gtgctggatt tgcgggatgt tgatgagaat     420
ttctgggcca gatggcctgg agcctgggcc ctgtcctgct cccagaggc catgagtaag      480
aggcagacag cagaggactg tccaaggacg ggagagcacc agcccttaaa ggtgttcata     540
gacatctgcc tcaaggaaat accccaggat gaatgcctga gatacctctt ccagtgggtt     600
taccaaagga gaggtttagt acacctgtgc tgtagtaagc tggtcaatta tctaacgcca     660
attaaatatc tcagaaagtc attgaaaata atatacatta atagtattgg ggagctggaa     720
attcacaaca cgtgctggcc acatctgata agaaagcttt attgttacct gaaggagatg     780
aagactcttt gcaaactcgt tttctccagg tgccatcatt acacgtcaga taatgaactc     840
gagggatggt tagtcaccag attcacctct gtgttcctca ggctggaaca cctccagttg     900
cttaaaataa aattgatcac cttcttcagt gggcacctgg aacagctgat caggtgcctc     960
cagaaccct tggagaactt ggaattaact tgtggcaacc tattagaaga ggacttgaag    1020
tgtctctccc agttcccaag cctcggttac ctaaagcatc tgaatctcag ctacgtgctg    1080
ctgttccgca tcagtcttga accctagga gctctgctag agaaaattgc tgcctctctc     1140
gagaccctcg tgttagaggg ctgtcagatc cactactccc aactcagtgc catcctgcct    1200
ggcctgagct gctgctccca gctcaccacc ttctactttg gcagcaattg catgtctatt    1260
gacgccctga aggacctgct gcgccacacc agtgggctga gcaagttaag cctggagacg    1320
tatcctgccc ctgaggagag tttgaattcc ttggttcgtg tcaattggga gatcttcacc    1380
ccacttcggg ctgagctgat gtgtacactg agggaattca ggcagcccaa gaggatcttc    1440
attggcccca ccccctgccc ttcctgtggc tcatcaccgt ctgaggaact ggagctccat    1500
ctttgctgct agggaaggcg tgccagtgg ggtagagaaa tccaaagttc tcttccaggc     1560
acttggacac taaatctac tatgtaggtg caaactattt ttctcttttc ttatttattt      1620
catttttaa taattccaaa at                                              1642
```

<210> SEQ ID NO 53
<211> LENGTH: 1862
<212> TYPE: DNA
<213> ORGANISM: Homo sapiens

<400> SEQUENCE: 53

```
acccaaagtc ttcaagcctg gagttcctgc ttggttcttc ctgaggtctg agcaccttct      60
agactacatc cagatctgtt ttccctgcag attcatgaag atgagcatcc ggactccacc     120
cagactcctg gagcttgcag gcggagcct gctgagggac caagctttgg ccatgtccac      180
cctggaggag ctgcccacag aacttttccc cccactgttc atggaggcct tcagcaggag     240
acgctgtgag gccctgaagc tgatggtgca ggcctggccc ttcgccgcc tccctctgag      300
gcctctgata aagatgcctt gtctggaggc cttccaagct gtgctcgatg gcttgatgc      360
actgcttacc caaggggttc gtcccaggag gtggaaactc caagtgctgg atttacagga    420
```

```
tgtctgtgag aacttctgga tggtttggtc tgaagctatg gcccatgggt gcttcctcaa    480
tgccaagagg aacaaaaaac cagtgcagga ctgtccaagg atgagaggac ggcagccctt    540
gactgtgttc gtagaacttt ggctcaagaa caggactctg gatgaatacc tcacctacct    600
ccttctatgg gtcaagcaga ggaaagattt actacacctg tgctgtaaga agctgaaaat    660
tttgggaatg cccttccgca atatcagaag catcctgaaa atggtgaacc tagactgtat    720
ccaggaggtg gaagtgaatt gcaagtgggt actgccatc ctgacacagt ttaccccata     780
cctgggccac atgaggaatc ttcagaagct cgttctctcc cacatggatg tctctcgcta    840
cgtttcccca gagcagaaga aggagattgt tacccagttc accactcagt cctcaagct    900 gcgctgcctc caaaagcttt atatgaactc tgtttctttc ctcgaaggcc acctggacca    960
gctgctcagc tgtctgaaga cctcgttaaa agtcctcaca ataactaact gtgtgctttt   1020
ggaatcagac ttgaagcatc tatcccagtg cccgagtatc agtcaactaa agaccctgga   1080
cctgagtggc atcagactga ccaattatag tcttgtgcct ctccaaattc tcctagaaaa   1140
agttgcagcc acccttgagt acctggattt agatgactgt ggcatcatag actcccaagt   1200
caacgccatc ctgcctgccc tgagccgctg ctttgagctc aacaccttca gcttctgtgg   1260
aaatcccatc tgcatggcca ccctggagaa cctgctgagc cacacaatca tactcaaaaa   1320
cttatgtgtg gagctgtatc ctgcccccg agagagttat ggtgctgatg gtactctctg   1380
ctggagcaga tttgctcaaa ttagggctga gctgatgaac agagtgaggg acttaaggca   1440
ccccaagagg atcttgttct gtactgacta ctgccctgac tgtggcaaca ggtcatttta   1500
tgacctggag gcagatcaat actgctgttg aatgcctgcc tatttggatg ggtatgtcaa   1560
acgctttctt ctggacactt ggaaactaaa acctaggtct taggtacatc ctaaagggag   1620
cacagaaccc atcatttcac acataggctc tgaaagtggg aaaggaaagc tgatcaagca   1680
ggggccggac ttgggggaaa tgttgccatg gattcgatgg actttgggg acctgtgtcc    1740 tgtagattcg aaaatgggaa tctgaatgtc tagagtggaa ttcaggcttg agaatacatg   1800
agggagttac tcttgcatgg atggttgtaa agaaacaatc agaaataaag gaaaactgag   1860
ca                                                                  1862
```

<210> SEQ ID NO 54
<211> LENGTH: 1844
<212> TYPE: DNA
<213> ORGANISM: Homo sapiens

<400> SEQUENCE: 54

```
gaactactgc ttgattctct gagagatccc agcaccctac aaactgagtc cagatctgag     60 tttcccttg cagattcatc aagatgagca tcagggcccc acccagactc ctggagctgg    120
caaggcagag gctgctgagg accaggcct tggccatctc caccatggag gagctgccca     180
gggagctctt cccacactg ttcatggagg ccttcagcag gagacgctgt gaaaccctga     240
aaacaatggt gcaggcctgg ccctttcaccc gcctccctct agggtccctg atgaagtcgc    300
ctcatctgga gtcattaaaa tctgtgctgg aagggggttga tgtgctgttg acccaagagg    360
ttcgccccag gcagtcaaaa cttcaagtgc tggacttgag gaatgtggat gagaacttct    420
gcgacatatt ttctggagct actgcatcct tcccggaggc tctgagtcag aagcaaacag    480
cagataactg tccagggaca ggcaggcagc agccattcat ggtgttcata gaccttttgc    540
tcaagaacag gacactagat gaatgcctca cccacctctt agagtgggc aagcagagaa    600
```

```
aaggcttact gcatgtgtgt tgccaggagc tgcaggtttt tggaatgccc atccacagta      660
tcatagaggt cctgaacatg gtggagcttg actgtatcca ggaggtggaa gtgtgctgcc      720
cctgggagct gtccactctt gtgaagtttg ccccttacct gggccagatg aggaatctcc      780
gcaaacttgt tctcttcaac atccgtgcat ctgcctgcat tccccagac aacaaggggc       840 agttcattgc ccgattcacc tctcagttcc tcaagctgga ctatttccag aatctgtcta      900
tgcactccgt ctcttttcctc gaaggccacc tggaccagct gctcaggtgt ctccaggcct     960
ccttggagat ggtcgttatg accgactgcc tgctgtcaga gtcggacttg aagcatctct     1020
cttggtgccc gagcatccgt caattaaagg agctggacct gagggtgtc acactgaccc      1080 atttcagccc tgagcccctc acaggtctgc tggagcaagt tgtggccacc ctgcagaccc     1140
tggacttaga ggactgtggg atcatggatt cccaactcag cgccatcctg cctgtcctga     1200
gccgctgctc ccagctcagc accttcagct tctgtgggaa cctcatctcc atggctgccc    1260
ttgagaacct gctgcgccac accgtcgggc tgagcaagct aagcctggag ctgtatcctg    1320
cccctctgga gagttatgac acccaggtgt ctctctgctg ggggagattt gctgaacttg    1380
gggctgagct gatgaagaca ctgagggact taaggcagcc caagatcatt gtgttctgca    1440
ccgtcccctg ccctcgctgt ggcatcaggg cctcctatga cctggagccc agtcactgcc    1500
tctgttgaat gcctgccatc agggtggata tatttcaagc tttcttctgg tcatttcgga    1560
gctgaaacct aggccatgag tgcatgttaa agggagcaca gacccatcgt ttcaaatgcc    1620
tcctcagtgt gaatgggaaa ggaatgagga tgcaggaggg gcaggactgg gggaaaagtt    1680
gacttggagt ggatgggctc tttagagacc tgtgtcccag agaatcagaa atgggaatct    1740
gaattgctag agtgagaatc agggaggaga gacacatgag agggttaccc ctgcacagat    1800
ggttgtaaag taacagtcag aaataaaggg aaactgagtg gaaa                     1844
```

<210> SEQ ID NO 55
<211> LENGTH: 1518
<212> TYPE: DNA
<213> ORGANISM: Homo sapiens

<400> SEQUENCE: 55

```
ttagttcttc ctgaggtctg agcaccctcc aaactgagtc cagatctgag tttttcctcg      60
gagatttgtc agaatgagcc tccaggcccc atccagactg ctggagctgg cagggcagag     120
cctgctgagg aaccagttct tgaccatctt caccctggat gagctgccca gggaggtctt     180
ccctctgatg ttcatggagg ccttcagcat gagacgtttt gaggccctga gctgatggt      240 gcaggcctgg cccttcctca gcctccctct gggatccctg atgaagacac ttcatctgga     300
gaccttgcaa gctgtcctga ggggactgta tacactggtg gcccagaagg ttcgccccag     360
gaggtggaaa cttcaagtgc tggatttgcg ggatgttgat gagaatttct ggaccatatg     420
gtctggagcc agggtcctct cctgctcccc agaggccatg agtaagaggc agacagtgga     480
ggactgtcca aggatgggag agcaccagcc cttgaaggtg ttcatagacc tctgcctaaa     540
ggaaagtaca ctggatgaat gcctgagcta cctttttggg tggatccact acagaagagg     600
cctagtgcac ctgtgttgta gtaaggtgca gaattactca atgcccactt caagtttcag     660
aaatctattg gaaaggatat acccagacag tatccaggag ttggaagtct ggaaaaagtg     720
ctctctcaat aaaacgggaa agtttgcccc ttacctgagc cagatgagca atcttcgtga     780
actcttttta gccttcggtt atgagcgtga gttgtacgtg agcgtccagt ggccgtgcat     840
tcctgacttg gactctccat tcctctgcct gtactacccc cagatgcttt atataaaaaa     900
```

```
gatcagtaat atcaaagagc acctggagca cctgctcagg tacctcaaga accccttggg      960
ggcctttata ttcagtgatg cttacctaac tgatcgggac atggagtgtc tgtctcagta     1020
cccaagcctc agtcagctaa aggagctgcg tctgattcat atcctaatgt ggaccaccca     1080
tcttgagccc cttggagttc tgctggagaa agttgctgct actctcaaga ccctcgtctt     1140
aaaggactgt cggatccagg accccaact cagggtcctc ctgcctgccc tgagccactg      1200
ttcccagctc accaccttca actttcatgg aaatgagacc tccatgaatg ctctgaaaga     1260
cctgctgcgt cacacaggcg ggctgagcaa gttaggcctg gagttgtatc ctgcccctct     1320
ggagagtctt gactacaagg gtcatgtcaa ttgggagatc ctcacccaa ttcgggctga      1380 gctgatgcgt acactcaggg aagtcaggca gcccaagagg atcttctttg gtcccgtccc     1440
ttgccctaac tgtggctcat ggccatctga gaaagtggac ttccatcttt gctcctaggg     1500
aaggcctggt tcgtggga                                                   1518
```

<210> SEQ ID NO 56
<211> LENGTH: 1597
<212> TYPE: DNA
<213> ORGANISM: Homo sapiens

<400> SEQUENCE: 56

```
acccaaagtc ttcaagcctg gagtttctgc ttggtttttc ctgaggtctg agcaccctgc       60
aaactgagtc cagatctggt aagtccctaa tctctgaaga tgagcatccg gactccaccc      120
agactcctgg agctggcggg gcggagcctg ctgaggacg aggccttggc catctccacc       180
ctggaggagc tgcccacgga acttttccc ccattgttca tggaggcctt cagcaggaga      240
cactgtgagg ccctgaagct gatggtgcag gcctggcctt cctccgcct tcctctgggg      300 tctctgatga aaaggccttg cccagagacc ttccaagctg tgctcgatgg gcttgatgca     360
ctgcttaccc acagggttcg tctcaggagg tggaaacttc aagtgctgga tttacaggat     420
gtcagtgaga acttctggat ggtttggtct gaagccatgg cccgtaggtg cttaccaaat    480
gccatgatga cagaaaaacc agtgcaggac tgtccaagga tgagaggaca gcagcccttg    540
actgtgttca tagacctttg cctcaagaac aggactctgg atgaatactt cacctgcctc    600
tttctatggg tcaagcagag ggaaggttta gtacacctgt gctgtaagaa gctgaaaatg    660
ttgggaatgc tcttccacaa tatcagaaac atcctgaaaa cagtcaacct agactgtatc    720
caggaggtgg aagtgaattg caattggaca ctgcccgtcc tggcagagtt taccccatac    780
ctcggccaga tgaggaatct tcggaagctc gttctctctg acatagattc tcgctacatt    840
tccccagagc agaagaagga gtttgttacc cagttcacca ctcagttcct caagctgcgc    900
tgcctccaaa agctttatat gaactctgtt tctttcctcg aaggccacct ggaccagatg    960
ctcagctgtc taaagacctc gttaaacatc ctcgcaataa ctaactgtgt gcttttggaa    1020
tcagacttga agcatctgtc caagtacccg agcattggtc aactaaagac cctggacctg    1080
agtggcacca gactggccaa tttcagcctt gtgccgctcc aagttctcct agaaaaagtt    1140
gcagccaccc ttgagtacct ggacttagat gactgtggca tcgtagactc ccaagtcaac    1200
gccatcctgc ctgccctgag ccgctgcttt gagctcacca ccttcagctt ccgtggaaat    1260
cccatctcca cggccaccct ggagaacctg ctgtgccaca caatcagact caacaactta    1320
tgcctggagc tgtatcctgc cccgcgggag agttatgatg ttcgtggtat cgtctgccgg    1380
agcagatttg cccaacttgg ggctgagctg atggggagag tgagggcctt aagggagccc    1440
```

```
gagaggatct tgttctgtac cgactactgc cctcagtgtg gcaacaggtc actttacgac    1500
ctggaggtag atcggtgttg ctgttgaatg cctgcctatt tgggtggata tatcaaactc    1560 tttttctga acacttgaaa actaaaacct aggtctt                              1597

<210> SEQ ID NO 57
<211> LENGTH: 1557
<212> TYPE: DNA
<213> ORGANISM: Homo sapiens

<400> SEQUENCE: 57
tctagagttt ttcactggag atttgtcaga atgagcctcc agtccccatc cagactcctg      60
gagctggcag ccagagcct gctgaggaac cagttcttga ccatcttcat cctggacgag    120
ctgcccaggg aggtcttccc tctgatgttc atggaggcct ccagcatgag acattttgag    180
gccctgaagc tgatggtgca ggcctggccc ttcctccgcc tccctctggg atccctgatg    240
aagacacctc atctggagac cttgcaagct gtgctgaagg acttgatac actgctggcc    300 cagaagcttc gccccaggag gtggaaactt caagtgctgg atttgcggga tgttgatggg    360
aatttctgga ctatatggtc tggagccagg gccctctcct gctccccaga ggccatgagt    420
aagaggcaga cagtggagga ctatccaagg acgggagagc accagccctt gaaggtgttc    480
atagacctct gccaaaagga agtacactg gatgaatgcc tgagctacct ctgcaggtgg    540
atccactaca gaagaggtct agtgcacctg tgttgtaata aggtgcagaa ttactcaatg    600
cccacttcaa gtttcagaaa tttattgaaa agggtatacc cagacagtat ccaggagttg    660
gaaattaaga gaaagtgctc tctgaataaa acaggaaagt ttgcccctta cttgagccag    720
atgagcaatc ttcgcaaaact ctttttagcc ttcggttatg acgatgagtt atatgtaagc    780
ggccaacagc agttcgttcc tgacttggac tgtccattcc tctgcctgta ctaccctcag    840
atgctttata aagaaagat cagtaatatc aaagagcacc tggagcacct gctcaggtgc    900
ctcaagaacc ccttgggaac ctttatattc tgtcatgctt acctagctga tcaggacatg    960
gagtgtctgt ctcagtaccc aagcctcagt cagctaaagg agctgcatct gattcatatc   1020
ctaatgtgga ccaccaatct tgagcccctt ggagctctgc tagagaaagt tgctgctact   1080
ctcgagatcc tcacgttaaa ggactgtcag atccaggact cccagctcag ggtcctcctg   1140
cctgccctga gccgctgctc ccagctcacc accttctact ttcgcggaaa tgagacctcc   1200
acgaatgctc tgaaagacct gctgtgtcac acaggtgggc tgagcaagtt aggtctggag   1260
ttgtatcctg cccctctgga gtgtcttgac aacaggggtc atgtcaattg ggagatcctc   1320
gccccaattc gggctgagct gatgtgtaca ctcagggaag tcaggcagcc caagaggatc   1380
ttttttggtc ccatcccctg cccttcctgt ggctcatggc catctgagaa agtggacttc   1440
catctttgct cttagtgaag gcctgattag tgggatggat atgctttctt caggacccrt   1500
aggcactaaa atctaggaca caggtgggtt tttttgtttt tttgttttttt ttttgat      1557

<210> SEQ ID NO 58
<211> LENGTH: 2123
<212> TYPE: DNA
<213> ORGANISM: Homo sapiens

<400> SEQUENCE: 58
ctgataagtt tgtctttttct ctggattttt cttgcagatt tatcaggatg agcttccagg     60
ccccacgcag actcctggag ctggcagggc agagcctgct gagggaccag gccttggcca   120
tctccgtcct ggatgagctg cccagggagc tcttcccccg actgttcgtg gaggccttca   180
```

```
ctagcagacg ctgcgaggtt ctgaaggtga tggtgcaggc ctggcccttc ccctgcctcc        240 ctctgggtc cctgatgaag acgcctgatc tggagatctt acattatgta gtggatggga         300
ttgattgcct gcttgcccaa aaggttcgcc ccaggaggtg aaacttcaa gtgctggaaa         360 tgcgggatgt tgatgagaat ttttggacca tatggtctgg agccaggccc ctgtcctgct        420
ccccagaggc catgagtaag agacagacag tggaggactg tccaaggaca ggagagaagc        480
agcccttgaa ggtgttcatg gatgtttgcc tcaaggaaaa atccgtggat gaagatctga       540
gcttcttctc tgggtgggtg cagcacagaa gacgttcagt acacctgtgc tgtactaagg       600
tggtaaatta ttcaatgaac attctaaatt tcagaaacat attagaaaca gtatacccag       660
acagtatcca agtattggaa atttggaaca tgtgctggcc gtgtatggta gcagaggtta       720
gccgttacct gagccagatg aagaatcttc gaaaactctt catctccgat ggctgtggtt       780
acctgccaag ctttgagagc caaggacagt tagttgctga attcagctct gtgttcctca       840
ggctggagta cctccagatg ctttatatga aaggatccg cttcttcgaa ggctacctgg        900
accagctgat caggtgcctc aagagcccgt tggagacatt ggcattaact tatggctccc      960
tagatgaaga ggacttgaaa tgtctgccct ggtacccaag tctcagtcaa ctgaagcagc      1020
tgaatctgag tcatggtaca ctgcgcttca tccgtcttga gccctccga gctctgctag       1080 agaaagttgc tgccactctt cagaccctct tcttagtgga ctgtgggatt gggtactcca      1140
aactcagggt catcctgcct gccctgagcc gctgctccaa cctcaccact ttctgctttc      1200
acggcaatga cacgtccatg gatggtctga aggacctgct cgccacaca ggcaggctga       1260 gcaatttgag cctggaaaca tatcctgccc ctcgggagag tcttgacaac aggggtcgtg      1320
tcatttcgga gctcctcacc ccacttcagg ctgagctgat gcgtatactg agggaagtaa      1380
gggagcccaa caggatcttc tttggtcccg tctcctgccc ttgctgtggc atgtcaccca      1440
ctgagcaact ggagttcaat ttttgcttgc ggggaaggcc tgcctagtgg ggtgaggta       1500 taaaaagctt tttctccagg cacttggaaa ctaaaatcta ggacatagat atcttttatt      1560 tttcttttc cttattttac aattttacag cttttattta aaatttgag acagggtttc        1620 cctatgttgt ccaggctggt ctcaaactct tacgcttaag ggagcccct gcttggcctc       1680 ccaagattct gggattacag gcataagcag ctgtgccggg tctataggtg tattataaag      1740
ggagcagaga aacctctgtt tcaggcatgt gctttctgtg agtgggaaaa aaaacacaaa       1800
aaaacccagc aggggggcagc actggggaaa aggttgaatg gagtcactga gactcaggga    1860
tctgtgtcct agacagtcag aaatagaacc tgaagttcta gagtgaagga gttatctcag     1920
caaggatgga tacaaagaaa cgtcggaagt aaagggaacc taaatggaaa ctctctgctg     1980
tccttcatga ttgattagcc tgtttcagca atttatacat cagaaatctt tagttcctga     2040
tgaattaaaa aaagaggtac tagttcatct gtgatttaag ttcatccgca ggaaataaag     2100
gaatcaaaat aaacttcatt ttg                                              2123
```

<210> SEQ ID NO 59
<211> LENGTH: 2100
<212> TYPE: DNA
<213> ORGANISM: Homo sapiens

<400> SEQUENCE: 59

```
acccacagca ctcattcctg gagctactgc ttggttccct gagaggtccc agaactctgc        60
aaagtgagtc cagcgctgac attcttcctg gtaccagtag aagcagatga ttgtgtttgc       120
```

| | |
|---|---|
| catgagagtg atacattttc cctggatttg tcttctagag attttcttg cagatctatc | 180 |
| aggatgagca tccaggcccc acccagactc ctggagctgg cagggcagag cctgctgaga | 240 |
| gaccaggcct tgtccatctc tgccatggag gagctgccca gggtgctcta tctcccactc | 300 |
| ttcatggagg ccttccgcag gagacacttc cagactctga cggtgatggt gcaggcctgg | 360 |
| cccttcacct gcctccctct gggatcactg atgaagacgc ttcatttgga gaccttaaaa | 420 |
| gcattgctgg aagggcttca tatgctgctt acacagaagg atcgcccag gaggtggaaa | 480 |
| cttcaagtgc tggatttgcg ggatgttgat gagaatttct gggccagatg gcctggagcc | 540 |
| tgggccctgt cctgcttccc agagaccatg agtaagaggc agacagcaga ggactgtcca | 600 |
| aggatgggag agcaccagcc cttaaaggtg ttcatagaca tctgcctcaa ggaaataccc | 660 |
| caggatgaat gcctgagata cctctttcag tgggtttacc aaaggagagg tttagtacac | 720 |
| ctgtgctgta gtaagctggt caattatcta acgccgatta acatctcag aaagtcattg | 780 |
| aaaataatat acctgaatag tattcaacag ctggaaattc gcaacatgtc ctggccacgt | 840 |
| ctgataagaa agcttcgttg ttacctgaag gagatgaaga atcttcgcaa actcgttttc | 900 |
| tccaggtgcc tccagaaccc cttggagaac ttggaattaa cttatggcta cctattggaa | 960 |
| gaagacatga agtgtctctc ccagtaccca agcctcggtt acctaaagca tctgaatctc | 1020 |
| agctacgtgc tgctgttccg catcagtctt gaaccctcg gagctctgct agagaaaatt | 1080 |
| gctgcctctc tcgaaaccct catcttggag ggctgtcaga tccactactc ccaactcagt | 1140 |
| gccatcctgc ctggcctgag ccactgctcc cagctcacca ccttctactt tggcagaaat | 1200 |
| tgtatgtcta tgggtgccct gaaggacctg ttgtgccaca ccagtgggct gagcaagtta | 1260 |
| agcctggaga cgtatcctgc ccctgaggag agtttgaatt ccttggttcg tgtcgattgg | 1320 |
| gagatcttcg ccctacttcg ggctgagctg atgtgtacac tgagggaagt caggcagccc | 1380 |
| aagaggatct tcattggtcc caccccctgc ccttcctgtg gctcatcacc gtctgaggaa | 1440 |
| ctggagctcc atctttgctg ctagggaagg cgtgcctagc ggggtagaga atccaaagt | 1500 |
| tctcttccag gcactgggac actaaaatct actatgtagg tgcaaactat ttttctcttt | 1560 |
| tcttatttat ttcattttt aataattcca aaattttat taaagacaat ttgagacagg | 1620 |
| gtttctctgt gttgctctgg gatcctcctg cctcagctgg gcttatggga tcctcctgcc | 1680 |
| tcagcttcct aaagtgctgg gattactggc atgagtgact gtgtccaggc acatgcaac | 1740 |
| ttaaaggaag cacagggaag tgctcagtgt gagggaaaaa aacataacag caggggcaa | 1800 |
| ggctggagga aaatgttgag atgacatcaa tgagaacttc agggacccgt gtcctacaga | 1860 |
| gtcggaaaga gaagctaaag ttctacagtg atgagaatgt tatccctgca aggatggtta | 1920 |
| ccaaggaata tcagaaataa agagcacctg aatgaaaact tttaacctgt tgtagcaatt | 1980 |
| tatccaccag aaatatctag ttattgagtt actgatggaa aaataatgaa atactacttt | 2040 |
| gtctgtgatt gagtttcagc tgtagaacat caaagcaacc aaatagaatt tgatcatttt | 2100 |

<210> SEQ ID NO 60
<211> LENGTH: 1508
<212> TYPE: DNA
<213> ORGANISM: Homo sapiens

<400> SEQUENCE: 60

| | |
|---|---|
| attcaggaag atgagcatcc ggactccacc cagactcctg gagctggcgg ggcggagcct | 60 |
| gctgagggac gaggccttgg ccatctccac cctggaggag ctgcccacgg aactttttcc | 120 |
| cccattgttc atggaggcct tcagcaggag acactgtgag gccctgaagc tgatggtgca | 180 |

```
ggcctggcct tcctccgcc ttcctctggg gtctctgatg aaaaggcctt gcccagagac      240
cttccaagct gtgcttgatg ggcttgatgc actgcttacc cacagggttc gtctcaggag      300
gtggaaactt caagtgctgg atttacagga tgtcagtgag aacttctgga tggtttggtc      360
tgaagccatg gcccgtaggt gcttaccaaa tgccatgatg aacagaaaac cagtgcagga      420
ctgtccaagg atgagaggac agcagcccctt gactgtgttc atagaccttt gcctcaagaa     480
caggactctg gatgaatact tcacctgcct ctttctatgg gtcaagcaga gggaaggttt      540
agtacacctg tgctgtaaga agctgaaaat gttgggaatg ctcttccaca atatcagaaa      600
catcctgaaa acagtcaacc tagactgtat ccaggaggtg gaagtgaatt gcaattggac      660
actgcccgtc ctggcagagt ttaccccata cctcggccag atgaggaatc ttcggaagct      720
cgttctctct gacatagatt ctcgctacat ttccccagag cagaagaagg agtttgttac      780
ccagttcacc actcagttcc tcaagctgcg ctgcctccaa aagctttata tgaactctgt      840
ttctttcctc gaaggccacc tggaccagat gctcagctgt ctaaagacct cgttaaacat      900
cctcgcaata actaactgtg tgcttttgga atcagacttg aagcatctgt ccaagtaccc      960
gagcattggt caactaaaga ccctggacct gagtggcacc agactggcca atttcagcct     1020
tgtgccgctc caagttctcc tagaaaaagt tgcagccacc cttgagtacc tggacttaga     1080
tgactgtggc atcgtagact cccaagtcaa cgccatcctg cctgccctga ccgctgctt      1140 tgagctcacc accttcagct ccgtggaaa tcccatctcc acggccaccc tggagaacct     1200
gctgtgccac acaatcagac tcaacaactt atgcctggag ctgtatcctg ccccgcggga     1260
gagttatgat gttcgtggta tcgtctgccg gagcagattt gcccaacttg gggctgagct     1320
gatggggaga gtgagggcct taagggagcc cgagaggatc ttgttctgta ccgactactg     1380
ccctcagtgt ggcaacaggt cactttacga cctggaggta gatcggtgtt gctgttgaat     1440
gcctgcctat ttgggtggat atatcaaact ctttttttctg aacacttgaa aactaaaacc    1500
taggtctt                                                              1508

<210> SEQ ID NO 61
<211> LENGTH: 1587
<212> TYPE: DNA
<213> ORGANISM: Homo sapiens

<400> SEQUENCE: 61
tctagagttt ttcactggag atttgtcaga atgagcctcc agtccccatc cagactcctg       60
gagctggcag gccagagcct gctgaggaac cagttcttga ccatcttcat cctggacgag      120
ctgcccaggg aggtcttccc tctgatgttc atggaggcct ccagcatgag acattttgag      180
gccctgaagc tgatggtgca ggcctggccc ttcctccgcc tccctctggg atccctgatg      240 aagacaccatc atctggagac cttgcaagct gtgctgaagg gacttgatac actgctggcc      300
cagaagcttc gccccaggag gtggaaactt caagtgctgg atttgcggga tgttgatggg      360
aatttctgga ctatatggtc tggagccagg gccctctcct gctccccaga ggccatgaga      420
aagaggcaga cagtggagga ctatccaagg acgggagagc accagccctt gaaggtgttc      480
atagacctct gccaaaagga aagtacactg atgaatgcc tgagctacct ctgcaggtgg      540
atccactaca gaagaggtct agtgcacctg tgttgtaata aggtgcagaa ttactcaatg      600
cccacttcaa gtttcagaaa tttattgaaa agggtatacc cagacagtat ccaggagttg      660
gaaattaaga gaaagtgctc tctgaataaa acaggaaagt ttgccccctta cttgagccag      720
```

```
atgagcaatc ttcgcaaact cttttttagcc ttcggttatg acgatgagtt atatgtaagc      780
ggccaacagc agttcgttcc tgacttggac tgtccattcc tctgcctgta ctaccctcag      840
atgctttata taagaaagat cagtaatatc aaagagcacc tggagcacct gctcaggtgc      900
ctcaagaacc ccttgggaac ctttatattc tgtcatgctt acctagctga tcaggacatg      960
gagtgtctgt ctcagtaccc aagcctcagt cagctaaagg agctgcatct gattcatatc     1020
ctaatgtgga ctaccaatct tgagccccct tggagctctgc tagagaaagt tgctgctact     1080
ctcgagatcc tcacgttaaa ggactgtcag atccaggact cccagctcag ggtcctcctg     1140
cctgccctga gccgctgctc ccagctcacc accttctact ttcgcggaaa tgagacctcc     1200
acgaatgctc tgaaagacct gctgtgtcac acaggtgggc tgagcaagtt aggtctggag     1260
ttgtatcctg cccctctgga gtgtcttgac aacaggggtc atgtcaattg ggagatcctc     1320
gccccaattc gggctgagct gatgtgtaca ctcagggaag tcaggcagcc caagaggatc     1380
ttttttggtc ccatcccctg cccttcctgt ggctcatggc catctgagaa agtggacttc     1440
catctttgct cttagtgaag gcctgattag tgggatggat atgctttctt caggacccct     1500
aggcactaaa atctaggaca caggtgggtt ttttttgtttt tttgtttttt tgttttgatg     1560
gagtctcgct ctgtccctca ggctaaa                                         1587

<210> SEQ ID NO 62
<211> LENGTH: 2123
<212> TYPE: DNA
<213> ORGANISM: Homo sapiens

<400> SEQUENCE: 62
ctgataagtt tgtcttttct ctggattttt cttgcagatt tatcaggatg agcttccagg       60
ccccacgcag actcctggag ctggcagggc agagcctgct gagggaccag gccttggcca      120
tctccgtcct ggatgagctg cccagggagc tcttcccccg actgttcgtg gaggccttca      180
ctagcagacg ctgcgaggtt ctgaaggtga tggtgcaggc ctggcccttc ccctgcctcc      240
ctctggggtc cctgatgaag acgcctgatc tggagatctt acattatgta gtggatggga      300
ttgattgcct gcttgcccaa aaggttcgcc ccaggaggtg gaaacttcaa gtgctggaaa      360
tgcgggatgt tgatgagaat ttttggacca tatggtctgg agccaggccc ctgtcctgct      420
ccccagaggc catgagtaag agacagacag tggaggactg tccaaggaca ggagagaagc      480
agcccttgaa ggtgttcatg gatgtttgcc tcaaggaaaa atccgtggat gaagatctga      540
gcttcttctc tgggtgggtg cagcacagaa gacgttcagt acacctgtgc tgtactaagg      600
tggtaaatta ttcaatgaac attctaaatt tcagaaacat attagaaaca gtatacccag      660
acagtatcca agtattggaa atttggaaca tgtgctggcc gtgtatggta gcagaggtta      720
gccgttacct gagccagatg aagaatcttc gaaaactctt catctccgat ggctgtggtt      780
acctgccaag ctttgagagc caaggacagt tagttgctga attcagctct gtgttcctca      840
ggctggagta cctccagatg ctttatatga aaggatccg cttcttcgaa ggctacctgg      900
accagctgat caggtgcctc aagagcccgt ggagacattt ggcattaact tatggctccc      960
tagatgaaga ggacttgaaa tgtctgccct ggtacccaag tctcagtcaa ctgaagcagc     1020
tgaatctgag tcatggtaca ctgcgcttca tccgtcttga gccctccga gctctgctag      1080 agaaagttgc tgccactctt cagacccctct tcttagtgga ctgtgggatt gggactcca      1140 aactcagggt catcctgcct gccctgagcc gctgctccaa cctcaccact ttctgctttc     1200
acggcaatga cacgtccatg gatggtctga aggacctgct gcgccacaca ggcaggctga     1260
```

```
gcaatttgag cctggaaaca tatcctgccc ctcgggagag tcttgacaac aggggtcgtg    1320
tcatttcgga gctcctcacc ccacttcagg ctgagctgat gcgtatactg agggaagtaa    1380
gggagcccaa caggatcttc tttggtcccg tctcctgccc ttgctgtggc atgtcaccca    1440
ctgagcaact ggagttcaat ttttgcttgc ggggaaggcc tgcctagtgg ggtggaggta    1500
taaaaagctt tttctccagg cacttggaaa ctaaaatcta ggacatagat atcttttatt    1560 tttcttttc cttatttac aattttacag cttttattta aaatttgag acagggtttc       1620 cctatgttgt ccaggctggt ctcaaactct tacgcttaag ggagccccct gcttggcctc    1680
ccaagattct gggattacag gcataagcag ctgtgccggg tctataggtg tattataaag    1740
ggagcagaga aacctctgtt tcaggcatgt gctttctgtg agtgggaaaa aaaacacaaa    1800
aaaacccagc aggggcagc actggggaaa aggttgaatg gagtcactga gactcaggga     1860
tctgtgtcct agacagtcag aaatagaacc tgaagttcta gagtgaagga gttatctcag    1920
caaggatgga tacaaagaaa cgtcggaagt aaagggaacc taaatggaaa ctctctgctg    1980
tccttcatga ttgattagcc tgtttcagca atttatacat cagaaatctt tagttcctga    2040
tgaattaaaa aaagaggtac tagttcatct gtgatttaag ttcatccgca ggaaataaag    2100
gaatcaaaat aaacttcatt ttg                                            2123
```

<210> SEQ ID NO 63
<211> LENGTH: 2164
<212> TYPE: DNA
<213> ORGANISM: Homo sapiens

<400> SEQUENCE: 63

```
acccacagca ctcattcctg gagctactgc ttggttccct gagaggtccc agaactctgc    60
aaagtgagtc cagcgctgag attttcttg cagatctatc aggatgagca tccaggcccc     120
acccagactc ctggagctgg cagggcagag cctgctgaga gaccaggcct tgtccatctc    180
tgccatggag gagctgccca gggtgctcta tctcccactc ttcatggagg ccttccgcag    240
gagacacttc cagactctga cggtgatggt gcaggcctgg cccttcacct gcctccctct    300
gggatcactg atgaagacgc ttcatttgga gaccttaaaa gcattgctgg aagggcttca    360
tatgctgctt acacagaagg atcgccccag gaggtggaaa cttcaagtgc tggatttgcg    420
ggatgttgat gagaatttct gggccagatg gcctggagcc tgggccctgt cctgcttccc    480
agagaccatg agtaagaggc agacagcaga ggactgtcca aggatgggag agcaccagcc    540
cttaaaggtg ttcatagaca tctgcctcaa ggaaataccc caggatgaat gcctgagata    600
cctctttcag tgggtttacc aaaggagagg tttagtacac ctgtgctgta gtaagctggt    660
caattatcta acgccgatta acatctcag aaagtcattg aaataatat acctgaatag      720 tattcaacag ctggaaattc gcaacatgtc ctggccacgt ctgataagaa agcttcgttg    780
ttacctgaag gagatgaaga atcttcgcaa actcgttttc tccaggtgcc atcattccat    840
gtcagataat gaactcgaag acggttagt caccaaattc agctctgtgt tcctcaggct     900
ggaacacctc cagttgctta aaataaaatt gatcaccttc ttcagtgggc acctggaaca    960
gctgatcagg tgcctccaga accccttgga gaacttggaa ttaacttatg ctacctatt     1020 ggaagaagac atgaagtgtc tctcccagta cccaagcctc ggttacctaa agcatctgaa    1080
tctcagctac gtgctgctgt tccgcatcag tcttgaaccc ctcggagctc tgctagaaa     1140 aattgctgcc tctctcgaaa ccctcatctt ggagggctgt cagatccact actcccaact    1200
```

| | | |
|---|---|---|
| cagtgccatc ctgcctggcc tgagccactg ctcccagctc accaccttct actttggcag | 1260 | |
| aaattgtatg tctatgggtg ccctgaagga cctgttgcgc cacaccagtg ggctgagcaa | 1320 | |
| gttaagcctg agacgtatc ctgcccctga ggagagtttg aattccttgg ttcgtgtcga | 1380 | |
| ttgggagatc ttcgccctac ttcgggctga gctgatgtgt acactgaggg aagtcaggca | 1440 | |
| gcccaagagg atcttcattg gtcccacccc ctgcccttcc tgtggctcat caccgtctga | 1500 | |
| ggaactggag ctccatcttt gctgctaggg aaggcgtgcc tagcggggta gagaaatcca | 1560 | |
| aagttctctt ccaggcactg ggacactaaa atctactatg taggtgcaaa ctattttct | 1620 | |
| cttttcttat ttatttcatt ttttaataat tccaaaattt ttattaaaga caatttgaga | 1680 | |
| cagggtttct ctgtgttgct ctgggatcct cctgcctcag ctgggcttat gggatcctcc | 1740 | |
| tgcctcagct tcctaaagtg ctgggattac tggcatgagt gactgtgtcc aggccacatg | 1800 | |
| caacttaaag gaagcacagg gaagtgctca gtgtgaggga aaaaacata acagcagggg | 1860 | |
| gcaaggctgg aggaaaatgt tgaggtgaca tcaatgagaa cttcagggac ccgtgtccta | 1920 | |
| cagagtcgga aagagaagct aaagttctac agtgatgaga atgttatccc tgcaaggatg | 1980 | |
| gttaccaagg aatatcagaa ataaagagca cctgaatgaa aacttttaac ctgttgtagc | 2040 | |
| aatttatcca ccagaaatat ctagttattg agttactgat ggaaaaataa tgaaatacta | 2100 | |
| ctttgtctgt gattgagttt cagctgtaga acatcaaagc aaccaaatag aatttgatca | 2160 | |
| tttt | 2164 | |

<210> SEQ ID NO 64
<211> LENGTH: 1863
<212> TYPE: DNA
<213> ORGANISM: Homo sapiens

<400> SEQUENCE: 64

| | | |
|---|---|---|
| acccaaagtc ttcaagcctg gagttcctgc ttggttcttc ctgaggtctg agcaccttct | 60 | |
| agactacatc cagatctgtt ttccctgcag attcatgaag atgagcatcc ggactccacc | 120 | |
| cagactcctg gagcttgcag ggcggagcct gctgagggac caagctttgg ccatgtccac | 180 | |
| cctggaggag ctgcccacag aacttttccc cccactgttc atggaggcct tcagcaggag | 240 | |
| acgctgtgag gccctgaagc tgatggtgca ggcctggccc ttccgccgcc tccctctgag | 300 | |
| gcctctgata aagatgcctt gtctggaggc cttccaagct gtgctcgatg gcttgatgc | 360 | |
| actgcttacc caagggttc gtcccaggag gtggaaactc caagtgctgg atttacagga | 420 | |
| tgtctgtgag aacttctgga tggtttggtc tgaagctatg gcccatgggt gcttcctcaa | 480 | |
| tgccaagagg aacaaaaaac cagtgcagga ctgtccaagg atgagaggac ggcagcccct | 540 | |
| gactgtgttc gtagaacttt ggctcaagaa caggactctg gatgaatacc tcacctacct | 600 | |
| ccttctatgg gtcaagcaga ggaaagattt actacacctg tgctgtaaga agctgaaaat | 660 | |
| tttgggaatg cccttccgca atatcagaag catcctgaaa atggtgaacc tagactgtat | 720 | |
| ccaggaggtg gaagtgaatt gcaagtgggt actgccatc ctgacacagt ttaccccata | 780 | |
| cctgggccac atgaggaatc ttcagaagct cgttctctcc cacatggatg tctctcgcta | 840 | |
| cgtttcccca gagcagaaga aggagattgt tacccagttc accactcagt tcctcaagct | 900 | |
| gcgctgcctc caaaagcttt atatgaactc tgtttcttc ctcgaaggcc acctggacca | 960 | |
| gctgctcagc tgtctgaaga cctgttaaa agtcctcaca ataactaact gtgtgctttt | 1020 | |
| ggaatcgac ttgaagcatc tatcccagtg cccgagtatc agtcaactaa agaccctgga | 1080 | |
| cctgagtggc atcagactga ccaattatag tcttgtgcct ctccaaattc tcctagaaaa | 1140 | |

```
agttgcagcc acccttgagt acctggattt agatgactgt ggcatcatag actcccaagt    1200
caacgccatc ctgcctgccc tgagccgctg ctttgagctc aacaccttca gcttctgtgg    1260
aaatcccatc tgcatggcca ccctggagaa cctgctgagc cacacaatca tactcaaaaa    1320
cttatgtgtg gagctgtatc ctgcccccg agagagttat ggtgctgatg gtactctctg    1380
ctggagcaga tttgctcaaa ttagggctga gctgatgaac agagtgaggg acttaaggca    1440
ccccaagagg atcttgttct gtactgacta ctgccctgac tgtggcaaca ggtcatttta    1500
tgacctggag gcagatcaat actgctgttg aatgcctgcc tatttggatg gtatgtcaa    1560 acgctttctt ctggacactt ggaaactaaa acctaggtct taggtacatc ctaaagggag    1620
cacagaaccc atcatttcac acataggctc tgaaagtggg aaaggaaagc tgatcaagca    1680
ggggccggac ttgggggaaa tgttgccatg gattcgatgg gactttgggg acctgtgtcc    1740
tgtagattcg aaaatgggaa tctgaatgtc tagagtggaa ttcaggcttg agaatacatg    1800
agggagttac tcttgcatgg atggttgtaa agaaacaatc agaaataaag gaaaactgag    1860
cag                                                                  1863

<210> SEQ ID NO 65
<211> LENGTH: 1855
<212> TYPE: DNA
<213> ORGANISM: Homo sapiens

<400> SEQUENCE: 65
acccaaagtc ttcaagcctg gagttcctgc ttggttcttc ctgaggactg agcaccttct      60
agactacatc cagatctgtt ttccctgcag attcgtgaag atgagcatcc ggactccacc     120
cagactcctg gagcttgcag gcggagcct gctgagggac caagccttgg ccatgtccac     180
cctggaggag ctgcccacag aacttttccc cccactgttc atggaggcct tcagcaggag     240
acgctgtgag gccctgaagc tgatggtgca ggcctggccc ttccgccgcc tccctctgag     300
gcctctgata aagatgcctt gtctggaggc cttccaagct gtgctcgatg ggctggatgc     360
actgcttacc caaggggttc atcccaggag gtggaaactt caagtgctgg atttacagga     420
tgtctgtgag aacttctgga tggtttggtc tgaagctatg gcccatgggt gcttcctcaa     480
tgccaagagg aacaaaaaac cagtgcagga ctgtccaagg atgagaggac agcagccctt     540
gactgtgttc gtagaacttt ggctcaagaa caggactctg gatgaatacc tcacctgcct     600
ccttctatgg gtcaagcaga ggaaagattt actacacctg tgctgtaaga agctgaaaat     660
tttgggaatg cccttccgca atatcagaag catcctgaaa atggtgaacc tagactgtat     720
ccaggaggtg gaagtgaatt gcaagtgggt actgcccatc ctgacacagt ttaccccata     780
cctgggccac atgaggaatc ttcagaagct cgttctctcc cacatggatg tctctcgcta     840
cgtttcccca gagcagaaga aggagattgt tacccagttc accactcagt tcctcaagct     900
gtgctgcctc caaaagcttt ctatgaactc tgtttctttc ctcgaaggcc acctggacca     960
gctgctcagc tgtctgaaga cctcgttaaa ggtcctcaca ataactaact gtgtgctttt    1020
ggaatcagac ttgaagcatc tatcccagtg cccgagtatc agtcaactaa agaccctgga    1080
cctgagtggc atcagactga ccaattacag tcttgtgcct ctccaaattc tcctagaaaa    1140
agttgcagcc acccttgagt acctggattt agatgactgt ggcatcatag actcccaagt    1200
caacgccatc ctgcctgccc tgagccgctg ctttgagctc aacaccttca gcttctgtgg    1260
aaatcccatc tccatggcca ccctggagaa cctgctgagc cacacaatca tactcaaaaa    1320
```

```
cttatgcgtg gagctgtatc ctgcccccg  ggagagttat gatgctgatg gtactctctg   1380
ctggagcaga tttgctcaaa ttagggctga gctgatgaag agagtgaggg acttaaggca   1440
ccccaagagg atcttgttct gtactgactg ctgccctgac tgtggcaaca ggtcatttta   1500
tgacctggag gcagatcaat gctgctgttg aatgcctgcc tatttgggtg gatatgtcaa   1560
acgctttctt ctggacactt ggaaactaaa acctaggtct taggtacatc ctatagggag   1620
cacagaaccc atcatttcac acatgggctc tgaaagtggg aaaggaaagg tgatcaagca   1680
ggggcaggac ttgggggaag tgttgccatg gattcgatgg gactttgggg acctgtgtcc   1740
tgtagagtgg aaaatgggaa tttgaatgtc tagagtggag gcttgagaat acttgaggga   1800
gttactcttg gatgcatggt tgtaaagaaa caatcagaaa taaggaaaa ctgag         1855
```

<210> SEQ ID NO 66
<211> LENGTH: 2104
<212> TYPE: DNA
<213> ORGANISM: Homo sapiens

<400> SEQUENCE: 66

```
gatttgtttt cttgcagatt tatgaggatg agcctacagg ccccacgcag actcctggag     60
ctggcagggc agagcctgct gggggaccag gccttggcca tctccatctt ggatgagctg    120
cccagggagc tcttcccccc actgttcgtg gaggccttca ctagcagacg ctgcgaggtt    180
ctgaaggtga tggtgcaggc ctggcccttc ccctgcctcc ctctgggtc cctgatgaag     240 acgcctgatc tggagatctt acattatgta gtggatggga ttgattgcct gcttgcccaa    300
aaggttcgcc ccaggaggcg gaaacttcaa gtgctggaat gcggatgt tgatgagaat      360 ttttggacca tatggtctgg agccaggccc ctgtcctgct ccccagaggc catgagtaag    420
aggcagacag tggaggactg tccaaggaca ggagagaagc agcccttgaa ggtgttcatg    480
gatgtttgcc tcaaggaaaa attcatggat gaagatctga gcttcttctc tgggtgggtc    540
cagcacagaa gaggttcagt acacctgtgc tgtactaagg tggtgaatta ttcaatgagc    600
attctaaatt tcagaaacat attggaaaca gtatacccag acagtatcca agtgttggaa    660
atttggaaca tgtgctggcc gtgtatgata gtagagttta tccgttacct gagccagatg    720
aggaatcttc gcaaactctt catctccgat ggctgtcgtt acctgctaag ctctgacagc    780
caagaacagt tagttgctga attcagctct gtgctcctca ggctggagta cctccagatg    840
ctttatgtaa gaagggtctg cttcttcaga ggccacctgg accagctgat caggtgcctc    900
aggagcccat ggagacatt ggcattaact tatggcttcc tagaaaaagt ggacttgaaa     960
tgtctgcccc ggtacccaag tctcagtcaa ctgaagcagc tgaatctgag tcatggtgca   1020
ctgcgcttca tccgtcttga gccctccga gctctgctag agaaagttgc tgccactctt    1080
cagaccctct tcttagtgga ctgtgggatt cgggactcca aactcagggt catcctgcct   1140
gccctgagct gctgctccaa cctcaccact ttctgttttc acggcaatga cacgtccatg   1200
gatggtctga aggacctgct gcgccacaca ggcaggctga gcaatttgag cctggaaaca   1260
tatcctgccc ctcgggagag tcttgatgac agggggtcgtg tcatttcgga gctcctcacc   1320
ccacttcagg ctgagctgat gcgtatactg agggaagtaa gggagcccaa aaggatcttc    1380
tttggtccgg tgtcctgccc ttgctgtggc acgtcgccca ctgagcaact ggagttcaat    1440
ttttgcttgt ggggaaggcc tgccagtgg ggtggaggta taaaaagctt tttctccagg    1500
cacttggaaa ctaaaatctg ggacatagat gtctttattt tttcttttc cttatttac     1560 aattttacag ttttttattta aaaatttgag acagggtttc cctatgttgt ccaggctggt   1620
```

-continued

| | |
|---|---|
| ctcaaactct tacgcttaag ggagccacct gcttggcctc ccaagattct gggattacag | 1680 |
| gcataagcag ctgtgccggg tctataggtg tattataaag ggagcagaga aacctctgtt | 1740 |
| tcaggcatgt gctttctgtg agtgggaaaa aaaacacaaa aaaacccagc aggggggcagc | 1800 |
| actgggaaaa aggttgaatg gagtcactga gactcaggga tctgtgtcct agacagtcag | 1860 |
| aaatagaaag ctgaagttct agagtgaagg agttatctca gcaaggatgg atacaaagaa | 1920 |
| acgtcggaag tagagggaac ctaaatggaa actctctgct gtccttcatg attgattagc | 1980 |
| ctgtttcagc aatttataca tcagaaatct ttagttcctg atgaattaaa aaaagaggta | 2040 |
| ctagttcatc tgtgatttag gttcatctgc aggaaataaa ggaatcaaaa taaacttcat | 2100 |
| tttg | 2104 |

<210> SEQ ID NO 67
<211> LENGTH: 1446
<212> TYPE: DNA
<213> ORGANISM: Homo sapiens

<400> SEQUENCE: 67

| | |
|---|---|
| atgaggatga gcctacaggc cccacgcaga ctcctggagc tggcagggca gagcctgctg | 60 |
| ggggaccagg ccttggccat ctccatcttg gatgagctgc ccagggagct cttcccccca | 120 |
| ctgttcgtgg aggccttcac tagcagacgc tgcgaggttc tgaaggtgat ggtgcaggcc | 180 |
| tggccccttcc cctgcctccc tctggggtcc ctgatgaaga cgcctgatct ggagatctta | 240 |
| cattatgtag tggatgggat tgattgcctg cttgcccaaa aggttcgccc caggaggtgg | 300 |
| aaacttcaag tgctggaatt gcgggatgtt gatgagaatt tttggaccat atggtctgga | 360 |
| gccaggcccc tgtcctgctc cccagaggcc atgagtaaga ggcagacagt ggaggactgt | 420 |
| ccaaggacag gagagaagca gcccttgaag gtgttcatgg atgtttgcct caaggaaaaa | 480 |
| ttcatggatg aagatctgag cttcttctct gggtgggtcc agcacagaag aggttcagta | 540 |
| cacctgtgct gtactaaggt ggtgaattat tcaatgagca ttctaaattt cagaaacata | 600 |
| ttggaaacag tatcccaga cagtatccaa gtgttggaaa tttggaacat gtgctggccg | 660 |
| tgtatgatag tagagtttag ccgttacctg agccagatga ggaatcttcg caaactcttc | 720 |
| atctccgatg gctgtcgtta cctgctaagc tctgacagcc aagaacagtt agttgctgaa | 780 |
| ttcagctctg tgctcctcag gctggagtac ctccagatgc tttatgtaag aagggtctgc | 840 |
| ttcttcagag gccacctgga ccagctgatc aggtgcctca ggagcccatt ggagacattg | 900 |
| gcattaactt atggcttcct agaaaaagtg gacttgaaat gtctgccccg gtacccaagt | 960 |
| ctcagtcaac tgaagcagct gaatctgagt catggtgcac tgcgcttcat ccgtcttgag | 1020 |
| cccctccgag ctctgctaga gaagttgct gccactcttc agaccctctt cttagtggac | 1080 |
| tgtgggattc gggactccaa actcagggtc atcctgcctg ccctgagctg ctgctccaac | 1140 |
| ctcaccactt tctgttttca cggcaatgac acgtccatgg atggtctgaa ggacctgctg | 1200 |
| cgccacacag gcaggctgag caatttgagc ctggaaacat atcctgcccc tcgggagagt | 1260 |
| cttgatgaca ggggtcgtgt catttcggag ctcctcaccc cacttcaggc tgagctgatg | 1320 |
| cgtatactga gggaagtaag ggagcccaaa aggatcttct ttggtccggt gtcctgccct | 1380 |
| tgctgtggca cgtcgcccac tgagcaactg gagttcaatt tttgcttgtg ggaaggcct | 1440 |
| gcctag | 1446 |

<210> SEQ ID NO 68

<211> LENGTH: 1425
<212> TYPE: DNA
<213> ORGANISM: Homo sapiens

<400> SEQUENCE: 68

| | | | | | |
|---|---|---|---|---|---|
| atgagcatca | gggccccacc | cagactcctg | gagctggcaa | ggcagaggct | gctgagggac | 60 |
| caggccttgg | ccatctccac | catggaggag | ctgcccaggg | agctcttccc | cacactgttc | 120 |
| atggaggcct | tcagcaggag | acgctgtgaa | accctgaaaa | caatggtgca | ggcctggcct | 180 |
| ttcacccgcc | tccctctagg | gtccctgatg | aagtcgcctc | atctggagtc | attaaaatct | 240 |
| gtgctggaag | gggttgatgt | gctgttgacc | caagaggttc | gccccaggca | gtcaaaactt | 300 |
| caagtgctgg | acttgaggaa | tgtggatgag | aacttctgcg | acatattttc | tggagctact | 360 |
| gcatccttcc | cggaggctct | gagtcagaag | caaacagcag | ataactgtcc | agggacaggc | 420 |
| aggcagcagc | cattcatggt | gttcatagac | ctttgtctca | agaacaggac | actagatgaa | 480 |
| tgcctcaccc | acctcttaga | gtggggcaag | cagagaaaag | gcttactgca | tgtgtgttgc | 540 |
| aaggagctgc | aggttttttgg | aatgcccatc | cacagtatca | tagaggtcct | gaacatggtg | 600 |
| gagcttgact | gtatccagga | ggtggaagtg | tgctgcccct | gggagctgtc | cactcttgtg | 660 |
| aagtttgccc | cttacctggg | ccagatgagg | aatctccgca | aacttgttct | cttcaacatc | 720 |
| cgtgcatctg | cctgcattcc | cccagacaac | aaggggcagt | tcattgcccg | attcacctct | 780 |
| cagttcctca | agctggacta | tttccagaat | ctgtctatgc | actccgtctc | tttcctcgaa | 840 |
| ggccacctgg | accagctgct | caggtgtctc | caggcctcct | ggagatggt | cgttatgacc | 900 |
| gactgcctgc | tgtcagagtc | ggacttgaag | catctctctt | ggtgcccgag | catccgtcaa | 960 |
| ttaaaggagc | tggacctgag | gggtgtcacg | ctgacccatt | tcagccctga | gcccctcaca | 1020 |
| ggtctgctgg | agcaagttgt | ggccaccctg | cagaccctgg | acttagagga | ctgtgggatc | 1080 |
| atggattccc | aactcagcgc | catcctgcct | gtcctgagcc | gctgctccca | gctcagcacc | 1140 |
| ttcagcttct | gtgggaacct | catctccatg | gctgcccttg | agaacctgct | cgccacacc | 1200 |
| gtcgggctga | gcaagctaag | cctggagctg | tatcctgccc | ctctggagag | ttatgacacc | 1260 |
| cagggtgctc | tctgctgggg | gagatttgct | gaacttgggg | ctgagctgat | gaagacaccg | 1320 |
| agggacttaa | ggcagcccaa | gatcattgtg | ttctgcaccg | tcccctgccc | tcgctgtggc | 1380 |
| atcagggcct | cctatgacct | ggagcccagt | cactgcctct | gttga | | 1425 |

<210> SEQ ID NO 69
<211> LENGTH: 1839
<212> TYPE: DNA
<213> ORGANISM: Homo sapiens

<400> SEQUENCE: 69

| | | | | | |
|---|---|---|---|---|---|
| ttcctgcttg | gttcttcctg | aggtctgagc | accttctaga | ctacatccag | atctgttttc | 60 |
| cctgcagatt | catgaagatg | agcatccgga | ttccacccag | actcctggag | cttgcgggcg | 120 |
| gagcctgctg | agggaccaag | ccttggccgt | ctccaccctg | gaggagctgc | ccacggaact | 180 |
| tttcccccca | ctgttcatgg | aggccttcag | caggagacgc | tgtgaggccc | tgaagctgat | 240 |
| ggtgcaggcc | tggcccttcc | gccgcctccc | tctgaggcct | ctgataaaga | tgccttgtct | 300 |
| ggaggccttc | caagctgtgc | tcgatgggct | tgatgcactg | cttacccaag | gggttcgtcc | 360 |
| caggagatgg | aaacttcaag | tgctggattt | acaggatgtc | tgtgagaact | tctggatggt | 420 |
| ttggtctgaa | gctatggccc | atgggtgctt | cctcaatgcc | aagaggaaca | aaacaccagt | 480 |
| gcaggactgt | ccaaggatga | gagaacggca | gcccttgact | gtgtttgtag | aactttggct | 540 |

```
caagaacagg actctggatg aatacctcac ctgcctcctt ctatgggtca agcagaggag      600
agatttacta cacctgtgct gtaagaagct gaaaattttg gaatgccct tccgcaatat       660 cagaagcatc ctgaaaatgg tgaacctaga ctgtatccag gaggtggaag tgaattgcaa      720
gtggatactg cccatcctga cacagtttac cccatacctg gccacttga ggaatcttca       780 gaagctcgtt ctctcccaca tggatgtctc tcgctacgtt tccccagagc agaagaagga      840
gattgttacc cagttcacca ctcagttcct caagctgcgc tgcctccaaa agctttatat      900
gaactctgtt tctttcctcg aaggccacct ggaccagctg ctcagctgtc tgaagacctc      960
gttaaaggtc ctcacaataa ctaactgtgt gcttttggaa tcagacttga agcatctctc     1020
ccagtgcccg agtatcagtc aactaaagac cctggacctg agtggcatca gactgaccaa     1080
ttacagtctt gtgcctctcc aaattctcct agaaaaagtt gcagccaccc ttgagtacct     1140
ggatttagat gactgtggca tcatagactc ccaagtcaac gccatcctgc ctgccctgag     1200
ccgctgcttt gagctcaaca ccttcagctt ctgtggaaat cccatctgca tggccaccct     1260
ggagaacctg ctgagccaca caatcatact caaaaactta tgcctggagc tgtatcctgc     1320
cccgcaggaa agttatggtg ctgatggtac tctctgctgg agcagatttg ctcaaattag     1380
ggctgagctg atgaagaaag tgaggcactt aaggcacccc aagaggatct tgttctgtac     1440
tgacaactgc cctgaccatg cgacaggtc attttatgac ctggaggcag atcaatactg      1500
ctgttgaatg cctgcctatt tggatgggta tgtcaaacgc tttcttctgg acacttggaa     1560
actaaaacct aggtcttagg tacatcctaa agggagcaca gaacccatcg tttcacacat     1620
gggctctgaa agtgggaaag gaaagctgat caagcagggg caggacttgg gggaaatgtt     1680
gccatggatt cgatgggact ttgggaacct gtatcctgta gagtcgaaaa tgggaatctg     1740
aatgtctaga gtggaattca ggcttgagaa tacatgaggg agttactctt gcatggatgg     1800
ttgtaaagaa acaatcagaa ataaaggaaa actgagcag                            1839
```

```
<210> SEQ ID NO 70
<211> LENGTH: 1476
<212> TYPE: DNA
<213> ORGANISM: Homo sapiens

<400> SEQUENCE: 70
```

```
gaggtggaaa cttcaagtgc tggatttaca ggatgtctgt gagaacttct ggatggtttg       60
gtctgaagct atggcccgtg ggtgcttcct caatgccaag aggaacaaaa aaccagtgca      120
ggactgtcca aggatgagag gacggcagcc cttgactgtg ttcgtagaac tttggctcaa      180
gaacaggact ctggatgaac acctcacctg cctccttcta gggtcaagc agaggaaaga      240 tttactacac ctgtgctgta agaagctgaa aattttggga tgcccttcc gcaatatcag       300 aagcatcctg aaaatggtga acctagactg tatccaggag gtggaagtga attgcaagtg      360
ggtactgccc atcctgacac agtttacccc atacctgggc acatgagga atcttcagaa       420 gctcgttctc tcccacatgg atgtctctcg ctacgtttcc ccagagcaga agaaggagat      480
tgttacccag ttcaccactc agttcctcaa gctgcactgc ctccaaaagc tttatatgaa      540 ctctgttttct ttcctcgaag gccacctgga ccagctgctc agctgtctga agacctcgtt    600
aaaggtcctc acaataacta actgtgtgct tttggaatca gacttgaagc atctatccca     660
gtgcccgagt atcagtcaac taaagaccct ggacctgagt ggcatcagac tgaccaatta     720
cagtcttgtg cctctccaaa ttctcctaga aaaagttgca gccacccttg agtacctgga     780
```

| | |
|---|---|
| tttagatgac tgtggcatca tagactccca agtcaacgcc atcctgcctg ccctgagccg | 840 |
| ctgctttgag ctcaacacct tcagcttctg tggaaatccc atctccatgg ccaccctgga | 900 |
| gaacctgctg agccacacaa tcatactcaa aacttatgc ctggagctgt atcctgcccc | 960 |
| acgggagagt tatggtgctg atggtactct ctgctggagc agatttactc agattagggc | 1020 |
| tgagctgatg aagagagtta gggacttaag gcaccccaag aggatcttgt tcggtactga | 1080 |
| ctactgccct gactgtggca acaggtcatt ttatgacctg gaggcagatc aatactgctg | 1140 |
| ttgaatgcct gcctatttgg atgggtatgt caaacgcttt cttctggaca cttggaaact | 1200 |
| aaaacctagg tcttaggtac atcctaaagg gagcacagaa cccatcgttt cacacatggg | 1260 |
| ctctgaaagt gggaaaggaa tgctgatcaa gcaggggcag gacttggggg aaatgttgcc | 1320 |
| atggattcga tgggactttg gggacctgta cctgtagag tcgaaaatgg gaatctgaat | 1380 |
| gtctagagtg gaattcaggc ttgagaatac atgagggagt tactcttgca tggatggttg | 1440 |
| taaagaaaca atcagaaata aaggaaaact gagcag | 1476 |

<210> SEQ ID NO 71
<211> LENGTH: 1720
<212> TYPE: DNA
<213> ORGANISM: Homo sapiens

<400> SEQUENCE: 71

| | |
|---|---|
| agcctggagt tcctgcttgg ttcttcctga ggactgagca ccttctagac tacatccaga | 60 |
| tctgttttcc ctgcagattc gtgaagatga gcatccggac tccacccaga ctcctggagc | 120 |
| ttgcagggcg gagcctgctg agggaccaag ccttggccat gtccaccctg gaggagctgc | 180 |
| ccacagaact tttccccca ctgttcatgg aggccttcag caggagacgc tgtgaggccc | 240 |
| tgaagctgat ggtgcaggcc tggccttcc gccgcctccc tctgaggcct ctgataaaga | 300 |
| tgccttgtct ggaggccttc caagctgtgc tcgatgggct ggatgcactg cttacccaag | 360 |
| gggttcatcc caggaggtgg aaacttcaag tgctggattt acaggatgtc tgtgagaact | 420 |
| tctggatggt ttggtctgaa gctatggccc gtgggtgctt cctcaatgcc aagaggaaca | 480 |
| aaacaccagt gcaggactgt ccaaggatga gaggacagca gcccttgact gtgttcgtag | 540 |
| aactttggct caagaacagg actctggatg aatacctcac ctgcctcctt ctatgggtca | 600 |
| agcagaggaa agatttacta cacctgtgct gtaagaagct gaaaatttg gaatgccct | 660 |
| tccgcaatat cagaagcatc ctgaaaatgg tgaacctaga ctgtatccag gaggtggaag | 720 |
| tgaattgcaa gtgggtactg cccatcctga cacagtttac cccatacctg gccacatga | 780 |
| ggaatcttca gaagctcgtt ctctcccaca tggatgtctc tcgctacgtt tccccagagc | 840 |
| agaagaagga gattgttacc cagttcacca ctcagttcct caagctgtgc tgcctccaaa | 900 |
| agctttctat gaactctgtt tctttcctcg aaggccacct ggaccagctg ctcagctgtc | 960 |
| tgaagacctc gttaaaggtc ctcacaataa ctaactgtgt gcttttggaa tcagacttga | 1020 |
| agcatctatc ccagtgcccg agtatcagtc aactaaagac cctggacctg agtggcatca | 1080 |
| gactgaccaa ttacagtctt gtgcctctcc aaattctcct agaaaaagtt gcagccaccc | 1140 |
| ttgagtacct ggatttagat gactgtggca tcatagactc ccaagtcaac gccatcctgc | 1200 |
| ctgccctgag ccgctgcttt gagctcaaca ccttcagctt ctgtggaaat cccatctcca | 1260 |
| tggccaccct ggagaacctg ctgagccaca atcatacat caaaaactta tgcgtggagc | 1320 |
| tgtatcctgc ccccgggag agttatgatg ctgatggtac tctctgctgg agcagatttg | 1380 |
| ctcaaattag ggctgagctg atgaagagag tgagggactt aaggcacccc aagaggatct | 1440 |

```
tgttctgtac tgactgctgc cctgactgtg gcaacaggtc attttatgac ctggaggcag     1500
atcaatgctg ctgttgaatg cctgcctatt tgggtggata tgtcaaacgc tttcttctgg     1560
acacttggaa actaaaacct aggtcttagg tacatcctat agggagcaca gaacccatca     1620
tttcacacat gggctctgaa agtgggaaag gaaggtgat caagcagggg caggacttgg       1680
gggaagtgtt gccatggatt cgatgggact ttggggacct                            1720
```

<210> SEQ ID NO 72
<211> LENGTH: 1840
<212> TYPE: DNA
<213> ORGANISM: Homo sapiens

<400> SEQUENCE: 72

```
ttcctgcttg gttcttcctg agatctgagc accttctaga ctacatccag atctgttttc      60
cctgcagatt catgaagatg agcatctgga ctccacccag actcctggag cttgcagggc     120
ggagcctgct aagggaccaa gctttggcca tgtccaccct ggaggagctg cccacagaac     180 ttttccccccc actgttcatg gaggccttca gcaggagacg ctgtgaggcc ctgaagctga     240
tggtgcagtc ctggcccttc cgccgcctcc ctctgaggcc tctgataaag atgccttgtc     300
tggaggcctt ccaagctgtg ctcgatgggc tggatgcact gcttaaccta ggggttcgtc     360
ccaggaggtg gaaacttcaa gtgctggatt tacaggatgt ctgtgagaac ttctggatgg     420
tttggtctga agctatggcc catgggtgct tcctcaatgc caagaggaac aaaaaaccag     480
tggaggactg tccaaggatg agaggacggc agcccttgac tgtgttcgta gaactttggc     540
tcaagaacag gactctggat gaatacctca cctgcctcct tctatgggtc aagcaggaga     600
aagatttact acacctgtgc tgtaagaagc tgaaaatttt gggaatgccc ttccgcaata     660
tcagaagcat cctgaaaatg gtgaacctag actgtatcca ggaggtggaa gtgaattgca     720
agtgggtact gccatcctg acacagttta ccccatacct gggccacatg aggaatcttc       780
agaaactcat tctctcccac atggatgtct ctcgctacgt tccccagag cagaagaagg        840 agattgttac ccagttcacc actcagttcc tcaagctgcg ctgcctccaa aagctttata     900
tgaactctgt ttctttcctc gaaggccacc tggaccagct gctcagctgt ctgaagacct     960
cgttaaagtt cctcacaata actaactgtg tgcttttgga atcagacttg aagcatctat    1020
cccagtgccc gagtatcagt caactaaaga ccctggacct gagtggcatc agactgacca    1080
attacagtct tgtgcctctc caaattctcc tagaaaaagt tgcagccacc cttgagtacc    1140
tggatttaga tgactgtggc atcatagact cccaagtcaa cgccatcttg cctgccctga    1200
gccgctgctt tgagctcaac accttcagct tctgtggaaa tcccatctgc atggccaccc    1260
tggagaacct gctgagccac acaatcatac tcaaaaactt atgcgtggag ctgtatcctg    1320
cccccccgga gagttatggt gctgatggta ctctctgctg gagcagattt gctcaaatta    1380
gggctgagct gatgaacaga gtgagggact aaggcaccc caagaggatc ttgttctgta     1440
ctgactactg ccctgactgt ggcaacaggt cattttatga cctggaggca gatcaatact    1500
gctgttgaat gcctgcctat ttggatgggt atgtcaaacg ctttcttctg gacacttgga    1560
aactaaaacc taggtcttag gtacatccta aagggagcac agaacccatc atttcacaca    1620
taggctctga aagtgggaaa ggaaagctga tcaagcaggg gccggacttg ggggaaatgt    1680
tgccatggat tcgatgggac tttggggacc tgtgtcctgt agagtcgaaa atgggaatct    1740
gaatgtctag agtggaattc aggcttgaga atacatgagg gagttactct tgcatggatg    1800
```

| | |
|---|---|
| gttgtaaaga aacaatcaga aataaaggaa aactgagcag | 1840 |

<210> SEQ ID NO 73
<211> LENGTH: 9396
<212> TYPE: DNA
<213> ORGANISM: Artificial Sequence
<220> FEATURE:
<223> OTHER INFORMATION: Synthetic construct

<400> SEQUENCE: 73

| | |
|---|---|
| cgcatagtta agccagtatc tgctccctgc ttgtgtgttg gaggtcgctg agtagtgcgc | 60 |
| gagcaaaatt taagctacaa caaggcaagg cttgaccgac aattgcatga agaatctgct | 120 |
| tagggttagg cgttttgcgc tgcttcgcga tgtacgggcc agatatacgc gttgacattg | 180 |
| attattgact agttattaat agtaatcaat tacggggtca ttagttcata gcccatatat | 240 |
| ggagttccgc gttacataac ttacggtaaa tggcccgcct ggctgaccgc ccaacgaccc | 300 |
| ccgcccattg acgtcaataa tgacgtatgt tcccatagta acgccaatag ggactttcca | 360 |
| ttgacgtcaa tgggtggagt atttacgtta aactgcccac ttggcagtac atcaagtgta | 420 |
| tcatatgcca agtacgcccc ctattgacgt caatgacggt aaatggcccg cctggcatta | 480 |
| tgcccagtac atgaccttat gggactttcc tacttggcag tacatctacg tattagtcat | 540 |
| cgctattacc atggtgatgc ggttttggca gtacatcaat gggcgtggat agcggtttga | 600 |
| ctcacgggga tttccaagtc tccacccccat tgacgtcaat gggagtttgt tttggcacca | 660 |
| aaatcaacgg gactttccaa atgtcgtaa caactccgcc ccattgacgc aaatgggcgg | 720 |
| taggcgtgta cggtgggagg tctatataag cagagctctc tggctaacta gagaacccac | 780 |
| tgcttactgg cttatcgaaa ttaatacgac tcactatagg gagacccaag ctggctagtt | 840 |
| aagctgagca tcaacaagtt tgtacaaaaa agcaggctcc gaattcgccc ttgacgcgcg | 900 |
| acgcgtgtcc tgctattctg tgcattgaaa catgtcatgt ctgtgtccct gatgttttac | 960 |
| ttgaagaata tggcatacaa gttccttctt ctttgcttta tagaatatat tttaaattat | 1020 |
| aataatttcc tctctaaaat aatgtttttg ttaagaccta ttaatttgtt ataaattttg | 1080 |
| ttgggattac aaatactttt ctgagaaaag tttgcatgtt gtacaaactc tattcatata | 1140 |
| aaataccttt tcatacaaaa gaagaattgc tgttttatcc ccattctaac tcttagtata | 1200 |
| aataaaataa tgcagtgggt tgttctgatg ctgcttatat tatcatgcta aatattggct | 1260 |
| tcttaatctg tggtcgtcca caaagtacag agccacacat ccaccaaatg atgttatttg | 1320 |
| aatattgtcc cgaaatacaa ctggttaaaa aaaaaaaaaa aaaaaaagc aacttgctat | 1380 |
| gactggtcat ctaagggaga aaggtggaat tgaggattaa agtgaagaga ttgctggtag | 1440 |
| aggaagagaa agaagaaaga agacttaagc ggagatggtt gccatgggaa gagatgaaat | 1500 |
| ataaattctt ggaacagaga aatagcaagt ataagggact tgatcgttgg ggaataagct | 1560 |
| gaaatagctg taaatctgcc ttatttaggc ttgagtttgt aaataaaata gctagattgt | 1620 |
| gttttttttt atatggacaa gctagcatta tggatcccctt ccaacagcaa caccaataa | 1680 |
| atgatttaaa agcatggctt ctaccttcct agtagtagcg gttccaggac aaccttactt | 1740 |
| ctatcatctt tttcttcttc ttcttcttga tgcttttgtg cttttttttt tttttttttt | 1800 |
| tttttttttt tttttttttt ttttggtgac accttctgtt catgcaagcc tggctatgtt | 1860 |
| tgagctctat ttgaaatcca gacttgcctc aaagtgatag agatgcttct gcatctgttt | 1920 |
| tctgatctag gattaagtgt gtagcaggga ttaaaggcac taacctcctt caagtaatct | 1980 |
| aattgctaaa ttgaattgtg cccttgaaat tcactttcag gaagaaaata gtgaacaaca | 2040 |

```
gtaaagtgtt tattgttctc atgaaaaaac actttcatct gaatgtttct tcttgttagt    2100
attgcattaa ttcattaata tactgaacat catcaatagc aaaaaaaaaa caaatgatac    2160
atttttacat ggtgagtcaa tcattgttgt aacaaatggc taattcattt gaagaatttg    2220
tagtgctttc tttgtcatgt ggcatttttt tttccataaa gggaagggca gctttaggtt    2280
taagcattca aaatttatgg ttttgtgaat gtaaaaaatt ttagaagttg taaatcactg    2340
attttccatc ctatttgggg taagggaaaa taaggttcta tgttttggac tgaagtttag    2400
cacaatctca gtgtttgaag ataaaacatc aacatgtgaa tttaggggtc acaattgaac    2460
ctatcaatta gcatgattgg acaaagcaat tcacaaaggc aaccacgttt aaatccacca    2520
ctctggaatt aatggcaagg atgtgtcaac ctgatccaca ctgtagggct attatgtcta    2580
ggcatacaag ggaaaaaaat tgtctctaga tgaagtaaaa gaaaacagag acagaaaaac    2640
aaaaaggatg tgtgaagtag tgaggtcact ctgggatgtc agcactgagg agttaaaagt    2700
tatatgattg tagtgcaaga tcattctgaa caagttagtg agattgtgag cagactagga    2760
taccatatag acacttgtaa aaaaacaaac aaaacaaaaa acaaatgaac aaaccaaaca    2820
tgagagagag atggaaagat agagaaaaca agagagaaca acaaagacca ccacattttg    2880
ccacaaattt taatctctcc ctagaataca gtcctcatat gatgtccatg ttttcgcaat    2940
aggcaatgca cattcctctc taccaaaaga tacaagttcc cttcagcctc catctttact    3000
atattgtgct acagacacct tatggattct tcctgcccta tctgatccca ctatcaagga    3060
ttctacagag ttcactgaag cacttagggt ccaatctctc tagaaaccag gaaattttaa    3120
caagttttca ttgactacta tgtgagaaca caggatcaga ggtcatagaa gataaatgcc    3180
aatcttggaa ttcctcttca gtgtggtact atttccattc actacagtga cttacaacac    3240
ttgactagga gatgatcttc ttccaaagaa gagtcaatca ttgcattaga gatgcaaaac    3300
tagagctgag ttaggattcc ttatgtgatt caatcagcag gaaaaaatgt cttccttat    3360 tttgtttgct tgcttgtatt tgattccccc ttttggcatt atctgttcct ctgggtcaga    3420
ctgaccttgg atctctgggc ttaataggca gtgctgggga ctactgactc tcctgattca    3480
atttctatta ctttgagtac tatggataaa atggtaatct gccccaccca ggaacaggag    3540
ttttgataga atcactgtgt gaatttaatc gtcatcagta actgactaac ggaagccagg    3600
cgctataaaa gggaaccaat cctaatagaa cctcagatga agcagagcca aggcagagac    3660
acacagtgcc tccctgggct tcttggcatc acccttgaag ttcaccggag aaagcagtga    3720
ggtggaggaa taggtaaact ttccttccta gtggtcttga atgtgtaagt atatgtgtat    3780
ttatgtgtgt gtatgtgtgt ttatttgtgg acttgtgaga agattcatca caattatggg    3840
gagatctcag tagttcaata ttgccttttg gaagctttcc tgatcaagag gttgattttt    3900
ctaaactcta agaaaactc tgagttggta atcattcagg tatgtgcgtg atatttgtt    3960 tgcctctctg tgaatttaat attcctgatt attcatttta aatatttct tatgaaagta    4020 ttattctctg gtgctttaga atgagacaga agggtgaaac ttaaatttg aggaacagca    4080 gaataactcc catctttcc aaaggggggaa cagacaacat tgctgtgttc ttaagatctc    4140
atgacagatc taagcaccct agatacagga ctttctggtt attgagtcaa ttttttttct    4200
acttttcagt tgttttgccc atttccaatt ccatgcaagc agattgaaag gactatagtg    4260
aaacatttac tgtcaggaac ccataaaacc atctgtgaca caaatctcat ttggttttgt    4320
gtttgttttg ttaacattaa ttatgtgttt cttccttttt taaattcaca gcttttacag    4380
```

| | |
|---|---|
| tacatccatc aactgttagc attttcgtaa agtcacaaaa cagatattaa actactatag | 4440 |
| ttgaatctttt cacaccattg tcaccacagt taacaagggc gaattcgacc cagctttctt | 4500 |
| gtacaaagtg gttgatgctg ttaacatggt gagcaagggc gaggagctgt tcaccggggt | 4560 |
| ggtgcccatc ctggtcgagc tggacggcga cgtaaacggc cacaagttca gcgtgtccgg | 4620 |
| cgagggcgag ggcgatgcca cctacggcaa gctgaccctg aagttcatct gcaccaccgg | 4680 |
| caagctgccc gtgccctggc ccaccctcgt gaccaccttc acctacggcg tgcagtgctt | 4740 |
| cgcccgctac cccgaccaca tgaagcagca cgacttcttc aagtccgcca tgcccgaagg | 4800 |
| ctacgtccag gagcgcacca tcttcttcaa ggacgacggc aactacaaga cccgcgccga | 4860 |
| ggtgaagttc gagggcgaca ccctggtgaa ccgcatcgag ctgaagggca tcgacttcaa | 4920 |
| ggaggacggc aacatcctgg ggcacaagct ggagtacaac tacaacagcc acaaggtcta | 4980 |
| tatcaccgcc gacaagcaga agaacggcat caaggtgaac ttcaagaccc gccacaacat | 5040 |
| cgaggacggc agcgtgcagc tcgccgacca ctaccagcag aacaccccca tcggcgacgg | 5100 |
| ccccgtgctg ctgcccgaca accactacct gagcacccag tccgccctga gcaaagaccc | 5160 |
| caacgagaag cgcgatcaca tggtcctgct ggagttcgtg accgccgccg ggatcactct | 5220 |
| cggcatggac gagctgtaca gtaatgata agtttaaacg ggggaggcta actgaaacac | 5280 |
| ggaaggagac ataccggaa ggaacccgcg ctatgacggc aataaaaaga cagaataaaa | 5340 |
| cgcacgggtg ttgggtcgtt tgttcataaa cgcggggttc ggtcccaggg ctggcactct | 5400 |
| gtcgataccc caccgagacc ccattggggc caatacgccc gcgtttcttc cttttcccca | 5460 |
| ccccacccc caagttcggg tgaaggccca gggctcgcag ccaacgtcgg ggcggcaggc | 5520 |
| cctgccatag cagatctgcg cagctggggc tctaggggt atccccacgc gccctgtagc | 5580 |
| ggcgcattaa gcgcggcggg tgtggtggtt acgcgcagcg tgaccgctac acttgccagc | 5640 |
| gccctagcgc ccgctccttt cgctttcttc ccttcctttc tcgccacgtt cgccggcttt | 5700 |
| ccccgtcaag ctctaaatcg ggggctccct ttagggttcc gatttagtgc tttacggcac | 5760 |
| ctcgacccca aaaaacttga ttagggtgat ggttcacgta gtgggccatc gccctgatag | 5820 |
| acggtttttc gccctttgac gttggagtcc acgttcttta atagtggact cttgttccaa | 5880 |
| actggaacaa cactcaaccc tatctcggtc tattcttttg atttataagg gattttgccg | 5940 |
| atttcggcct attggttaaa aaatgagctg atttaacaaa aatttaacgc gaattaattc | 6000 |
| tgtggaatgt gtgtcagtta gggtgtggaa agtccccagg ctccccagca ggcagaagta | 6060 |
| tgcaaagcat gcatctcaat tagtcagcaa ccaggtgtgg aaagtcccca ggctccccag | 6120 |
| caggcagaag tatgcaaagc atgcatctca attagtcagc aaccatagtc cgcccctaa | 6180 |
| ctccgcccat cccgcccta actccgccca gttccgccca ttctccgccc catggctgac | 6240 |
| taatttttttt tatttatgca gaggccgagg ccgcctctgc ctctgagcta ttccagaagt | 6300 |
| agtgaggagg ctttttttgga ggcctaggct tttgcaaaaa gctcccggga gcttgtatat | 6360 |
| ccatttttcgg atctgatcag cacgtgttga caattaatca tcggcatagt atatcggcat | 6420 |
| agtataatac gacaaggtga ggaactaaac catggccaag cctttgtctc aagaagaatc | 6480 |
| caccctcatt gaaagagcaa cggctacaat aacagcatc cccatctctg aagactacag | 6540 |
| cgtcgccagc gcagctctct ctagcgacgg ccgcatcttc actggtgtca atgtatatca | 6600 |
| ttttactggg ggaccttgtg cagaactcgt ggtgctgggc actgctgctg ctgcggcagc | 6660 |
| tggcaacctg acttgtatcg tcgcgatcgg aaatgagaac aggggcatct tgagcccctg | 6720 |
| cggacggtgc cgacaggtgc ttctcgatct gcatcctggg atcaaagcca tagtgaagga | 6780 |

```
cagtgatgga cagccgacgg cagttgggat tcgtgaattg ctgccctctg gttatgtgtg   6840
ggagggctaa gcacttcgtg gccgaggagc aggactgaca cgtgctacga gatttcgatt   6900
ccaccgccgc cttctatgaa aggttgggct tcggaatcgt tttccgggac gccggctgga   6960
tgatcctcca gcgcgggat ctcatgctgg agttcttcgc ccaccccaac ttgtttattg   7020
cagcttataa tggttacaaa taaagcaata gcatcacaaa tttcacaaat aaagcatttt   7080
tttcactgca ttctagttgt ggtttgtcca aactcatcaa tgtatcttat catgtctgta   7140
taccgtcgac ctctagctag agcttggcgt aatcatggtc atagctgttt cctgtgtgaa   7200
attgttatcc gctcacaatt ccacacaaca tacgagccgg aagcataaag tgtaaagcct   7260
ggggtgccta atgagtgagc taactcacat taattgcgtt gcgctcactg cccgctttcc   7320
agtcgggaaa cctgtcgtgc cagctgcatt aatgaatcgg ccaacgcgcg gggagaggcg   7380
gtttgcgtat tgggcgctct tccgcttcct cgctcactga ctcgctgcgc tcggtcgttc   7440
ggctgcggcg agcggtatca gctcactcaa aggcggtaat acggttatcc acagaatcag   7500
gggataacgc aggaaagaac atgtgagcaa aaggccagca aaaggccagg aaccgtaaaa   7560
aggccgcgtt gctggcgttt ttccataggc tccgcccccc tgacgagcat cacaaaaatc   7620
gacgctcaag tcagaggtgg cgaaacccga caggactata agataccag gcgtttcccc   7680
ctggaagctc cctcgtgcgc tctcctgttc gaccctgcc gcttaccgga tacctgtccg   7740
cctttctccc ttcgggaagc gtggcgcttt ctcatagctc acgctgtagg tatctcagtt   7800
cggtgtaggt cgttcgctcc aagctgggct gtgtgcacga accccccgtt cagcccgacc   7860
gctgcgcctt atccggtaac tatcgtcttg agtccaaccc ggtaagacac gacttatcgc   7920
cactggcagc agccactggt aacaggatta gcagagcgag gtatgtaggc ggtgctacag   7980
agttcttgaa gtggtggcct aactacggct acactagaag aacagtattt ggtatctgcg   8040
ctctgctgaa gccagttacc ttcggaaaaa gagttggtag ctcttgatcc ggcaaacaaa   8100
ccaccgctgg tagcggtggt ttttttgttt gcaagcagca gattacgcgc agaaaaaaag   8160
gatctcaaga agatcctttg atcttttcta cggggtctga cgctcagtgg aacgaaaact   8220
cacgttaagg gattttggtc atgagattat caaaaaggat cttcacctag atccttttaa   8280
attaaaaatg aagttttaaa tcaatctaaa gtatatatga gtaaacttgg tctgacagtt   8340
accaatgctt aatcagtgag gcacctatct cagcgatctg tctatttcgt tcatccatag   8400
ttgcctgact ccccgtcgtg tagataacta cgatacggga gggcttacca tctggcccca   8460
gtgctgcaat gataccgcga gacccacgct caccggctcc agatttatca gcaataaacc   8520
agccagccgg aagggccgag cgcagaagtg gtcctgcaac tttatccgcc tccatccagt   8580
ctattaattg ttgccgggaa gctagagtaa gtagttcgcc agttaatagt ttgcgcaacg   8640
ttgttgccat tgctacaggc atcgtggtgt cacgctcgtc gtttggtatg gcttcattca   8700
gctccggttc ccaacgatca aggcgagtta catgatcccc catgttgtgc aaaaaagcgg   8760
ttagctcctt cggtcctccg atcgttgtca gaagtaagtt ggccgcagtg ttatcactca   8820
tggttatggc agcactgcat aattctctta ctgtcatgcc atccgtaaga tgcttttctg   8880
tgactggtga gtactcaacc aagtcattct gagaatagtg tatgcggcga ccgagttgct   8940
cttgcccggc gtcaatacgg gataataccg cgccacatag cagaacttta aaagtgctca   9000
tcattggaaa acgttcttcg gggcgaaaac tctcaaggat cttaccgctg ttgagatcca   9060
gttcgatgta acccactcgt gcacccaact gatcttcagc atcttttact ttcaccagcg   9120
```

```
tttctgggtg agcaaaaaca ggaaggcaaa atgccgcaaa aaagggaata agggcgacac    9180
ggaaatgttg aatactcata ctcttcctit ttcaatatta ttgaagcatt tatcagggtt    9240
attgtctcat gagcggatac atatttgaat gtatttagaa aaataaacaa ataggggttc    9300
cgcgcacatt tccccgaaaa gtgccacctg acgtcgacgg atcgggagat ctcccgatcc    9360
cctatggtgc actctcagta caatctgctc tgatgc                              9396
```

USE OF ZSCAN4 AND ZSCAN4-DEPENDENT GENES FOR DIRECT REPROGRAMMING OF SOMATIC CELLS

CROSS REFERENCE TO RELATED APPLICATIONS

This application is a U.S. National Phase patent application of PCT/US2012/037643 filed May 11, 2012, which claims priority to U.S. Provisional Application Ser. No. 61/486,004 filed May 13, 2011 and U.S. Provisional Application Ser. No. 61/529,055 filed Aug. 30, 2011, the contents of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 699442000500SeqList.txt, date recorded: Nov. 13, 2013.

FIELD

This disclosure concerns the identification of Zscan4 as an early embryonic factor required for direct reprogramming of somatic cells. This disclosure further concerns the use of Zscan4 and Zscan4-dependent genes for production of induced pluripotent stem (iPS) cells, iPS cells produced by this method, and methods of using the generated iPS cells.

BACKGROUND

Induced pluripotent stem cells hold great promise as a source of patient-specific cells in regenerative medicine, but there are many challenges that must be overcome before this technology can be applied effectively in clinical therapies (Hanna et al., Cell 143:508-525, 2010; Yamanaka, Cell 137:13-17, 2009; Stadtfeld et al., Genes Dev 24:2239-2263, 2010). One critical issue is the use of an oncogene, c-Myc (M), together with other three factors KOS (Klf4, Oct4, Sox2) to generate induced pluripotent stem (iPS) cells. The ectopic overexpression of KOS alone leads to a low efficiency of iPS cell formation (Takahashi and Yamanaka, Cell 126:663-676, 2006). However, the use of oncogenes raises serious concern about tumorigenicity of iPS cells and long-term safety in potential clinical use of iPS cells. Indeed, recent reports show that even after successful reprogramming, iPS cells tend to show low genome stability and premature cellular senescence upon differentiation (Feng et al., Cell Stem Cell 4:301-312, 2009; Hu et al., Proc Natl Acad Sci USA 107:4335-4340, 2010). However, increasing cell proliferation and suppressing genome stability by c-Myc seems to be inseparable from efficient induced pluripotent stem cell (iPSC) formation (Zhao et al., Cell Stem Cell 3:475-479, 2008). Thus, a fundamental challenge that must be addressed is how to increase efficiency of iPS cell generation without sacrificing genome stability. Without resolving this issue, iPS cells may never be usable in clinical practice.

The Zscan4 (zinc finger and scan domain-containing protein 4) gene was identified by expression profiling of all preimplantation stages of mouse embryos using a large-scale cDNA sequencing project (Ko et al., Development 127: 1737-1749, 2000; Sharov et al., PLoS Biol 1:E74, 2003) and DNA microarray analysis (Hamatani et al., Dev Cell 6:117-131, 2004). In mice, Zscan4 consists of 6 paralog genes (Zscan4a to Zscan4f) and 3 pseudogenes (Zscan4-ps1 to Zscan4-ps3) clustered on an approximately 850 kb region of chromosome 7. Among the six paralogs, the open reading frames of Zscan4c, Zscan4d, and Zscan4f encode a SCAN domain as well as all four zinc finger domains, suggesting their potential role as transcription factors. A high expression peak of Zscan4 marks the late 2-cell stage of mouse embryos. Zscan4 expression, normally below detection threshold in blastocysts, is reactivated in vitro in a small fraction of embryonic stem (ES) cells in culture. It has previously been demonstrated that Zscan4 acts critically in the formation of proper blastocysts (Falco et al., Dev Biol 307:539-550, 2007; PCT Publication No. WO 2008/118957) and is required for the maintenance of genome stability and normal karyotype in ES cells (Zalzman et al., Nature 464: 858-863, 2010; PCT Publication No. WO 2011/028880).

SUMMARY

Disclosed herein is the finding that Zscan4 initiates direct reprogramming of somatic cells by reactivating early embryonic genes. Forced expression of Zscan4 in somatic cells, along with other previously described reprogramming factors, leads to the efficient production of high quality induced pluripotent stem (iPS) cells. It is also disclosed herein that expression of the Zscan4-dependent genes Patl2, Pramel6, Piwil2 and D5Ertd577e in somatic cells promotes induction of iPS cells.

Provided herein is an ex vivo method of producing an iPS cell by reprogramming of a somatic cell. The method includes contacting the somatic cell with a Zscan4, or a Zscan4-dependent gene, and at least one reprogramming factor, thereby producing an iPS cell. In some embodiments, the Zscan4-dependent gene is selected from Patl2, Pramel6, Piwil2 and D5Ertd577e. In some embodiments, the method includes contacting the somatic cell with at least two, at least three, or at least four reprogramming factors. The reprogramming factors for use in the disclosed methods include, but are not limited to, c-Myc, Klf4, Oct4, Sox2, Lin28 and Nanog. In some embodiments, the method includes contacting the somatic cell with a Zscan4, at least one Zscan4-dependent gene and at least one reprogramming factor. Also provided are isolated iPS cells produced according to the methods disclosed herein. Use of the isolated iPS cells for therapeutic applications is further provided by the present disclosure.

Also provided herein are methods of identifying mature and/or high quality iPSCs in a cell population by transfecting the cell population with an expression vector comprising a Zscan4 promoter operably linked to a reporter gene, wherein expression of the reporter gene in a cell of the cell population identifies the cell as a mature and/or high-quality iPSC. Further provided is a method of isolating mature iPSCs from a cell population, comprising transfecting the cell population with an expression vector comprising a Zscan4 promoter operably linked to a reporter gene, and separating cells expressing the reporter gene from the cell population, thereby isolating mature iPSCs.

The foregoing and other objects and features of the disclosure will become more apparent from the following detailed description, which proceeds with reference to the accompanying figures.

BRIEF DESCRIPTION OF THE DRAWINGS

FIG. 1A depicts a schematic of the structure of pCAG-Zscan4cERT2 plasmid used to make murine embryonic fibroblast (MEF)-ZERT cells. FIG. 1B depicts a schematic representation of experimental procedures for iPSC generation. FIG. 1C depicts representative pictures of 6-well plates stained for ALP 20 days after the doxycycline (Dox) induction. Alkaline phosphatase (ALP) positive colonies were counted (mean±S.E.M.) and the results are shown in the graph on the right. FIG. 1D depicts the efficiency of iPSC formation examined after different Tamoxifen (Tmx) treatments. FIG. 1E also depicts the efficiency of iPSC formation examined after different Tamoxifen (Tmx) treatments. ALP-positive colonies were counted 20 days after the induction (mean±S.E.M.). Different letters denote significant differences between groups (P<0.05).

FIG. 2A depicts a schematic representation of procedures for secondary MEFs generation. FIG. 2B depicts representative cell morphologies during the first 6 days of Dox and Tmx treatments. Pictures of cells after ALP-staining on day 17 are shown. FIG. 2C depicts the efficiency of iPSC formation examined after different Tmx treatments. ALP-positive colonies were counted 13 days after Dox induction. Different letters denote significant differences between groups (P<0.05).

FIG. 3 shows microarray analysis of the early phase of iPSC formation from the MEF-KOS-ZERT$^{2nd}$ cells. FIG. 3A depicts scatter-plots showing pair-wise comparison between Dox+ Tmx− (KOS factors) and Dox− Tmx− (No factor); Dox+ Tmx+ (ZKOS factors) and Dox− Tmx+ (No factor); Dox− Tmx+ (No factor) and Dox− Tmx− (No factor); and Dox+ Tmx+ (ZKOS factors) and Dox+ Tmx− (KOS factors) conditions. Cells were harvested on day 1, 3, and 6 after beginning the Dox or Tmx treatment. Figures in each scatter plot represent the number of genes that showed statistically significant differences between the conditions (FDR≤0.05, fold-change≥2). A list of non-redundant 231 genes were obtained by combining 12 (day 1), 90 (day 3), and 178 (day 6) genes that were more highly expressed in Dox+ Tmx+ (ZKOS) condition than in Dox+ Tmx− (KOS) condition. FIG. 3B depicts a heatmap showing the fold-difference of expression levels of 231 genes between Tmx+ and Tmx− conditions. The fold difference for each gene was calculated by dividing the expression level (Tmx+) by the expression level (Tmx−). Among 231 genes, Pramel6 showed the highest fold-difference: 10.2-fold on day 3 (see Table 1). Results obtained by searching the EST database for 231 genes are shown as symbols after gene names: Red circle, genes expressed predominantly in oocytes; blue circle, genes expressed predominantly in preimplantation embryos (1-cell to blastocysts); pink square, genes expressed predominantly in testes or ovaries. FIG. 3C depicts a heatmap showing expression patterns of 201 genes (a subset of 231 genes) found in the NIA Gene Expression Atlas (Sharov et al., *BMC Genomics* 12:102, 2011) (22 different adult organs/tissues and cultured cells, from left to right: brain, cerebellum, eyes, skeletal muscle, heart, bone, liver, kidney, bladder, skin, visceral fat, lung, small intestine, large intestine, stomach, placenta, ovary, oocyte, testis, MEF cells, ESCs, and iPSCs). Bar graphs show the gene expression levels of two representative genes (Patl2 and D13Ertd608e) among these tissues. FIG. 3D depicts a heatmap showing the expression patterns of 99 genes (a subset of 231 genes) found in the GNF database (Su et al., *Proc Natl Acad Sci USA* 99:4465-4470, 2002) (62 different organs/tissues). Bar graphs show the gene expression levels of two representative genes (Pramel6 and D5Ertd577e) among these tissues. FIG. 3E depicts a summary diagram showing events occurring during Zscan4-mediated iPSC formation.

FIG. 4A depicts growth curves of MEF-WT and MEF-ZERT cultured and passaged in Tmx+ and Tmx− conditions. FIG. 4B depicts scatter-plots showing global gene expression differences between Tmx+ and Tmx− conditions 48 hours after Tmx treatment. FIG. 4C depicts DNA methylation patterns of the promoter region of Oct4 gene. FIG. 4D depicts a summary diagram of the Zscan4 effect on MEFs.

FIG. 5A depicts a schematic representation of procedures for MEF-ZERT generation. A pCAG-Zscan4cERT2 vector was transfected into V6.5 embryonic stem (ES) cells to make Zscan4ERT2 ES cells (ES-ZERT). ES-ZERT cells were microinjected into blastocysts from the ICR mice to generate male chimeric mice, which were subsequently mated with the ICR female mice. E13.5 embryos were dissected out from the pregnant ICR female mice and used to generate mouse embryo fibroblasts (MEFs). MEFs were subjected to genotyping and quantitative RT-PCR. MEFs that carried pCAGZscan4cERT2 DNA and expressed the exogenous Zscan4c were designated as MEF-ZERT and MEFs that did not were designated MEF-WT (wild type). FIG. 5B depicts expression levels of Zscan4c in a series of MEFs (MEF-ZERT and MEF-WT) were examined by qRT-PCR. FIG. 5C depicts expression levels of Zscan4c in a different series of MEFs (MEF-ZERT and MEF-WT) were examined by qRT-PCR. Data in triplicate were represented as mean±S.E.M. after calculating a ratio between the expression levels of Zscan4c and those of Gapdh. The following MEF lines were used in the studies disclosed herein: MEF-ZERT (#A2, #A7, #B5); MEF-WT (#A3).

FIG. 6A depicts a schematic presentation of experimental procedures. A piggyBac vector (PB-TET-MKOS) carrying doxycycline (Dox)-inducible Myc (M), Klf4 (K), Oct4 (O), and Sox2 (S), was transfected into MEF-ZERT and MEF-WT, respectively. The cells were cultured under the Dox+ Tmx− or Dox+ Tmx+ condition for 14 days, fixed, and stained for alkaline phosphatase (ALP). FIG. 6B depicts phase-contrast microscopic images showing morphological changes of MEF-ZERT cells during the MKOS-mediated iPSC colony formation. FIG. 6C depicts representative pictures of 6-well plates stained for ALP. FIG. 6D depicts iPSC colonies that were scored based on their authentic ES cell morphology and ALP-staining (mean±S.E.M.). *, P<0.05.

FIG. 7A shows several iPSC colonies that were picked from the wells prepared in parallel with the experiment shown in FIG. 6C and propagated in the ES cell culture condition on feeder cells: one iPSC clone from the MEF-WT (Dox+ Tmx−); three iPSC clones from the MEF-WT (Dox+ Tmx+); two iPSC clones from the MEF-ZERT (Dox+ Tmx−); and three iPSC clones from the MEF-ZERT (Dox+ Tmx+). These iPSC clones, MEF-WT cells, MEF-ZERT cells, and V6.5 ES cells were subjected to RT-PCR analysis with pluripotency gene markers: endogenous Oct4 (Pou5f1), endogenous Sox2, Nanog, Zfp42 (Rex1), and Dax1 (Nr0b1). Gapdh was used as a control. FIG. 7B depicts a representative phase-contrast image of the iPSC clone (#5B+1) derived from the MEF-ZERT cells with MKOS under Tmx+ condition (i.e., with MKOS factors plus Zscan4 (ZMKOS factors)). FIG. 7C depicts a microscopic image of the iPSC clone (#5B+1) after staining with ALP. FIG. 7D depicts fluorescence microscopic images of the iPSC clone (#5B+1) after staining with antibodies against SSEA-1 and NANOG. Pictures (right) are the same images after merging with DAPI-staining. FIG. 7E depicts a microscopic image showing embryoid bodies (day 4) generated from the iPSC clone (#5B+1); ×200. FIG. 7F depicts fluorescence images of the iPSCs after in vitro differentiation from the embryoid body shown in FIG. 7E, and stained with antibodies against αSMA (mesoderm), AFP (endoderm), GATA4 (endoderm), and βIII-tubulin (ectoderm). Pictures (right) are the same images after merging with DAPI-staining. Scale bar, 100 mm. FIG. 7G depicts an E13.5 embryo derived from the iPSC by the 4N complementation.

FIG. 8A depicts a schematic representation of experimental procedures. A PB-MKOS vector together with a PB-TET-DsRed (control), PB-TET-Zscan4, or PB-TET-Zscan4ERT2 vector was transfected into the MEF-WT cells (C57BL/6Jx12956/SvEvTac). The cells were cultured for 14 days under the Dox+ condition (for the PB-TET-Zscan4ERT2 vector, Dox+ Tmx− or Dox+ Tmx+ condition), fixed, and stained for the ALP. FIG. 8B depicts a representative pictures of 6-well plates stained for ALP. FIG. 8C depicts ALP-positive colonies that were scored. Transfections and Dox inductions were performed in triplicate. Data from two independent experiments are shown. Data are represented as mean±S.E.M. (triplicate wells); *, P<0.01.

FIG. 9A depicts several iPSC colonies that were picked from the wells prepared in parallel with the experiment shown in FIG. 8B and propagated in the ES cell culture condition on feeder cells: five iPSC clones from the MEF-WT (MKOS: #A2, #A3, #A4, #A5, #A6); four iPSC clones from the MEF-WT (ZMKOS: #B1, #B3, #B5, #B6). These iPSC clones and MEF-WT cells were subjected to RT-PCR analysis with pluripotency gene markers: endogenous Oct4 (Pou5f1), endogenous Sox2, Nanog, Zfp42 (Rex1), and Dax1 (Nr0b1). Gapdh was used as a control. FIG. 9B depicts a representative phase-contrast image of the iPSC clone (#B5) after staining with ALP. FIG. 9C depicts a microscopic image showing embryoid bodies (day 4) generated from the iPSC clone (#B5). FIG. 9D depicts fluorescence microscopic images of the iPSC clone (#B5) after in vitro differentiation from the embryoid body shown in FIG. 9C, and stained with antibodies against αSMA (mesoderm), AFP (endoderm), GATA4 (endoderm), and βIII-tubulin (ectoderm). Pictures (right) are the same images after merging with DAPI-staining. Scale bar, 100 μm.

FIG. 10A depicts several iPSC colonies that were picked from the wells prepared in parallel with the experiment shown in FIG. 8B and propagated in the ES cell culture condition on feeder cells: five iPSC clones from the MEF-WT (MKOS+Zscan4ERT2, Tmx− condition: #C1, #C2, #C3, #C5, #C6); four iPSC clones from the MEF-WT (MKOS+Zscan4ERT2, Tmx+: #D2, #D3, #D5, #D6). These iPSC clones and control MEF-WT cells were subjected to RT-PCR analysis with pluripotency gene markers: endogenous Oct4 (Pou5f1), endogenous Sox2, Nanog, Zfp42 (Rex1), and Dax1 (Nr0b1). Gapdh was used as a control. FIG. 10B depicts a representative phase-contrast image of the iPSC clone (#D3) after staining with ALP. FIG. 10C depicts a microscopic image showing embryoid bodies (day 4) generated from the iPSC clone (#D3). FIG. 10D depicts fluorescence microscopic images of the iPSC clone (#D3) after in vitro differentiation from the embryoid body shown in FIG. 10C, and stained with antibodies against α SMA (mesoderm), AFP (endoderm), GATA4 (endoderm), and βIII-tubulin (ectoderm). Pictures (right) are the same images after merging with DAPI-staining. Scale bar, 100 μm.

FIG. 11A depicts a schematic representation of a piggyBac vector (PB-TET-hZSCAN4) carrying human ZSCAN4 open reading frame (ORF) under the Dox-inducible promoter. A PB-TET-MKOS vector together with either PB-TET-hZSCAN4 or a control PB-DsRed vector were cotransfected to MEF-WT cells (C57BL/6Jx12956/SvEvTac). The experimental design was essentially the same as that shown in FIG. 8A. The cells were cultured for 14 days, fixed, and stained for ALP. FIG. 11B depicts representative pictures of 6-well plates stained for ALP. FIG. 11C depicts additional representative pictures of 6-well plates stained for ALP. ALP+ colonies were scored. Data are represented as mean±S.E.M. in triplicate; *, P<0.01. (B) and (C) are representatives of three independent experiments.

FIG. 13A depicts several iPSC colonies that were picked from the wells prepared in parallel with the experiment shown in FIG. 1C and propagated in the ES cell culture condition on feeder cells: four iPSC clones from the MEF-ZERT (KOS factors and Tmx+ condition, i.e., ZKOS factors: #2, #4, #7, #8). These iPSC clones and control MEF-ZERT cells were subjected to RT-PCR analysis with pluripotency gene markers: endogenous Oct4 (Pou5f1), endogenous Sox2, Nanog, Zfp42 (Rex1), and Dax1 (Nr0b1). Gapdh was used as a control. FIG. 13B depicts a representative phase-contrast image of the iPSC clone (#7) after staining with ALP. FIG. 13C depicts an E13.5 embryo derived from the iPSC clone (#7) by the 4N complementation.

FIG. 14A shows that following the experimental procedure shown in FIG. 2A, iPSC colonies were generated by transfecting the MEF-WT (C57BL/6Jx129S6/SvEvTac) with piggyBac vectors (PB-TET-KOS and PB-TET-Zscan4ERT2-IRES-HisDsRed) and culturing the cells for 30 days under the Dox+Tmx+ condition. Under fluorescence microscope, Zscan4ERT2+ iPS colonies could be identified by red-fluorescence. The two red iPSC colonies were picked from the wells and propagated in the ES cell culture condition on feeder cells, resulting in the establishment of two iPSC clones (MEF-WT with the ZKOS factors: #2, #4). These iPSC clones and control MEF-WT cells were subjected to RT-PCR analysis with pluripotency gene markers: endogenous Oct4 (Pou5f1), endogenous Sox2, Nanog, Zfp42 (Rex1), and Dax1 (Nr0b1). Gapdh was used as a control. FIG. 14B depicts a representative phase-contrast image of the iPSC clone (#2). FIG. 14C depicts a representative phase-contrast image of the iPSC clone (#2) after staining with ALP. FIG. 14D depicts fluorescence microscopic images of the iPSC clone (#2) after staining with antibodies against SSEA-1 and NANOG. Pictures (right) are the same images after merging with DAPI-staining. FIG. 14E depicts a microscopic image showing embryoid bodies (day 4) generated from the iPSC clone (#2). FIG. 14F depicts fluorescence images of the iPSC clone (#2) after in vitro differentiation from the embryoid body shown in FIG. 14E, and stained with antibodies against αSMA (mesoderm), AFP (endoderm), GATA4 (endoderm), and βIII-tubulin (ectoderm). Pictures (right) are the same images after merging with DAPI-staining. Scale bar, 100 μm. FIG. 14G depicts E13.5 embryos derived from the iPSC clone (#2) by the 4N complementation. These embryos were used to generate the secondary MEFs (MEF-KOS-ZERT$^{2nd}$) as described in FIG. 2A.

FIG. 15A depicts a scatter-plot showing pair-wise comparison between iPSC (ZKOS#2) and MEF-WT. FIG. 15B depicts a scatter-plot showing pair-wide comparison between iPSC (ZKOS#2) and V6.5 ESC. Spots in color represent genes whose expression show statistically significant difference between samples (FDR=0.05, fold-change>2).

FIG. 17 depicts a list of primers used in the studies disclosed herein (SEQ ID NOs: 15-37).

FIG. 18 shows that iPSCs generated with Zscan4 are of high quality based on the karyotype and tetraploid complementation assay. FIG. 18A depicts a table of the results of a tetraploid complementation assay. FIG. 18B depicts images of karyotypes. FIG. 18C depicts images of live embryos derived from iPSC. Karyotype analysis of randomly selected iPSC lines clearly showed that iPSCs generated with Zscan4 were of higher quality than iPSCs generated without Zscan4. In addition, iPSCs generated with Zscan4 could form entire live embryos by the tetraploid complementation assay, which is the most stringent test for the pluripotency of iPS cells.

FIG. 19A depicts a schematic representation of procedures to examine Zscan4 expression during iPSC formation. TA1 ES cells, F1 hybrid strain (C57BL/6Jx129S6/SvEvTac). A piggyBac transfection involves a main vector PB-TET-MKOS (shown), PB-CAG-rtTA (a tetracycline transactivator), and pCyL43 (transposase). FIG. 19B depicts phase-contrast microscopic images during the formation of cell colonies with authentic ES-like morphology (denoted MOR+). Day 0 is set when doxycycline (Dox) is added to the complete ES medium 24 hours after a piggyBac transfection. FIG. 19C depicts fluorescence images (left), fluorescence images merged with phase-contrast images (middle), and flow cytometry charts (right) of two representative cell clones established from MOR+ colonies and cultured in the absence of Dox. FIG. 19D depicts the appearance of EM+ cells (represented as "+") in the culture. Fraction of EM+ cells was measured by the flow cytometry on day 28.

FIG. 20A depicts nanog-immunohistochemistry on ESCs and MEFs. Nanog-immunohistochemistry with a DAB (3,3'-diaminobenzidine) reporter showed staining patterns comparable to Nanog-immunohistochemistry with an Alexa-fluorescence reporter: absence of Nanog in MEFs and presence of Nanog in ESCs. When Nanog is not used as one of the exogenous iPSC factors, the activation of Nanog expression has been used as an indication of reprogramming to authentic iPSCs. FIG. 20B depicts a comparison of scoring methods for reprogrammed cells by MKOS factors between MOR+ ALP+ phenotype and NANOG+ phenotype. Similar number of colonies was obtained by both methods, indicating that MOR+ ALP+ can be used to score iPSC colonies reprogrammed by MKOS factors on a piggyBac vector. MEFs (B6DBA1F1) plated on gelatin-coated 6-well plates at a density of 1×10⁵ cells/well were used. FIG. 20C depicts additional support for the generation of authentic iPSC colonies reprogrammed by the MKOS factors on a piggyBac vector from MEFs carrying a GFP reporter driven by the Oct4 promoter (Stemgent, USA). Images of three representative MOR+ colonies are shown. FIG. 20D depicts a comparison of scoring methods for reprogrammed cells by the ZMKOS factors between MOR+ ALP+ phenotype and NANOG+ phenotype. Similar number of colonies was obtained by both methods, indicating that MOR+ ALP+ can be used to score iPSC colonies reprogrammed by ZMKOS factors on piggyBac vectors. MEFs (B6DBA1F1) plated on gelatin-coated 6-well plates at a density of 1×10⁵ cells/well were used. FIG. 20E depicts additional support for the generation of authentic iPSC colonies reprogrammed by ZMKOS factors on piggyBac vectors from MEFs carrying a GFP reporter driven by the Oct4 promoter (Stemgent, USA). Images of three representative MOR+ colonies are shown.

FIG. 22A depicts a bar graph showing increased iPS colony formation from mouse embryonic fibroblast (MEF) by Zscan4c, Patl2 and Pramel6. FIG. 22B depicts a bar graph showing increased iPS colony formation from MEF by Piwil2. FIG. 22C depicts a bar graph showing increased iPS colony formation from MEF by Zscan4c, Patl2 and D5Ertd577e. The efficiency of iPS colony formation was scored based on their authentic ES cell morphology and alkaline phosphatase (ALP) staining 14 days after transfection (mean±S.E.M.). The experiments were performed in triplicate. Different letters (a or b) denote significant differences between groups (P<0.05).

SEQUENCE LISTING

Figure 1:
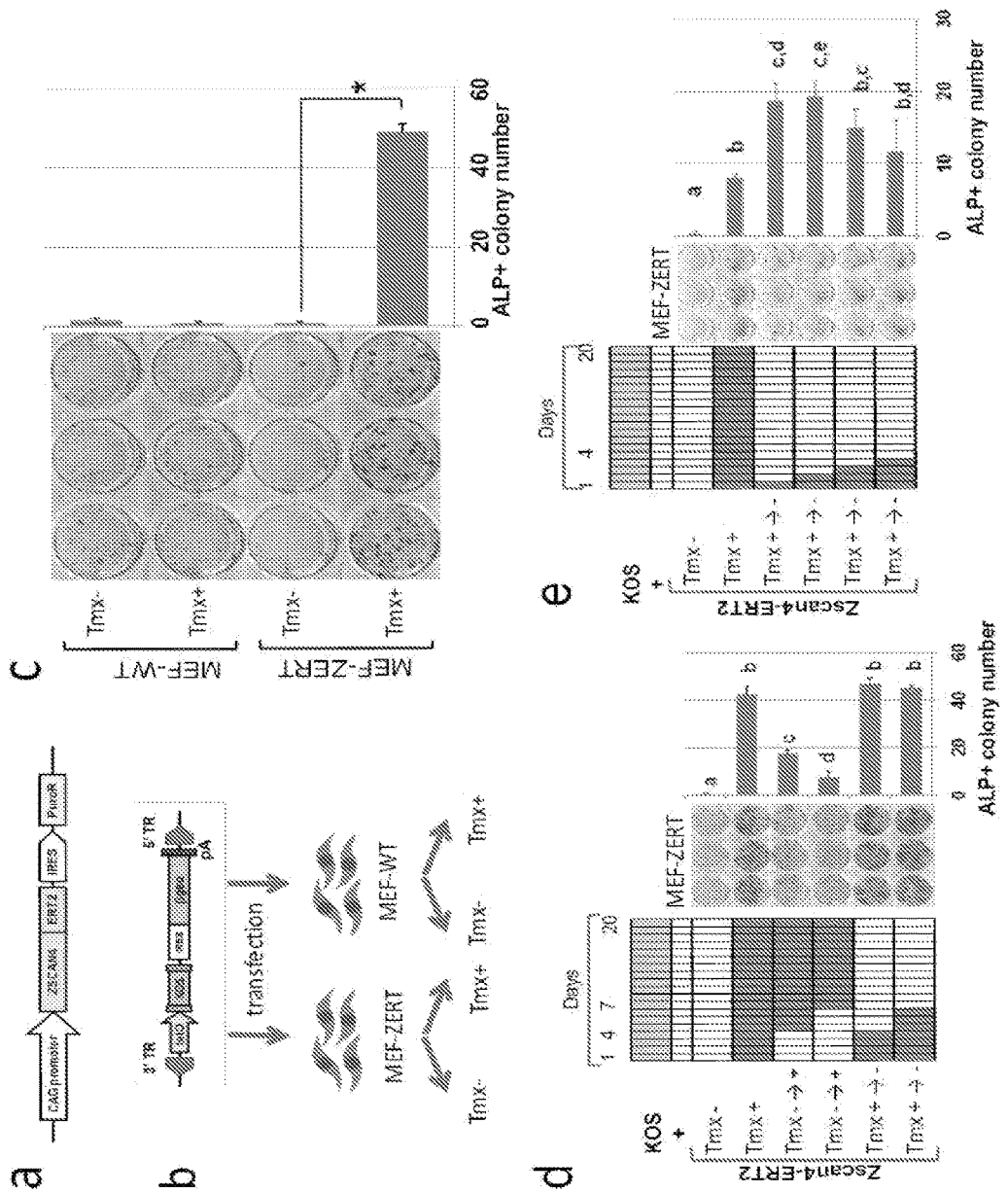
FIG. 1 shows that Zscan4 enhances iPSC formation without Myc.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Aug. 26, 2011, 212 KB, which is incorporated by reference herein. In the accompanying sequence listing:

SEQ ID NOs: 1 and 2 are nucleotide and amino acid sequences of human ZSCAN4.

SEQ ID NOs: 3 and 4 are nucleotide and amino acid sequences of mouse Zscan4a.

SEQ ID NOs: 5 and 6 are nucleotide and amino acid sequences of mouse Zscan4b.

SEQ ID NOs: 7 and 8 are nucleotide and amino acid sequences of mouse Zscan4c.

SEQ ID NOs: 9 and 10 are nucleotide and amino acid sequences of mouse Zscan4d.

SEQ ID NOs: 11 and 12 are nucleotide and amino acid sequences of mouse Zscan4e.

SEQ ID NOs: 13 and 14 are nucleotide and amino acid sequences of mouse Zscan4f.

SEQ ID NOs: 15-37 are primer sequences.

SEQ ID NOs: 38 and 39 are the nucleotide and amino acid sequences of mouse Patl2 (GenBank Accession No. NM_026251).

SEQ ID NOs: 40 and 41 are the nucleotide and amino acid sequences of mouse Pramel6 (GenBank Accession No. NM_178249).

SEQ ID NOs: 42 and 43 are the nucleotide and amino acid sequences of mouse Piwil2 (GenBank Accession No. NM_021308).

SEQ ID NOs: 44 and 45 are the nucleotide and amino acid sequences of mouse D5Ertd577e (GenBank Accession No. NM_177187).

SEQ ID NOs: 46 and 47 are the nucleotide and amino acid sequences of human Patl2 respectively (GenBank Accession No. NM_001145112).

SEQ ID NOs: 48 and 49 are the nucleotide and amino acid sequences of human Piwil2 (GenBank Accession No. NM_001135721).

SEQ ID NO: 50 is the nucleotide sequence of human PRAMEF1 (GenBank Accession No. NM_023013).

SEQ ID NO: 51 is the nucleotide sequence of human PRAMF12 (GenBank Accession No. NM_001080830).

SEQ ID NO: 52 is the nucleotide sequence of human PRAMEF2 (GenBank Accession No. NM_023014).

SEQ ID NO: 53 is the nucleotide sequence of human PRAMEF15 (GenBank Accession No. NM_001098376).

SEQ ID NO: 54 is the nucleotide sequence of human PRAMEF8 (GenBank Accession No. NM_001012276).

SEQ ID NO: 55 is the nucleotide sequence of human PRAMEF10 (GenBank Accession No. NM_001039361).

SEQ ID NO: 56 is the nucleotide sequence of human PRAMEF20 (GenBank Accession No. NM_001099852).

SEQ ID NO: 57 is the nucleotide sequence of human PRAMEF17 (GenBank Accession No. NM_001099851).

SEQ ID NO: 58 is the nucleotide sequence of human PRAMEF19 (GenBank Accession No. NM_001099790).

SEQ ID NO: 59 is the nucleotide sequence of human PRAMEF14 (GenBank Accession No. NM_001099854).

SEQ ID NO: 60 is the nucleotide sequence of human PRAMEF21 (GenBank Accession No. NM_001100114).

SEQ ID NO: 61 is the nucleotide sequence of human PRAMEF16 (GenBank Accession No. NM_001045480).

SEQ ID NO: 62 is the nucleotide sequence of human PRAMEF18 (GenBank Accession No. NM_001099850).

SEQ ID NO: 63 is the nucleotide sequence of human PRAMEF13 (GenBank Accession No. NM_001024661).

SEQ ID NO: 64 is the nucleotide sequence of human PRAMEF9 (GenBank Accession No. NM_001010890).

SEQ ID NO: 65 is the nucleotide sequence of human PRAMEF5 (GenBank Accession No. NM_001013407).

SEQ ID NO: 66 is the nucleotide sequence of human PRAMEF3 (GenBank Accession No. NM_001013692).

SEQ ID NO: 67 is the nucleotide sequence of human PRAMEF22 (GenBank Accession No. NM_001100631).

SEQ ID NO: 68 is the nucleotide sequence of human PRAMEF7 (GenBank Accession No. NM_001012277).

SEQ ID NO: 69 is the nucleotide sequence of human PRAMEF11 (GenBank Accession No. NM_001146344).

SEQ ID NO: 70 is the nucleotide sequence of human PRAME (Ensembl: WI2-2994D6.2; ENSG00000229571).

SEQ ID NO: 71 is the nucleotide sequence of human PRAMEF6 (GenBank Accession No. NM_001010889).

SEQ ID NO: 72 is the nucleotide sequence of human PRAMEF4 (GenBank Accession No. NM_001009611).

SEQ ID NO: 73 is the nucleotide sequence of the Zscan4-Emerald expression vector (9396 bp). The starting nucleotide of the Zscan4c promoter sequence is 906 and the ending nucleotide is 4468.

DETAILED DESCRIPTION

I. Abbreviations

ALP alkaline phosphatase
D5Ertd577e DNA segment, Chr 5, ERATO Doi 577, expressed
Dox doxycycline
ES embryonic
hCG human chorionic gonadotropin
iPS induced pluripotent stem
iPSC induced pluripotent stem cell
IRES internal ribosomal entry site
KOS Klf4, Oct4, Sox2
LIF leukemia inhibitory factor
MEF murine embryonic fibroblast
MKOS Myc, Klf4, Oct4, Sox2
NT nuclear transplantation
ORF open reading frame
Patl2 protein associated with topoisomerase II homolog 2
PCR polymerase chain reaction
Piwil2 piwi-like homolog 2
PMSG pregnant mare serum gonadotropin
PRAME preferentially expressed antigen in melanoma
Pramel6 preferentially expressed antigen in melanoma like 6
qPCR quantitative PCR
RT-PCR reverse transcriptase PCR
Tmx Tamoxifen
WT wild type
ZKOS Zscan4, Klf4, Oct4, Sox2
Zscan4 zinc finger and scan domain-containing protein 4

II. Terms and Methods

Unless otherwise noted, technical terms are used according to conventional usage. Definitions of common terms in molecular biology may be found in Benjamin Lewin, *Genes V,* published by Oxford University Press, 1994 (ISBN 0-19-854287-9); Kendrew et al. (eds.), *The Encyclopedia of Molecular Biology,* published by Blackwell Science Ltd., 1994 (ISBN 0-632-02182-9); and Robert A. Meyers (ed.),

*Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Agent: Any protein, nucleic acid molecule, compound, small molecule, organic compound, inorganic compound, or other molecule of interest. In some embodiments, the "agent" is any agent that increases expression of Zscan4. In particular examples, the agent is a retinoid or an agent that induces oxidative stress.

c-Myc: A transcription factor that plays a role in cell cycle progression, apoptosis and cellular transformation, and has been previously reported to function as a reprogramming factor. Nucleic acid and protein sequences of c-Myc for a number of different species are known in the art. For example, mouse c-Myc nucleic acid and protein sequences include GenBank accession numbers NM_010849 and NP_034979, respectively; and human c-Myc nucleic acid and protein sequences include GenBank accession numbers NM_002467 and NP_002458, respectively. c-Myc is also known as v-myc myelocytomatosis viral oncogene homolog, MYC and myelocytomatosis oncogene.

Cell-penetrating peptide (CPP): A type of polypeptide that facilitates transduction of proteins, nucleic acids or other compounds across membranes in a receptor-independent manner (Wadia and Dowdy, *Curr Protein Pept Sci* 4(2):97-104, 2003). Typically, CPPs are short polycationic sequences that can facilitate cellular uptake of compounds to which they are linked into endosomes of cells. Examples of CPPs include poly-arginine tags and protein transduction domains (such as HIV-1 Tat).

Contacting: Placement in direct physical association; includes both in solid and liquid form. As used herein, "contacting" is used interchangeably with "exposed." In some cases, "contacting" includes transfecting, such as transfecting a nucleic acid molecule into a cell.

Degenerate variant: A polynucleotide encoding a polypeptide, such as a Zscan4 polypeptide, that includes a sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged.

Differentiation: Refers to the process by which a cell develops into a specific type of cell (for example, muscle cell, skin cell etc.). Differentiation of pluripotent stem cells refers to the development of the cells toward a specific cell lineage. As a cell becomes more differentiated, the cell loses potency, or the ability to become multiple different cell types.

DNA segment, Chr 5, ERATO Doi 577, expressed (D5Ertd577e): A gene located on chromosome 5 of the mouse genome. Nucleotide and amino acid sequences of D5Ertd577e are available, such as in the NCBI database under Gene ID 320549. Exemplary mRNA and protein sequences are provided herein as SEQ ID NOs: 44 and 45, respectively (GenBank Accession No. NM_177187). Predicted human orthologs of D5Ertd577e include members of the preferentially expressed antigen in melanoma family (PRAMEF), for example PRAMEF1, PRAMF12, PRAMEF2, PRAMEF15, PRAMEF8, PRAMEF10, PRAMEF20, PRAMEF17, PRAMEF19, PRAMEF14, PRAMEF21, PRAMEF16, PRAMEF18, PRAMEF13, PRAMEF9, PRAMEF5, PRAMEF3, PRAMEF22, PRAMEF7, PRAMEF11, WI2-2994D6.2, PRAMEF6 and PRAMEF4 (nucleotide sequences for each of the orthologs is set forth herein as SEQ ID NOs: 50-72).

Encapsulated: As used herein, a molecule "encapsulated" in a nanoparticle refers to a molecule (such as a Zscan4 nucleic acid or protein) that is either contained within the nanoparticle or attached to the surface of the nanoparticle, or a combination thereof.

ERT2: A protein comprising a mutated ligand binding domain of the human estrogen receptor that does not bind its natural ligand (17β-estradiol) at physiological concentrations, but is highly sensitive to nanomolar concentrations of tamoxifen or its metabolite 4-hydroxytamoxifen (4OHT) (Feil et al., *Biochem Biophys Res Commun* 237(3):752-757, 1997).

Fusion protein: A protein containing at least a portion of two different (heterologous) proteins. In some examples such proteins are generated by expression of a nucleic acid sequence engineered from nucleic acid sequences encoding at least a portion of two different (heterologous) proteins. To create a fusion protein, the nucleic acid sequences must be in the same reading frame and contain no internal stop codons.

Heterologous: A heterologous polypeptide or polynucleotide refers to a polypeptide or polynucleotide derived from a different source or species.

Host cells: Cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used.

Introducing: In the context of the present disclosure, "introducing" a nucleic acid molecule or a protein into a cell encompasses any means of delivering the nucleic acid molecule or protein into the cell. For example, nucleic acid molecules can be transfected, transduced or electroporated into a cell. Delivery of proteins into cells can be achieved, for example, by fusing the protein to a cell-penetrating peptide, such as a peptide with a protein transduction domain (such as HIV-1 Tat), or a poly-arginine peptide tag (Fuchs and Raines, *Protein Science* 14:1538-1544, 2005).

Induced pluripotent stem (iPS) cells: A type of pluripotent stem cell artificially derived from a non-pluripotent cell, such as an adult somatic cell, by inducing a "forced" expression of certain transcription factor genes (generally referred to in the art as "reprogramming factors," "nuclear reprogramming factors," or "somatic cell reprogramming factors"). iPS cells can be derived from any organism, such as a mammal. In some embodiments, iPS cells are produced from mice, rats, rabbits, guinea pigs, goats, pigs, cows, non-human primates or humans. Human and murine derived iPS cells are exemplary.

iPS cells are similar to ES cells in many respects, such as the expression of certain stem cell genes and proteins, chromatin methylation patterns, doubling time, embryoid body formation, teratoma formation, viable chimera formation, and potency and differentiability. Methods for producing iPS cells are known in the art (exemplary methods are discussed below in section V). For example, iPS cells are typically derived by delivery of certain stem cell-associated genes (such as Oct-3/4 (Pouf51) and Sox2) into non-pluripotent cells, such as adult fibroblasts. Delivery can be achieved through viral vectors, such as retroviruses, lentiviruses, or adenoviruses; transfection of plasmid vectors; or delivery of reprogramming factor mRNA or protein. For example, cells can be transfected with Oct3/4, Sox2, Klf4, and c-Myc using a retroviral system or with OCT4, SOX2, NANOG, and LIN28 using a lentiviral system. After 3-4 weeks, small numbers of transfected cells begin to become morphologically and biochemically similar to pluripotent stem cells, and are typically isolated through morphological selection, doubling time, or through a reporter gene and antibiotic selection. Methods of producing iPS cells from adult human cells have been previously described (see for example, Yu et al., *Science* 318(5854):1224, 2007; Takahashi et al., *Cell* 131(5):861-72, 2007; U.S. Patent Application Publication Nos. 2008/0280362, 2009/0068742, 2009/0227032, 2009/0047263 and 20100279404).

Isolated: An isolated nucleic acid has been substantially separated or purified away from other nucleic acid sequences and from the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids. Similarly, "isolated" proteins have been substantially separated or purified from other proteins of the cells of an organism in which the protein naturally occurs, and encompasses proteins prepared by recombination expression in a host cell as well as chemically synthesized proteins. Similarly, "isolated" cells have been substantially separated away from other cell types.

Klf4: A transcription factor previously reported to function as a reprogramming factor. Nucleic acid and protein sequences of Klf4 for a number of different species are known in the art. For example, mouse Klf4 nucleic acid and protein sequences include GenBank accession numbers NM_010637 and NP_034767, respectively; and human Klf4 nucleic acid and protein sequences include GenBank accession numbers NM_004235 and NP_004226, respectively. Klf4 is also known as kruppel-like factor 4.

Lin28: A transcription factor previously reported to function as a reprogramming factor. Nucleic acid and protein sequences of Lin28 for a number of different species are known in the art. For example, mouse Lin28 nucleic acid and protein sequences include GenBank accession numbers NM_145833 and NP_665832, respectively; and human Lin28 nucleic acid and protein sequences include GenBank accession numbers NM_024674 and NP_078950, respectively. Lin28 is also known as lin-28 homolog A (LIN28A) and Lin-28.

Linker: One or more nucleotides or amino acids that serve as a spacer between two molecules, such as between two nucleic acid molecules or two peptides (such as in a fusion protein). In some examples a linker is 1 to 100 amino acids, such as 1 to 50 or 5 to 10 amino acids.

Nanog: A transcription factor previously reported to function as a reprogramming factor. Nucleic acid and protein sequences of Nanog for a number of different species are known in the art. For example, mouse Nanog nucleic acid and protein sequences include GenBank accession numbers NM_028016 and NP_082292, respectively; and human Nanog nucleic acid and protein sequences include GenBank accession numbers NM_024865 and NP_079141, respectively. Nanog is also known as Nanog homeobox.

Nanoparticle: A particle less than about 1000 nanometers (nm) in diameter. Exemplary nanoparticles for use with the methods provided herein are made of biocompatible and biodegradable polymeric materials. In some embodiments, the nanoparticles are PLGA nanoparticles. As used herein, a "polymeric nanoparticle" is a nanoparticle made up of repeating subunits of a particular substance or substances. "Poly(lactic acid) nanoparticles" are nanoparticles having repeated lactic acid subunits. Similarly, "poly(glycolic acid) nanoparticles" are nanoparticles having repeated glycolic acid subunits.

Non-human animal: Includes all animals other than humans. A non-human animal includes, but is not limited to, a non-human primate, a farm animal such as swine, cattle, and poultry, a sport animal or pet such as dogs, cats, horses, hamsters, rodents, such as mice, or a zoo animal such as lions, tigers or bears. In one example, the non-human animal is a mouse.

Oct4: A transcription factor that plays a role in embryonic development, especially during early embryogenesis. Oct4 is necessary for embryonic stem cell potency and has been previously reported to function as a reprogramming factor. Nucleic acid and protein sequences of Oct4 for a number of different species are known in the art. For example, mouse Oct4 nucleic acid and protein sequences include GenBank accession numbers NM_013633 and NP_038661, respectively; and human Oct nucleic acid and protein sequences include GenBank accession numbers NM_002701 and NP_002692, respectively. Oct4 is also known as POU domain class 5 transcription factor 1 (Pou5f1), Oct3 and Oct3/4.

Operably linked: A first nucleic acid sequence is operably linked to a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and where necessary to join two protein coding regions, in the same reading frame.

Piwi-like homolog 2 (Piwil2): A gene belonging to the Argonaute family of proteins, which function in development and maintenance of germline stem cells. Nucleotide and amino acid sequences of Piwil2 are available, such as in the NCBI database under Gene ID 57746 (mouse) and Gene ID 55124 (human). Exemplary mouse mRNA and protein sequences are provided herein as SEQ ID NOs: 42 and 43, respectively (GenBank Accession No. NM_021308). Exemplary human mRNA and protein sequences are provided herein as SEQ ID NOs: 48 and 49, respectively (GenBank Accession No. NM_001135721).

Pluripotent/pluripotency: A "pluripotent" cell is a cell that can form all of an organism's cell lineages (endoderm, mesoderm and ectoderm), including germ cells. Pluripotent cells can give rise to any fetal or adult cell type, but cannot form an entire organism autonomously due to the inability to form extraembryonic tissue (such as placenta).

Poly-arginine peptide tag: A short peptide (generally 7 to 11 residues) comprised of arginine residues that facilitates delivery of larger molecules (such as proteins and nucleic acid molecules) into cells (see, for example, Fuchs and Raines, *Protein Science* 14:1538-1544, 2005).

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide, such as a Zscan4. Biologically functional fragments, for example, can vary in size from a polypeptide fragment as small as an epitope capable of binding an antibody molecule to a large polypeptide capable of participating in the characteristic induction or programming of phenotypic changes within a cell, including affecting cell proliferation or differentiation. An "epitope" is a region of a polypeptide capable of binding an immunoglobulin generated in response to contact with an antigen. Thus, smaller peptides containing the biological activity of Zscan4, or conservative variants of Zscan4, are thus included as being of use.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Examples of conservative substitutions are shown below:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, should be minimized in order to preserve the functional and immunologic identity of the encoded protein. Thus, in several non-limiting examples, a Zscan4 polypeptide includes at most two, at most five, at most ten, at most twenty, or at most fifty conservative substitutions. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide.

Preferentially expressed antigen in melanoma like 6 (Pramel6): A gene located on chromosome 2 of the mouse genome. Nucleotide and amino acid sequences of Pramel6 are available, such as in the NCBI database under Gene ID 347711. Exemplary mRNA and protein sequences are provided herein as SEQ ID NOs: 40 and 41, respectively (GenBank Accession No. NM_178249). Predicted human orthologs of Pramel6 include members of the preferentially expressed antigen in melanoma family (PRAMEF), for example PRAMEF1, PRAMF12, PRAMEF2, PRAMEF15, PRAMEF8, PRAMEF10, PRAMEF20, PRAMEF17, PRAMEF19, PRAMEF14, PRAMEF21, PRAMEF16, PRAMEF18, PRAMEF13, PRAMEF9, PRAMEF5, PRAMEF3, PRAMEF22, PRAMEF7, PRAMEF11, WI2-2994D6.2, PRAMEF6 and PRAMEF4 (nucleotide sequences for each of the orthologs is set forth herein as SEQ ID NOs: 50-72).

Progenitor cells: Oligopotent or unipotent cells that differentiate into a specific type of cell or cell lineage. Progenitor cells are similar to stem cells but are more differentiated and exhibit limited self renewal.

Promoter: Nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor).

Protein associated with topoisomerase II homolog 2 (Patl2): A gene conserved in human, mouse, chimpanzee, dog, cow, chicken and zebrafish. Nucleotide and amino acid sequences of Patl2 are available, such as in the NCBI database under Gene ID 67578 (mouse) and Gene ID 197135 (human). Exemplary mouse mRNA and protein sequences are provided herein as SEQ ID NOs: 38 and 39, respectively (GenBank Accession No. NM_026251). Exemplary human mRNA and protein sequences are provided herein as SEQ ID NOs: 46 and 47, respectively (GenBank Accession No. NM_001145112).

Protein transduction domains: Small cationic peptides that facilitate entry of larger molecules (proteins, nucleic acid molecules etc.) into a cell by a mechanism that is independent of classical endocytosis.

Recombinant: A recombinant nucleic acid or polypeptide is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Reprogramming: In the context of the present disclosure, "reprogramming" a somatic cell refers to the process of converting a partially or fully differentiated somatic cell into a pluripotent cell (i.e., an iPS cell). Because reprogrammed somatic cells possess ES cell-like properties, it is believed that iPS cells can replace ES cells in a number of regenerative medicine applications.

Reprogramming factor: A gene or gene product that when exogenously expressed or introduced into a somatic cell is capable of promoting a pluripotent state. A number of reprogramming factors have been described in the art including, but not limited to, c-Myc, Klf4. Oct4, Sox2, Lin28 and Nanog. Although c-Myc, Klf4, Oct4, Sox2, Lin28 and Nanog are currently the most commonly used reprogramming factors, the term also encompasses other genes and gene products with the same functional effect of promoting the pluripotent state. For example, in some cases, Sox1, Sox3, L-myc, N-myc, and Klf2 can be used as reprogramming factors. Reprogramming factors are also referred to in the art as "nuclear reprogramming factors," "somatic cell reprogramming factors" and "pluripotency genes."

Retinoids: A class of chemical compounds that are related chemically to vitamin A. Retinoids are used in medicine, primarily due to the way they regulate epithelial cell growth. Retinoids have many important and diverse functions throughout the body including roles in vision, regulation of cell proliferation and differentiation, growth of bone tissue, immune function, and activation of tumor suppressor genes. Examples of retinoids include, but are not limited to, all-trans retinoic acid (atRA), 9-cis retinoic acid (9-cis RA), 13-cis RA and vitamin A (retinol).

Quality of an iPS cell: As used herein, an iPS cell of high quality refers to an iPS cell having a normal karyotype and/or possessing the ability to form a live embryo (such as in a tetraploid complementation assay). High quality iPS cells are highly pluripotent.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

Somatic cell: Any cell of the body. In standard terminology, "somatic cell" generally excludes germ cells. However, in the context of the present disclosure, the "somatic cell" that can be used in the disclosed methods to produce an iPS cell is any cell, including germ cells present during development and early embryonic cells. In some embodiments, the somatic cell is a tissue stem cell, progenitor cell or differentiated cell. Fibroblasts (including embryonic fibroblasts, adult fibroblasts and cardiac fibroblasts) have commonly been used for generating iPS cells. However, a number of other cell types have been described, including oral mucosa, cord blood cells, lymphocytes (e.g., T cells and B cells), stromal cells, neural progenitor cells, adipose cells, keratinocytes, neural stem cells, meningiocytes, adipose stem cells, hepatocytes, gastric cells, pancreatic beta cells, peripheral blood cells, fetal hepatocytes, adipocytes and limbal cells (Parameswaran et al., *Stem Cells* 29(7):1013-1020, 2011; U.S. Patent Application Publication No. 2010/0279404). In some embodiments, the somatic cell is a neural stem cell, a hematopoietic stem cell, a mesenchymal stem cell, an adipose stem cell, a fibroblast, a lymphocyte (such as a T cell or B cell), a hepatocyte, an epithelial cell, a muscle cell, an adipose cell, a cardiomyocyte, a pancreatic β cell, a keratinocyte, an amniotic cell, a peripheral blood cell, a platelet, or an astrocyte.

Sox2: A transcription factor involved in the regulation of embryonic development and in the determination of cell fate. Sox 2 (sex determining region Y-box 2) has been previously reported to function as a reprogramming factor. Nucleic acid and protein sequences of Sox2 for a number of different species are known in the art. For example, mouse Sox2 nucleic acid and protein sequences include GenBank accession numbers NM_011443 and NP_035573, respectively; and human Sox2 nucleic acid and protein sequences include GenBank accession numbers NM_003106 and NP_003097, respectively.

Subject: Living multi-cellular vertebrate organisms, a category that includes human and non-human mammals.

Tissue stem cell: Undifferentiated cells found throughout the body after embryonic development that multiply by cell division to replenish dying cells and regenerate damaged tissues. Tissue stem cells are also known as somatic stem cells or adult stem cells.

Transfecting or transfection: Refers to the process of introducing nucleic acid into a cell or tissue. Transfection can be achieved by any one of a number of methods, such as, but not limited to, liposomal-mediated transfection, electroporation and injection.

Vector: A nucleic acid molecule as introduced into a host cell, thereby producing a transformed host cell. A vector may include nucleic acid sequences that permit it to replicate in a host cell, such as an origin of replication (DNA sequences that participate in initiating DNA synthesis). For example, an expression vector contains the necessary regulatory sequences to allow transcription and translation of inserted gene or genes. A vector may also include one or more selectable marker genes and other genetic elements known in the art. Vectors include, for example, virus vectors and plasmid vectors.

Zscan4: A group of genes that have previously been identified as exhibiting 2-cell-specific expression and ES cell-specific expression (PCT Publication No. WO 2008/118957) and have been shown to promote telomere elongation and genome stability (Zalzman et al., *Nature* 464(7290): 858-863, 2010; PCT Publication No. WO 2011/028880). In the context of the present disclosure, "Zscan4" includes both human ZSCAN4 and mouse Zscan4. In the mouse, the term "Zscan4" refers to a collection of genes including three pseudogenes (Zscan4-ps1, Zscan4-ps2 and Zscan4-ps3) and six expressed genes (Zscan4a, Zscan4b, Zscan4c, Zscan4d, Zscan4e and Zscan4f). Among the six paralogs, the open reading frames of Zscan4c, Zscan4d, and Zscan4f encode a SCAN domain as well as all four zinc finger domains, suggesting their potential role as transcription factors. Zscan4 refers to Zscan4 polypeptides and Zscan4 polynucleotides encoding the Zscan4 polypeptides. Exemplary Zscan4 sequences are set forth herein as SEQ ID NOs: 1-14, and are disclosed in PCT Publication Nos. WO 2008/118957 and WO 2011/028880, which are herein incorporated by reference.

Zscan4-dependent gene: A gene whose expression is regulated by Zscan4. In some embodiments of the present disclosure, a Zscan4-dependent gene refers to any of the 231 genes (listed in Table 1) that were identified as upregulated during the early phase (day 1-day 6) of iPSC formation in a Zscan4-dependent manner (see Example 1 below). In particular examples, the Zscan4-dependent gene is Patl2, Pramel6, Piwil2 or D5Ertd577e. In non-limiting examples, the Zscan4-dependent gene is mouse Patl2, mouse Pramel6, mouse Piwil2 or mouse D5Ertd577e; or human PATL2 or human PIWIL2; or a human ortholog of mouse Pramel6 or mouse D5Ertd577e (such as a member of the PRAME family).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Reprogramming of somatic cells by nuclear transplantation (NT) occurs within a few cell divisions (Egli et al., Curr Biol 19:1403-1409, 2009), whereas reprogramming of somatic cells into induced pluripotent stem (iPS) cells by the forced expression of four factors, Myc, Klf4, Oct4, and Sox2 (MKOS) requires about 3 weeks (Takahashi and Yamanaka, Cell 126:663-676, 2006; Hanna et al., Cell 143:508-525, 2010; Stadtfeld and Hochedlinger, Genes Dev 24:2239-2263, 2010; Gonzalez et al., Nat Rev Genet 12:231-242, 2011), with their continuous application for at least the first 8-10 days (Wernig et al., Nat Biotechnol 26:916-924, 2008; Plath and Lowry, Nat Rev Genet 12:253-265, 2011). Although a requirement for additional embryonic factors present in the NT environment has been suggested for the efficient formation of iPS cells (Hanna et al., Nature 462:595-601, 2009), no such factors have been reported yet. Previously, it was shown that Zscan4, expressed specifically in 2-cell embryos and only about 5% of ES cells at a given time (Falco et al., Dev Biol 307:539-550, 2007), acts critically in the formation of proper blastocysts (Falco et al., Dev Biol 307:539-550, 2007) and in the maintenance of genome stability and telomeres in ES cells (Zalzman et al., Nature 464:858-863, 2010). It is disclosed herein that Zscan4 can replace oncogenic Myc and produce a comparable number of iPSC colonies from mouse embryo fibroblasts (MEFs) when coexpressed with Klf4, Oct4, and Sox2.

Furthermore, unlike other factors, Zscan4 was required only for the initial day during the formation of iPSCs. Global expression profiling of iPSC-derived, homogeneously-inducible secondary MEFs revealed that a small difference in the transcriptome caused by the overexpression of Zscan4 determines whether MEFs become iPS cells. Though few in number, many of these upregulated genes exhibit preimplantation embryo-specific expression. Without Klf4, Oct4, and Sox2, the overexpression of Zscan4 did not itself convert MEFs to iPSCs, but it reduced the proliferation of MEFs and caused partial but rapid DNA demethylation on the promoters of Oct4. It is further disclosed herein that at least four of the identified Zscan4-dependent genes also are capable of promoting iPSC formation when co-expressed with MKOS factors.

Taken together, the studies disclosed herein have established that Zscan4 is a previously unidentified transiently acting natural factor that facilitates the reprogramming process. The Zscan4-mediated reprogramming process recapitulates at least a part of NT-mediated reprogramming process through the reactivation of the early embryonic program.

IV. Overview of Several Embodiments

Disclosed herein is the finding that Zscan4 initiates direct reprogramming of somatic cells by reactivating early embryonic genes. In particular, it is disclosed that forced expression of Zscan4 in somatic cells, along with other previously described reprogramming factors, leads to the efficient production of high quality iPS cells. It is further disclosed herein that forced expression of any of the Zscan4-dependent genes Patl2, Pramel6, Piwil2 and D5Ertd577e, in combination with previously described reprogramming factors, promotes formation of iPS colonies.

Provided herein is an ex vivo method of producing an iPS cell by reprogramming of a somatic cell. The method includes contacting the somatic cell with a Zscan4 or a Zscan4-dependent gene and at least one reprogramming factor, thereby producing an iPS cell. In some embodiments, the Zscan4-dependent gene is selected from the genes listed in Table 1. In specific non-limiting embodiments, the Zscan4dependent gene is selected from Patl2, Pramel6, Piwil2 and D5Ertd577e. In some embodiments, the method includes contacting the somatic cell with at least two, at least three, or at least four reprogramming factors. Reprogramming factors (also known in the art as somatic cell reprogramming factors, nuclear reprogramming factors, pluripotency genes or stem cell-associated genes) have been described in the art and appropriate reprogramming factors can be selected by one of skill. In particular examples, the at least one, at least two, at least three or at least four reprogramming factors are selected from c-Myc, Klf4. Oct4, Sox2, Lin28 and Nanog. In some cases, the reprogramming factors include one or more of Sox 1, Sox3, L-myc, N-myc or Klf2. For example, Sox 1 and Sox3 may be used to replace Sox2; L-myc or N-myc may be used to replace c-Myc; and/or Klf2 may be used to replace Klf4.

In several non-limiting examples, the somatic cell is contacted with two, three or four reprogramming factors, wherein (i) the four reprogramming factors are c-Myc, Klf4. Oct4 and Sox2; (ii) the four reprogramming factors are Lin28, Nanog, Oct4 and Sox2; (iii) the three reprogramming factors are Klf4, Oct4 and Sox2; or (iv) the two reprogramming factors are Oct4 and Sox2.

Zscan4, the Zscan4-dependent gene(s) and the reprogramming factor(s) can be introduced to the somatic cell using any suitable method known in the art that results in delivery of the Zscan4 or Zscan4-dependent gene(s) and the reprogramming factor(s) into the cell. The method of delivery of the Zscan4 and/or Zscan4-dependent gene(s) need not be the same method used for delivery of the reprogramming factor(s). In some embodiments, contacting the somatic cell with a Zscan4 comprises introducing a nucleic acid molecule encoding a Zscan4 protein into the somatic cell. In some embodiments, contacting the somatic cell with a Zscan4-dependent gene comprises introducing a nucleic acid molecule encoding a Zscan4-dependent gene protein into the somatic cell. In some embodiments, contacting the somatic cell with at least one reprogramming factor comprises introducing a nucleic acid molecule encoding at least one reprogramming factor protein into the somatic cell.

For embodiments in which at least two reprogramming factors are contacted with the somatic cell by introducing a nucleic acid molecule encoding the reprogramming factors, the reprogramming factors can be delivered using a single nucleic acid molecule (such as a single viral vector or plasmid containing the nucleic acid molecule) or as separate nucleic acid molecules (such as a separate vector or plasmid for each reprogramming factor). Similarly, the Zscan4 nucleic acid molecule, or Zscan4-dependent gene nucleic acid molecule, can be delivered to the somatic cell as a separate nucleic acid molecule or can be included with the nucleic acid molecule encoding the reprogramming factor(s).

In some embodiments, the nucleic acid molecule encoding the Zscan4 or Zscan4-dependent gene, and/or the nucleic acid molecule encoding the at least one reprogramming factor, comprises a viral vector. Exemplary viral vectors include, but are not limited to retrovirus vectors, lentivirus vectors and adenovirus vectors. However, the choice of viral vector may vary depending upon, for example, the type of somatic cell to be used and the particular application for which the iPS cell will be used. One of skill in the art is capable of selecting an appropriate viral vector for introduction of the Zscan4 or the Zscan4-dependent gene, and reprogramming factor(s).

In other embodiments, the nucleic acid molecule comprises a plasmid vector. In specific examples, the plasmid vector is an episomal plasmid vector capable of autonomous replication.

In some examples, the nucleic acid molecule introduced to the somatic cell is encapsulated in a nanoparticle.

In other embodiments, the nucleic acid molecule encoding the Zscan4, the Zscan4-dependent gene, or the at least one reprogramming factor comprises mRNA encoding the Zscan4 protein, the Zscan4-dependent gene protein or the reprogramming factor protein.

In some embodiments, contacting the somatic cell with a Zscan4 comprises introducing a Zscan4 protein into the somatic cell. In some embodiments, contacting the somatic cell with a Zscan4-dependent gene comprises introducing a Zscan4dependent gene protein into the somatic cell. In some embodiments, contacting the somatic cell with at least one reprogramming factor comprises introducing a reprogramming factor protein into the somatic cell. In some examples, the Zscan4 protein, Zscan4-dependent gene protein or reprogramming factor protein is encapsulated in a nanoparticle. In other examples, the Zscan4 protein, Zscan4dependent gene protein or reprogramming factor protein is fused to a cell-penetrating peptide (CPP). A number of different CPPs are known in the art, and are discussed in greater detail below.

In particular examples, the cell-penetrating peptide comprises a protein transduction domain, such as the human immunodeficiency virus (HIV) Tat protein. In other examples, the cell-penetrating peptide comprises a poly-arginine peptide tag. The poly-arginine tag can vary in size, but in some cases is about 7 to about 11 arginine residues.

Delivery of the Zscan4 or Zscan4-dependent gene and the reprogramming factor(s) (regardless of whether delivery includes delivery of a nucleic acid molecule, vector, mRNA or protein) can occur simultaneously or sequentially. In some embodiments, the Zscan4 or Zscan4-dependent gene is delivered prior to delivery of the at least one reprogramming factor. In addition, in some cases, depending on the method of delivery, the Zscan4 or Zscan4-dependent gene and/or the reprogramming factor(s) is delivered at least twice, at least three times or at least four times to allow for a sufficient duration of expression to permit induction of the pluripotent state. In some embodiments, the methods disclosed herein include continuous expression of the reprogramming factor(s) (or presence of the reprogramming factor(s) protein) for at least 3 days, at least 4 days, at least 5 days, at least 6 days, at least 7 days, at least 8 days, at least 9 days, or at least 10 days. In some embodiments, the method includes continuous expression of Zscan4 (or presence of the Zscan4 protein) for at least one day, at least two days or at least three days. In some embodiments, the method includes continuous expression of the Zscan4-dependent gene (or presence of the Zscan4dependent gene protein) for at least one day, at least two days or at least three days.

In some embodiments of the disclosed method, the somatic cell is a murine cell. In other embodiments, the somatic cell is a human cell.

The somatic cell used in the disclosed method can be any type of cell, including a tissue stem cell, a progenitor cell or a differentiated cell. In some embodiments, the tissue stem cell is a neural stem cell, a hematopoietic stem cell, a mesenchymal stem cell or an adipose stem cell. In some embodiments, the differentiated cell is a fibroblast, lymphocyte (such as a T cell or a B cell), hepatocyte, epithelial cell, muscle cell, adipose cell, cardiomyocyte, pancreatic β cell, keratinocyte, amniotic cell, peripheral blood cell, platelet, or astrocyte.

In some embodiments, the method comprises contacting the somatic cell with a Zscan4 and at least one reprogramming factor. In particular embodiments, the Zscan4 is murine Zscan4, such as Zscan4c, Zscan4d or Zscan4f. In some examples, the murine Zscan4 is Zscan4c. In specific non-limiting example, the Zscan4c amino acid sequence is at least 95% identical to SEQ ID NO: 8; the Zscan4c amino acid sequence comprises SEQ ID NO: 8; or the Zscan4c amino acid sequence consists of SEQ ID NO: 8. In some examples, the Zscan4c is encoded by a nucleotide sequence at least 95% identical to SEQ ID NO: 7; is encoded by a nucleotide sequence comprising SEQ ID NO: 7; or is encoded by a nucleotide sequence consisting of SEQ ID NO: 7.

In other embodiments, the Zscan4 is human ZSCAN4. In some examples, the ZSCAN4 amino acid sequence is at least 80%, at least 85%, at least 90%, at least 95%, at least 96%, at least 97%, at least 98% or at least 99% identical to SEQ ID NO: 2; the ZSCAN4 amino acid sequence comprises SEQ ID NO: 2; or the ZSCAN4 amino acid sequence consists of SEQ ID NO: 2. In some examples, ZSCAN4 is encoded by a nucleotide sequence at least 80%, at least 85%, at least 90%, at least 95%, at least 96%, at least 97%, at least 98% or at least 99% identical to SEQ ID NO: 1; ZSCAN4 is encoded by a nucleotide sequence comprising SEQ ID NO: 1; or ZSCAN4 is encoded by a nucleotide sequence consisting of SEQ ID NO: 1.

In some embodiments, the method includes contacting the somatic cell with a Patl2 and at least one reprogramming factor. In particular embodiments, the Patl2 is mouse Patl2. In some examples, the mouse Patl2 amino acid sequence is at least 80%, at least 85%, at least 90%, at least 95%, at least 96%, at least 97%, at least 98% or at least 99% identical to SEQ ID NO: 39; the Patl2 amino acid sequence comprises SEQ ID NO: 39; or the Patl2 amino acid sequence consists of SEQ ID NO: 39. In some examples, mouse Patl2 is encoded by a nucleotide sequence at least 80%, at least 85%, at least 90%, at least 95%, at least 96%, at least 97%, at least 98% or at least 99% identical to SEQ ID NO: 38; Patl2 is encoded by a nucleotide sequence comprising SEQ ID NO: 38; or Patl2 is encoded by a nucleotide sequence consisting of SEQ ID NO: 38.

In particular embodiments, the Patl2 is human Patl2. In some examples, the human Patl2 amino acid sequence is at least 80%, at least 85%, at least 90%, at least 95%, at least 96%, at least 97%, at least 98% or at least 99% identical to SEQ ID NO: 47; the Patl2 amino acid sequence comprises SEQ ID NO: 47; or the Patl2 amino acid sequence consists of SEQ ID NO: 47. In some examples, human Patl2 is encoded by a nucleotide sequence at least 80%, at least 85%, at least 90%, at least 95%, at least 96%, at least 97%, at least 98% or at least 99% identical to SEQ ID NO: 46; Patl2 is encoded by a nucleotide sequence comprising SEQ ID NO: 46; or Patl2 is encoded by a nucleotide sequence consisting of SEQ ID NO: 46.

In some embodiments, the method includes contacting the somatic cell with a Pramel6 and at least one reprogramming factor. In some examples, the Pramel6 amino acid sequence is at least 80%, at least 85%, at least 90%, at least 95%, at least 96%, at least 97%, at least 98% or at least 99% identical to SEQ ID NO: 41; the Pramel6 amino acid sequence comprises SEQ ID NO: 41; or the Pramel6 amino acid sequence consists of SEQ ID NO: 41. In some examples, Pramel6 is encoded by a nucleotide sequence at least 80%, at least 85%, at least 90%, at least 95%, at least 96%, at least 97%, at least 98% or at least 99% identical to SEQ ID NO: 40; Pramel6 is encoded by a nucleotide sequence comprising SEQ ID NO: 40; or Pramel6 is encoded by a nucleotide sequence consisting of SEQ ID NO: 40. In other examples, the Zscan4-dependent gene is a human ortholog of Pramel6. In particular examples, the human ortholog of Pramel6 is encoded by a nucleotide sequence at least 80%, at least 85%, at least 90%, at least 95%, at least 96%, at least 97%, at least 98% or at least 99% identical to any one of SEQ ID NOs: 50-72.

In some embodiments, the method includes contacting the somatic cell with a Piwil2 and at least one reprogramming factor. In particular embodiments, the Piwil2 is mouse Piwil2. In some examples, the mouse Piwil2 amino acid sequence is at least 80%, at least 85%, at least 90%, at least 95%, at least 96%, at least 97%, at least 98% or at least 99% identical to SEQ ID NO: 43; the Piwil2 amino acid sequence comprises SEQ ID NO: 43; or the Piwil2 amino acid sequence consists of SEQ ID NO: 43. In some examples, mouse Piwil2 is encoded by a nucleotide sequence at least 80%, at least 85%, at least 90%, at least 95%, at least 96%, at least 97%, at least 98% or at least 99% identical to SEQ ID NO: 42; Piwil2 is encoded by a nucleotide sequence comprising SEQ ID NO: 42; or Piwil2 is encoded by a nucleotide sequence consisting of SEQ ID NO: 42.

In particular embodiments, the Piwil2 is human Piwil2. In some examples, the human Piwil2 amino acid sequence is at least 80%, at least 85%, at least 90%, at least 95%, at least 96%, at least 97%, at least 98% or at least 99% identical to SEQ ID NO: 49; the Piwil2 amino acid sequence comprises SEQ ID NO: 49; or the Piwil2 amino acid sequence consists of SEQ ID NO: 49. In some examples, human Piwil2 is encoded by a nucleotide sequence at least 80%, at least 85%, at least 90%, at least 95%, at least 96%, at least 97%, at least 98% or at least 99% identical to SEQ ID NO: 48; Piwil2 is encoded by a nucleotide sequence comprising SEQ ID NO: 48; or Piwil2 is encoded by a nucleotide sequence consisting of SEQ ID NO: 48.

In some embodiments, the method comprises contacting the somatic cell with a D5Ertd577e and at least one reprogramming factor. In some examples, the D5Ertd577e amino acid sequence is at least 80%, at least 85%, at least 90%, at least 95%, at least 96%, at least 97%, at least 98% or at least 99% identical to SEQ ID NO: 45; the D5Ertd577e amino acid sequence comprises SEQ ID NO: 45; or the D5Ertd577e amino acid sequence consists of SEQ ID NO: 45. In some examples, D5Ertd577e is encoded by a nucleotide sequence at least 80%, at least 85%, at least 90%, at least 95%, at least 96%, at least 97%, at least 98% or at least 99% identical to SEQ ID NO: 44; D5Ertd577e is encoded by a nucleotide sequence comprising SEQ ID NO: 44; or D5Ertd577e is encoded by a nucleotide sequence consisting of SEQ ID NO: 44. In other examples, the Zscan4-dependent gene is a human ortholog of D5Ertd577e. In particular examples, the human ortholog of D5Ertd577e is encoded by a nucleotide sequence at least 80%, at least 85%, at least 90%, at least 95%, at least 96%, at least 97%, at least 98% or at least 99% identical to any one of SEQ ID NOs: 50-72.

In alternative embodiments, the method includes contacting the somatic cell with an agent that increases expression of endogenous Zscan4 and contacting the cell with at least one reprogramming factor, thereby producing an iPS cell. It has previously been demonstrated that retinoids and oxidative stress increase transient expression of Zscan4 (see, PCT Publication No. WO 2011/028880). Thus, in particular examples, the agent is a retinoid, such as, but not limited to, all-trans retinoic acid, 9-cis retinoic acid, 13-cis retinoic acid and vitamin A. In other examples, the agent induces oxidative stress.

Further provided herein are isolated iPS cells produced according to the methods disclosed herein. Also provided are non-human animals (such as mice) produced from an iPS cell generated according to the disclosed methods.

The isolated iPS cells produced by the disclosed methods can be used for a variety of research and therapeutic purposes. For example, the iPS cells can be used in any regenerative medicine application as a replacement for ES cells or other stem cells. The number of iPS cells to be used and the mode of administration will vary depending upon the particular disease or disorder to be treated. In particular examples, about $1 \times 10^6$, about $2 \times 10^6$ or about $2 \times 10^6$ cells are injected. The iPS cells can be used either in the pluripotent state, or the cells can be differentiated to produce the desired cell type (such as neurons, muscle cells or cells of a particular organ). Methods of differentiating undifferentiated ES cells in vitro are known and can be applied to the differentiation of iPS cells. For example US Patent Application Publication No. 2006/0194321 describes differentiation of ES cells into endodermal cells (e.g., pancreatic); US Patent Application Publication No. 2004/0014209 describes differentiation of ES cells into cardiac cells; US Patent Application Publication No. 2008/0194023 describes differentiation of ES cells into vascular smooth muscle cells; and US Patent Application Publication No. 2011/0117062 describes differentiating ES cells into retinal pigment epithelial cells.

Examples of disorders or diseases that can benefit from administration of iPS cells (or iPS cells that have been differentiated to a particular cell type) include autoimmune diseases, and diseases in which cell regeneration is beneficial, such as neurologic injuries (such as brain or spinal cord injuries, or damage from stroke) or neurodegenerative disorders, as well as blindness, deafness, tooth loss, arthritis, myocardial infarctions, bone marrow transplants, baldness, Crohn's disease, diabetes, and muscular dystrophy. Exemplary neurodegenerative diseases include, for example, adrenoleukodystrophy (ALD), alcoholism, Alexander's disease, Alper's disease, Alzheimer's disease, amyotrophic lateral sclerosis (Lou Gehrig's Disease), ataxia telangiectasia, Batten disease (also known as Spielmeyer-Vogt-Sjögren-Batten disease), bovine spongiform encephalopathy (BSE), Canavan disease, cerebral palsy, Cockayne syndrome, Corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease (Spinocerebellar ataxia type 3), Multiple System Atrophy, multiple sclerosis, narcolepsy, Niemann Pick disease, Parkinson's disease, Pelizaeus-Merzbacher Disease, Pick's disease, primary lateral sclerosis, prion diseases, progressive supranuclear palsy, Refsum's disease, Sandhoff disease, Schilder's disease, subacute combined degeneration of spinal cord secondary to Pernicious Anaemia, Spielmeyer-Vogt-Sjögren-Batten disease (also known as Batten disease), spinocerebellar ataxia, spinal muscular atrophy, Steele-Richardson-Olszewski disease, Tabes dorsalis, toxic encephalopathy. Exemplary autoimmune diseases that can benefit from the iPS provided herein include but are not limited to, rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, and pernicious anemia.

Also provided herein are methods of identifying mature and/or high quality iPSCs in a cell population by transfecting the cell population with an expression vector comprising a Zscan4 promoter operably linked to a reporter gene, wherein expression of the reporter gene in a cell of the cell population identifies the cell as a mature and/or high-quality iPSC. Further provided is a method of isolating mature iPSCs from a cell population, comprising transfecting the cell population with an expression vector comprising a Zscan4 promoter operably linked to a reporter gene, and separating cells expressing the reporter gene from the cell population, thereby isolating mature iPSCs.

In some embodiments, the cell population comprises iPSCs, embryonic fibroblasts, adult fibroblasts, or a combination thereof.

In some embodiments, the Zscan4 promoter comprises the Zscan4c promoter. In some examples, the Zscan4c promoter is at least 80%, at least 85%, 90%, at least 95%, at least 96%, at least 97%, at least 98% or at least 99% identical to the nucleotide sequence set forth as nucleotides 906-4468 of SEQ ID NO: 73. In some embodiments, the reporter gene encodes a fluorescent protein, such as GFP or a derivative thereof (e.g. Emerald). Alternatively, the reporter gene encodes a drug (e.g., antibiotic)-selectable marker, and the non-Zscan4-expressing cells are killed by adding the appropriate drug (e.g., hygromycin, neomycin, etc.). In specific non-limiting examples, the nucleotide sequence of the expression vector is at least 80%, at least 85%, 90%, at least 95%, at least 96%, at least 97%, at least 98% or at least 99% identical to the nucleotide sequence set forth as SEQ ID NO: 73. In specific examples, the expression vector comprises the nucleotide sequence of SEQ ID NO: 73.

V. Methods of Introducing Zscan4, Zscan4-Dependent Genes and Reprogramming Factors into Somatic Cells A number of methods have been described in the art for delivery of reprogramming factors to somatic cells for the generation of iPSCs (for reviews, see Lai et al., *J Assist Reprod Genet* 28(4):291-301, 2011; Parameswaran et al., *Stem Cells* 29(7):1013-1020, 2011; Müller et al., *Mol Ther* 17(6):947-953, 2009). The methods include several broad categories, including introduction of nucleic acid molecules encoding the reprogramming factors using a viral vector (such as integrating or non-integrating viral vectors) or a plasmid vector, delivery of mRNA molecules encoding the reprogramming factors, or direct delivery of the reprogramming factor proteins. Each of these methods has been described in the art and is therefore within the capabilities of one of skill in the art. A brief summary of each method that can be used to deliver Zscan4, a Zscan4-dependent gene and/or one or more reprogramming factors to a somatic cell is provided below. It is not necessary for Zscan4 or the Zscan4dependent gene and each of the reprogramming factors to be delivered by the same method. For example, delivery of Zscan4 (or Zscan4-dependent gene) mRNA can be combined with vector-mediated delivery of the reprogramming factor(s).

A. Viral Vectors

The initial experiments carried out to produce iPSCs used retrovirus vectors (e.g., Moloney murine leukemia virus (MMLV)-based vectors) to deliver the reprogramming factors to murine and human somatic cells (Takahashi et al., *Cell* 126:663-666, 2006; Takahashi et al., *Cell* 31:861-872, 2007; Okita et al., *Nature* 313-317, 2007; Park et al., *Nature* 451:141-146; U.S. Patent Application Publication No. 2009/0047263). Subsequent studies utilized lentivirus vectors (Brambrink et al., *Cell Stem Cell* 2:151-159, 2008; Wernig et al., *Nat Biotechnol* 26:916-924, 2008; Stadtfeld et al., *Science* 322:945-949, 2008), which had the advantage of being able to infect both dividing and non-dividing cells, thereby improving the rate of cell transduction. In addition, lentiviruses can be pseudotyped to expand viral tropism. For example, pseudotyping with vesicular stomatitis virus glycoprotein (VSVg) enables infection of a wide range of cell types (Lai et al., *J Assist Reprod Genet* 28(4):291-301, 2011). Lentiviruses also allow for both constitutive and inducible expression of the reprogramming factors. Examples of drug-inducible lentivirus expression systems are described by Hockmeyer et al. (*Cell Stem Cell* 3:346-353, 2008) and Wernig et al. (*Nat Biotechnol* 26:916-924, 2008).

Lentiviruses include, but are not limited to, human immunodeficiency virus (such as HIV-1 and HIV-2), feline immunodeficiency virus, equine infectious anemia virus and simian immunodeficiency virus. Other retroviruses include, but are not limited to, human T-lymphotropic virus, simian T-lymphotropic virus, murine leukemia virus, bovine leukemia virus and feline leukemia virus. Methods of generating retrovirus and lentivirus vectors and their uses have been well described in the art (see, for example, U.S. Pat. Nos. 7,211,247; 6,979,568; 7,198,784; 6,783,977; and 4,980,289).

Non-integrating viral vectors, such as adenovirus vectors, have also been used to deliver reprogramming factor nucleic acid molecules to cells. For example adenovirus vectors, which remain in episomal form in cells, have been successfully used to deliver to produce iPS cells from mouse fibroblasts and liver cells by delivery of Oct4, Sox2, Klf4, and c-Myc (Stadtfeld et al., *Science* 322:945-949, 2008).

B. Plasmid Vectors

In some instances, it is desirable to use non-viral vectors, such as to avoid integration into the host cell genome. Thus, Zscan4, the Zscan4-dependent gene and/or one or more reprogramming factors can be delivered to a somatic cell using one or more plasmid vectors. Plasmid vectors are episomally maintained and generally exhibit a short duration of gene expression (Lai et al., *J Assist Reprod Genet* 28(4):291-301, 2011). As one example, Okita et al. (*Science* 322:949-953, 2008) describe the use of the pCX plasmid, containing a CAG promoter, for the expression of reprogramming factors in somatic cells. In this study, fibroblasts were serially transfected with two plasmids, one expressing c-Myc and the other expressing Oct4, Klf4 and Sox2. A later study by Gonzalez et al. (*Proc Natl Acad Sci USA* 106:8918-8922, 2009) successfully used a single polycistronic plasmid encoding all four reprogramming factors (c-Myc, Oct4, Klf4 and Sox2) to generate iPS cells.

Episomal plasmid vectors are a further option for introducing Zscan4 or the Zscan4-dependent gene and reprogramming factors into somatic cells. Episomal plasmid vectors are capable of replicating themselves autonomously as extrachromosomal elements, and therefore exhibit prolonged gene expression in target cells. An episomal plasmid vector derived from the Epstein Barr virus (oriP/EBNA1) has been used to reprogram human somatic cells by expression of OCT4, SOX2, NANOG, LIN28, c-MYC and KLF4 (Yu et al., *Science* 324:797-801, 2009).

Selection of an appropriate vector is well within the capabilities of one of skill in the art. Expression vectors typically contain an origin of replication, a promoter, and optionally include specific genes to allow for phenotypic selection of the transformed cells (e.g. an antibiotic resistance cassette). Generally, the expression vector will include a promoter. The promoter can be inducible or constitutive. The promoter can also be tissue specific. Exemplary promoters include the CAG promoter, thymidine kinase promoter (TK), metallothionein I, polyhedron, neuron specific enolase, thyrosine hyroxylase, beta-actin, CMV immediate early promoter, or other promoters. Optionally, an enhancer element is also included, and can generally be located anywhere on the vector and still have an enhancing effect on gene expression.

Plasmid vectors can be introduced into somatic cells using any suitable method. In some embodiments, the vector is delivered to a cell by transfection using a lipid of cationic polymer. In particular examples, the transfection reagent is LIPOFECTAMINE™, or a similar reagent. In other examples, delivery is achieved using the nucleofection transfection technology (Amaxa, Cologne, Germany). This technology is based on an electroporation technique using the NUCLEOFECTOR™ delivery device to introduce DNA directly into the host cell nucleus (Lakshmipathy et al., *Stem Cells* 22:531-543, 2004). In yet another example, the transfection reagent comprises poly-β-amino esters. Montserrat et al. (*J Biol Chem* 286(14):12417-12428, 2011) describe the production of iPS cells from human fibroblasts by delivery of a polycistronic CAG-promoter driven plasmid expressing Oct4, Sox2, Klf4 and c-Myc using poly-β-amino esters as the transfection reagent.

C. Excision Strategies

Excision of exogenous reprogramming factors from genomic integration sites can be desirable. Two excision-based methods have been previously described, CreloxP recombination and piggyBac transposition. Soldner et al. (*Cell* 136:964-977, 2009) described the use of the Crelox system to produce iPS cells free of viral reprogramming factors. This strategy included positioning a loxP site in the 3' LTR of a lentivirus vector that contained a Dox-inducible minimal CMV promoter to drive expression of the reprogramming factors. During proviral replication, loxP was duplicated into the 5' LTR, resulting in genomic integration of the reprogramming factors flanked by two loxP sites. Transient expression of Cre-recombinase resulted in excision of the floxed reprogramming factors.

The piggyBac transposon is capable of excising itself without leaving any remnants of exogenous DNA in the cell genome (Elick et al., *Genetica* 98:33-41, 1996; Fraser et al., *Insect Mol Biol* 5:141-151, 1996). Using this method, iPS cells have been generated from fibroblasts by delivery of a polycistronic construct carrying reprogramming factor genes linked with a 2A peptide linker positioned between the piggyBac transposon 5' and 3' terminal repeats. Precise excision of the integrated reprogramming genes is observed upon expression of the transposase (Kaji et al., *Nature* 458:771-775, 2009; Wang et al., *Proc Natl Acad Sci USA* 105:9290-9295, 2008; Yusa et al., *Nat Methods* 6:363-369, 2009).

D. mRNA

Another strategy for introducing Zscan4, a Zscan4-dependent gene and/or one or more reprogramming factors to a somatic cell is by delivery of mRNA encoding Zscan4, the Zscan4-dependent gene or the reprogramming factor(s). iPSCs have been generated from multiple different human cell types by administration of synthetic mRNA encoding reprogramming factors (Warren et al., *Cell Stem Cell* 7(5): 618-630, 2010). In the study by Warren et al., the mRNA was modified to overcome innate antiviral responses and was delivered repeatedly to achieve pluripotency.

E. Protein

It is also possible to introduce Zscan4, the Zscan4-dependent gene and/or the reprogramming factors by directly delivering the respective proteins to the somatic cells. Protein delivery can be accomplished using, for example, electroporation, microinjection, cationic lipids or nanoparticles according to standard methods. Alternatively, the proteins can be modified by fusion with a cell-penetrating peptide (CPP) to facilitate entry of the protein into the cell. The use of CPPs and nanoparticles is discussed in greater detail below.

1. Cell-Penetrating Peptides (CPPs)

CPPs are a family of polypeptides that facilitate transduction of proteins, nucleic acids or other compounds across membranes in a receptor-independent manner (Wadia and Dowdy, *Curr. Protein Pept. Sci.* 4(2):97-104, 2003). Typically, CPPs are short polycationic sequences that can facilitate cellular uptake of compounds to which they are linked into endosomes of cells.

The capacity of certain peptides to deliver proteins or nucleic acids into cells was originally described for the HIV-encoded Tat protein, which was shown to cross membranes and initiate transcription. It was then discovered that the portion of the Tat protein that was required for the transduction of the protein was only an 11 amino acid polypeptide, referred to as the Tat peptide. When fused with other proteins, the Tat peptide has been demonstrated to deliver these proteins, varying in size from 15 to 120 kDa, into cells in tissue culture (Frankel and Pabo, *Cell* 55(6): 1189-93, 1988; Green and Loewenstein, *J. Gen. Microbiol.* 134(3):849-55, 1988; Vives et al., *J. Biol. Chem.* 272(25): 16010-7, 1997; Yoon et al., *J. Microbiol.* 42(4):328-35, 2004; Cai et al., *Eur. J. Pharm. Sci.* 27(4):311-9, 2006).

Other known CPPs include PENETRATIN™, a 16 amino acid peptide derived from the third helix of the *Drosophila* Antennapedia homeobox gene (U.S. Pat. No. 5,888,762; Derossi et al., *J. Biol. Chem.* 269:10444-10450, 1994; Schwarze et al., *Trends Pharmacol. Sci.* 21:45-48, 2000); transportan, a 27 amino acid chimeric peptide comprised of 12 amino acids from the N-terminus of the neuropeptide galanin and the 14-amino acid protein mastoparan, connected via a lysine (U.S. Pat. No. 6,821,948; Pooga, *FASEB J.* 12:67-77, 1998; Hawiger, *Curr. Opin. Chem. Biol.* 3:89-94, 1999); peptides from the VP22 protein of herpes simplex virus (HSV) type 1 (Elliott et al., *Cell* 88:223-233, 1997); the UL-56 protein of HSV-2 (U.S. Pre-Grant Publication No. 2006/0099677); and the Vpr protein of HIV-1 (U.S. Pre-Grant Publication No. 2005/0287648). In addition, a number of artificial peptides also are known to function as CPPs, such as poly-arginine, poly-lysine and others (see, for example, U.S. Pre-Grant Publication Nos. 2006/0106197; 2006/0024331; 2005/0287648; and 2003/0125242; Zhibao et al., *Mol. Ther.* 2:339-347, 2000; and Laus et al. *Nature Biotechnol.* 18:1269-1272, 2000).

Zhou et al. (*Cell Stem Cell* 4:381-384, 2009) describe the successful generation of iPS cells by fusing purified recombinant reprogramming factors OCT4, SOX2, KLF4 and c-MYC to poly-arginine peptide tags. Mouse embryonic fibroblasts were transduced with the recombinant four times and cultured in the presence of the histone deacetylase inhibitor, valproic acid (VPA) for 30-35 days. In addition, Kim et al. (*Cell Stem Cell* 4:472-476, 2009) describe reprogramming of human fetal fibroblasts by transduction of OCT4, SOX2, KLF4 and c-MYC proteins fused to the HIV-TAT protein transduction domain.

2. Nanoparticles

Nanoparticles are submicron (less than about 1000 nm) sized drug delivery vehicles that can carry encapsulated drugs such as synthetic small molecules, proteins, peptides, cells and nucleic acid based biotherapeutics for either rapid or controlled release. A variety of molecules (e.g., proteins, peptides and nucleic acid molecules) can be efficiently encapsulated in nanoparticles using processes well known in the art.

In some examples, the Zscan4 protein, the Zscan4-dependent gene protein and/or a reprogramming factor protein is encapsulated by a nanoparticle to aid in delivery to the cells. Suitable nanoparticles for use with the disclosed methods are known in the art and are described briefly below.

The nanoparticles for use with the methods described herein can be any type of biocompatible nanoparticle, such as biodegradable nanoparticles, such as polymeric nanoparticles, including, but not limited to polyamide, polycarbonate, polyalkene, polyvinyl ethers, and cellulose ether nanoparticles. In some embodiments, the nanoparticles are made of biocompatible and biodegradable materials. In some embodiments, the nanoparticles include, but are not limited to nanoparticles comprising poly(lactic acid) or poly(glycolic acid), or both poly(lactic acid) and poly(glycolic acid). In particular embodiments, the nanoparticles are poly(D,L-lactic-co-glycolic acid) (PLGA) nanoparticles.

Other biodegradable polymeric materials are contemplated for use with the methods described herein, such as poly(lactic acid) (PLA) and polyglycolide (PGA). Additional useful nanoparticles include biodegradable poly(alkylcyanoacrylate) nanoparticles (Vauthier et al., *Adv. Drug Del. Rev.* 55: 519-48, 2003).

Various types of biodegradable and biocompatible nanoparticles, methods of making such nanoparticles, including PLGA nanoparticles, and methods of encapsulating a variety of synthetic compounds, proteins and nucleic acids, has been well described in the art (see, for example, U.S. Publication No. 2007/0148074; U.S. Publication No. 20070092575; U.S. Patent Publication No. 2006/0246139; U.S. Pat. No. 5,753,234; U.S. Pat. No. 7,081,489; and PCT Publication No. WO/2006/052285).

The following examples are provided to illustrate certain particular features and/or embodiments. These examples should not be construed to limit the disclosure to the particular features or embodiments described.

EXAMPLES

Example 1

Zscan4 is an Early Embryonic Factor Required for Direct Reprogramming of Somatic Cells This example describes the finding that Zscan4 initiates direct reprogramming of somatic cells by reactivating early embryonic genes.

Methods

Plasmid Vector Construction

To construct a pCAG-Zscan4-ERT2 plasmid, an entire open reading frame (ORF: 506a.a.) of the mouse Zscan4c gene (Falco et al., *Dev Biol* 307:539-550, 2007) was fused with ERT2 (a mutated ligand-binding domain of the human estrogen receptor (Feil et al., *Proc Natl Acad Sci USA* 93:10887-10890, 1996); 314 a.a.) and cloned into XhoI/NotI sites of a plasmid (pPyCAGBstXI-IP; Niwa et al., *Gene* 108:193-199, 1991). The resultant plasmid vector (pCAG-Zscan4-ERT2) expresses a Zscan4c-ERT2 fusion protein and a Puromycin-resistant protein driven by a strong CAG promoter (FIG. 1A). PiggyBac vectors (PB-TET-IRES-βgeo, PB-TET-MKOS, and PB-CAG-rtTA; Kaji et al., *Nature* 458:771-775, 2009; Woltjen et al., *Nature* 458:766-770, 2009) were purchased from Addgene. ORFs of Klf4-Oct4-Sox2 (KOS), Zscan4c, Zscan4cERT2 or DsRed were PCR-amplified by using a high-fidelity DNA polymerase (Pfx50 or Platinum Pfx from Invitrogen) and attB1/2 primers (FIG. 17) from PB-TET-MKOS or pCAG-Zscan4-ERT2 and cloned into a pDONR221 vector, respectively (Invitrogen). Subsequently, these DNA fragments were inserted into a PB-TET-IRES-βgeo destination vector thorough the Gateway System (Invitrogen). To construct a PB-TETZscan4c-ERT2-IRES-Histidinol dehydrogenase (His)-DsRed vector, an IRES-His-DsRed fusion protein was excised from a pBR-CAG-cHA-IRES-HisDsRed vector (Niwa et al., *Gene* 108:193-199, 1991) by ApaI and BamHI (blunt-ended) and inserted into an ApaI/EcoRI (blunt-ended) site of a PB-TET-Zscan4c or PB-TET-Zscan4cERT2 vector, respectively. To construct a PB-TET-IRES-HisDsRed destination vector, an attR1R2 ccdB cassette was excised from a PB-TET destination vector with ApaI and SacII and inserted into an ApaI/SacII site of a PB-TET-Zscan4cERT2-HisDsRed vector. An ORF of human ZSCAN4 was amplified by PCR using attB1/2 primers (FIG. 17) from pReceiver-M50-ZSCAN4 (Genecopoeia) and cloned into a pDONR221 vector (Invitrogen). This fragment was inserted into a PB-TET-IRES-HisDsRed destination vector through the Gateway System (Invitrogen).

Generation of ES-ZERT Cells

V6.5 ES (Eggan et al., *Proc Natl Acad Sci USA* 98:6209-6214, 2001) cells derived from an F1 hybrid strain (C57BL/6×129/Sv) were purchased from Thermo Scientific Open Biosystem. ES cells were cultured at 37° C. in 5% $CO_2$ in the complete ES medium: DMEM, 15% FBS, 1000 U/ml leukemia inhibitory factor (LIF) (ESGRO, Chemicon), 1 mM sodium pyruvate, 0.1 mM non-essential amino acids, 2 mM GlutaMAX™, 0.1 mM β-mercaptoethanol, penicillin, and streptomycin. V6.5 ES cells ($5 \times 10^5$ cells) in suspension were cotransfected with 2 μg of a linearized pCAGZscan4-ERT2 vector and 0.4 μg of PL452 vector (a neomycin-resistant gene driven by a PGK promoter; Liu et al., *Genome Res* 13:476-484, 2003) using Effectene™ (QIAGEN) according to the manufacturer's protocol, and plated in 100 mm cell culture dishes. After selecting with G418 for 8 days, resulting ES cell colonies were picked, expanded, and frozen. Subsequently, an ES-ZERT cell clone was selected based on the results of genotyping, qPCR, and puromycin-resistance.

Generation of ZERT Chimeric Mice

ICR females (Charles River, 8-12 weeks old) were used for superovulation by pregnant mare serum gonadotropin (PMSG) (Sigma) followed by human chorionic gonadotropin (hCG; Sigma) administration 48 hours later. After hCG administration, females were mated with ICR males and 2-cell embryos were collected by flushing oviducts. Recovered embryos were cultured to the blastocyst stage in KSOM (Millipore) medium for 3 days at 37° C. in 5% $CO_2$. ES-ZERT cells (10-15 cells) were injected into 2N blastocysts and then transferred to E2.5 recipient females. After genotyping the pups, ZERT chimeric mice carrying a pCAG-Zscan4-ERT2 DNA were established.

MEF Isolation

MEF-ZERT cells and MEF-WT cells were isolated from E13.5 embryos, which were obtained by crossing male ZERT mice to female ICR mice (FIG. 5A). MEF-WT (C57BL/6Jx129S6/SvEvTac) cells were isolated from E13.5 embryos, which were obtained by crossing between male 129SvEvTac mice and female C57BL/6J mice. These cells were plated into 10-cm plate in DMEM supplemented with 10% FBS, 1 mM sodium pyruvate, 0.1 mM non-essential amino acids, 2 mM GlutaMAX™, 0.1 mM β-mercaptoethanol, penicillin and streptomycin.

Cell Growth Analysis

To determine growth rate under Tamoxifen (Tmx)– or Tmx+ conditions, MEFs were passaged at a density of $3 \times 10^5$ cells/10 cm-plate in triplicate every 3 days. Live cells were scored using trypan blue.

PiggyBac-Transfection and iPSC Generation iPSCs were generated as previously reported (Kaji et al., *Nature* 458:771-775, 2009; Woltjen et al., *Nature* 458:766-770, 2009) with some modifications. Briefly, MEFs were plated on gelatin-coated 6-well plates at a density of $1 \times 10^5$ cells/well in complete ES medium. After 24 hour incubation, MEFs were transfected with 1.6 μg of each plasmid, which were pCyL43 (Sanger institute; Wang et al., *Proc Natl Acad Sci USA* 105:9290-9295, 2008), CAG-rtTA and PB-TET-MKOS or -KOS with or without PB-TET-Zscan4c or PB-TET-Zscan4cERT2, using Xfect (Clontech). After 24 hour, cells were fed with the complete ES medium with Doxycycline (Dox: 1.5 μg/ml) and with or without 200 nM 4-hydroxytamoxifen (Tmx). Colonies were picked after 12 days post-Dox induction and propagated as iPSCs in the complete ES medium with Dox (1.5 μg/ml), until Dox-independency was observed in replicate wells. Culture medium was changed every day.

Alkaline Phosphatase Staining

Cells were stained using Leukocyte Alkaline Phosphatase kit (Sigma) according to the manufacturer's protocol.

In Vitro Differentiation

Cells were dissociated by Accutase (Chemicon), counted, and propagated using the hanging drop method (200 single cells per 25 μl) in the ES medium without LIF for 4 days. Embryoid bodies, formed in the hanging drop, were transferred to gelatin-coated 24-well plates and cultured for 7 days, before being fixed with 4% paraformaldehyde.

Immunocytochemistry

Cells were fixed with 4% paraformaldehyde for 20 min and permeabilized with 0.2% triton-X 100 for 15 minutes. Cells were blocked with FX Signal Enhancer (Invitrogen). Primary antibody was added and incubated overnight at 4° C. (SSEA-1 (500:1, Invitrogen), Nanog (500:1, BETHYL laboratories), α-smooth muscle actin (a SMA 1:1000, R&D), α-fetoprotein (AFP 1:500, R&D), GATA-4 (1:200, Santa Cruz) or βIII-tubulin (1:500, Millipore)). Alexa488 anti-mouse IgG or IgM (Invitrogen) or Alexa-594 anti-Rabbit IgG (Invitrogen) were used as secondary antibodies. Nuclei were visualized with DAPI (Roche).

Nanog Immunohistochemistry

Nanog expression of ESC or iPSC colonies was detected by the Envision system-HRP kit (Dako, USA) according to the manufacturer's instructions. In brief, cells were washed by PBS and fixed in Acetone/Methanol (1:1) for 20 minutes at 4° C. After PBS washing, peroxidase blocking was applied to remove exogenous peroxidase in cells for 5 minutes. Cells were blocked by 1% BSA for 10 minutes at room temperature and then incubated for 1 hour at room temperature with the primary anti-Nanog antibody (Bethyl, USA) diluted 1:500 in the blocking solution. The bound antibody was visualized with a peroxidase labeled polymer for 30 minutes and substrate chromogen for 5 minutes under an Axiovert microscope.

RT-PCR, Quantitative PCR, and Genotyping PCR

One μg of total RNA was reverse-transcribed using Superscript III reverse transcriptase (Invitrogen). qPCR analysis was performed for 10 ng cDNA/well in triplicate using SYBR™ green master mix (Applied Biosystems) according to the manufacturer's protocol. Reactions were run on 7900HT or 7500 system (Applied Biosystems). Genotyping PCR was performed using TITANIUM Taq PCR kit (Clontech). Primers are shown in FIG. 17.

Karyotype Analysis iPS cells were treated with 0.1 μg/ml colcemid (Invitrogen) for 3 hours to induce the metaphase arrest, treated with 0.56% KCl and fixed with Methanol:Glacial Acetic acid (3:1). Slides were air-dried before Giemsa staining.

Tetraploid Complementation

ICR females (Charles River, 8-12 week old) were used for superovulation by PMSG (Sigma), followed by hCG (Sigma) administration 48 hours later. After hCG administration, females were mated with male ICR mice and 2-cell embryos were collected by flushing oviducts. Recovered embryos were cultured in KSOM (Millipore) medium for 3 days at 37° C. in 5% $CO_2$. Collected 2-cell embryos were directly transferred into 0.3M Mannitol solution and aligned automatically by alternate current (AC) pulse in an electrofusion chamber. Then two direct current (DC) pulses with 140 V/mm were applied for 40 μs using LF101 Electro Cell Fusion Generator. Fused embryos (4N) that had one blastomere were collected at 60 minutes of cultivation and then continued to culture in KSOM medium until they reached the blastocyst stage. iPS cells (10-15 cells) were injected into 4N blastocysts to assess their developmental potency and then transferred to E2.5 recipient females. Pups were harvested by cesarean section at E13.5.

Isolation of Secondary MEFs and Induction of Secondary iPSCs

Secondary MEFs were isolated from E13.5 embryos, which were harvested by tetraploid complementation. Secondary MEFs were plated on gelatin-coated 6-well plates at a density of 1×10$^5$ cells/well in the complete ES medium. After 24 hour incubation, secondary MEFs were fed with complete ES medium with or without Dox (1.5 μg/ml) and with or without 200 nM Tmx. Culture medium was changed every day. Withdrawal of drugs (Dox or Tmx) was always followed by 1× washing by PBS before changing culture medium.

Microarray Data Analysis

Expression profiling was carried out as described (Nishiyama et al., *Cell Stem Cell* 5, 420-433, 2009) using the whole-genome 60-mer oligonucleotide microarrays (Agilent; Carter et al., *Genome Biol* 6:R61, 2005). Data analysis and visualization were carried out by the NIA Array Analysis Software (Sharov et al., *Bioinformatics* 21:2548-2549, 2005). Heatmaps were generated with MultiExperiment Viewer (Mev) v4.2 (Saeed et al., *Methods Enzymol* 411: 134-193, 2006). The data were normalized in each row (gene) in the Gene/Row Adjustment of the program. The color scale was set from −3 to +3 based on the normalized data. The map displayed is from HCL (Hierarchical clustering) of MeV4.2. All the microarray data have been submitted to the public database GEO (accession number GSE28436).

Bisulfite Sequencing

Genomic DNAs were extracted using DNeasy (Qiagen). Bisulfite conversion of genomic DNA was performed with EpiTect plus (QIAGEN) according to the manufacturer's protocol. Amplified products were purified by gel extraction and cloned into pCR 2.1 vector (Invitrogen). PCR primers are shown in FIG. 17. Randomly picked clones were sequenced with M13 forward or reverse primers. Sequencing data were analyzed using QUMA[36] (online at http://quma.cdb.riken.jp/top/index.html; Kumaki et al., *Nucleic Acids Res* 36:W170-175, 2008). Data were excluded as low quality, if >5% unconverted CpHs or >10% alignment mismatches.

Statistical Analysis

Data were evaluated using ANOVA with Scheffé's post hoc analysis for multiple comparisons and t tests for two groups. $P<0.05$ was accepted as statistically significant.

Results

Figure 19:
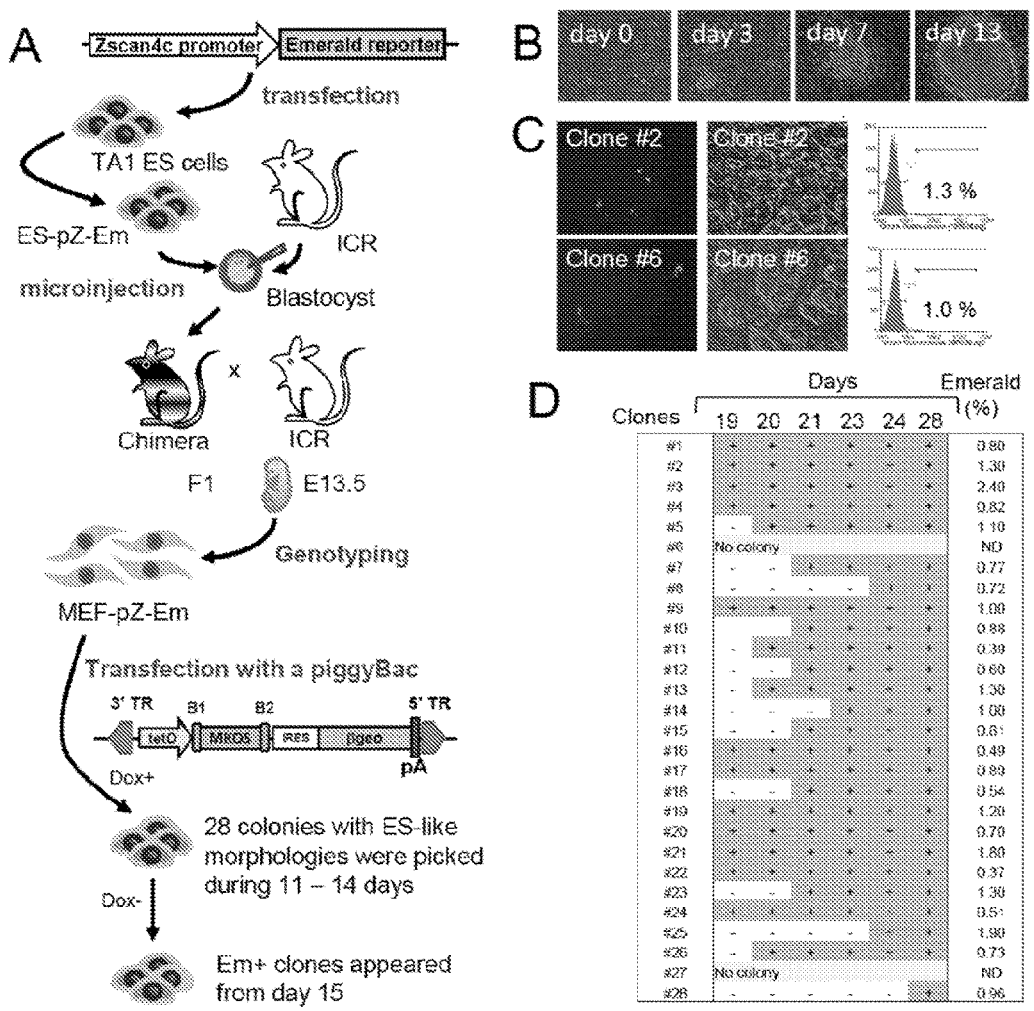
FIG. 19 shows that Zscan4 is not expressed during early phase of iPSC formation, but reactivated later in iPSC cells.

To investigate whether Zscan4 is reactivated during iPSC formation, mouse ES cells were generated that carry an Emerald (EM: a GFP variant) reporter driven by a 3.5 kb Zscan4 promoter (Zscan4-Emerald; SEQ ID NO: 73), which can reproduce the expression pattern of endogenous Zscan4 in mouse ES cells (Zalzman et al., *Nature* 464:858-863, 2010; PCT Publication No. WO 2011/028880). Chimeric mice produced by injecting the ES cells (named ES-pZ-EM) into blastocysts, were used to generate E13.5 embryos, which were subsequently used to derive mouse embryo fibroblasts (MEFs). The MEFs confirmed for the presence of an Emerald reporter by genotyping were named MEF-pZ-EM cells (FIG. 19A). Emerald fluorescence was not detectable in the MEF-pZ-EM cells, indicating that Zscan4 is not expressed in MEFs.

A piggyBac vector (PB-TET-MKOS) (Kaji et al., *Nature* 458:771-775, 2009; Woltjen et al., *Nature* 458:766-770, 2009) carrying doxycycline (Dox)-inducible Myc (M), Klf4 (K), Oct4 (O), and Sox2 (S) was then transfected into the MEF-pZ-EM cells, and then the cells were cultured in ES cell media supplemented with Dox. As reported, colonies with an authentic ES-like morphology (denoted herein MOR+) were clearly visible by day 13 (FIG. 19B). The cells were observed under fluorescence microscopes every day, but no EM+ cells were found in the culture. Twenty-eight MOR+ colonies were picked and passaged into ES cell culture media without Dox 11 to 14 days after the piggyBac transfection. Two clones did not survive, but the other 26 clones proliferated to form MOR+ colonies. Colonies with EM+ cells began to appear from the day 15 and by day 28 all the colonies showed the presence of EM+ cells in the same pattern as typical F1 hybrid ES cell lines: a small number (1.0±0.5%, S.E.M.) of EM+ cells (FIGS. 19C and 19D). The data indicate that iPSCs, once formed, gained the expression pattern of Zscan4 similar to ESCs, suggesting a close similarity between iPSC and ESCs. Importantly, Zscan4 was not activated during the early phase of iPSC formation by the MKOS factors. Consistent with this finding, reanalysis of the published microarray data (Samavarchi-Tehrani et al., *Cell Stem Cell* 7:64-77, 2010; Sridharan et al., *Cell* 136:364-377, 2009) did not reveal the activation of Zscan4 during the early phase of iPSC formation.

Figure 20:
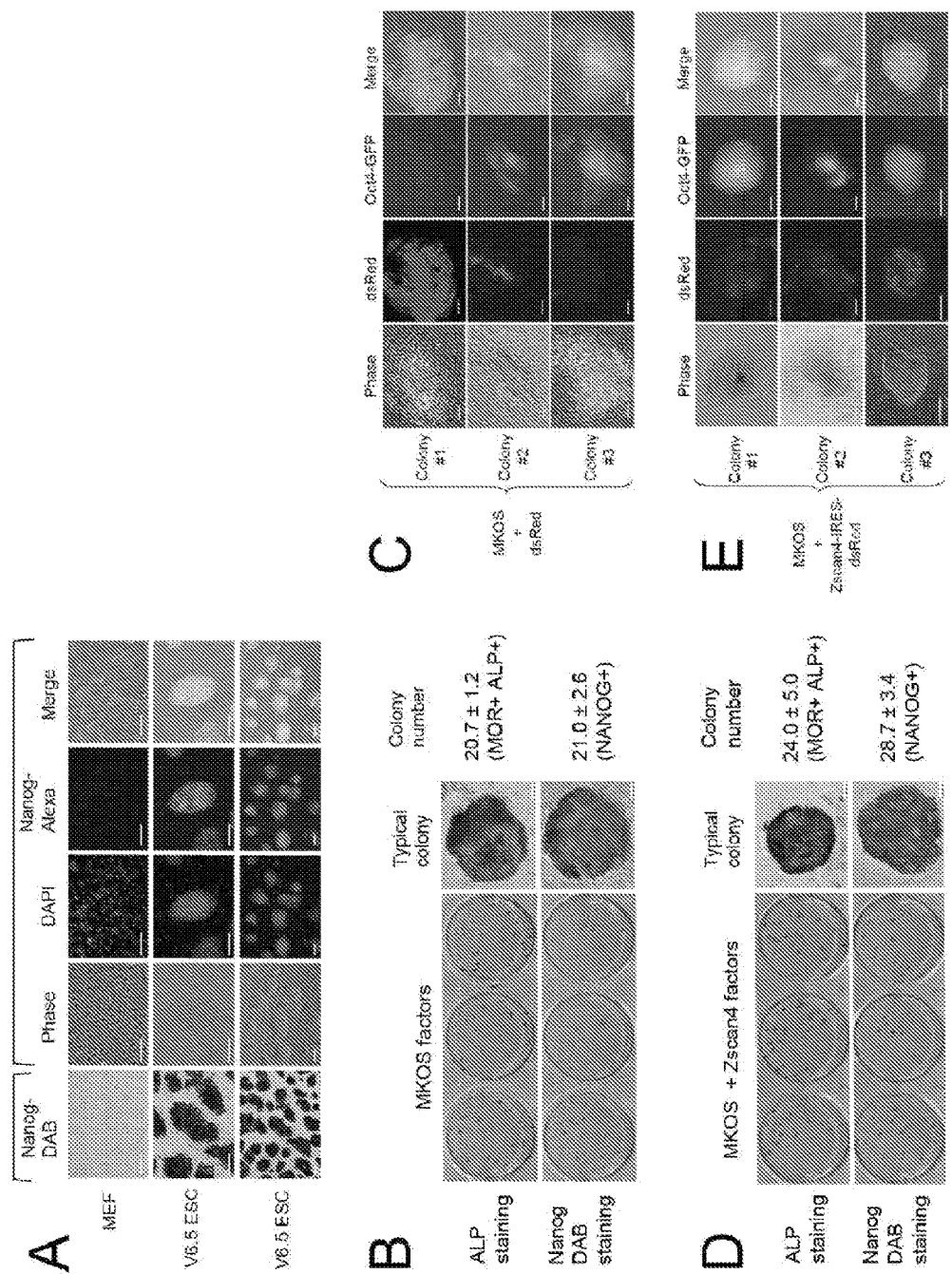
FIG. 20 depicts the validation of a MOR+ ALP+ phenotype for scoring authentic iPSC colonies generated by a piggyBac vector system.

The data also indicate that, as reported previously (Kaji et al., *Nature* 458:771775, 2009; Woltjen et al., *Nature* 458: 766-770, 2009), the production of iPSC by a piggyBac vector carrying MKOS factors was robust and the majority of MOR+ colonies indeed became the authentic iPSCs, as confirmed by the same unique expression pattern of Zscan4 as typical ES cells. This notion was further supported by the presence of a pluripotency marker NANOG (FIGS. 20A and 20B), which was not used as an exogenous iPSC factor, and the expression of a GFP marker under the control of the Oct4 promoter (Brambrink et al., *Cell Stem Cell* 2:151-159, 2008) (FIG. 20C) in the majority of MOR+ colonies generated by the PB-TET-MKOS. Therefore, in the subsequent experiments, the MOR+ phenotype combined with the alkaline phosphatase staining (ALP+) was primarily used to score the number of authentic iPSCs.

Figure 5:
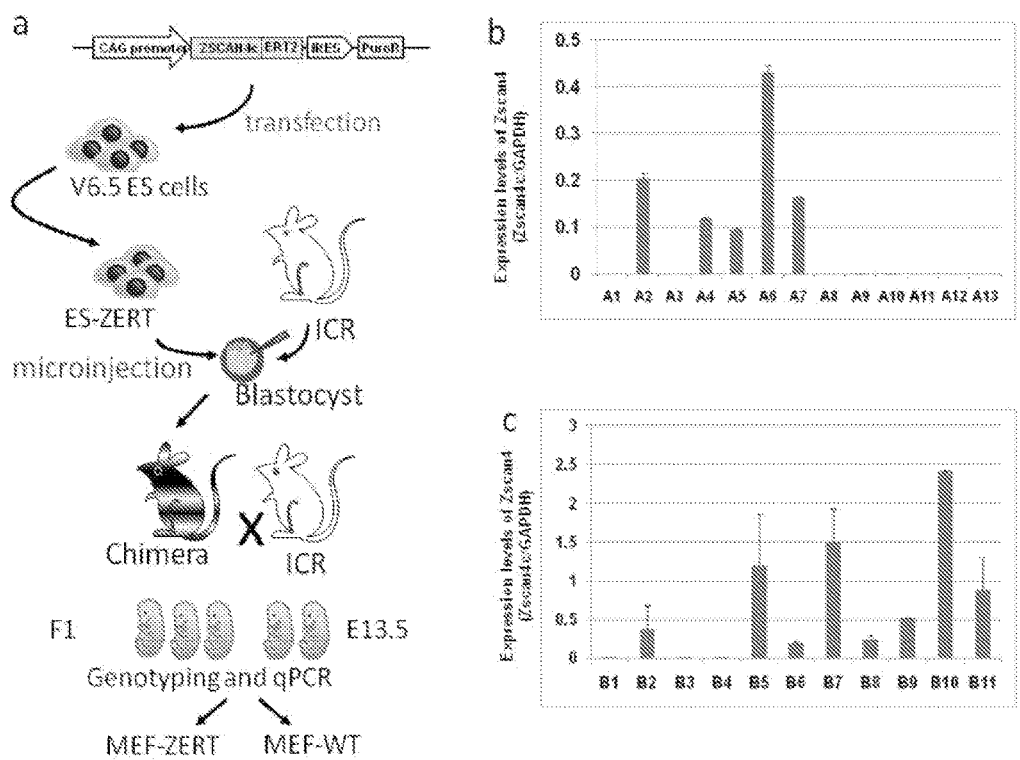
FIG. 5 depicts the generation and characterization of MEF-ZERT cell lines.
Figure 6:
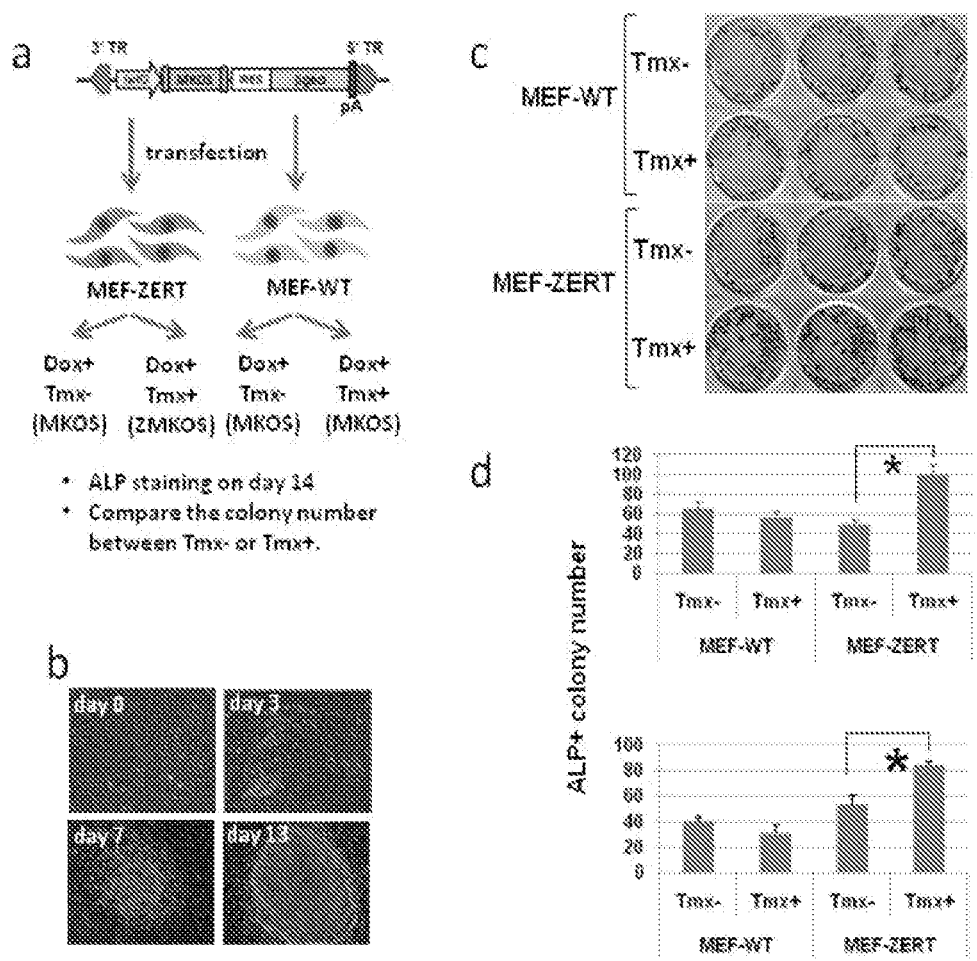
FIG. 6 shows that Zscan4 enhances MKOS-mediated iPSC colony formation from the MEF-ZERT cells.
Figure 7:
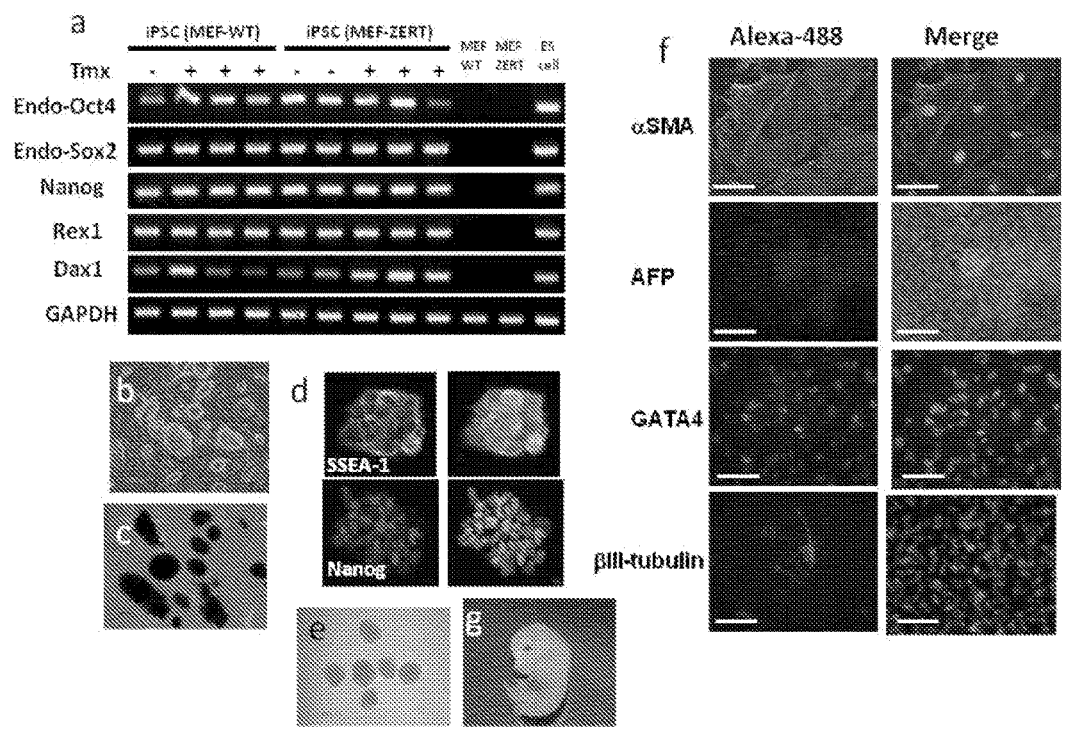
FIG. 7 depicts the characterization of iPSCs generated from the MEF-WT and MEF-ZERT cells with a PB-TET-MKOS vector.
Figure 8:
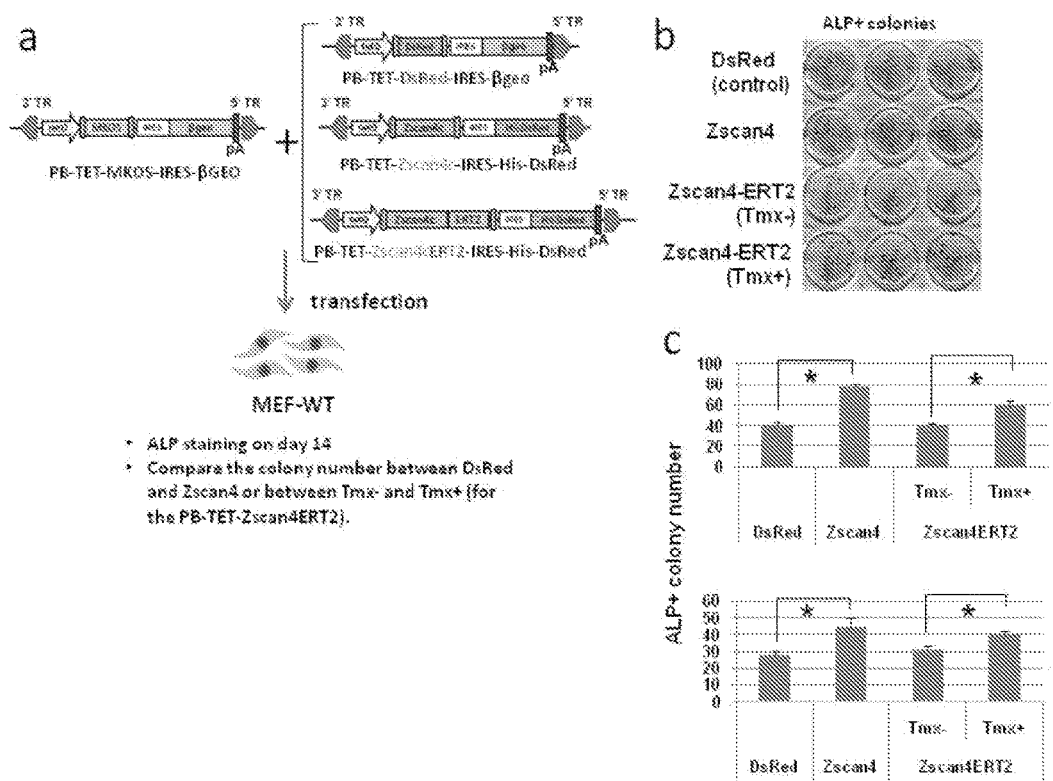
FIG. 8 shows that Zscan4 enhances MKOS-mediated iPSC colony formation from the MEF-WT cells.
Figure 9:
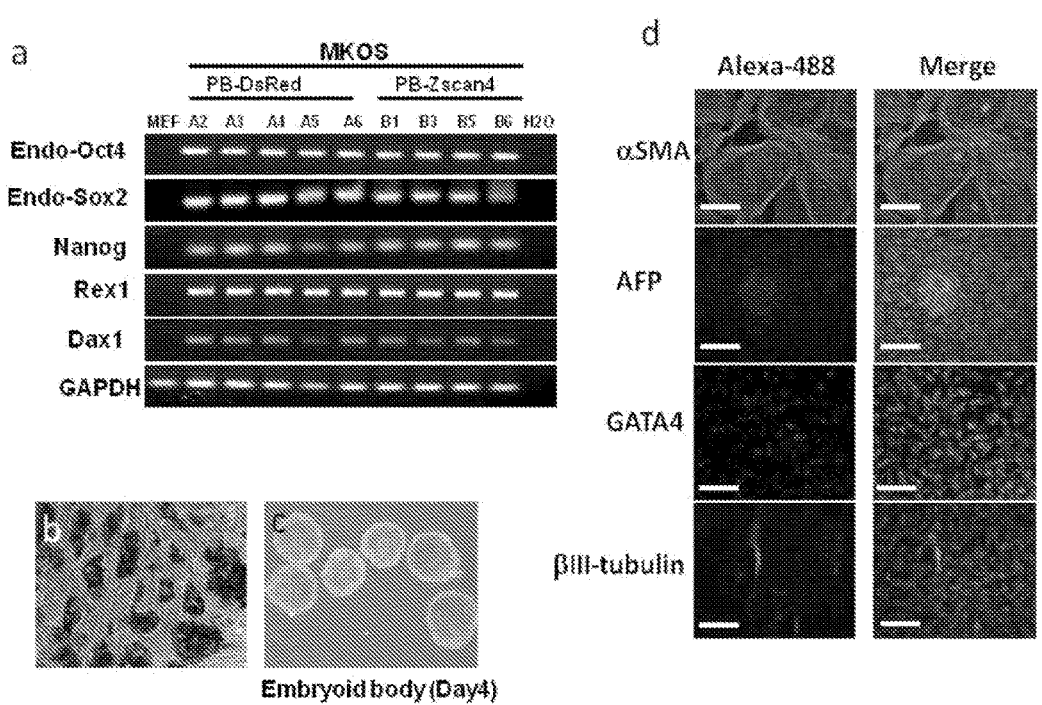
FIG. 9 depicts the characterization of iPSC clones derived from the MEF-WT with MKOS and Zscan4.
Figure 10:
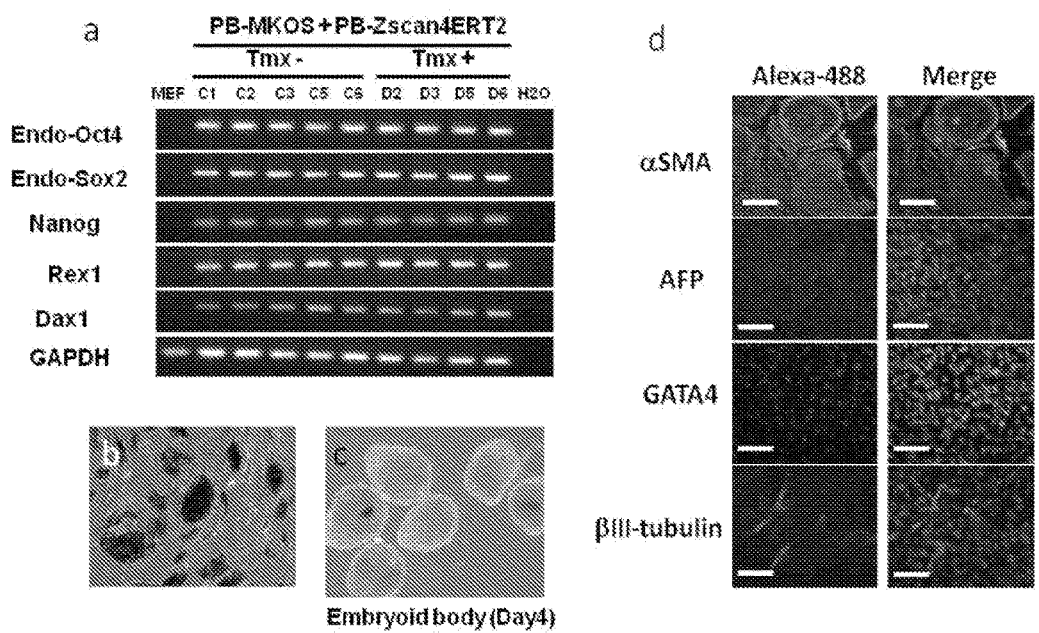
FIG. 10 depicts that characterization of iPSC clones derived from the MEF-WT with MKOS and Zscan4ERT2 (Tmx+).
Figure 11:
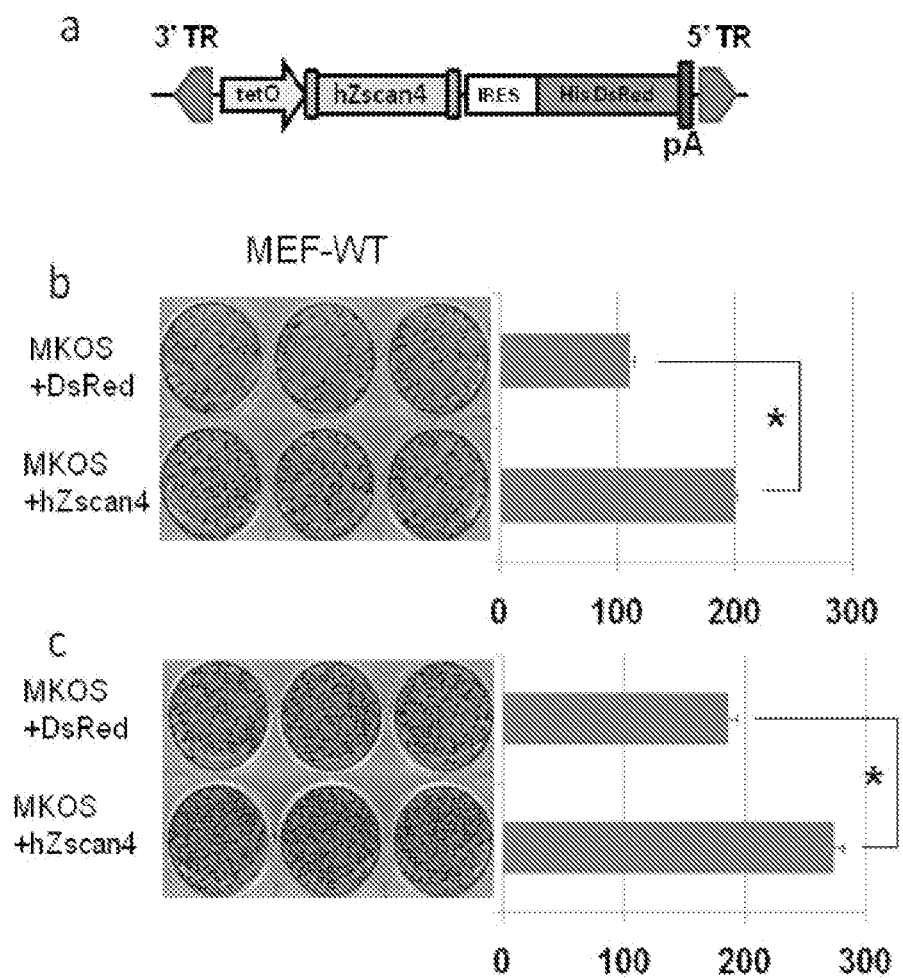
FIG. 11 shows human ZSCAN4 functions in the same manner as mouse Zscan4. By contrast to mouse Zscan4 that consists of 6 paralogous genes and 3 pseudogenes (Falco et al., *Dev Biol* 307:539-550, 2007), the human genome has only one ZSCAN4 gene copy. To investigate if human ZSCAN4 has similar functions to mouse Zscan4, the efficiency of iPSC formation was compared between mouse Zscan4 and human ZSCAN4.

Considering the critical roles of Zscan4 in 2-cell embryos (Falco et al., *Dev Biol* 307:539-550, 2007) and ES cells (Zalzman et al., *Nature* 464:858-863, 2010), it was hypothesized that Zscan4 could enhance the efficiency and quality of iPS cells. To test this notion, MEFs (named MEF-ZERT) were generated in which mouse Zscan4c fused to ERT2 (a mutated ligand-binding domain of the human estrogen receptor, which can be activated by the presence of tamoxifen [Tmx]; Feil et al., *Proc Natl Acad Sci USA* 93:10887-10890, 1996) was constantly expressed under a strong and ubiquitous CAG-promoter (Niwa et al., *Gene* 108:193-199, 1991) (FIG. 1A, FIG. 5). Next the effect of Zscan4 on iPSC formation was tested by transfecting a piggyBac vector (PB-TET-MKOS; Kaji et al., *Nature* 458:771-775, 2009; Woltjen et al., *Nature* 458:766-770, 2009) carrying doxycycline (Dox)-inducible Myc (M), Klf4 (K), Oct4 (O), and Sox2 (S), into control MEF-WT and MEF-ZERT cells and culturing them with or without Tmx in standard iPSC generation conditions (Dox+) (FIG. 6A). By day 13, colonies with ES-like morphologies were clearly visible (FIG. 6B). iPSC colonies were scored based on their authentic ES cell morphology and ALP-staining. In the control MEF-WT, the efficiency of iPSC formation was slightly lower in the Tmx+ condition than the Tmx− condition (FIGS. 6C and 6D). By contrast, in the MEF-ZERT cells, Tmx+ conditions increased the number of iPSC colonies by 1.5- to 2-fold, suggesting that the continuous presence of Zscan4 can enhance the efficiency of iPSC formation by the MKOS factors (FIG. 6C and FIG. 6D). The formation of authentic iPSCs was confirmed by the RT-PCR analysis of pluripotency genes, alkaline-phosphatase (ALP) staining of colonies, immunohistochemistry of pluripotency markers, embryoid body formation, and the ability to differentiate into three germ layers (FIG. 7). Similar enhancement of iPSC formation by Zscan4 was observed on wild-type MEF cells (MEF-WT), excluding the possibility that enhancement of iPSC formation is a unique feature of MEF-ZERT cells (FIGS. 8, 9 and 10). It was also determined that the human ZSCAN4 gene functions similar to mouse Zscan4 in the iPSC formation (FIG. 11).

Figure 12:
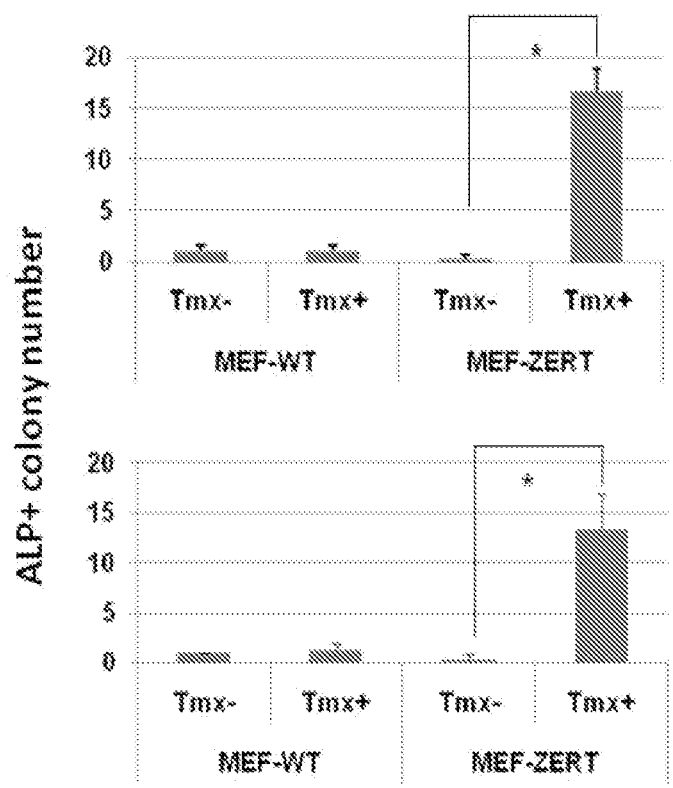
FIG. 12 shows that Zscan4 enhances iPSC colony formation without Myc. The charts shown represent two of the three replications for the experiments shown in FIG. 1B. The third data set is shown in FIG. 1C. A piggyBac vector (PB-TET-KOS) carrying Klf4 (K), Oct4 (O), and Sox2 (S) was transfected into the MEF-ZERT. The cells were cultured for 20 days under Dox+ Tmx− or Dox+ Tmx+ condition, fixed, and stained for ALP. ALP+ colonies were scored and presented in the bar chart. For each experiment, the transfection and Dox-induction were performed in triplicate. Data are represented as mean±S.E.M. (triplicate wells); *, P<0.01.
Figure 13:
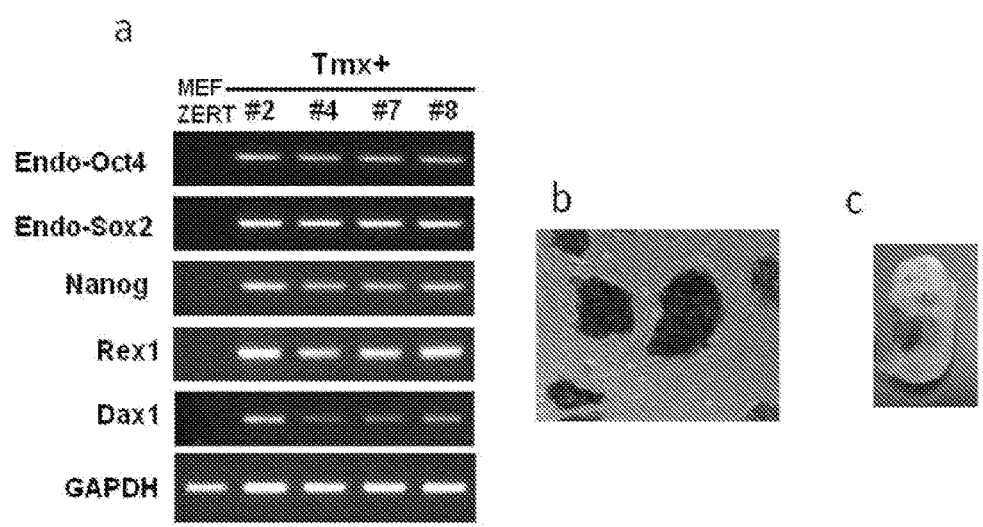
FIG. 13 depicts the characterization of iPSC clones derived from the MEF-ZERT with KOS factors.

Previous studies have shown that oncogene Myc (Feng et al., Cell Stem Cell 4:301-312, 2009; Hu et al., Proc Natl Acad Sci USA 107:4335-4340, 2010), which increases cell proliferation and suppresses genome stability, is required for the efficient iPSC formation (Takahashi and Yamanaka, Cell 126:663-676, 2006; Hanna et al., Cell 143:508-525, 2010). To test whether Zscan4 (Z) can enhance the iPSC formation without Myc, MEF-WT and MEF-ZERT cells were transfected with a PB-TET-KOS vector carrying Dox-inducible KOS factors and the cells were cultured in the Dox+ Tmx+ or Dox+ Tmx− conditions for 2 weeks (FIG. 1B). As expected, MEF-WT cells produced only a small number of ALP+ iPSC colonies (FIG. 1C). However, MEF-ZERT cells produced 40-o 70-fold more iPSC colonies in Dox+ Tmx+ (i.e., ZKOS) conditions than control Dox+ Tmx− (i.e., KOS) conditions (FIG. 1C). The result was confirmed in independent experiments (FIG. 12) and the quality of iPSCs generated with ZKOS factors was also demonstrated (FIG. 13). The number of iPSC colonies generated by ZKOS factors (FIG. 1C) was comparable to that generated by MKOS factors (FIG. 6). Thus, in combination with KOS factors, Zscan4 can replace Myc for iPSC formation.

To clarify further a role of Zscan4 in reprogramming, studies were carried out to determine when and how long Zscan4 is required. It has been shown that efficient iPSC formation requires the ectopic overexpression of MKOS factors at least for 9 days (Wernig et al., Nat Biotechnol 26:916-924, 2008; Sridharan et al., Cell 136:364-377, 2009). Using the Tmx− inducible system of Zscan4 expression in MEF-ZERT cells, which was independent of the Dox-inducible expression of KOS factors, it was possible to vary the time of exposure to Zscan4 (FIG. 1B). The absence of Zscan4 for the first 4 or 7 days (i.e., adding the Tmx from day 4 or 7) significantly reduced the number of iPSC colonies, whereas the presence of Zscan4 only for the first 4 or 7 days (i.e., removing the Tmx after day 4 or 7) was sufficient to produce the number of iPSC colonies comparable to that obtained by the presence of Zscan4 for 20 days (FIG. 1D). Further experiments with progressive shortening of the exposure established that Zscan4 is required only for the initial day of iPSC formation (FIG. 1E). These data indicate that, unlike other factors, Zscan4 is involved in the early phase of reprogramming.

Figure 2:
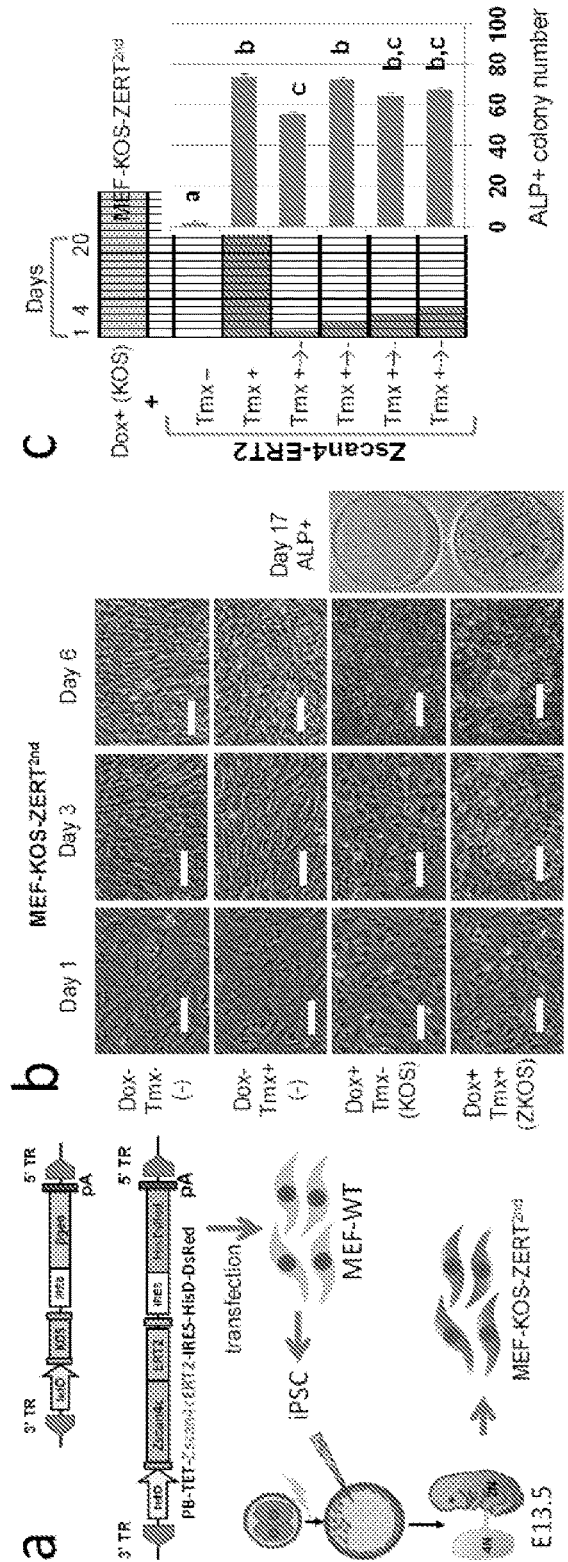
FIG. 2 shows the generation of secondary MEFs and induction of secondary iPSCs.
Figure 14:
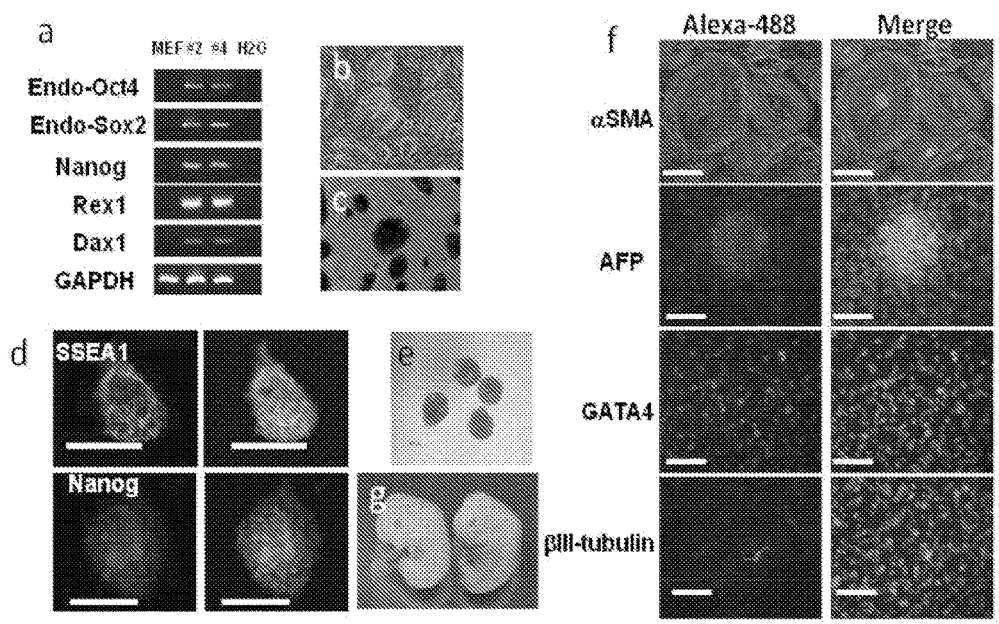
FIG. 14 depicts the generation and characterization of iPSC clones derived from the MEF-WT with the KOS factors and Zscan4ERT2 under the Tmx+ condition.
Figure 15:
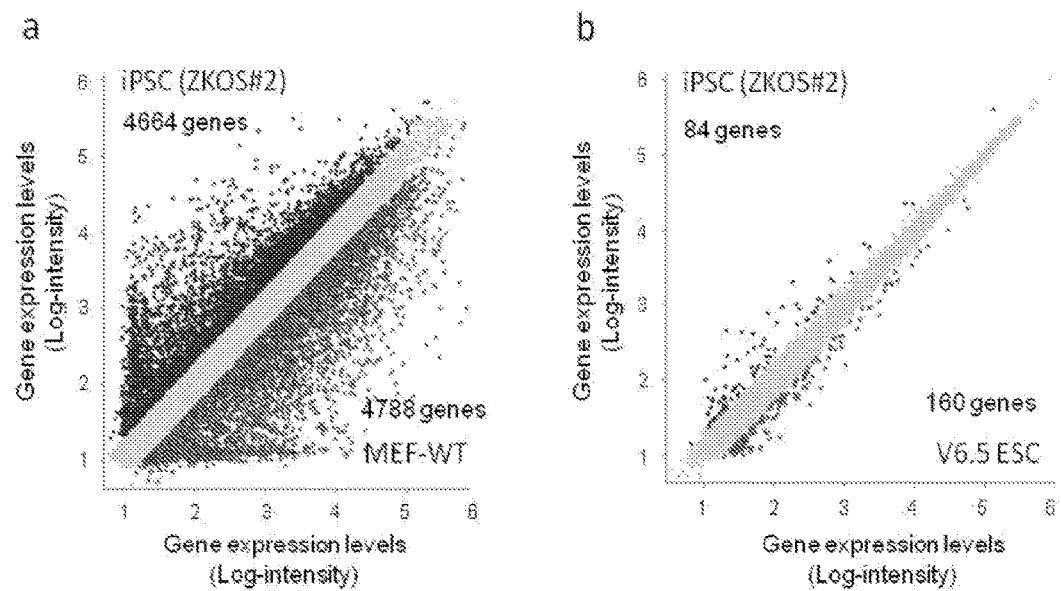
FIG. 15 shows a comparison of global gene expression profiles between iPSC, ESC and MEF. Global expression profiles of the iPSC clone (ZKOS#2), V6.5 ESC, and MEF-WT were generated by using DNA microarrays.

It has been shown that the secondary MEF system facilitates the analysis of early events leading to iPSC formation, because every cell carries inducible iPSC factors (Wernig et al., Nat Biotechnol 26:916-924, 2008; Hanna et al., Nature 462:595-601, 2009). Therefore, secondary MEF cells were generated by injecting iPSCs (clone #2, FIG. 14) produced with ZKOS factors into tetraploid (4N) blastocysts. The result was production of 2 live E13.5 embryos (FIG. 14G), which were subsequently used to derive the secondary MEFs (named MEF-KOS-ZERT$^{2nd}$) (FIG. 2A). As the embryos were entirely derived from the iPSCs in tetraploid complementation system (Nagy et al., Development 110: 815-821, 1990), the results demonstrated that iPSCs generated with ZKOS factors were fully pluripotent. This iPSC clone also showed >80% normal karyotype and global gene expression profiles indistinguishable from ES cells (FIG. 15). Without ZKOS induction (i.e., Dox− Tmx− and Dox− Tmx+ conditions), ALP+ iPSC colonies were not formed from the MEF-KOS-ZERT$^{2nd}$ cells by day 17 (FIG. 2B).

By contrast, the forced expression of ZKOS factors (Dox+ Tmx+ condition) produced a large number (approximately 400) of ALP+ iPSC colonies, whereas the KOS factor only (Dox+ Tmx− condition) produced a much smaller number (about 20) of ALP+ iPSC colonies (FIG. 2B). Interestingly, even the KOS factors alone caused dramatic changes in the MEF morphology by day 1: cells became flatter and lost typical spindle-shape of MEFs (FIG. 2B). However, ES colony-like structures started to form by day 6 only in the Dox+ Tmx+ condition (i.e., the forced expression of ZKOS factors) (FIG. 2B). Furthermore, the secondary MEF system also confirmed that Zscan4 is required only for the initial day of iPSC formation (FIG. 2C).

Consistent with a dramatic morphological change, the forced expression of KOS alone (Dox+ Tmx−) altered the transcriptomes of MEF-KOS-ZERT$^{2nd}$ significantly by day 1: upregulation of 1730 genes and downregulation of 947 genes (FIG. 3A, first row). By day 3 and 6, the number of expression-altered genes further increased. However, considering that these conditions (Dox+ Tmx−) produced only a small number of iPSCs after 17 days in culture, these transcriptome alterations were not sufficient to convert MEFs to iPSCs. By contrast, a comparison between the iPSC-producing ZKOS condition (Dox+ Tmx+) and the KOS condition (Dox+ Tmx−) revealed only a minor transcriptome difference (FIG. 3A, fourth row): 28 genes by day 1, 162 genes by day 3, and 237 genes by day 6. That such a small difference in transcriptome yielded such a great difference in the number of iPSC colonies was astounding, highlighting the critical contribution of these genes to the early phase of iPSC formation. After combining lists of these genes, 231 distinct genes were obtained that were more highly expressed in the ZKOS condition than in the KOS condition (with the statistical significance of FDR≤0.05, fold-change≥2) (FIG. 3A). For these 231 genes, the fold-differences between Tmx+ (i.e., Zscan4+) and Tmx− (i.e., Zscan4−) were calculated, subjected to the hierarchical clustering, and presented as a heatmap (FIG. 3B, Table 1).

TABLE 1

| | \multicolumn{6}{c}{Genes upregulated in the ZKOS condition} | | | | | |
|---|---|---|---|---|---|---|
| Gene Symbol | Day 1 Dox− (Tmx+/Tmx−) | Day 1 Dox+ (Tmx+/Tmx−) | Day 3 Dox− (Tmx+/Tmx−) | Day 3 Dox+ (Tmx+/Tmx−) | Day 6 Dox− (Tmx+/Tmx−) | Day 6 Dox+ (Tmx+/Tmx−) |
| Pramel6 | 1.05 | 1.12 | 0.74 | 10.23 | 0.89 | 9.33 |
| E330017A01Rik | 1.00 | 0.83 | 1.00 | 2.40 | 1.00 | 7.76 |
| Lce3f | 1.20 | 0.89 | 0.81 | 1.35 | 1.70 | 6.76 |
| Trim31 | 0.98 | 1.41 | 0.93 | 6.31 | 0.59 | 1.48 |
| BC094916 | 1.00 | 0.83 | 1.00 | 1.26 | 1.00 | 5.89 |
| Galnt13 | 1.10 | 1.12 | 1.10 | 0.87 | 1.10 | 5.89 |
| Podnl1 | 0.89 | 0.58 | 0.89 | 5.75 | 0.89 | 1.10 |
| Patl2 | 1.00 | 1.20 | 0.91 | 3.80 | 1.17 | 5.50 |
| Esx1 | 1.00 | 1.58 | 0.93 | 1.26 | 1.02 | 4.90 |
| AF067063 | 0.98 | 1.62 | 0.76 | 2.40 | 1.55 | 4.79 |
| 9130409J20Rik | 1.12 | 1.10 | 1.00 | 1.41 | 1.07 | 4.79 |
| 1700003E24Rik | 1.41 | 1.70 | 0.91 | 3.47 | 0.89 | 4.68 |
| 4930558C23Rik | 1.05 | 2.40 | 0.95 | 3.63 | 1.02 | 4.47 |
| D5Ertd577e | 1.07 | 1.23 | 0.93 | 4.47 | 1.17 | 4.17 |
| Trim42 | 1.00 | 0.63 | 1.00 | 4.47 | 1.00 | 2.51 |
| A930002C04Rik | 1.05 | 0.56 | 1.55 | 0.60 | 1.10 | 4.47 |
| Dppa2 | 1.00 | 1.02 | 0.79 | 2.45 | 1.12 | 4.07 |
| Gm22 | 1.02 | 4.07 | 1.05 | 0.87 | 0.95 | 1.10 |
| Aadac | 1.00 | 3.98 | 0.83 | 2.19 | 1.02 | 1.86 |
| LOC677440 | 0.98 | 0.93 | 0.69 | 3.98 | 1.12 | 2.88 |
| Mageb7-ps (EG637027) | 0.93 | 1.95 | 0.93 | 3.98 | 0.91 | 1.15 |
| D13Ertd608e | 1.07 | 1.62 | 0.98 | 3.89 | 0.98 | 1.74 |
| Abca12 | 1.00 | 1.26 | 1.00 | 2.19 | 0.93 | 3.89 |
| Nlrp4c | 0.95 | 1.91 | 1.17 | 3.89 | 1.26 | 0.63 |
| Slc6a14 | 1.10 | 1.23 | 0.72 | 1.82 | 0.78 | 3.80 |
| 9030625G05Rik | 0.81 | 0.81 | 1.66 | 3.80 | 0.81 | 1.10 |
| C130073F10Rik | 0.98 | 1.20 | 1.05 | 2.88 | 1.05 | 3.72 |
| Cphx | 0.95 | 1.74 | 0.91 | 3.72 | 0.95 | 1.62 |
| Lce1f | 1.23 | 1.29 | 1.00 | 1.05 | 0.78 | 3.63 |
| 4930459C07Rik | 1.00 | 1.05 | 1.00 | 0.87 | 1.00 | 3.55 |
| AU018829 | 1.15 | 1.48 | 0.71 | 2.57 | 1.05 | 3.55 |
| 4930519F16Rik | 1.20 | 1.00 | 1.00 | 0.95 | 1.00 | 3.55 |
| Calcoco2 | 1.00 | 1.07 | 0.78 | 1.91 | 1.20 | 3.47 |
| Cyp2a4 | 1.00 | 0.85 | 1.00 | 1.45 | 1.02 | 3.47 |
| Mogat1 | 0.91 | 1.10 | 0.98 | 0.98 | 1.07 | 3.47 |
| Gdpd2 | 1.29 | 3.47 | 1.10 | 1.05 | 0.85 | 1.00 |
| Il1f5 | 1.00 | 1.51 | 1.00 | 2.57 | 1.00 | 3.39 |
| Nr5a2 | 1.10 | 1.32 | 0.81 | 3.24 | 1.02 | 3.31 |
| LOC434660 | 1.29 | 1.74 | 0.68 | 2.40 | 0.98 | 3.31 |
| Trim43b (EG666747) | 0.79 | 0.91 | 1.00 | 1.26 | 1.00 | 3.31 |
| Sp8 | 1.00 | 1.20 | 1.00 | 2.88 | 1.17 | 3.24 |
| Slc28a1 | 1.05 | 1.66 | 0.95 | 3.24 | 1.05 | 2.19 |
| Ubtfl1 (B020006M18Rik) | 1.10 | 1.23 | 0.76 | 1.78 | 0.68 | 3.24 |
| LOC434136 | 1.12 | 1.07 | 0.76 | 1.17 | 0.98 | 3.24 |
| C1qtnf9 | 1.15 | 1.12 | 0.79 | 0.98 | 0.91 | 3.16 |
| 1600029D21Rik | 1.00 | 1.23 | 1.07 | 3.09 | 1.12 | 3.02 |
| Tcl1 | 0.89 | 1.07 | 0.95 | 2.34 | 1.02 | 3.09 |
| Cdx2 | 1.70 | 1.23 | 1.07 | 1.95 | 0.85 | 3.09 |
| Khdc1c | 1.00 | 1.12 | 1.00 | 1.45 | 1.00 | 3.09 |
| Tarm1 (9930022N03Rik) | 0.89 | 0.95 | 1.00 | 1.26 | 1.00 | 3.09 |
| 4732457N14 | 1.00 | 1.32 | 0.87 | 2.34 | 1.48 | 3.02 |
| AU015836 | 0.93 | 0.78 | 1.15 | 3.02 | 0.95 | 2.29 |
| Anxa10 | 0.69 | 3.02 | 1.00 | 1.82 | 1.00 | 1.23 |
| D630045M09Rik | 0.98 | 1.07 | 1.23 | 1.82 | 1.55 | 3.02 |
| Prdm13 | 1.17 | 0.91 | 0.71 | 1.70 | 0.87 | 3.02 |
| Mx1 | 1.17 | 2.95 | 1.20 | 1.02 | 1.12 | 0.91 |
| Obox6 | 0.98 | 1.20 | 0.87 | 2.88 | 1.10 | 2.69 |
| LOC668206 | 1.12 | 1.55 | 0.87 | 2.19 | 0.95 | 2.88 |
| LOC432715 | 0.98 | 1.15 | 0.87 | 2.88 | 1.02 | 2.51 |
| Mmp8 | 0.89 | 2.88 | 0.79 | 1.55 | 1.15 | 1.35 |
| 4933411G11Rik | 1.26 | 0.91 | 0.95 | 1.20 | 0.91 | 2.88 |
| D730045A05Rik | 1.15 | 0.63 | 1.35 | 1.45 | 0.87 | 2.88 |
| Fgf20 | 1.00 | 0.65 | 1.00 | 1.10 | 1.35 | 2.88 |
| Spink5 | 1.10 | 0.58 | 1.26 | 1.02 | 1.10 | 2.88 |
| Gabrr3 | 1.00 | 1.00 | 1.00 | 2.24 | 1.00 | 2.82 |
| 4930430J02Rik | 0.95 | 1.35 | 0.91 | 2.82 | 0.93 | 1.86 |
| Crct1 | 1.02 | 1.12 | 1.07 | 1.10 | 1.12 | 2.82 |
| Cdcp1 | 1.29 | 1.26 | 0.87 | 2.82 | 1.00 | 2.75 |
| 4933402E13Rik | 0.95 | 1.05 | 0.87 | 2.00 | 1.05 | 2.82 |
| Rptn | 1.29 | 1.70 | 1.10 | 1.12 | 1.55 | 2.75 |
| Stox1 | 0.93 | 0.91 | 0.91 | 1.86 | 1.02 | 2.75 |

TABLE 1-continued

| Genes upregulated in the ZKOS condition | | | | | | |
|---|---|---|---|---|---|---|
| Gene Symbol | Day 1 Dox− (Tmx+/Tmx−) | Day 1 Dox+ (Tmx+/Tmx−) | Day 3 Dox− (Tmx+/Tmx−) | Day 3 Dox+ (Tmx+/Tmx−) | Day 6 Dox− (Tmx+/Tmx−) | Day 6 Dox+ (Tmx+/Tmx−) |
| Trim43a (EG547109) | 1.23 | 0.49 | 1.41 | 1.86 | 0.91 | 2.75 |
| Gpx2-ps1 | 1.00 | 0.83 | 1.00 | 1.45 | 1.00 | 2.75 |
| LOC677115 | 1.15 | 0.79 | 1.15 | 1.17 | 0.76 | 2.75 |
| Ankrd22 | 0.98 | 1.35 | 0.81 | 2.69 | 1.07 | 2.09 |
| LOC625360 | 0.98 | 1.05 | 0.81 | 2.69 | 1.02 | 2.00 |
| Trpv3 | 1.00 | 1.00 | 1.00 | 1.32 | 1.00 | 2.69 |
| RP23-438H3.2 | 1.35 | 1.05 | 0.98 | 1.91 | 0.93 | 2.69 |
| Kremen2 | 1.00 | 1.05 | 0.91 | 1.38 | 0.69 | 2.69 |
| Ldhc | 1.07 | 1.95 | 0.91 | 2.63 | 1.00 | 2.04 |
| A530040E14Rik | 1.26 | 1.20 | 0.83 | 2.63 | 1.12 | 2.34 |
| Zp3 | 1.20 | 1.15 | 2.04 | 2.34 | 1.15 | 2.63 |
| AF067061 | 0.91 | 0.71 | 1.07 | 2.34 | 1.10 | 2.63 |
| Fam155a (AW121567) | 0.95 | 1.48 | 1.10 | 2.63 | 1.29 | 1.48 |
| Sftpd | 0.98 | 1.00 | 0.87 | 1.55 | 1.02 | 2.63 |
| Sox30 | 1.17 | 1.10 | 1.17 | 1.20 | 0.81 | 2.63 |
| Pof1b | 0.98 | 1.00 | 0.89 | 2.29 | 1.07 | 2.57 |
| B930018H19 | 1.55 | 1.15 | 1.07 | 1.91 | 1.26 | 2.57 |
| Slc39a4 | 0.98 | 1.02 | 1.10 | 1.74 | 1.15 | 2.57 |
| Spnb3 | 1.07 | 0.98 | 1.07 | 1.70 | 1.10 | 2.57 |
| LOC672264 | 0.98 | 0.79 | 1.51 | 1.66 | 0.87 | 2.57 |
| D10Bwg1379e | 1.12 | 0.79 | 1.23 | 1.45 | 0.91 | 2.57 |
| Tmprss11d | 1.00 | 1.00 | 1.10 | 1.23 | 1.00 | 2.57 |
| 1700065L07Rik | 0.85 | 2.57 | 0.62 | 0.91 | 0.76 | 0.91 |
| Slc23a3 | 1.10 | 1.35 | 1.05 | 2.14 | 1.00 | 2.51 |
| 2210418O10Rik | 1.02 | 0.98 | 0.91 | 2.24 | 1.05 | 2.51 |
| Tcstv3 | 0.83 | 0.78 | 1.02 | 2.40 | 0.95 | 2.51 |
| Slc46a2 | 0.93 | 1.29 | 0.74 | 1.51 | 0.74 | 2.51 |
| Mszf81 | 0.98 | 1.20 | 1.00 | 1.32 | 1.15 | 2.51 |
| Nlrp4e | 1.05 | 1.26 | 0.89 | 2.51 | 1.02 | 1.12 |
| 4931429I11Rik | 1.12 | 2.51 | 1.00 | 1.10 | 1.00 | 1.17 |
| Khdc1a | 1.00 | 0.91 | 1.00 | 1.07 | 1.00 | 2.51 |
| Adcyap1 | 1.29 | 0.76 | 1.29 | 1.20 | 1.58 | 2.51 |
| Mnx1 | 0.87 | 0.78 | 1.20 | 0.98 | 0.91 | 2.51 |
| Cgn | 1.02 | 1.70 | 1.05 | 2.45 | 1.10 | 2.40 |
| Wfdc15a | 0.55 | 1.35 | 0.71 | 1.95 | 0.91 | 2.45 |
| Tcstv1 | 1.15 | 0.89 | 0.87 | 2.40 | 1.26 | 2.45 |
| B020031M17Rik | 1.10 | 0.93 | 1.17 | 2.29 | 1.12 | 2.45 |
| Fam25c (2200001I15Rik) | 1.00 | 1.62 | 1.05 | 1.55 | 0.95 | 2.45 |
| Lce1d | 0.78 | 1.10 | 1.00 | 2.45 | 1.00 | 2.00 |
| AI848258 | 1.02 | 1.12 | 0.74 | 2.45 | 1.07 | 1.32 |
| Slc44a4 | 0.95 | 1.02 | 1.07 | 1.41 | 1.05 | 2.45 |
| Slc34a3 | 1.00 | 0.81 | 1.51 | 1.58 | 0.87 | 2.45 |
| Nr0b1 | 0.98 | 1.41 | 1.00 | 2.40 | 1.00 | 2.09 |
| Bex6 | 1.48 | 1.10 | 0.89 | 2.40 | 1.07 | 2.40 |
| Adh4 | 0.89 | 1.41 | 0.83 | 1.95 | 1.15 | 2.40 |
| C130026I21Rik | 1.41 | 0.83 | 1.91 | 2.19 | 1.07 | 2.40 |
| Adad2 | 1.10 | 1.32 | 0.87 | 1.55 | 1.10 | 2.40 |
| LOC673289 | 0.65 | 0.62 | 1.02 | 2.40 | 0.91 | 1.95 |
| Sst | 0.98 | 0.98 | 0.78 | 1.58 | 0.76 | 2.40 |
| E230016M11Rik | 1.12 | 1.26 | 0.93 | 2.40 | 0.85 | 1.07 |
| Slc38a5 | 1.05 | 1.12 | 0.89 | 1.17 | 1.00 | 2.40 |
| Fasl | 1.17 | 0.95 | 0.95 | 1.26 | 0.98 | 2.40 |
| 4930538E20Rik | 1.00 | 1.12 | 1.00 | 0.91 | 1.12 | 2.40 |
| Gpr111 | 1.02 | 1.00 | 1.00 | 1.00 | 1.00 | 2.40 |
| Gtsf1 | 1.05 | 1.05 | 1.10 | 0.91 | 1.15 | 2.40 |
| Cfc1 | 1.02 | 1.48 | 0.89 | 2.34 | 0.95 | 1.74 |
| Fbxo15 | 1.26 | 1.07 | 0.98 | 1.95 | 1.10 | 2.34 |
| Plbd1 (1100001H23Rik) | 1.05 | 0.95 | 1.10 | 2.04 | 1.15 | 2.34 |
| Gm8016 (EG666272) | 0.91 | 0.91 | 0.89 | 2.34 | 0.85 | 1.86 |
| Mageb8-ps (EG436212) | 1.00 | 1.00 | 1.00 | 1.70 | 1.12 | 2.34 |
| Zbtb32 | 0.83 | 1.23 | 0.93 | 1.41 | 1.02 | 2.34 |
| Eif1a | 0.98 | 0.81 | 1.00 | 2.34 | 1.12 | 1.78 |
| 2010109I03Rik | 1.00 | 1.00 | 0.58 | 1.41 | 1.00 | 2.34 |
| BC066135 | 0.87 | 1.15 | 1.00 | 1.23 | 0.95 | 2.34 |
| Vstm2a | 1.00 | 1.00 | 1.17 | 2.34 | 0.95 | 0.98 |
| Prom2 | 0.74 | 0.59 | 1.17 | 1.38 | 1.10 | 2.34 |
| Hoxc13 | 1.00 | 0.85 | 0.87 | 2.34 | 0.85 | 0.98 |
| LOC665276 | 1.00 | 1.00 | 1.00 | 0.69 | 1.00 | 2.34 |
| Ankrd56 | 0.89 | 1.35 | 0.87 | 1.78 | 1.00 | 2.29 |

TABLE 1-continued

| | Genes upregulated in the ZKOS condition | | | | | |
|---|---|---|---|---|---|---|
| Gene Symbol | Day 1 Dox− (Tmx+/Tmx−) | Day 1 Dox+ (Tmx+/Tmx−) | Day 3 Dox− (Tmx+/Tmx−) | Day 3 Dox+ (Tmx+/Tmx−) | Day 6 Dox− (Tmx+/Tmx−) | Day 6 Dox+ (Tmx+/Tmx−) |
| Tnk1 | 1.07 | 0.83 | 0.87 | 2.29 | 1.32 | 2.14 |
| Prss8 | 0.68 | 1.00 | 1.02 | 1.95 | 1.32 | 2.29 |
| Shisa3 | 1.32 | 1.41 | 0.83 | 2.29 | 1.23 | 1.35 |
| Fndc3c1 (Gm784) | 1.17 | 1.17 | 1.02 | 1.51 | 1.15 | 2.29 |
| Btnl9 | 1.29 | 0.51 | 0.98 | 2.09 | 1.32 | 2.29 |
| Vmn1r15 (V1rc6) | 1.41 | 1.35 | 1.00 | 1.00 | 1.26 | 2.29 |
| Mmp19 | 0.91 | 1.05 | 0.98 | 2.29 | 0.91 | 0.91 |
| Dkkl1 | 1.00 | 1.45 | 0.98 | 2.24 | 1.02 | 1.74 |
| Gli1 | 0.98 | 1.10 | 0.95 | 2.04 | 0.91 | 2.24 |
| Tceal7 | 1.26 | 1.05 | 1.17 | 2.24 | 1.07 | 2.00 |
| 1700024P16Rik | 1.07 | 1.12 | 1.10 | 1.91 | 1.00 | 2.24 |
| Trim6 | 1.15 | 1.15 | 1.00 | 1.82 | 1.07 | 2.24 |
| Piwil2 | 1.17 | 1.48 | 0.81 | 1.45 | 1.02 | 2.24 |
| Isg15 | 1.23 | 1.32 | 0.95 | 1.58 | 1.17 | 2.24 |
| Gm5576 (EG434050) | 0.85 | 0.98 | 1.00 | 1.78 | 0.91 | 2.24 |
| Cldn7 | 0.93 | 0.93 | 0.98 | 1.78 | 1.10 | 2.24 |
| Tmem30b | 0.93 | 0.59 | 1.07 | 2.24 | 0.93 | 2.09 |
| Lce3c | 1.07 | 1.23 | 1.15 | 1.38 | 1.02 | 2.24 |
| D030018L15Rik | 0.93 | 1.26 | 1.12 | 1.32 | 0.79 | 2.24 |
| 1700042O10Rik | 1.02 | 0.95 | 1.10 | 1.32 | 1.05 | 2.24 |
| LOC672673 | 0.95 | 1.10 | 0.91 | 1.15 | 0.89 | 2.24 |
| 1700003M02Rik | 0.81 | 1.35 | 0.79 | 2.24 | 1.45 | 0.87 |
| 1700008A04Rik | 0.91 | 1.20 | 1.23 | 0.95 | 1.74 | 2.24 |
| Gm5891 (EG545929) | 0.83 | 0.85 | 0.89 | 2.09 | 1.35 | 2.19 |
| Gm9124 (EG668356) | 0.79 | 1.20 | 1.02 | 2.19 | 1.05 | 1.74 |
| Crb3 | 1.12 | 2.19 | 1.02 | 1.58 | 1.12 | 1.35 |
| Rab25 | 0.78 | 0.91 | 0.98 | 1.91 | 0.87 | 2.19 |
| EG226955 | 0.69 | 1.02 | 1.20 | 2.19 | 1.55 | 1.70 |
| Gm3336 (2410018E23Rik) | 1.10 | 0.93 | 1.55 | 1.74 | 1.00 | 2.19 |
| 2310007B03Rik | 0.89 | 1.35 | 0.98 | 1.32 | 1.45 | 2.19 |
| Sp110 | 1.00 | 0.98 | 1.00 | 1.66 | 1.07 | 2.19 |
| Gldc | 1.02 | 1.05 | 0.98 | 1.32 | 1.07 | 2.19 |
| Lce1a1 | 1.20 | 1.23 | 0.87 | 1.00 | 0.83 | 2.19 |
| Meox1 | 0.83 | 1.07 | 1.02 | 1.10 | 1.00 | 2.19 |
| Pglyrp3 | 1.10 | 1.15 | 1.00 | 1.00 | 0.95 | 2.19 |
| Gpr115 | 1.10 | 1.07 | 1.66 | 1.00 | 0.65 | 2.19 |
| Muc4 | 1.00 | 2.19 | 1.00 | 1.00 | 1.00 | 0.98 |
| LOC626773 | 1.12 | 0.83 | 1.51 | 1.02 | 0.40 | 2.19 |
| B230217J21Rik | 1.10 | 0.91 | 1.70 | 0.65 | 0.83 | 2.19 |
| Mbl2 | 1.15 | 1.62 | 0.71 | 2.14 | 0.50 | 1.62 |
| 1700016G22Rik | 1.05 | 1.78 | 0.81 | 1.41 | 1.51 | 2.14 |
| Hsh2d | 1.07 | 1.05 | 0.72 | 2.14 | 1.48 | 2.09 |
| Usp43 | 1.35 | 1.02 | 0.83 | 2.14 | 1.02 | 1.95 |
| Mal2 | 1.15 | 2.14 | 1.02 | 1.45 | 1.10 | 1.45 |
| Ssxb2 | 0.79 | 0.85 | 0.78 | 2.14 | 0.66 | 1.95 |
| Prdm1 | 1.12 | 1.15 | 1.12 | 1.58 | 0.98 | 2.14 |
| LOC233184 | 1.00 | 1.00 | 0.95 | 2.14 | 1.02 | 1.66 |
| 1700110K17Rik | 0.56 | 1.26 | 1.10 | 2.14 | 0.81 | 1.38 |
| BC013672 | 0.81 | 1.26 | 0.95 | 1.35 | 1.62 | 2.14 |
| Cldn6 | 0.98 | 1.00 | 1.07 | 1.55 | 1.05 | 2.14 |
| RP23-67E6.3 | 0.87 | 0.93 | 1.45 | 1.58 | 0.95 | 2.14 |
| Pdc | 0.87 | 1.00 | 0.76 | 1.41 | 0.98 | 2.14 |
| Speer1-ps1 | 0.89 | 1.26 | 1.05 | 1.15 | 1.17 | 2.14 |
| 4933438K21Rik | 1.10 | 1.20 | 0.93 | 1.10 | 0.87 | 2.14 |
| Tas2r137 | 1.41 | 0.81 | 0.95 | 2.14 | 0.79 | 1.45 |
| Tns4 | 1.12 | 1.02 | 0.95 | 1.07 | 1.20 | 2.14 |
| Tcte2 | 1.29 | 0.87 | 0.95 | 1.05 | 0.81 | 2.14 |
| Gpr152 | 1.35 | 0.68 | 1.15 | 0.74 | 0.83 | 2.14 |
| LOC623810 | 1.00 | 0.60 | 1.00 | 0.46 | 1.00 | 2.14 |
| Rhox4c | 0.95 | 1.74 | 0.74 | 2.09 | 0.95 | 1.45 |
| Tsga8 | 1.55 | 1.41 | 0.72 | 1.66 | 1.15 | 2.09 |
| Epcam(Tacstd1) | 1.02 | 1.15 | 0.93 | 2.09 | 1.07 | 1.86 |
| Bex1 | 0.93 | 1.17 | 1.02 | 1.78 | 1.00 | 2.09 |
| Spint1 | 1.05 | 1.26 | 1.23 | 1.62 | 0.78 | 2.09 |
| Gc | 1.20 | 1.10 | 0.71 | 1.78 | 1.02 | 2.09 |
| D7Ertd183e | 1.51 | 1.55 | 1.07 | 0.93 | 0.76 | 2.09 |
| Bcl2l14 | 1.00 | 1.15 | 1.02 | 1.20 | 1.12 | 2.09 |
| Scel | 1.07 | 1.00 | 1.12 | 1.07 | 1.23 | 2.09 |
| Robo4 | 0.76 | 0.83 | 1.12 | 1.20 | 0.98 | 2.09 |

TABLE 1-continued

Genes upregulated in the ZKOS condition

| Gene Symbol | Day 1 Dox−<br>(Tmx+/Tmx−) | Day 1 Dox+<br>(Tmx+/Tmx−) | Day 3 Dox−<br>(Tmx+/Tmx−) | Day 3 Dox+<br>(Tmx+/Tmx−) | Day 6 Dox−<br>(Tmx+/Tmx−) | Day 6 Dox+<br>(Tmx+/Tmx−) |
|---|---|---|---|---|---|---|
| Ttll10 | 0.78 | 0.83 | 0.52 | 0.93 | 1.12 | 2.09 |
| Cyp26b1 | 1.17 | 0.91 | 0.83 | 0.76 | 0.89 | 2.09 |
| BC024997 | 0.95 | 1.78 | 1.00 | 2.04 | 1.32 | 1.70 |
| Btn1a1 | 1.10 | 1.66 | 1.00 | 1.74 | 1.29 | 2.04 |
| 9330159N05Rik | 1.45 | 1.45 | 1.12 | 1.58 | 1.38 | 2.04 |
| 1810019J16Rik | 1.05 | 1.12 | 0.93 | 2.04 | 1.07 | 1.91 |
| Capsl | 0.89 | 1.23 | 0.89 | 1.78 | 0.95 | 2.04 |
| A630095N17Rik | 1.12 | 1.29 | 0.95 | 1.45 | 1.07 | 2.04 |
| Grb7 | 0.95 | 0.98 | 1.05 | 1.55 | 0.98 | 2.04 |
| LOC671025 | 1.07 | 1.07 | 1.12 | 1.35 | 1.20 | 2.04 |
| Gm44 | 1.51 | 0.79 | 1.05 | 2.04 | 1.17 | 1.62 |
| Pard6b | 0.93 | 0.98 | 1.17 | 1.20 | 1.07 | 2.04 |
| I730030J21Rik | 1.07 | 1.05 | 1.20 | 2.04 | 1.35 | 1.05 |
| Gpr112 | 1.00 | 0.91 | 1.00 | 1.17 | 1.00 | 2.04 |
| Psg27 | 0.95 | 0.95 | 1.00 | 2.04 | 0.93 | 1.07 |
| Mctp2 | 1.00 | 1.00 | 1.00 | 1.00 | 1.00 | 2.04 |
| Il1f9 | 1.00 | 1.05 | 1.00 | 0.85 | 0.95 | 2.04 |
| Colec10 | 1.02 | 1.00 | 1.26 | 0.56 | 1.07 | 2.04 |
| Syt2 | 1.00 | 0.79 | 1.15 | 0.49 | 1.00 | 2.04 |
| 1700013H16Rik | 1.10 | 1.23 | 0.85 | 2.00 | 1.10 | 1.48 |
| LOC673795 | 1.00 | 1.00 | 1.00 | 1.51 | 1.00 | 2.00 |
| Rab39 | 1.17 | 0.69 | 1.12 | 1.38 | 1.07 | 2.00 |

Figure 16:
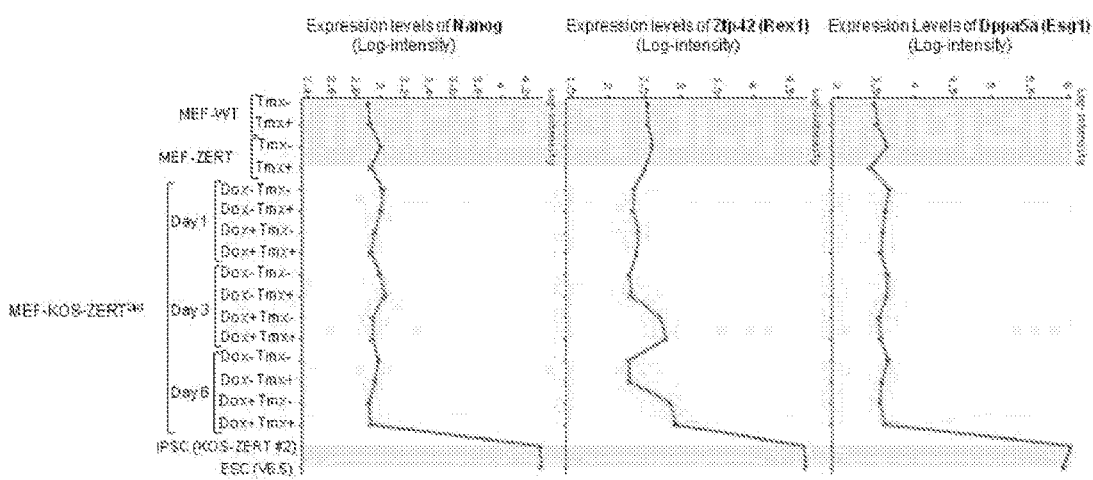
FIG. 16 depicts expression levels of pluripotency genes—Nanog, Zfp42, and Dppa5a during initial phase of induction in the secondary MEFs. Gene expression levels were obtained from DNA microarray analysis and plotted by the NIA ANOVA tool (Sharov et al., *Bioinformatics* 21:2548-2549, 2005).

Some of these genes were originally identified from only preimplantation embryos through large-scale cDNA sequencing projects (Ko et al., *Development* 127:1737-1749, 2000), e.g., Pramel6, D5Ertd577e, D13Ertd608e, Tcstv1 (Struwe and Solter, 1998, GenBank accession AF067057.1), Trim43a (Stanghellini et al., 2009), and Trim43b (Stanghellini et al., *Gene Expr Patterns* 9:595-602, 2009). Accordingly, the public Expressed Sequence Tags (ESTs) database (NCBI/NIH) was searched and d the number of EST hits for each gene was scored. A significant fraction of the 231 genes was indeed expressed predominantly in early embryos and closely related gonads (testis and ovary): 27 genes in preimplantation stage (1-cell-blastocysts); 14 genes in oocytes; and 37 genes in testis/ovary (FIG. 3B). The preimplantation- and gonad-specific expression of these genes was also confirmed by the expression patterns in the NIA Gene Expression Atlas (Sharov et al., *BMC Genomics* 12:102, 2011) (FIG. 3C) and the GNF database (Su et al., *Proc Natl Acad Sci USA* 99:4465-4470, 2002) (FIG. 3D). Interestingly, most of these genes showed little or no expression in MEFs, ESCs, and iPSCs (FIG. 3C), indicating that these genes are activated transiently in the early phase of iPSC formation, but then downregulated once iPSCs are fully formed. These genes may thus represent the earliest markers for eventual iPSC formation from MEFs, because they were fully activated as early as day 1, 3, or 6, when typical pluripotency markers such as Nanog, Zfp42 (also known as Rex1), and Dppa5a (also known as Esg1) were still silent (FIG. 16).

The early activation of preimplantation-specific genes seems to be unique to Zscan4-mediated iPSC formation. Indeed, previous microarray studies of the secondary MEF system using piggyBac MKOS factors have not identified the activation of preimplantation-specific genes as the critical features of iPSC-forming transcriptome changes (Samavarchi-Tehrani et al., *Cell Stem Cell* 7:64-77, 2010). For example, most of the 231 critical genes identified were not activated transiently during the early phase of MKOS-based iPSC formation. These data indicate that Zscan4-mediated iPSC formation takes a different path from standard MKOS-mediated iPSC formation: the former path is more strongly associated with the genetic program occurring in the preimplantation embryos than the latter path.

Figure 4:
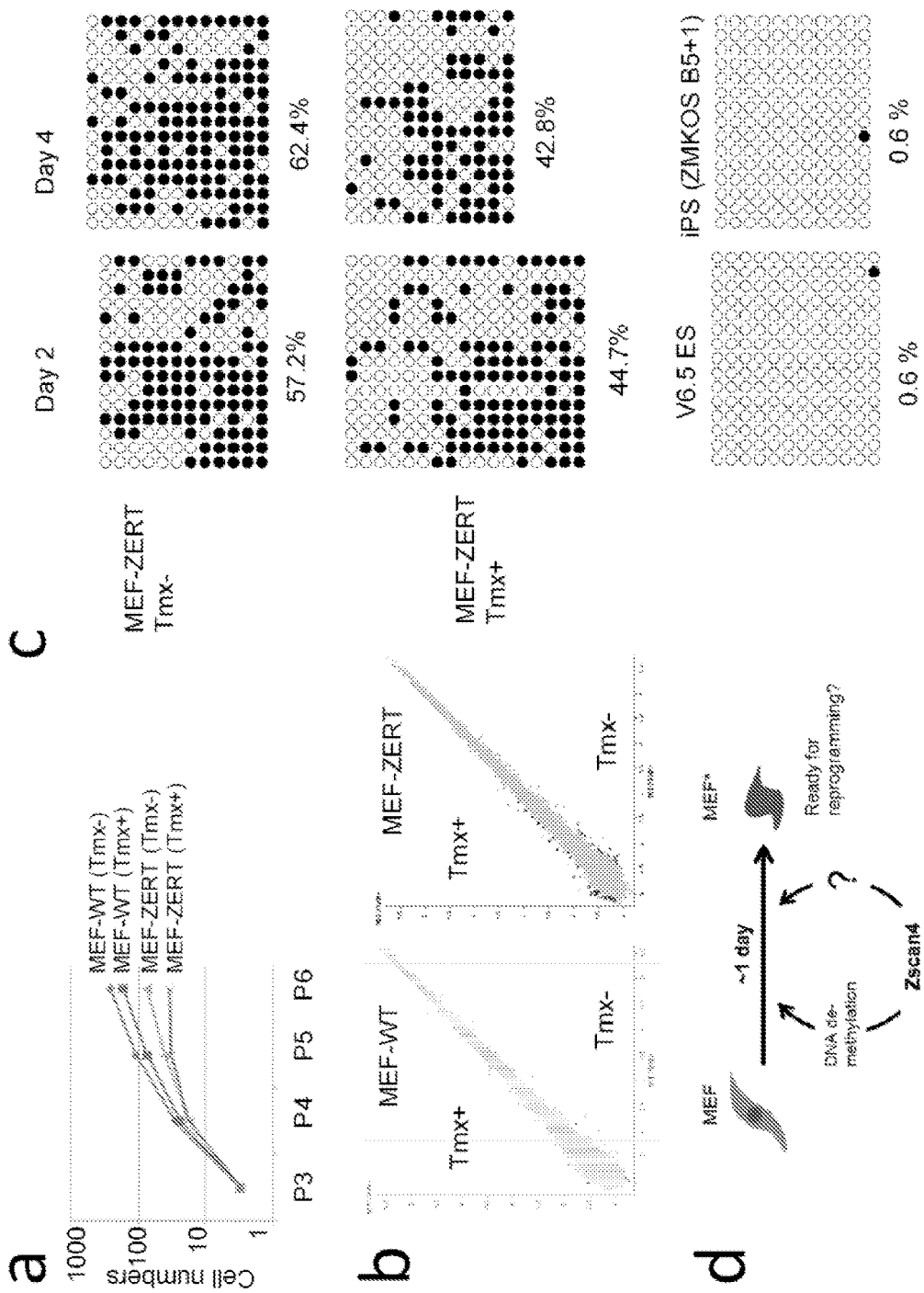
FIG. 4 depicts the characterization of MEF-ZERT cells and summary diagrams.

To further investigate the action of Zscan4, the effect of Zscan4 alone on the MEFs was examined using the MEF-ZERT cells. Cell growth curves showed that Tmx slowed down the proliferation of MEF-ZERT significantly, but had only a minor effect on wild-type MEF (MEF-WT) (FIG. 4A). Evidently, although Zscan4 is not usually expressed there, it can function in MEFs and negatively affect their proliferation. Zscan4 alone, however, did not convert MEFs into iPSCs. In fact, the microarray analysis showed that a short-term treatment of Tmx had almost no effect on the transcriptome of both MEF-ZERT and MEF-WT (FIG. 4B). Next, DNA methylation patterns for Oct4 promoters was examined by the bisulfite sequencing method. Consistent with previous reports, the established iPSC, similar to ES cells, showed almost no DNA methylation (FIG. 4C). Interestingly, Tmx− treatment decreased DNA methylation levels from ~60% to ~44% by day 2, indicating a partial but rapid demethylation of DNAs by Zscan4 in MEFs. These data suggest that the expression of Zscan4 quickly alters the epigenetic status of the genome (e.g., open chromatin conformation) by a mechanism that is as yet unidentified, and renders MEF susceptible to the effects of the forced expression of KOS factors (FIG. 4D).

Several lines of evidence indicate that Zscan4 is the missing early factor that initiates the cellular reprogramming (FIG. 3E). First, Zscan4 is a gene expressed specifically in late 2-cell embryos, blastomeres of which has been shown to have a potent reprogramming activity in the NT cloning experiments (Egli et al., *Curr Biol* 19:1403-1409, 2009). Second, Zscan4-mediated reprogramming activates other preimplantation-specific genes in MEFs, seemingly recapitulating the genetic program occurring transiently during preimplantation embryo development and NT embryo development. Third, Zscan4 alone can induce the rapid DNA demethylation in MEFs. This is in accord with the requirement of DNA demethylation for reprogramming in iPSC (Mikkelsen et al., *Nature* 454:49-55, 2008), NT (Simonsson and Gurdon, *Nat Cell Biol* 6:984-990, 2004), and heterokaryons (Bhutani et al., *Nature* 463:1042-1047, 2010).

Fourth, Zscan4 replaces Myc in enhancing the efficiency of iPSC formation with KOS factors. Unlike Myc, which is required for at least the first 5 days of iPSC formation (Sridharan et al., *Cell* 136:364-377, 2009), Zscan4 is required for only the initial day of iPSC formation—long before the expression of core pluripotency transcription factors such as Nanog. In addition, unlike Myc and other iPSC-promoting conditions (e.g., repression of P53; Tapia and Scholer, *J Exp Med* 207:2045-2048, 2010), which stimulate the proliferation of MEFs, destabilize genome integrity (Hanna et al., *Cell* 143:508-525, 2010; Stadtfeld and Hochedlinger, *Genes Dev* 24:2239-2263, 2010; Nakagawa et al., *Proc Natl Acad Sci USA* 107:14152-14157, 2010), and raise concerns about long-term stability of iPSCs in culture (Hu et al., *Proc Natl Acad Sci USA* 107:4335-4340, 2010; Feng et al., *Stem Cells* 28:704-712, 2010), Zscan4 represses the proliferation of MEFs and promotes the genome stability and maintenance of normal karyotype in ES cells (Zalzman et al., *Nature* 464:858-863, 2010). Therefore, these results indicate that Zscan4 is an "initiating" factor with distinct properties that can help to reprogram cells while preserving genome stability.

Example 2 iPSCs Generated with Zscan4 are of High Quality

Several studies were carried out to evaluate the quality of the iPSCs generated by expression of Zscan4, including a tetraploid complementation assay, which is the most stringent test for the pluripotency of iPS cells. A karyotype analysis of iPSCs generated with or without forced expression of Zscan4 was also performed. The results are shown in FIG. 18. Karyotype analysis of randomly selected iPSC lines clearly showed that iPSCs generated with Zscan4 were of higher quality than iPSCs generated without Zscan4. In addition, iPSCs generated with Zscan4 could form entire live embryos by the tetraploid complementation assay. The success rate for iPSCs in the tetraploid complementation assay is usually much lower than what was achieved by expression of Zscan4. Furthermore, this high success rate was achieved with the standard fetal calf serum-based culture condition, whereas the reported success has been achieved by using the special cell culture condition (KSR medium), which is known to dramatically enhance the pluripotency of ES/iPSC cells (see for example, Li et al., *Cell Res* 21(3):550-553, 2011).

Example 3

Zscan4-Dependent Genes Increase the Efficiency of iPSC Formation

As discussed in Example 1, 231 genes were identified that are upregulated during the early phase (day 1-day 6) of iPSC formation in a Zscan4-dependent manner. Since many of these genes are preimplantation- or germline-specifically expressed, it was hypothesized that these genes would also enhance the efficiency of iPSC formation.

Figure 21:
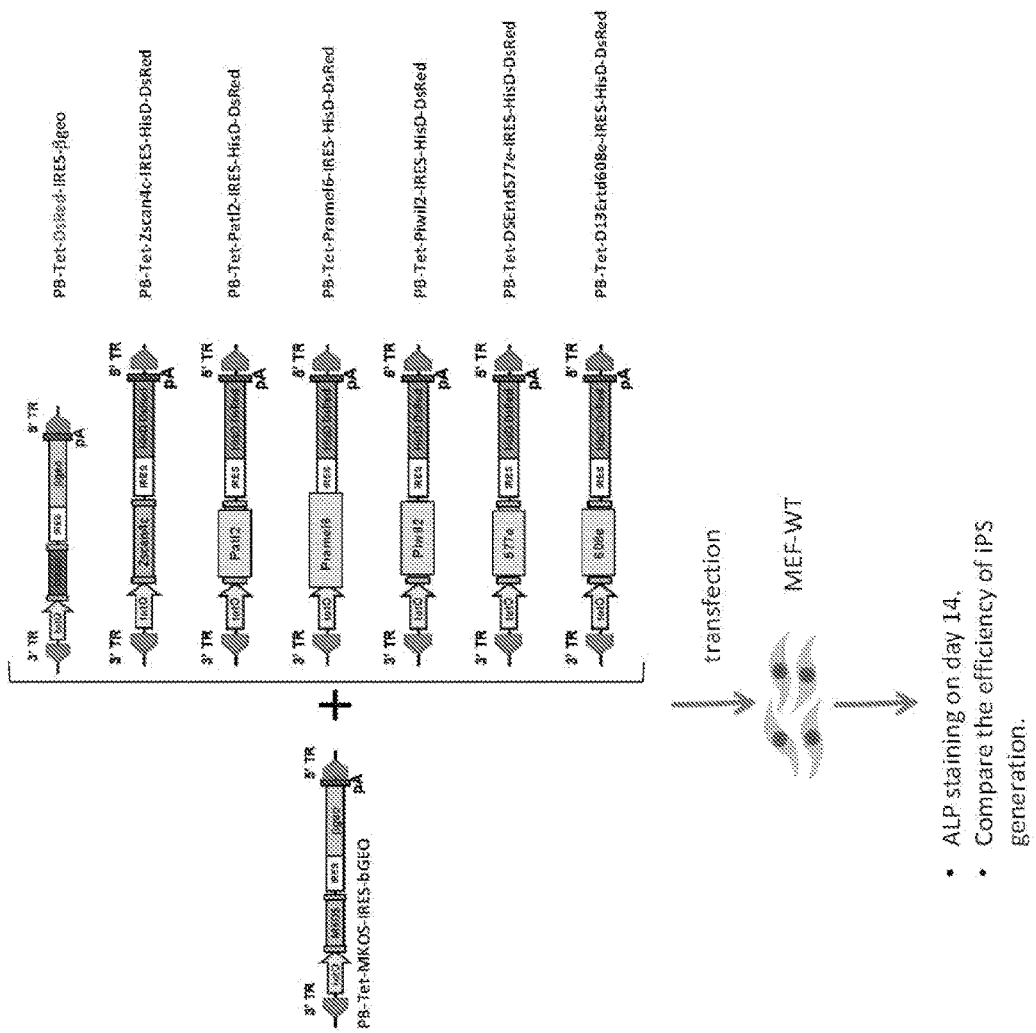
FIG. 21 depicts a schematic of the experimental procedure and constructs used for testing the effect of several Zscan4-dependent genes on the efficiency of iPSC formation.
Figure 22:
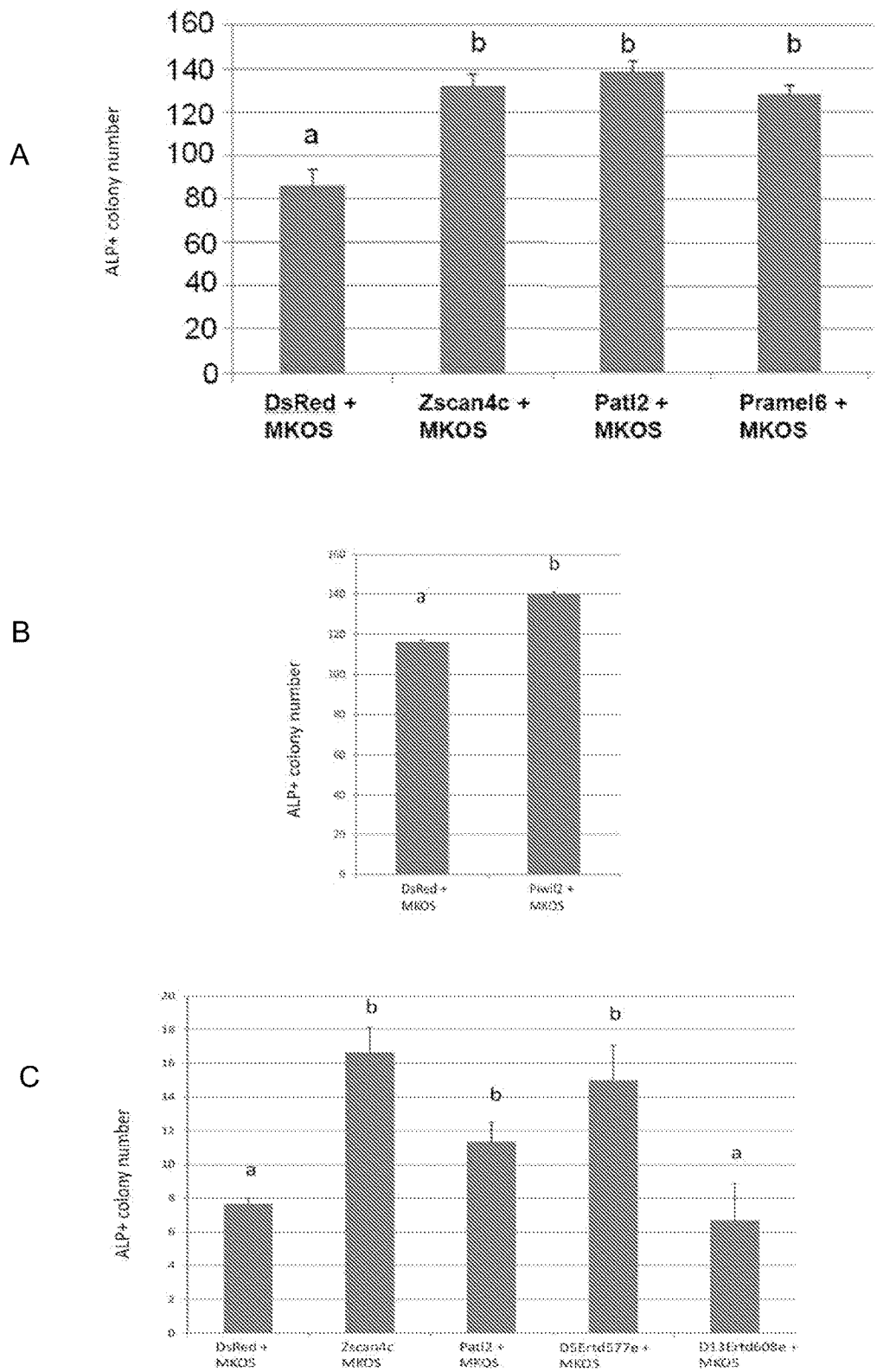
FIG. 22 shows the efficiency of iPS colony formation by Zscan4 and Zscan4-dependent genes.

To test this notion, a piggyBac vector containing MKOS factors (Myc, Klf4, Oct4, and Sox2) and a piggyBac vector containing either DsRed (Control), Zscan4c (positive control), Patl2, Pramel6, Piwil2, D5Ertd577e, or D13Ertd608e, were transfected into wild-type mouse embryo fibroblast (MEF-WT) cells (FIG. 21). The efficiency of iPSC formation was scored based on their authentic ES cell morphology and alkaline phosphatase (ALP) staining 14 days after transfection (mean±S.E.M.) (FIGS. 22A-22C).

The results showed that Patl2, Pramel6, Piwil2, and D5Ertd577e increase the efficiency of iPSC formation. These effects were very similar to what was observed with Zscan4.

In view of the many possible embodiments to which the principles of the disclosed invention may be applied, it should be recognized that the illustrated embodiments are only examples of the disclosure and should not be taken as limiting the scope of the disclosure. Rather, the scope of the disclosure is defined by the following claims. We therefore claim as our invention all that comes within the scope and spirit of these claims.

The invention claimed is:

1. An ex vivo method of producing an induced pluripotent stem (iPS) cell by reprogramming of a somatic cell, comprising contacting the somatic cell with (1) a zinc finger and scan domain-containing protein 4 (Zscan4) or a Zscan4-dependent gene selected from the group consisting of protein associated with topoisomerase II homolog 2 (Pat12), preferentially expressed antigen in melanoma like 6 (Pramel6), piwi-like homolog 2 (Piwil2), and DNA segment, Chr 5, ERATO Doi 577, and expressed (D5Ertd577e), or a protein encoded by the Zscan4-dependent gene and (2) at least four reprogramming factors, thereby producing an iPS cell, wherein the at least four reprogramming factors are v-myc myelocytomatosis viral oncogene homolog (c-Myc), kruppel-like factor 4 (Klf4), POU domain class 5 transcription factor 1 (Oct4), and sex determining region Y-box 2 (Sox2), or the at least four reprogramming factors are Oct4, Sox2, lin-28 homolog A (Lin28), and Nanog homeobox (Nanog), and wherein the somatic cell is a mouse somatic cell, a rat somatic cell, a non-human primate somatic cell, or a human somatic cell.

2. The method of claim 1, wherein contacting the somatic cell with the Zscan4 or the Zscan4-dependent gene comprises introducing a nucleic acid molecule encoding either Zscan4 protein or the protein encoded by the Zscan4-dependent gene into the somatic cell.

3. The method of claim 2, wherein the nucleic acid molecule comprises a viral vector.

4. The method of claim 3, wherein the viral vector is a retrovirus vector, a lentivirus vector or an adenovirus vector.

5. The method of claim 2, wherein the nucleic acid molecule comprises a plasmid vector.

6. The method of claim 2, wherein the nucleic acid molecule is encapsulated in a nanoparticle.

7. The method of claim 2, wherein the nucleic acid molecule comprises mRNA encoding either the Zscan4 protein or the protein encoded by the Zscan4-dependent gene, or mRNA encoding the reprogramming factor proteins.

8. The method of claim 1, wherein contacting the somatic cell with at least four reprogramming factors comprises introducing one or more nucleic acid molecules encoding at least four reprogramming factor proteins into the somatic cell.

9. The method of claim 1, wherein contacting the somatic cell with the Zscan4 or the protein encoded by the Zscan4-dependent gene comprises introducing a Zscan4 protein or the protein encoded by the Zscan4-dependent gene into the somatic cell.

10. The method of claim 9, wherein the Zscan4 protein or the protein encoded by the Zscan4-dependent gene, or four reprogramming factor proteins, is encapsulated in a nanoparticle.

11. The method of claim 9, wherein the Zscan4 protein or the protein encoded by the Zscan4-dependent gene, or four reprogramming factor proteins, is fused to a cell-penetrating peptide, a protein transduction domain or a poly-arginine peptide tag.

12. The method of claim 1, wherein contacting the somatic cell with at least four reprogramming factors comprises introducing four reprogramming factor proteins into the somatic cell.

13. The method of claim 1, wherein the somatic cell is a murine cell or a human cell.

14. The method of claim 1, wherein the somatic cell is a tissue stem cell, a progenitor cell or a differentiated cell, wherein the tissue stem cell is a neural stem cell, a hematopoietic stem cell, a mesenchymal stem cell or an adipose stem cell, and wherein the differentiated cell is a fibroblast, lymphocyte, hepatocyte, epithelial cell, muscle cell, adipose cell, cardiomyocyte, pancreatic β cell, keratinocyte, amniotic cell, peripheral blood cell, platelet, or astrocyte, and wherein the lymphocyte is a T cell or B cell.

15. The method of claim 1, wherein the Zscan4 is murine Zscan4c and wherein the Zscan4c amino acid sequence is at least 95% identical to SEQ ID NO: 8.

16. The method of claim 1, wherein the Zscan4 is human ZSCAN4 and wherein the ZSCAN4 amino acid sequence is at least 95% identical to SEQ ID NO: 2.

17. The method of claim 1, wherein the Pat12 is mouse Pat12 and wherein the Pat12 amino acid sequence is at least 95% identical to SEQ ID NO: 39.

18. The method of claim 1, wherein the Pat12 is human Pat12 and wherein the Pat12 amino acid sequence is at least 95% identical to SEQ ID NO: 47.

19. The method of claim 2, wherein the Pramel6 amino acid sequence is at least 95% identical to SEQ ID NO: 41.

20. The method of claim 1, wherein the Piwil2 is mouse Piwil2 and wherein the Piwil2 amino acid sequence is at least 95% identical to SEQ ID NO: 43.

21. The method of claim 1, wherein the Piwil2 is human Piwil2 and wherein the Piwil2 amino acid sequence is at least 95% identical to SEQ ID NO: 49.

22. An isolated iPS cell produced according to the method of claim 1.

23. An ex vivo method of producing an induced pluripotent stem (iPS) cell by reprogramming of a somatic cell, comprising contacting the somatic cell with (1) a zinc finger and scan domain-containing protein 4 (Zscan4) or a Zscan4-dependent gene selected from the group consisting of protein associated with topoisomerase II homolog 2 (Pat12), preferentially expressed antigen in melanoma like 6 (Pramel6), piwi-like homolog 2 (Piwil2), and DNA segment, Chr 5, ERATO Doi 577, and expressed (D5Ertd577e), or a protein encoded by the Zscan4-dependent gene and (2) at least three or at least four reprogramming factors, thereby producing an iPS cell, wherein the at least three or at least four reprogramming factors are selected from the group consisting of v-myc myelocytomatosis viral oncogene homolog (c-Myc), kruppel-like factor 4 (Klf4), POU domain class 5 transcription factor 1 (Oct4), sex determining region Y-box 2 (Sox2), lin-28 homolog A (Lin28), and Nanog homeobox (Nanog), and wherein the somatic cell is a mouse somatic cell, a rat somatic cell, a non-human primate somatic cell, or a human somatic cell.

* * * * *